US012805725B2

(12) United States Patent
Donner et al.

(10) Patent No.: US 12,805,725 B2

(45) Date of Patent: Nov. 24, 2026

(54) POSTERIOR-INFERIOR SACROILIAC JOINT FUSION PROCEDURE EMPLOYING AN IMPLANT HAVING A PAIR OF FIXATION MEMBERS CONNECTED BY A BRIDGE

(71) Applicant: JCBD, LLC, Fort Collins,, CO (US)

(72) Inventors: Edward Jeffrey Donner, Fort Collins, CO (US); Christopher Thomas Donner, Banner, WY (US)

(73) Assignee: JCBD, LLC

(*) Notice: Subject to any disclaimer, the term of this patent is extended or adjusted under 35 U.S.C. 154(b) by 0 days.

(21) Appl. No.: 18/909,492

(22) Filed: Oct. 8, 2024

(65) Prior Publication Data

US 2025/0025050 A1 Jan. 23, 2025

Related U.S. Application Data

(63) Continuation of application No. 17/706,312, filed on Mar. 28, 2022, now Pat. No. 12,150,733, which is a (Continued)

(51) Int. Cl.

| | |
|---|---|
| ***A61B 17/88*** | (2006.01) |
| ***A61B 5/00*** | (2006.01) |
| ***A61B 17/17*** | (2006.01) |
| ***A61B 17/70*** | (2006.01) |
| ***A61B 17/84*** | (2006.01) |
| *A61B 17/02* | (2006.01) |

(Continued)

(52) U.S. Cl.

CPC .......... *A61B 5/0057* (2013.01); *A61B 5/4528* (2013.01); *A61B 5/4571* (2013.01); *A61B 17/1757* (2013.01); *A61B 17/7055* (2013.01); *A61B 17/7077* (2013.01); *A61B 17/84* (2013.01); *A61B 17/8872* (2013.01); *A61B 5/6847* (2013.01); *A61B 5/6891* (2013.01); *A61B 2017/0275* (2013.01); *A61B 17/90* (2021.08); *A61F 2002/30995* (2013.01)

(58) Field of Classification Search

CPC ... A61B 5/0057; A61B 5/4528; A61B 5/4571; A61B 5/6847; A61B 5/6891; A61B 17/1757; A61B 17/7055; A61B 17/7077; A61B 17/84; A61B 17/8872; A61B 17/90; A61B 2017/0275; A61F 2002/30995

USPC ......... 606/279, 90, 102, 104, 105, 99, 86 A; 623/17.11, 18.11, 22.11, 22.12, 23.39

See application file for complete search history.

(56) References Cited

U.S. PATENT DOCUMENTS 12,150,733 B2 * 11/2024 Donner .............. A61B 17/1757
2011/0238181 A1 * 9/2011 Trieu ................. A61B 17/7055 623/17.11

(Continued)

FOREIGN PATENT DOCUMENTS

WO WO-2014074853 A1 * 5/2014 ............ A61F 2/4611

*Primary Examiner* — Eduardo C Robert
*Assistant Examiner* — David C Comstock
(74) *Attorney, Agent, or Firm* — Polsinelli PC

(57) ABSTRACT

A sacroiliac joint fusion procedure and implant designed for fixation in the dense bone of the SI joint inferior to the extra-articular recess. The implant includes an opening extending across the sacroiliac joint space, an iliac fixation member and a sacral fixation member connected to one another by a bridge where the pair of fixation members extend further distally than the bridge.

11 Claims, 91 Drawing Sheets

Related U.S. Application Data continuation of application No. 16/282,114, filed on Feb. 21, 2019, now Pat. No. 11,284,798, which is a continuation-in-part of application No. 15/789,602, filed on Oct. 20, 2017, now Pat. No. 10,492,688, which is a continuation of application No. 14/723,384, filed on May 27, 2015, now Pat. No. 9,801,546.

(60) Provisional application No. 62/633,205, filed on Feb. 21, 2018, provisional application No. 62/003,053, filed on May 27, 2014.

(51) Int. Cl.
*A61B 17/90* (2006.01)
*A61F 2/30* (2006.01)

(56) References Cited

U.S. PATENT DOCUMENTS

2012/0296428 A1* 11/2012 Donner .............. A61B 17/7043
623/17.11
2014/0277165 A1* 9/2014 Katzman ............ A61B 17/1671
606/279

* cited by examiner

POSTERIOR-INFERIOR SACROILIAC JOINT FUSION PROCEDURE EMPLOYING AN IMPLANT HAVING A PAIR OF FIXATION MEMBERS CONNECTED BY A BRIDGE

CROSS REFERENCE TO RELATED APPLICATIONS

The present application is a continuation application of U.S. application Ser. No. 17/706,312, filed Mar. 28, 2022, which application is a continuation application of U.S. application Ser. No. 16/282,114, filed Feb. 21, 2019, now U.S. Pat. No. 11,284,798, which application is a continuation-in-part application of U.S. patent application Ser. No. 15/789,602, filed Oct. 20, 2017, now U.S. Pat. No. 10,492,688, which application is a continuation application of U.S. patent application Ser. No. 14/723,384 filed May 27, 2015, now U.S. Pat. No. 9,801,546, which application claims the benefit of U.S. Provisional Application 62/003,053, which was filed May 27, 2014, entitled "SYSTEMS FOR AND METHODS OF TREATING A MUSCULOSKELETAL JOINT." application Ser. No. 16/282,114 also claims the benefit of U.S. Provisional Application No. 62/633,205, filed Feb. 21, 2018. The contents of all the above-mentioned patent applications are hereby incorporated by reference in their entireties for all purposes.

TECHNICAL FIELD

Aspects of the present disclosure relate to medical apparatus and methods. More specifically, the present disclosure relates to devices and methods for diagnosing and treating a sacroiliac joint.

BACKGROUND

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different methods encompassing an anterior approach, a posterior approach, and a lateral approach with or without percutaneous screw or other type implant fixation.

A general overview of anatomy, function, pathology and certain treatment options are shown and discussed in "Surgery for the Painful, Dysfunctional Sacroiliac Joint", copyrighted 2015 and edited by Drs. Bruce Dall, Sonia Eden, Michael Rahl and with chapters authored by Drs. E. J. Donner, Arnold Graham Smith, Michael Moore and David Polly. This book is hereby incorporated by reference in its entirety.

Improvements to sacroiliac joint fusion involve systems and methods for non-transverse delivery of an implant into the sacroiliac joint are described in U.S. patent application Ser. No. 12/998,712, filed May 23, 2011 entitled SACROILIAC JOINT FIXATION FUSION SYSTEM; Ser. No. 13/236,411, filed Sep. 19, 2011 entitled SYSTEMS FOR AND METHODS OF FUSING A SACROILIAC JOINT; and Ser. No. 13/475,695, filed May 18, 2012, entitled SYSTEMS FOR AND METHODS OF FUSING A SACROILIAC JOINT; and Ser. No. 13/945,053, filed Jul. 18, 2013, entitled SYSTEMS FOR AND METHODS OF FUSING A SACROILIAC JOINT; and Ser. No. 13/946,790, filed Jul. 19, 2013, entitled SYSTEMS FOR AND METHODS OF FUSING A SACROILIAC JOINT; and Ser. No. 14/216,975, filed Mar. 17, 2014, entitled SYSTEMS AND METHODS FOR FUSING A SACROILIAC JOINT AND ANCHORING AN ORTHOPEDIC APPLIANCE; and Ser. No. 14/447,612, filed Jul. 31, 2014, entitled SYSTEMS FOR AND METHODS OF FUSING A SACROILIAC JOINT; and Ser. No. 16/133,605, filed Sep. 17, 2018, entitled "SYSTEMS FOR AND METHODS OF PREPARING AND FUSING A SACROILIAC JOINT". All of application Ser. Nos. 12/998,712, 13/236,411, 13/475,695, 13/945,053, 13/946,790, 14/216,975, and 14/447,612 are herein incorporated by reference in their entirety.

To determine whether a sacroiliac joint is a source of pain, an injection of analgesics into a sacroiliac joint can be performed by a physician and a patient's subjective measurement of pain can be recorded before, during and for some time after the intervention. The injection may reduce or substantially eliminate pain temporarily. If the injection substantially reduces the pain then the physician could conclude that the sacroiliac joint is indeed a source of the patient's pain.

Other conventional methods for determining sacroiliac joint pain include physical manipulation of body parts within close proximity to the joint which can be meant to stress the sacroiliac joint and thereby provoke pain in hopes of eliciting a reproduction of the patient's accustomed pain. The sacroiliac pain provocation tests can include distraction, right or left sided thigh thrusts, right or left sided Gaenslen's test, compression, and sacral thrust.

The pain referral pattern associated with sacroiliac joint pain can be confused with other etiologies of the pain due to overlapping pain referral patterns. For example, lumbar spinal disc herniations, lumbosacral facet pathologies, femoral acetabular impingement and other musculoskeletal or medical conditions may cause confusingly similar pain referral patterns.

A significant problem with certain conventional methods, which include the injection of material within the joint, for determining sacroiliac pain may be that the physician has introduced an amount of analgesic or other combined substances into the joint which exceeds the capacity of the joint and the solution could then go beyond the joint and or affect other parts of the body. Similarly, without regard to the amount of solution injected, the solution can leave the joint and affect other structures. For example, if the analgesic solution affects the sciatic nerve, the lumbosacral trunk, the L4 nerve root, the sacral plexus, or the S1, S2 or S3 nerves, all of which are in close proximity to the sacroiliac joint, and, for example, if the patient's pain is due to some condition of one of these nerves which has a similar pain referral pattern as sacroiliac joint pain, the sensitivity and specificity of the diagnostic procedure can be grossly misleading.

Another substantial problem with conventional methods which include manipulation of body parts near the joint can be that the structures targeted by the provocative tests are not the only structures affected. One or more different innervated structures in close proximity to the sacroiliac joint could also be stressed by these tests and refer pain or other symptoms into the lower back, pelvis or lower extremities thereby complicating the diagnosis.

As seen in FIGS. 1A-1B, external pelvic fixators 5 are conventionally used to stabilize and rest a traumatized sacroiliac joint 3 until healed or asymptomatic (e.g., 6-12 weeks). External pelvic fixators 5 are conventionally recommended to diagnose and determine whether sacroiliac joint fusion would be a treatment option if the patient received pain relief from temporary stabilization of the sacroiliac joint 3.

However, the external pelvic fixators 5 require multiple pins 2 placed in, e.g., the ilium 1 bilaterally (i.e., in both ilia) which is associated with significant risk and morbidity including but not limited to pain, infection and the inconvenience to the patient and medical person due to a bulky external frame around the pelvis. Another problem with conventional procedures can be that there may be no or an insufficient reduction in the movements of a sacroiliac joint 3. For example, an insufficient reduction in the movements of a sacroiliac joint 3 may be due to the extended distance from the fixation point provided by the external fixator relative to the sacroiliac joint 3 being evaluated. The complication rate for definitive and temporary conventional pelvic external fixation has been reported to be rather significant.

Referring to FIG. 1C, other conventional techniques for fixation of the joint 3 may include placement of rods or screws 4 across a sacroiliac joint 3 within the ilium 1 and sacrum 0 defining the sacroiliac joint 3. Yet further conventional techniques and implants may distract the joint and may thereby alter the tension of the surrounding ligamentous structure. Problems associated with these and other conventional techniques used primarily for sacroiliac joint fusion may include the difficulty of removal of the implants, namely, because the implants and the associated conventional methods of use are generally intended for insertion only. That is, the implants, rods, and screws described with reference to the conventional art are not configured for temporary use or for diagnostic purposes. Explanation of the implants, rods, or screws are generally not intended and is generally only utilized when complications arise. For example, the rods shown in FIG. 1C may disrupt the interosseous ligament which the sacroiliac joint 3 depends on, in part, for stability in a healthy patient. As another example, other conventional implants and method may significantly disrupt the inner and outer table of the ilium, the cortical surface of the sacrum and may remove a significant volume of the bone of the sacrum and ilium.

Accordingly, there is a need in the art for systems and methods of diagnosing and treating a sacroiliac joint that minimally and temporarily disrupts the patient's anatomical structure and tissues. It is with these thoughts in mind, among others, that the present disclosure involving systems and methods of diagnosing and treating a sacroiliac joint were developed.

SUMMARY

Aspects of the present disclosure may involve a method of diagnosing and treating a sacroiliac joint of a patient, the method may include delivering a first member into the ilium via a first posterior approach, delivering a second member into the sacrum via a second posterior approach, coupling the first and second members to a pliers, and manipulating the first member relative to the second member via the pliers to determine an ailment of the sacroiliac joint.

In certain instances, the pliers are a dual-axis pliers may include first and second handles, first and second head portions, and a pair of joints adjustably coupling the first and second handles and the first and second head portions, the pair of joints facilitating rotation of the first and second head portions about first and second axes, the first and second axes are generally perpendicular to each other.

In certain instances, the pliers may include first and second handles, first and second head portions, and a first joint adjustably coupling the first and second handles and the first and second head portions, the pliers are expanding pliers such that movement of the first and second handles closer together via rotation about a first axis of the first joint causes the first and second head portions to move apart from each other.

In certain instances, the pliers further may include a second joint adjustably coupling the first and second handles and the first and second head portions, the second joint facilitates rotation of the first and second head portions about a second axis of the second joint, the second axis being generally perpendicular to the first axis.

In certain instances, the pliers further may include at least one stud member configured to be engaged and disengaged with the first joint, engagement of the stud member with the first joint limits rotation of the pliers to the first axis of the first joint, and disengagement of the stud member with the first joint permits rotation of the pliers to the first axis of the first joint and the second axis of the second joint.

Aspects of the present disclosure may involve a method of diagnosing and treating a sacroiliac joint of a patient, the method may include delivering a first member into the ilium via a first posterior approach, delivering a second member into the sacrum via a second posterior approach, coupling the first and second members to a first and second guide blocks, respectively, of a clevis guide, and manipulating the first member relative to the second member via the clevis guide to determine an ailment of the sacroiliac joint.

In certain instances, the clevis guide may include a pair of prongs adjustably coupled to the first and second guide blocks.

In certain instances, the first guide block may include rotationally coupled to the pair of prongs, and the second guide block may include rotationally and slidingly coupled to the pair of prongs so as to permit parallel alignment of the first and second guide blocks.

In certain instances, manipulation of the first member relative to the second member via the clevis guide may include relative longitudinal displacement of the first and second members.

In certain instances, the first guide block may include a first through-hole and a first screw-lock to secure the first member in a first position within the first through-hole, the second guide block may include a second through-hole and a second screw-lock to secure the second member in a second position within the second through-hole.

Aspects of the present disclosure may involve a method of diagnosing and treating a sacroiliac joint of a patient, the method may include delivering a first member into the sacrum via a first posterior approach, sliding a first dilator over the first member, sliding a sleeve of a first guide of a parallel pin guide over the first dilator, positioning a second guide of the parallel pin guide so as to target the ilium, inserting a second dilator into the second guide, and delivering a second member into the ilium via guidance by the second dilator.

In certain instances, the first and second members are guide wires, and the method further may include delivering first and second bone pins, respectively into the locations of the first and second members.

In certain instances, further may include manipulating the first and second bone pins relative to each other in order to determine a condition of the sacroiliac joint.

In certain instances, further may include using at least one of a pliers and a clevis guide to manipulate the first and second bone pins relative to each other in order to determine a condition of the sacroiliac joint.

In certain instances, further may include inserting a pair of radiographic contrasting members into radiographic guide holes of the parallel pin guide, and aligning the radiographic contrasting members with the sacroiliac joint.

In certain instances, aligning the radiographic contrasting members with the sacroiliac joint may include done under radiographic imaging.

In certain instances, aligning the radiographic contrasting members with the sacroiliac joint causes the second guide of the parallel pin guide to target the ilium.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 55I is an inferior view of the sacrum and the ilium with the clevis guide secured to the pair of pins (positioned in the sacrum and ilium where the guide wires were previously).

DETAILED DESCRIPTION

Figure 1A:
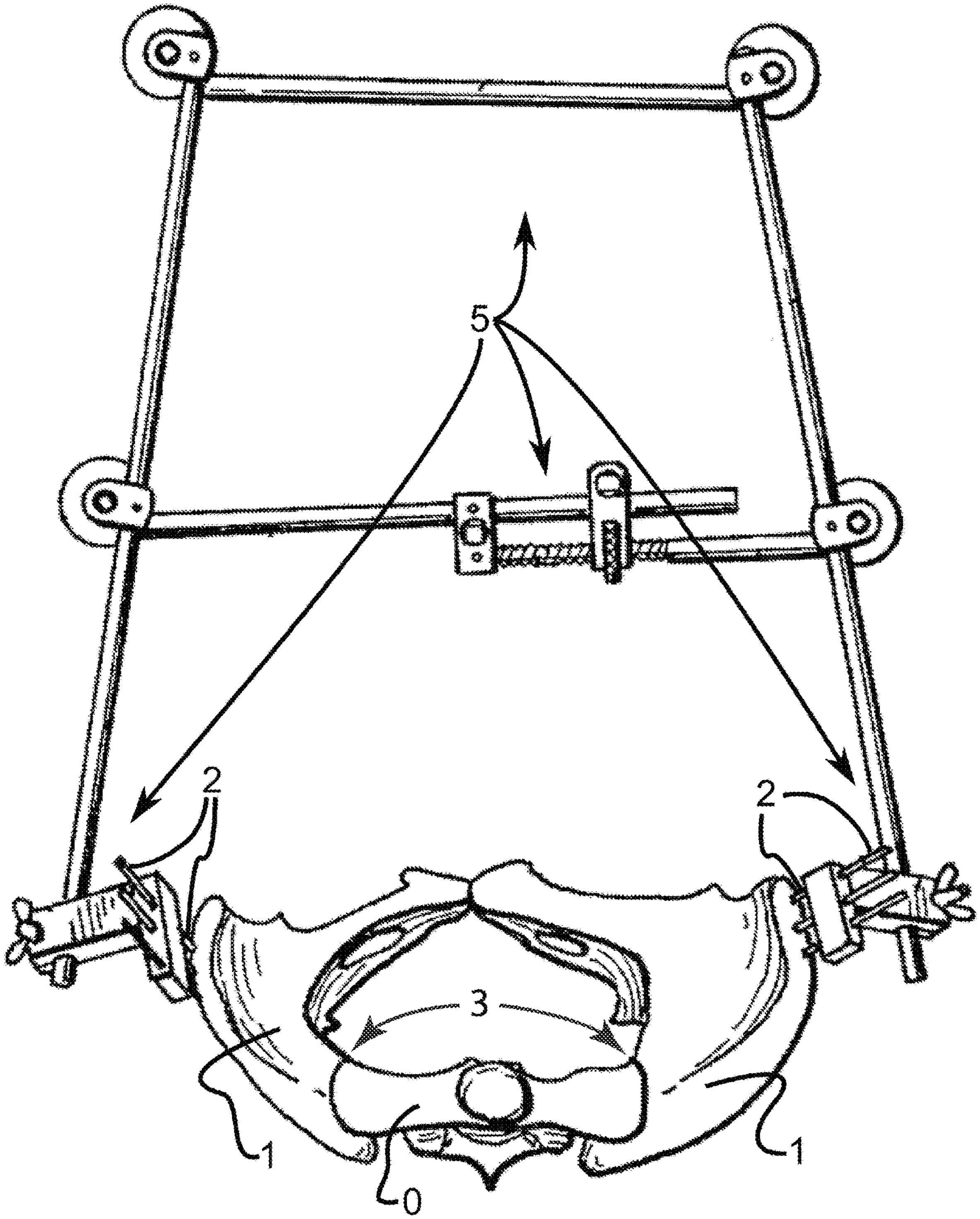
FIG.1A (CONVENTIONAL ART)
FIG. 1A is a superior view of a pelvic region and a conventional method and device for temporarily stabilizing the sacroiliac joint.
Figure 1B:
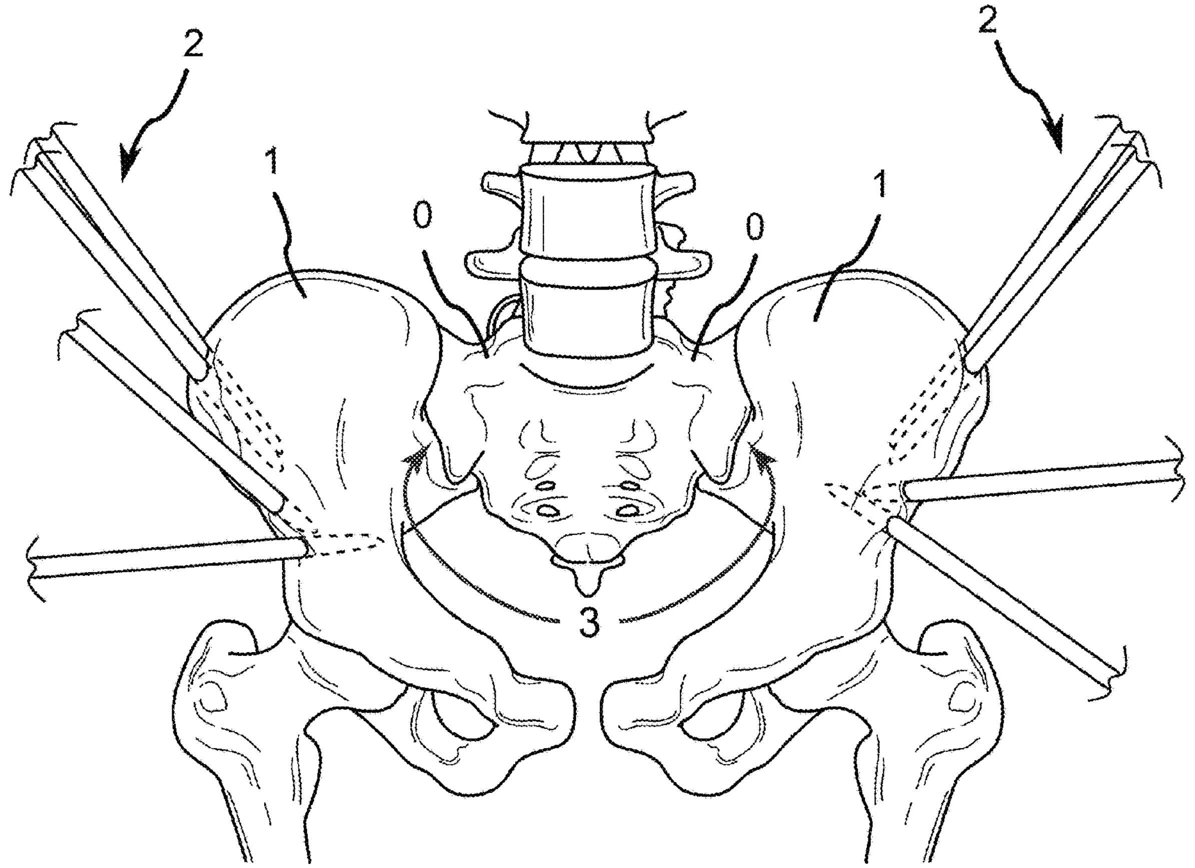
FIG.1B (CONVENTIONAL ART)
FIG. 1B is an anterior view of the pelvic region and the conventional method and device for temporarily stabilizing the sacroiliac joint of FIG. 1A.
Figure 1C:
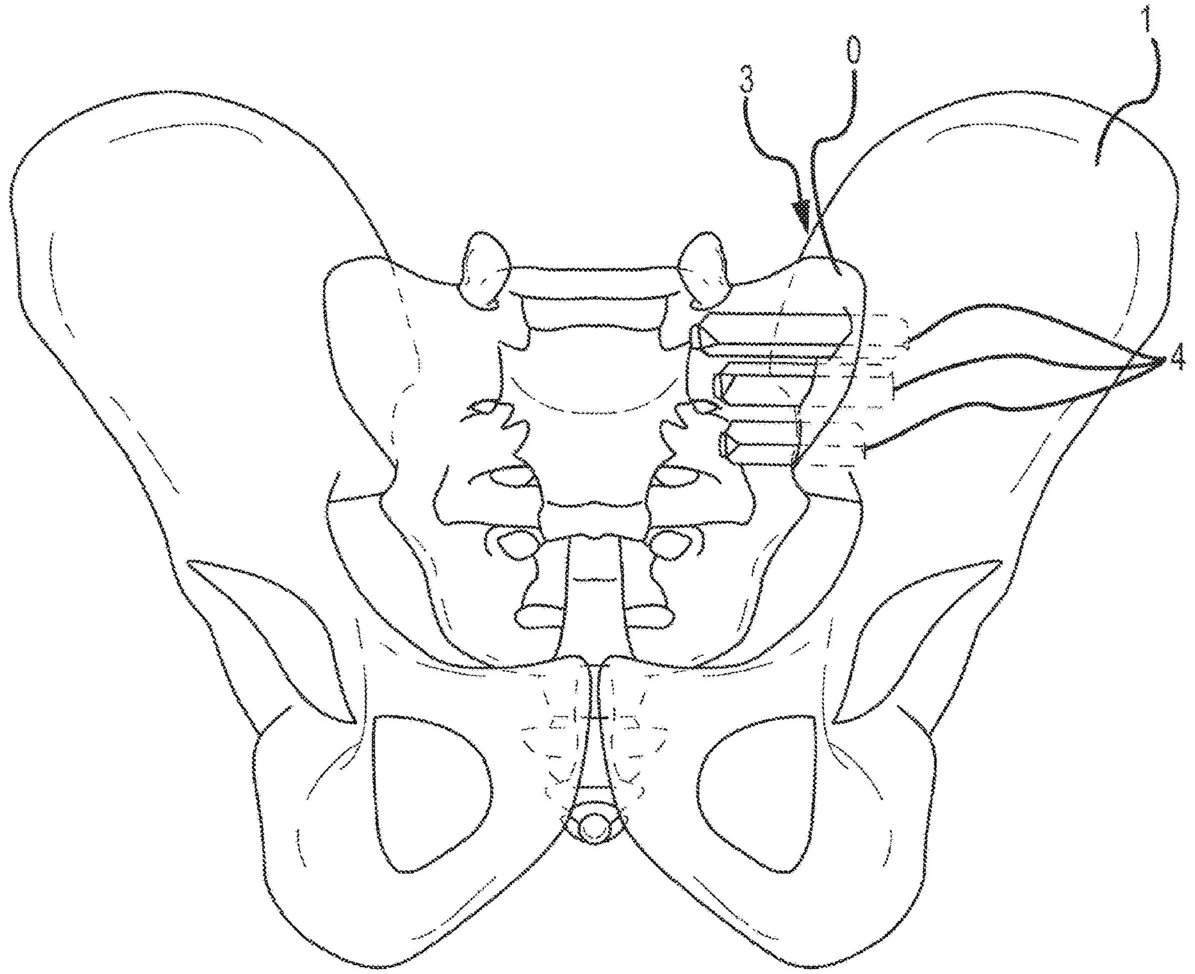
FIG.1C (CONVENTIONAL ART)
FIG. 1C is an anterior view of the pelvic region and a conventional method and device for permanently stabilizing the sacroiliac joint.

Implementations of the present disclosure involve a system for diagnosing and treating a sacroiliac joint disorder or ailment. In particular, the system may include a diagnostic tool for manipulating a pair of rods temporarily implanted or engaged with the hip region of the patient. A first rod may engage with or be delivered into the sacrum and a second rod may be delivered parallel to the first rod and may engage with or be delivered into the ilium. The rods may span an intra-articular region or extra-articular region of the sacroiliac joint. The diagnostic tool may be used to grasp and manipulate the rods such that the sacrum and ilium are manipulated relative to each other. Through manipulation of the diagnostic tool, the ilium may be, for example, translated proximally, distally, cranial, or caudal relative to the sacrum. Additionally, the ilium may be, for example, rotated in various planes relative to the sacrum via the diagnostic tool. Alternatively, and in certain embodiments, the rods may be manipulated by hand without the aid of the diagnostic tool. The manipulation of the sacrum and ilium via the rods may be beneficial for a medical professional to diagnose a sacroiliac joint disorder because, for example, the rods may isolate the forces exerted to specific areas of the hip region (e.g., sacrum, ilium or lumbosacral spine). In certain instances, the diagnosis may indicate that stabilization of the joint is necessary.

The joint may be stabilized in several ways. For example, the rods may be replaced by anchor or shorter rods and the rods may be coupled together, beneath the patient's skin. If a suitable amount of pain is reduced by this procedure, this may indicate that permanent fixation of the joint should alleviate or substantially reduce the pain.

As another example of joint fixation and while the rods are in place in the sacrum and ilium, the rods may act as an alignment system for the subsequent delivery of a temporary implant. More particularly, a sleeve may be fitted over the rods and an insert may be fitted within the sleeve to guide a particular implant for delivery into the sacroiliac joint. The implant may be delivered via a posterior approach into the sacroiliac joint and the implant may be delivered such that a portion of the implant bridges the joint and affixes into a portion of each of the sacrum and the ilium. In certain implementations, the implant may include an open distal end such that a majority of the body of the implant occupies the sacrum and the ilium with the open portion of the implant occupying the sacroiliac joint space so as to minimally disrupt the cartilage in the joint space.

The temporary implant may remain in the patient for a period of time to determine if a subsequent, permanent implant is needed. For example, if the temporary implant successfully treats the disorder, the implant may be removed in favor of implanting a permanent implant such as those described in U.S. patent application Ser. Nos. 14/447,612; 13/475,695; 13/236,411; 12/998,712; and Ser. No. 16/133, 605, all of which are incorporated by reference in their entireties into the present application. Accordingly, if a subsequent implant is to be delivered into the joint space, the joint may be prepared according to the systems, tools, and methods described in U.S. patent application Ser. Nos. 14/514,221, and 16/133,605 which is hereby incorporated by reference into the present application in its entirety. Or, the implant may remain implanted and a subsequent implant may or may not be delivered into the sacroiliac joint.

In particular instances, a portion or entirety of a sacroiliac joint may be treated, stabilized, or replaced by an implant, system and/or method as described in U.S. patent application Ser. No. 14/127,119, filed Dec. 17, 2013, entitled "Sacroiliac Joint Implant System" and incorporated herein by reference in its entirety.

In certain instances, when a patient may have pain in the region near the sacroiliac joint, a fluid injection method may be used to inject pain medicine in the sacroiliac joint. When using the fluid injection method, it may be difficult to accurately determine if the pain arises from the sacroiliac joint or other regions, because the fluid may leak to other nearby regions. The pain medicine may leak into other nearby regions and relieve the pain in those regions such that even if the pain is reduced, it is difficult to determine if the pain truly comes from the sacroiliac joint.

Current diagnostic procedures may not be accurate enough to determine whether the root cause of the pain comes from the sacroiliac joint. As a result, a surgeon may place an implant in the sacroiliac joint, which may not be necessary or helpful for relieving the patient's pain, or possibly subjecting the patient to unnecessary potential complications.

The present diagnostic system provides a diagnostic system that can generate localized forces to cause movement of the sacroiliac joint. The diagnostic system may assist to accurately determine the need of an implant in the sacroiliac joint (or other treatment), either by stabilizing the joint to reduce the pain in a patient or by reproducing the pain in the patient via the localized forces to mobilize the joint or cause movement of the joint. This diagnostic system and method may provide accurate diagnostics on whether an implant is needed, thus, reducing the possibility of an unnecessary implant being implanted into the sacroiliac joint.

The present disclosure provides a diagnostic system that can be used to mobilize the sacroiliac joint of a patient to reproduce or stimulate pain in the patient. The patient may provide feedback on whether the pain is similar to his or her familiar pain pattern. If the pain in the patient can be reproduced by manipulating the movement of the sacroiliac joint, this suggests that fusion, fixation, stabilization, or other treatment of the joint (e.g., with an implant) may be helpful to reduce the pain. Various methods and means may be used to mobilize the sacroiliac joint. For example, the diagnostic system may include pins, rods, or bars that may be inserted or engaged with the sacrum or ilium at different locations to cause particular movements of the sacroiliac joint. The pins or bars may have a distal end portion that can engage a larger region of the ilium or sacrum to cause the movement. For example, the distal end portion may extend from the pin in a radial direction such that the distal end portion may have a larger surface area. The distal end portion may be a 2D or 3D plate. The diagnostic system may also include screws that are inserted in the ilium or sacrum. One shaft may be used to couple to one screw while another shaft may be coupled to another screw. The shafts may be used to cause movements or stabilization of the joint. The distal portion may be a hook. The distal portion may be configured to reversibly expand (i.e., similar to a molly bolt or toggle bolt).

The present disclosure also provides a diagnostic system that can help determine if stabilizing the sacroiliac joint of a patient helps with reducing pain or other symptoms in the patient. The diagnostic system may include diagnostic pins coupled together that may be temporarily placed in the patient to stabilize the joint and to determine if the patient may have reduced pain. The pins may remain in the patient for a given period of time to determine if stabilization of the joint via the pins is effective at reducing pain. Instructions may be given to the patient to perform, e.g., single leg stands, squats, sitting, rolling on side, movement of leg in various directions, an activity which causes accustomed symptoms. The patient may do certain work out routines on a running machine or cycling machine to provide feedback on whether the pain is reduced. The patient may also be instructed to live a regular daily life to provide feedback on whether the pain is reduced. The diagnostic system may also include delivering tools for implanting into the joint.

I. System for Fusion of the Sacroiliac Joint

Figures 2A, 2B, 2C:
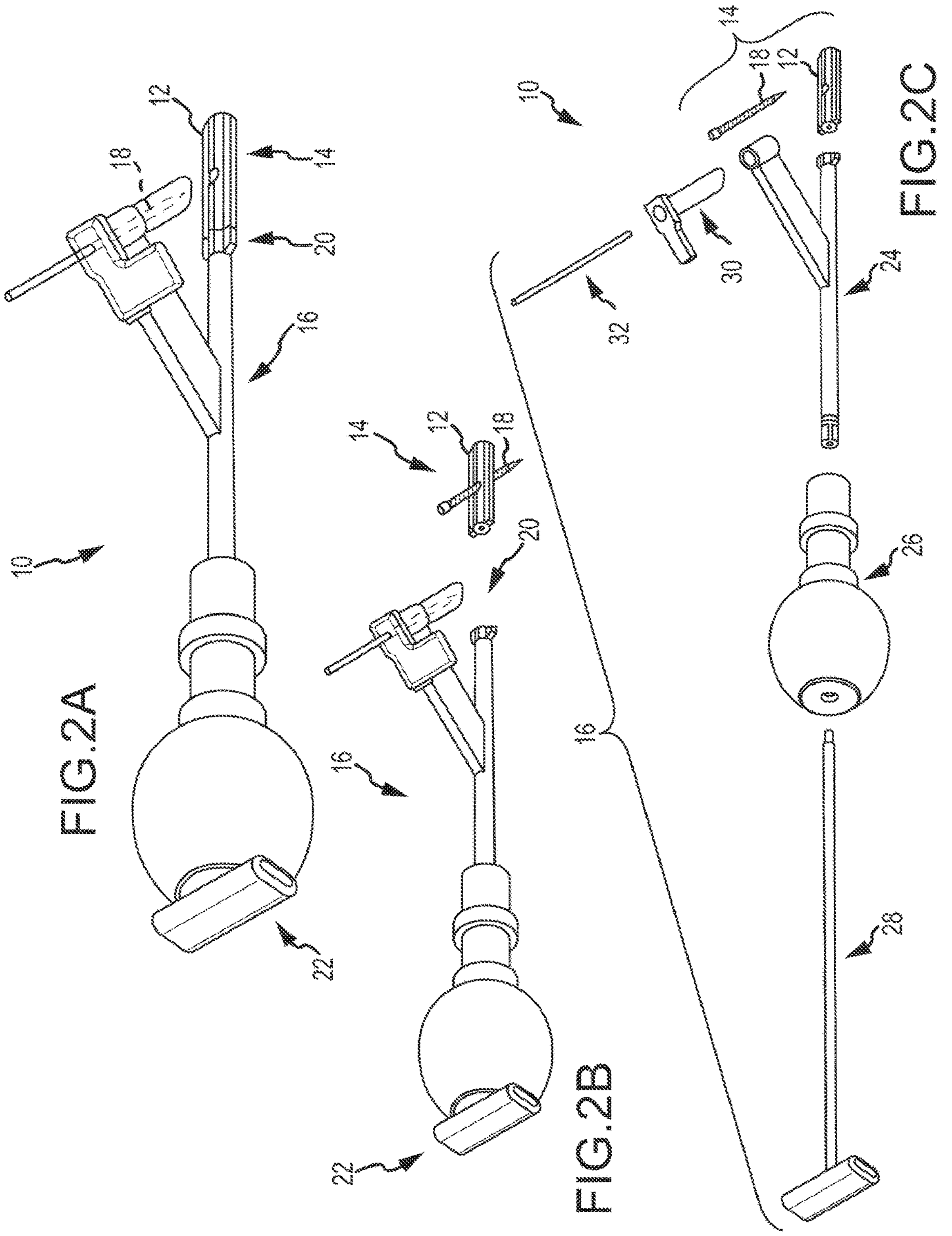
FIG. 2A is an isometric view of an example system for fusing a sacroiliac joint.
FIG. 2B is the same view as FIG. 2A, except the delivery tool and implant assembly are decoupled from each other.
FIG. 2C is the same view as FIG. 2A, except the system is exploded to better illustrate its components.

To begin a detailed discussion of a system 10 for delivering an implant 12 into the sacroiliac joint, reference is made to FIGS. 2A-2C. FIG. 2A is an isometric view of the system 10. FIG. 2B is the same view as FIG. 2A, except an implant assembly 14 of the system 10 is separated from a delivery tool 16 of the system 10. FIG. 2C is the same view as FIG. 2A, except the system 10 is shown exploded to better illustrate the components of the system 10.

As can be understood from FIGS. 2A and 2B, the system 10 includes a delivery tool 16 and an implant assembly 14 for implanting at the sacroiliac joint via the delivery tool 16, the implant assembly 14 being for fusing the sacroiliac joint. As indicated in FIG. 2C, the implant assembly 14 includes an implant 12 and an anchor element 18 (e.g., a bone screw or other elongated body). As discussed below in greater detail, during the implantation of the implant assembly 14 at the sacroiliac joint, the implant 12 and anchor element 18 are supported by a distal end 20 of the delivery tool 16, as illustrated in FIG. 2A. The delivery tool 16 is used to deliver the implant 12 into the sacroiliac joint space. The delivery tool 16 is then used to cause the anchor element 18 to extend through the ilium, sacrum and implant 12 generally transverse to the sacroiliac joint and implant 12. The delivery tool 16 is then decoupled from the implanted implant assembly 14, as can be understood from FIG. 2B. As illustrated in FIGS. 2A-2C, the delivery tool 16 further includes a proximal end 22 opposite the distal end 20, an arm assembly 24, a handle 26, an implant retainer 28, a sleeve 30 and a trocar or guidewire 32. While in the embodiment of FIGS. 2A-2C, the delivery tool 16 is fixed and non-adjustable and configured to deliver the anchoring element 18 in a single orientation relative to the implant 12, the delivery tool 16 may be adjustable and configured to deliver the anchoring elements 18 within a range of orientations relative to the implant 12 that will orient the anchoring element 18 either within a bore of the implant 12, or adjacent implant 12 as described in U.S. patent application Ser. No. 14/447,612, filed Jul. 31, 2014, entitled SYSTEMS FOR AND METHODS OF FUSING A SACROILIAC JOINT, which is hereby incorporated by reference in its entirety.

In particular embodiments, first and second articular faces of the implant 12 may be selected to match the contour of the joint space of the sacroiliac joint within which the implant 12 is to be inserted. For example, the sacral, medial or first articular faces of the implant may be configured to be generally convex to match the contour of a sacral auricular boney surface or to match the contour of an extra-articular region of a sacrum (e.g., a sacral fossa). In one aspect and referring to portions of the anatomy shown FIG. 5C, the sacral, medial or first articular face of the implant 12 may be generally a surface negative of the articular surfaces 1016 of the extra-articular region 3007 and/or articular region 1044 of the sacrum 1004. As another example, the lateral, iliac or second articular face of the implant 12 may be configured to be generally concave to match the contour of an iliac auricular boney surface or to match the contour of an extra-articular region of an ilium (e.g., an iliac tuberosity). In one aspect, the lateral, iliac or second articular face of the implant 12 may be generally a surface negative of the articular surfaces 1016 of the extra-articular region 3007 and/or articular region 1044 of the ilium 1005.

Figure 3:
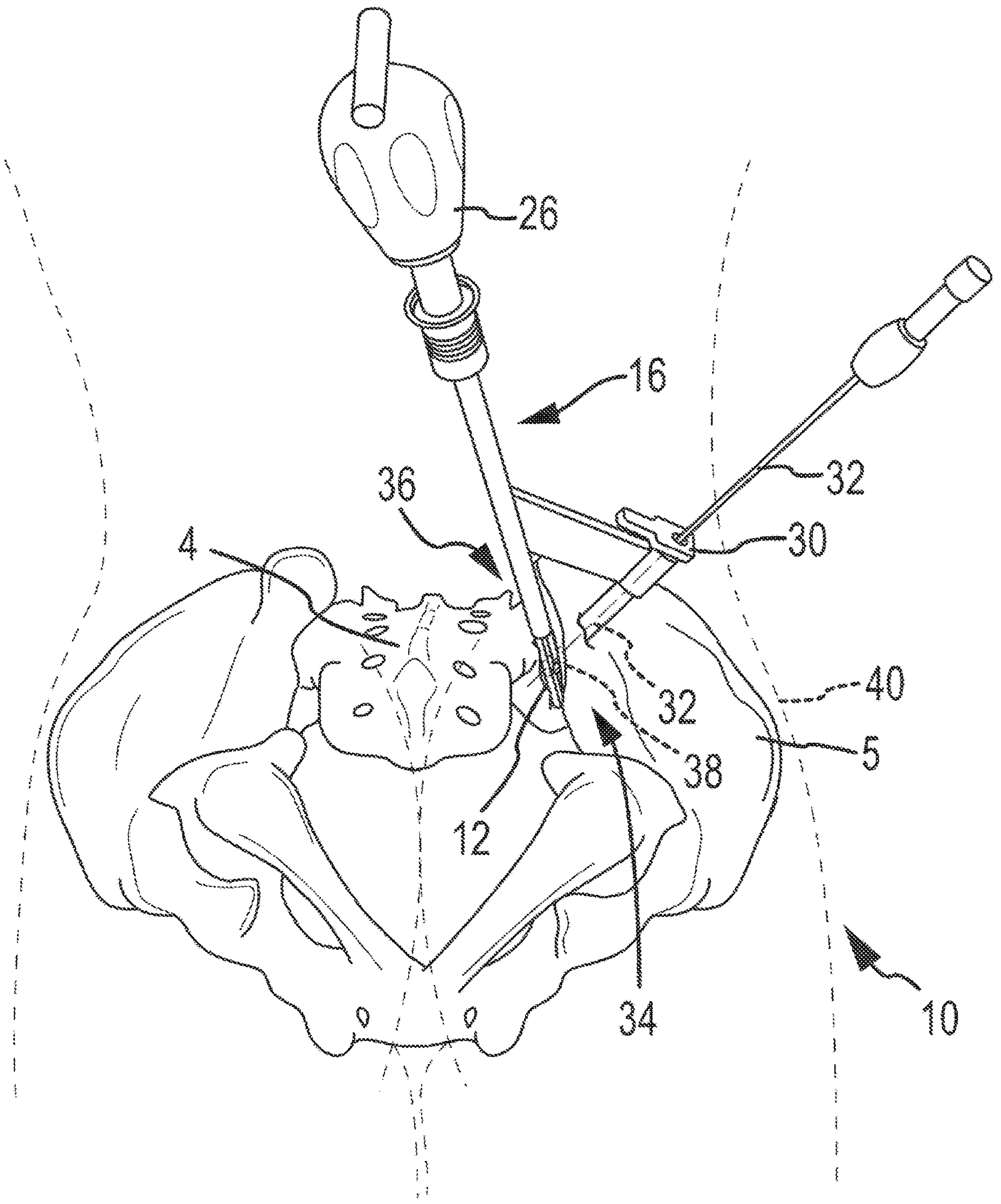
FIG. 3 is a posterior-inferior view of a sacroiliac joint with a patient body shown in broken line.
Figure 4:
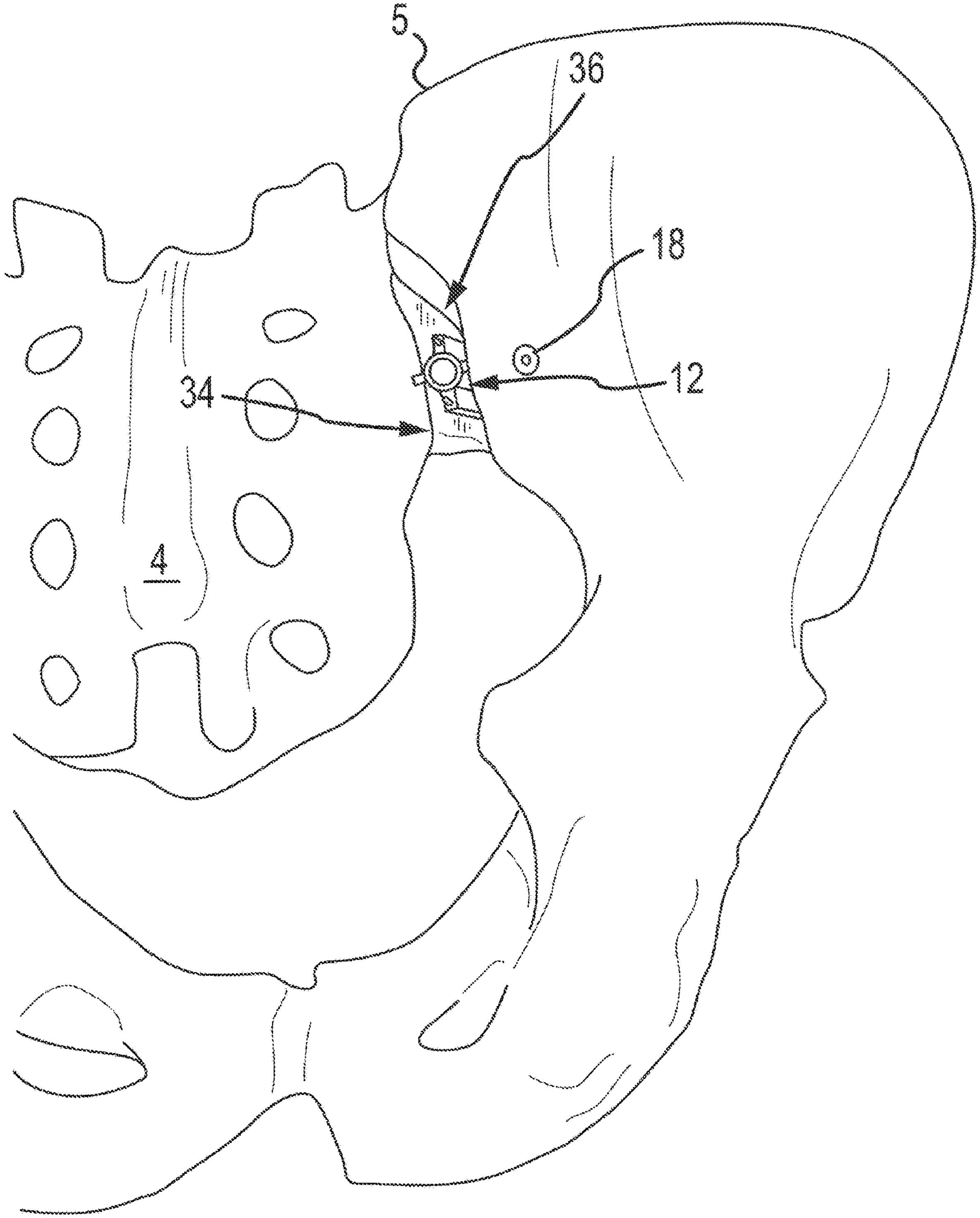
FIG. 4 is a close-up view of the implant and anchor element in the sacroiliac joint.

A system as described in FIGS. 2A-2C may be used in a surgical procedure via a posterior approach, as seen in FIGS. 3-4. As can be understood from FIG. 3, which is a posterior-inferior view of a sacroiliac joint 36 with a patient 40 shown in broken line, the delivery tool 16 is positioned to deliver the implant 12 into a caudal region 34 of the sacroiliac joint 36 and the anchoring element 18 through the ilium 5 and into the bore 38 of the implant 12. Referring to FIG. 4, the implant 12 and anchoring element 18 have been inserted into the caudal region 34 of the sacroiliac joint 36 and the delivery tool 16 has been removed.

Figure 5A:
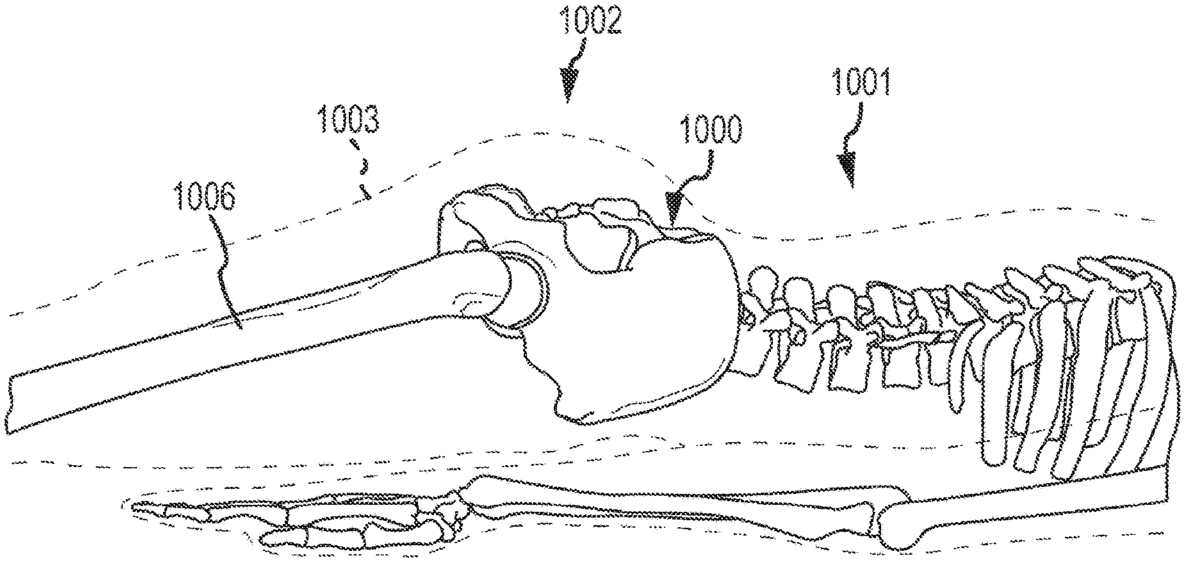
FIG. 5A is a right lateral view of a hip region of a patient lying in a prone position, wherein the soft tissue surrounding the skeletal structure of the patient is shown in dashed lines.
Figure 5B:
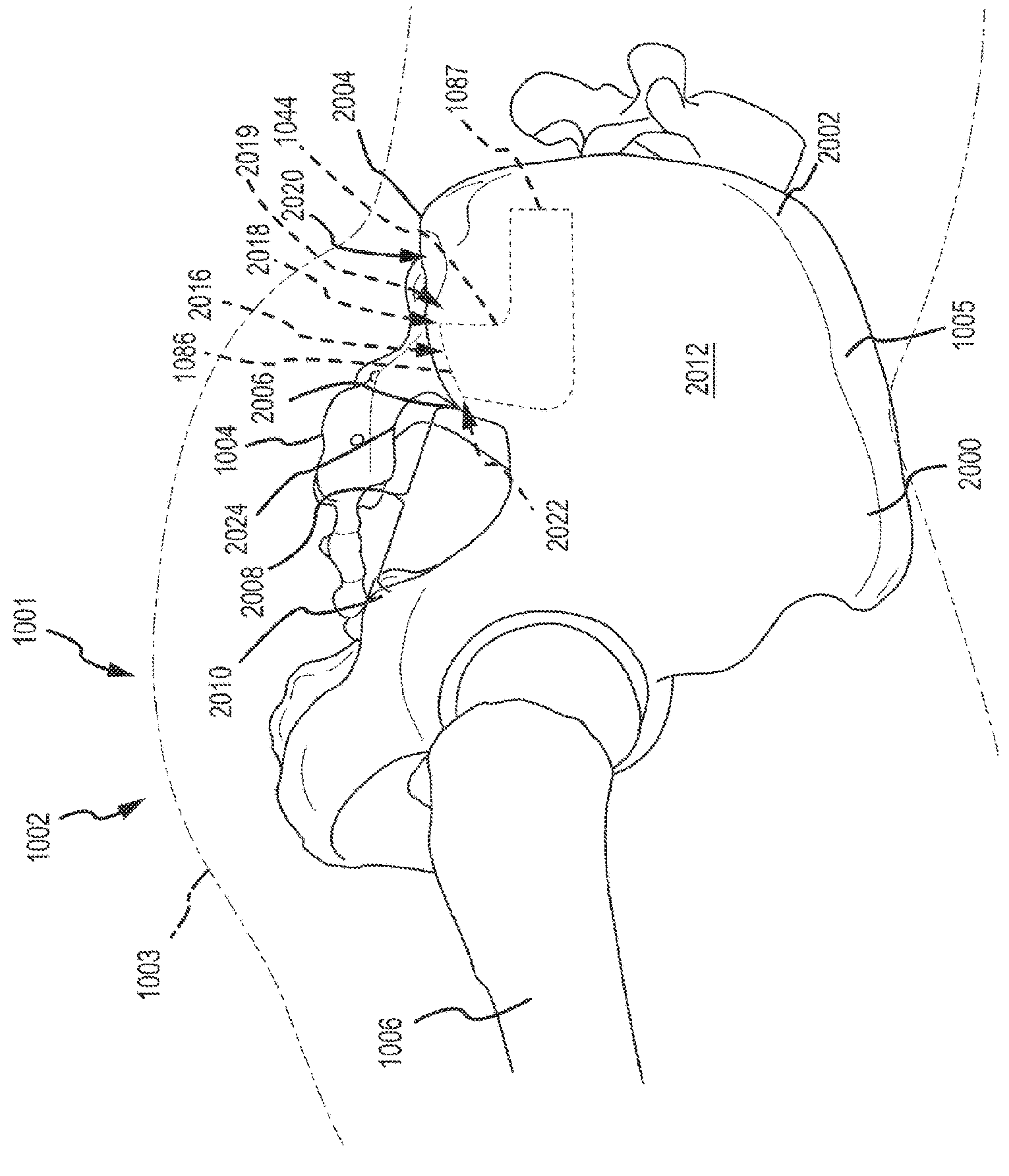
FIG. 5B is an enlarged view of the hip region of FIG. 5A.
Figure 5C:
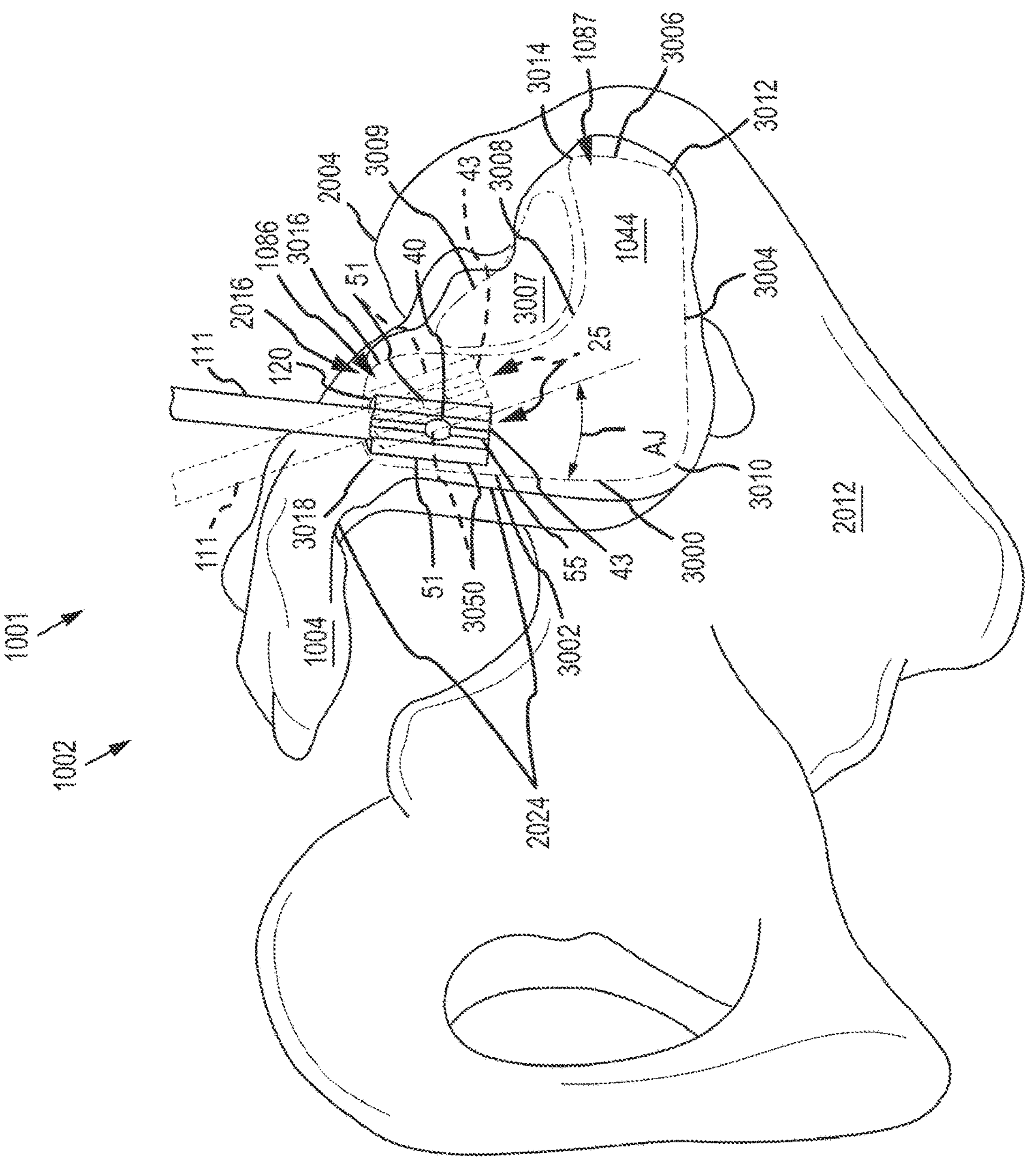
FIG. 5C is generally the same view as FIG. 5B, except that the ilium is removed to show the sacroiliac joint space boundary defined along the sacrum and an implant positioned for implantation within the joint space.

With further reference to the boney anatomy shown in FIG. 5C, a system as described herein may be used in a surgical procedure via an anterior approach (e.g., such that the surgical pathway includes traversing an anterior boundary segment 3004 and/or traversing an anterior-inferior corner 3010) and may further include positioning an implant into a sacroiliac joint such that: 1) the implant longitudinal axis a) is generally parallel to a sacroiliac joint inferior boundary segment 3002, or b) points towards a posterior superior iliac spine, or c) point towards a posterior inferior iliac spine, or d) points toward a sacroiliac extra-articular region; or, 2) the distal end of the implant generally lies within a) a caudal region of the sacroiliac joint articular region, or b) an extra-articular portion of the sacroiliac joint, or c) a cranial portion or cephalad region of the sacroiliac joint articular region.

Additionally, a system as described herein may be used in a surgical procedure via an approach which includes a surgical pathway which transverses a sacroiliac joint inferior boundary segment 3002, e.g., as described in U.S. patent application Ser. No. 13/945,053, filed Jul. 18, 2013, entitled SYSTEMS AND METHODS OF FUSING A SACROILIAC JOINT, which is hereby incorporated by reference in its entirety. A surgical procedure via this pathway may further include positioning an implant into a sacroiliac joint such that: 1) the implant longitudinal axis a) is transverse to a sacroiliac joint inferior boundary segment 3002, or b) points towards a posterior superior iliac spine, or c) point towards a posterior inferior iliac spine, or d) points toward a sacroiliac extra-articular region, or e) points towards a sacroiliac joint anterior boundary segment 3004, or f) points towards either superior boundary segment corner 3014 or 3012 or somewhere in-between; or, 2) the distal end of the implant generally lies within a) a caudal region of the sacroiliac joint articular region, or b) an extra-articular portion of the sacroiliac joint, or c) a cranial portion or cephalad region of the sacroiliac joint articular region.

Furthermore, in certain embodiments, an implant 12 may be inserted along a generally arcuate path. Accordingly, a surgical preparation technique and tools may be utilized while operating in an arcuate path. The implant arcuate path may follow and generally match the surgical preparation arcuate path and the path arc may include a radius of between approximately 3 cm to 6 cm. The portion of the path having an arcuate path including a radius of between approximately 3 cm to 6 cm may reside substantially in the plane of the sacroiliac joint or in a plane in close proximity and generally parallel thereto. Furthermore, the arcuate path may generally or substantially reside in sacroiliac joint articular region 1044. Additionally, an implant may be selected for use during the procedure which substantially matches the radius or curvature of the arcuate or curved insertion path or surgical preparation path.

In certain embodiments, after drilling or otherwise producing an opening through an ilium (or sacrum) leading toward or into a sacroiliac joint, a sleeve may guide (alone or along with another cannulated tool, e.g., a needle) a bone paste, bone marrow aspirate, stem cells, allograft or any biocompatible material or substance into the sacroiliac joint space via a path with a trajectory which may be generally transverse to the plane of the sacroiliac joint. The sleeve may be caused to form a seal with a bone defining the sacroiliac joint, e.g. the ilium. The seal may be created by impacting a proximal end of sleeve which may, for example, cause the sleeve to slightly penetrate the cortex of the outer table of the ilium. Alternatively, a cannulated tool such as a large gauge needle or tube may either be interference fit within a hole in the ilium or the needle or tube may have a threaded distal end which may be threaded into the bore formed in the ilium. A plunger or bone tamp may be forced through a sleeve to advance the bone paste or other material into the sacroiliac joint space, adjacent/around the implant and/or into the bone graft window of the implant.

Subsequently, an anchor such as a bone screw may be advanced via the sleeve into engagement with an opening formed in the ilium and driven across the sacroiliac joint and further into the sacrum. Alternatively, a bone plug may be positioned into the opening formed in the ilium in order to occlude the passageway between the outer cortex of the ilium and the implanted bone paste or other material positioned generally in the plane of the joint.

II. Methods of Preparing the Sacroiliac Joint for Fusion

The following discussion will focus on various methods of diagnosing and treating a sacroiliac joint ailment utilizing the tools and devices discussed previously.

A. Preoperative Planning for a Diagnostic and/or Surgical Procedure

Prior to any joint treatment, preparation or fusion, a surgeon or other medical person may diagnose a particular ailment of the sacroiliac joint and select a suitable procedure to treat the sacroiliac joint, e.g., fusion, fixation, stabilization, replacement, resurfacing, restructuring, repairing, or altering of boney ligamentous or capsular tissue. The procedure may include fusing the joint with or without delivering an implant in the joint space. A diagnostic and/or treatment procedure may be planned and/or conducted (and, e.g., the surgeon may select an implant configuration for delivery into the sacroiliac joint region of the patient) based on preoperative or intraoperative data. The data may be the result of post-processing of raw or other imaging data (e.g. CT or MRI DICOM files). The post-processing may include the use of a software program (e.g., 3DSLICER available from http://www.slicer.org) that may be used for medical image processing and 3D visualization of image data. Other data may include the patient's weight, activity level, spinal alignment, posture and general health.

The preoperative or intraoperative data may assist in the planning and selecting of desirable implant and final anchor positioning, trajectories (e.g., starting and stopping points on patient's soft tissue and near or within bone tissue), anchor, number, configurations and dimensions (e.g., length, cannulation, apertures, cross sectional geometry, surface treatments, diameter, head size, washer, thread pitch), implant types, number, configurations and dimensions, and joint preparation tool types, dimensions, and configurations. A particularly system for preparing and fusing the sacroiliac joint may be selected, for example, for a hypermobile joint, which may include an implant or fusion system that is resistant to the expected forces (magnitude and vector) present at that particular patient's sacroiliac joint. The determination of fixation sufficiency may be calculated based on the patient's data and also on the performance results of various bench and/or finite element analysis ("FEA") tested implant assembly (or individual components) configurations. For example, a calculated anchor and/or implant trajectory may be considered and determined from certain patient imaging and post-processing data with an overlayed implant assembly. Further, the implant assembly footprint within the joint plane may be selected as a lower percent of total joint surface area to permit sufficient boney fusion across the joint while maintaining a sufficient implant sacral and iliac face surface area to prevent implant subsidence.

Specific measurements and characteristics of the patient's anatomy may influence the selection of a particular joint fusion system. For example, the patient's bone density may be measured at numerous locations in proximity to and surrounding the elements of the implant assembly. Lower bone density (e.g., osteopenia, osteoporosis) corresponding to a T-score lower than −1, sacroiliac joint instability, or hypermobility may require the use of an implant assembly with a greater amount of keel (or a particular keel configuration) (i.e., the material cross section as defined by thickness of the keel and its length along implant longitudinal axis and also keels extending a greater distance into both bones defining the sacroiliac joint) and anchor extending across the sacroiliac joint and into the ilium and sacrum. Additionally, the relative angles between the implant longitudinal axis and anchor or anchors, and also the relative angles between multiple anchors (e.g., parallel, divergent, convergent) may be preselected based on the patient's anatomy.

A comparison of the preoperative or intraoperative data (e.g., sacroiliac joint surface area, joint mobility, loading, bone density, desirable anatomic pathways) and the selected implant assembly and joint preparation tools may be conducted to ensure or validate compatibility before the manufacture ships the implant system and/or before the surgeon employs the system in a surgical procedure. After implant assembly and preparation tools validation, the selected assemblies may be shipped to the surgeon and the surgeon may proceed with the surgical fusion procedure utilizing the selected assemblies.

Similarly, various aspects of the diagnostic tools (discussed herein) may be selected based on the same or similar data and/or studies. Additionally, placement of the various components of the diagnostic systems in to the sacroiliac joint region and/or the amount of displacement of one bone relative to another may be chosen or guided by one or more of the following: the anchor trajectory and placement may be guided and confirmed with imaging studies before the end of the surgical procedure or afterwards. For example, a surgeon may use fluoroscopy (and/or arteriography) to obtain an anteroposterior view, lateral view, an inlet view, an outlet-oblique view, Judet views of the pelvis, an internal (obturator) oblique view, a Ferguson view, an external (iliac) oblique view or other relevant views and further use radiographic boney landmarks such as the superimposed greater sciatic notches, superimposed iliac cortical densities or alar slope, sacral promontory, first sacral endplate, sacral foramina, arcuate sacral lines, iliopectineal line, ilioishial line, acetabular teardrop lines bony corridors of S1 or S2, superimposed acetabula, ventral and dorsal surfaces of the sacrum, etc.; or using an angiogram to identify vascular structures such as the superior gluteal artery, internal iliac artery and vein, iliolumbar vein, etc.

B. Fusion of the Sacroiliac Joint Via Implant Delivery

The following is an overview of the anatomy and methods of fusing the joint. To begin, reference is made to FIGS. 5A-5B, which depict various bone landmarks adjacent, and defining, the sacroiliac joint 1000 of a patient 1001.

Reference is first made to FIG. 5A, which is a right lateral view of a hip region 1002 of a patient 1001 lying prone, wherein the soft tissue 1003 surrounding the skeletal structure 1006 of the patient 1001 is shown in dashed lines. Delivery of an implant into the sacroiliac joint 1000 and, thus, preparing of the joint 1000 for delivery of the implant may be conducted via a posterior approach to the hip region 1002. FIG. 5B, which is an enlarged view of the hip region 1002 of FIG. 5A, depicts a lateral view of the patient's hip region 1002 and reveals certain features of the ilium 1005, including the anterior superior iliac spine 2000, the iliac crest 2002, the posterior superior iliac spine 2004, the posterior inferior iliac spine 2006, the greater sciatic notch 2008 extending from the posterior inferior iliac spine 2006 to the ischial spine 2010, and the tubercle of the iliac crest 2012.

The sacroiliac joint articular region or intra-articular region 1044 is shown in dashed lines. The articular region 1044 is a portion of the sacroiliac joint 1000 formed between articular surfaces of the ilium 1005 and sacrum 1004. The articular region 1044 is typically covered in a thin plate of cartilage and is surrounded by a fibrous capsule containing synovial fluid.

Boundaries of the sacroiliac joint articular region 1044 are as follows. A posterior inferior access region 2016 of the sacroiliac joint articular region 1044 has a superior end 2018 on the sacroiliac joint line 2019 that is between approximately 0 mm and approximately 40 mm inferior the posterior inferior overhang 2020 of the posterior superior iliac spine 2004. The posterior inferior access region 2016 of the sacroiliac joint articular region 1044 has an inferior end 2022 on the sacroiliac joint line that is at approximately the intersection of the posterior inferior iliac spine 2006 with the lateral anterior curved boundary 2024 of the sacrum 1004. In other words, the posterior inferior access region 2016 of the sacroiliac joint articular region 1044 has an inferior end 2022 on the sacroiliac joint line that is at approximately the superior beginning of the greater sciatic notch 2008.

Still referring to FIG. 5B, the sacroiliac joint articular region 1044 roughly defines an L-shape or boot-shape that includes a caudal region 1086 and a cranial region 1087. Access into the caudal region 1086 of the sacroiliac joint may be accomplished via the posterior inferior access region 2016 that extends between corners defined by the superior end 2018 and the inferior end 2022. Access into the cranial region 1087 may be accomplished by continual, anterior travel in the caudal region 1086 until the articular region 1044 turns superiorly into the cranial region 1087.

To begin a discussion of implant delivery into the sacroiliac joint articular region 1044, reference is made to FIG. 5C, which is a close-up lateral side view of the hip region 1002 of a patient 1001 with a nearest ilium 1005 removed in order to show the sacroiliac joint boundary 3000 defined along the sacrum 1004 and outlining the sacroiliac joint articular region 1044, and an implant 25 positioned for implantation within the sacroiliac joint articular region 1044.

As seen in FIG. 5C, boundaries along the sacroiliac joint articular region 1044 include an inferior boundary segment 3002, an anterior boundary segment 3004, a superior boundary segment 3006, and a posterior boundary segment 3008. The inferior boundary segment 3002 is immediately adjacent, and extends along, the sciatic notch 2024.

The inferior boundary segment 3002 and anterior boundary segment 3004 intersect to form an anterior-inferior corner 3010. The anterior boundary segment 3004 and superior boundary segment 3006 intersect to form an anterior-superior corner 3012. The superior boundary segment 3006 and posterior boundary segment 3008 intersect to form a superior-posterior corner 3014. The posterior boundary segment 3008 and posterior inferior access region 2016 intersect to form a superior-posterior corner 3016 of the posterior inferior access region 2016. The inferior boundary segment 3002 and posterior inferior access region 2016 intersect to form an inferior-posterior corner 3018 of the posterior inferior access region 2016.

The inferior boundary segment 3002 extends between corners 3010 and 3018. The anterior boundary segment 3004 extends between corners 3010 and 3012. The superior boundary segment 3006 extends between corners 3012 and 3014 and provides an access into the cranial portion 1087 of the sacroiliac joint. The posterior boundary segment 3008 extends between corners 3014 and 3016. The posterior inferior access region 2016 extends between corners 3016 and 3018 and provides an access into the caudal region 1086 of the sacroiliac joint.

The posterior boundary segment 3008 separates the articular region 1044 and the extra-articular region 3007, which includes the sacral fossa on the sacrum 1004 and the corresponding iliac tuberosity on the ilium 1005 and defined by the extra-articular region boundary 3009.

In one aspect and as seen in FIG. 5C, the implant 25 may be delivered via an implant arm 111 of a delivery tool into the caudal region 1086 of the sacroiliac joint articular region 1044. As shown via the implant 25 and implant arm 111 shown in solid lines, in one embodiment, the implant 25 enters the posterior inferior access region 2016, and is further advanced into the caudal region 1086 of the sacroiliac joint articular region 1044, in an orientation such that the implant arm 111 and wide planar members 51 are in the joint plane and the longitudinally extending edge 3050 of the wide planar member 51 next to the inferior boundary segment 3002 is generally parallel to, and immediately adjacent to, the inferior boundary segment 3002. Thus, the distal end 43 of the implant is heading generally perpendicular to, and towards, the anterior boundary segment 3004.

As shown in FIG. 5C via the implant 25 and implant arm 111 shown in dashed lines, in one embodiment, the implant 25 enters the posterior inferior access region 2016, and is further advanced into the caudal region 1086 of the sacroiliac joint articular region 1044, in an orientation such that the implant arm 111 and wide planar members 51 are in the joint plane and the longitudinally extending edge 3050 of the wide planar member 51 next to the inferior boundary segment 3002 is somewhere between being generally parallel to the inferior boundary segment 3002 (as illustrated by the solid-lined implant 25 in FIG. 5C) or forming an angle AJ with the inferior boundary segment 3002 of up to approximately 50 degrees. Thus, the distal end 43 of the implant shown in dashed lines can be said to head anywhere from generally perpendicular to, and towards, the anterior boundary segment 3004 to heading generally towards the superior-anterior corner 3012, or points in between.

In one embodiment, the implant 25 may be first directed into the joint space as illustrated by the solid-lined implant 25 in FIG. 5C after which the implant 25 is rotated within the joint space to be positioned somewhere between, and including, angled position depicted by the dashed-lined implant 25. In other embodiments, the implant 25 may be first directed into the joint space as illustrated by the dashed-lined implant 25 in FIG. 5C after which the implant 25 is rotated within the joint space to be positioned somewhere between, and including, the parallel position depicted by the solid-lined implant 25. Thus, an implant 25 may be delivered non-transversely (i.e., within the joint and not across the joint) into the caudal region 1086, the cranial portion 1087, or partially within each of the caudal and cranial regions 1086, 1087 of the sacroiliac joint articular region 1044. Further details of the implant delivery can be found in related applications, mentioned previously, such as U.S. patent application Ser. No. 12/998,712, which is incorporated by reference herein in its entirety.

Figure 5D:
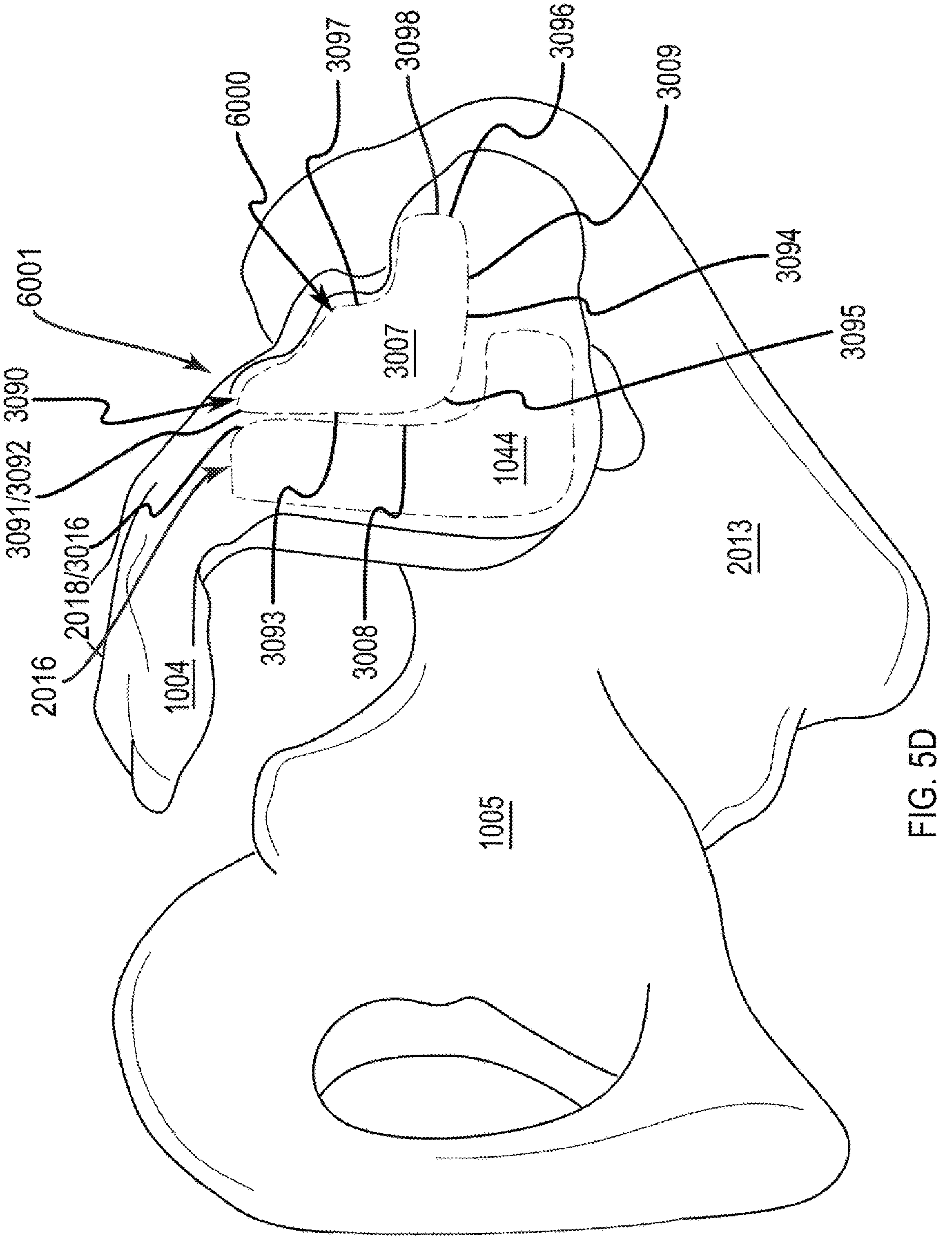
FIG. 5D is a lateral side view of the pelvic region of a patient with a nearest ilium removed to clearly show the regions of the sacroiliac joint.

Reference is now made to FIGS. 5D, which depicts a close-up lateral view of the hip region 1002 of FIG. 5C, except the implant is not shown. In particular, FIG. 5D shows additional anatomical features of the extra-articular region 3007 of the joint. As seen in the figure, the extra-articular region boundary 3009 has a caudal boundary segment 3093, an anterior boundary segment 3094, and a posterior boundary segment 3097. The caudal boundary segment 3093 and the anterior boundary segment 3094 separate the intra-articular region 1044 and the extra-articular region 3007. The posterior boundary segment 3097 is immediately adjacent and extends along the sacroiliac joint line 2019. The caudal and anterior boundary segments 3093, 3094 intersect to form an anterior-inferior corner 3095. The caudal boundary segment 3093 intersects with the posterior boundary segment 3097 to form a posterior-inferior corner 3091. The anterior boundary segment 3094 of the extra-articular boundary 3009 intersects with the posterior boundary segment 3097 for form a posterior-anterior corner 3096.

The sacroiliac extra-articular region 3007 has an extra-articular recess access region 6000, which spans the posterior boundary segment 3097 and has an inferior end 3092 (i.e., generally coincident with posterior inferior corner 3091) and a superior end 3098 located near the posterior anterior corner 3096 along the sacroiliac joint line 2019.

The extra-articular access region 6000 has an extra-articular posterior-inferior access region 6001 that has an inferior end 3092 along the sacroiliac joint line 2019. The inferior end 3092 is generally coincident with the posterior inferior corner 3091. The inferior end 3092 is immediately adjacent both the superior-posterior corner 3016 and the superior end 2018 of the posterior inferior access region 2016.

Figure 5E:
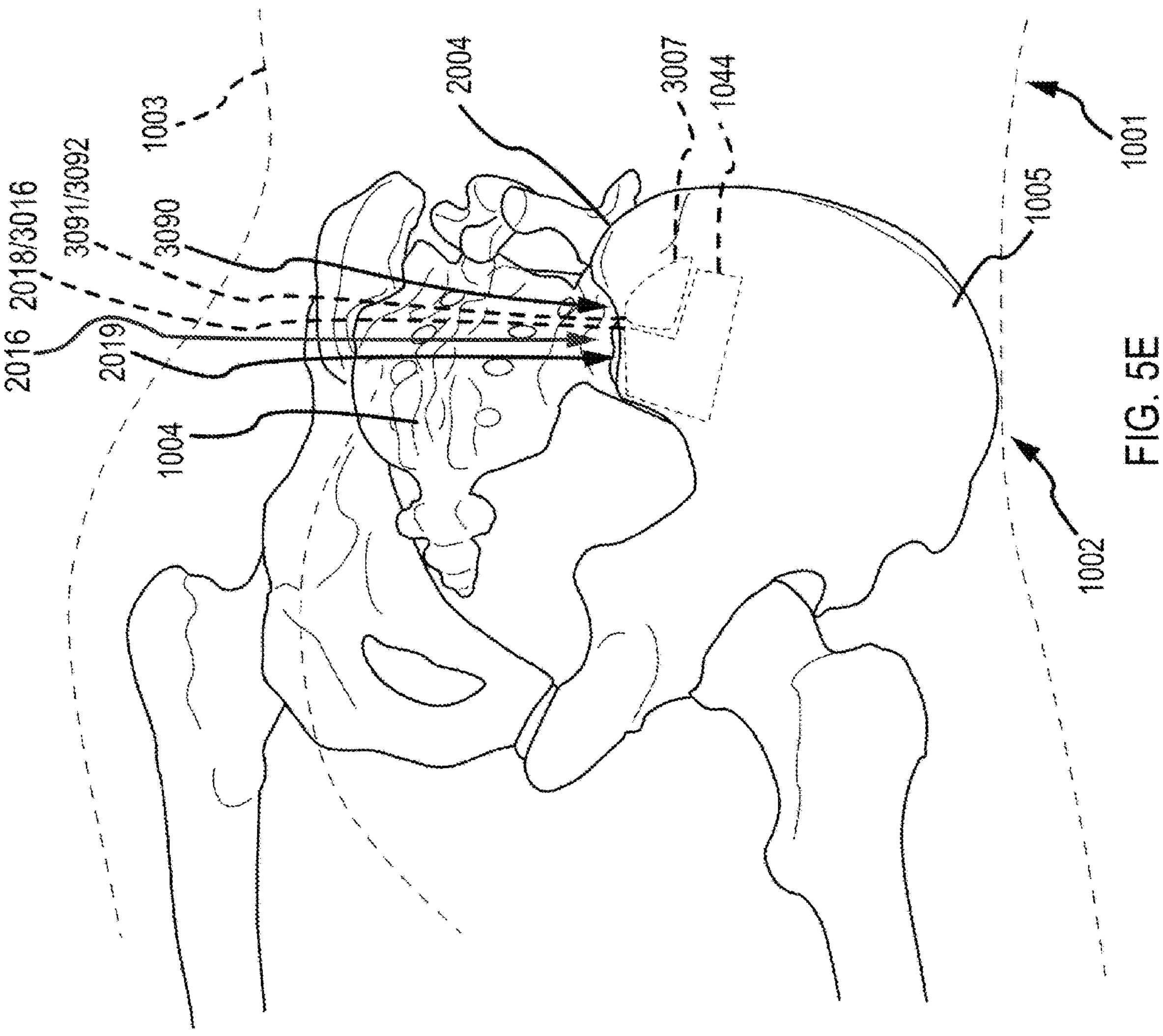
FIG. 5E is a lateral posterior view of the hip region of the patient showing the regions of the sacroiliac joint.
Figure 5F:
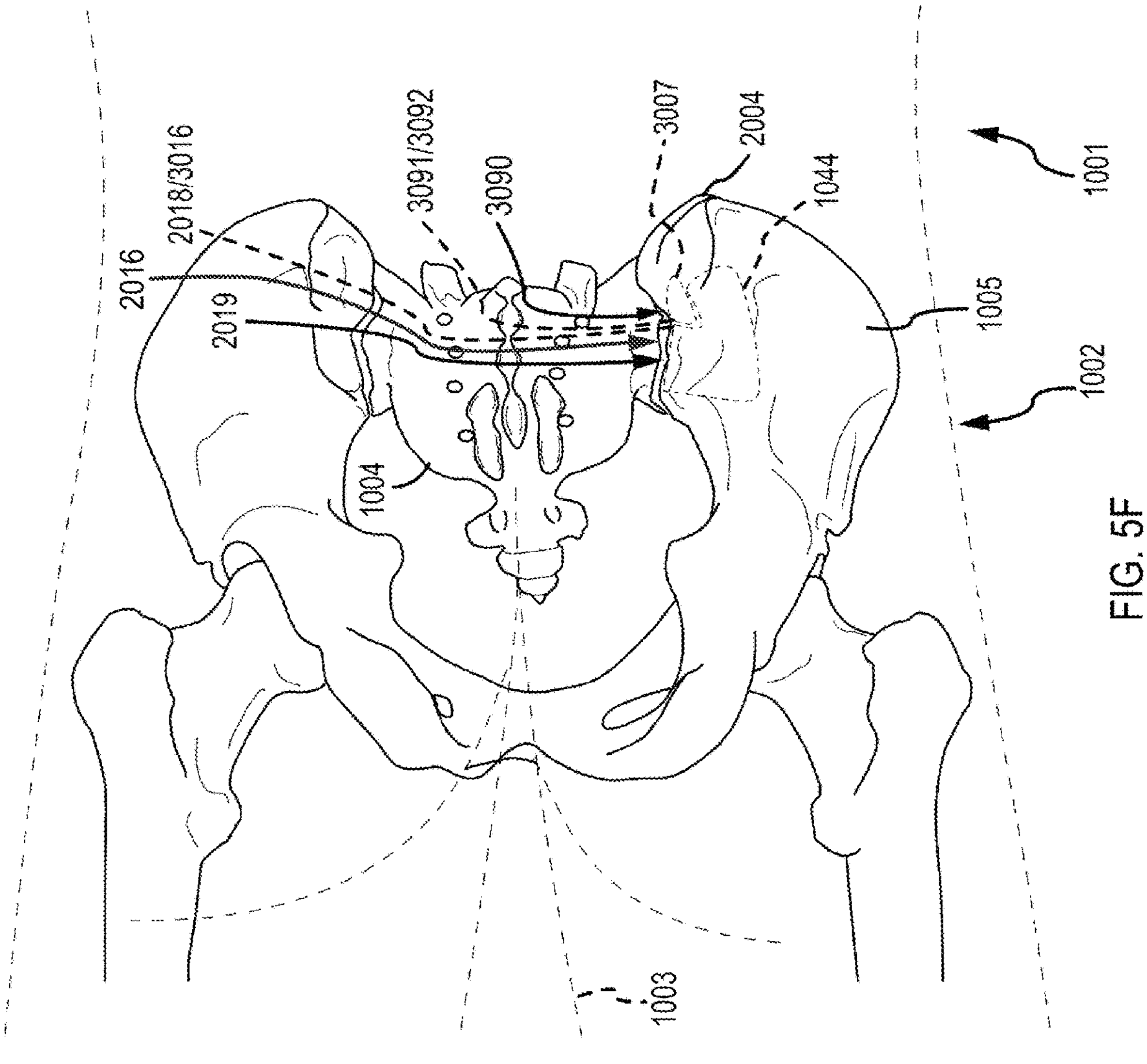
FIG. 5F is a posterior view of the hip region of the patient showing the regions of the sacroiliac joint.

Reference is now made to FIGS. 5E-5F, which depict, respectively, a lateral-posterior view and a posterior view of the hip region 1002 of the patient 1001. These figures include many of the anatomical features referred to in FIGS. 5B-5C and the some of the additional anatomical features described in FIG. 5D. For example, the articular region 1044 and extra-articular region 3007 are shown in dashed line with many of their respective boundaries identified in each figure. FIG. 5E depicts the posterior inferior access region 3090 of the sacroiliac joint extra-articular region 3007 and inferior end 3092 of the extra-articular posterior inferior access on the sacroiliac joint line 2019. The posterior inferior access region 2016 of the intra-articular region 1044 has the superior end 2018 on the sacroiliac joint line 2019 that is immediately adjacent the inferior end 3092 of the caudal boundary segment 3093 of the extra-articular region 3007.

C. Preparing the Sacroiliac Joint for Fusion

Now that an overview of the relevant anatomical landmarks and an example fusion procedure has been described, the discussion may now focus on preparing the sacroiliac joint for a fusion procedure. In doing so, reference will be made to FIGS. 6A-6D, among additional figures, which are steps in the methodology and illustrated in the same transverse cross section taken in along a plane extending medial-lateral and anterior posterior. In this cross section, articular surfaces 1016 are covered by a thick layer of articular cartilage with a joint space existing between them, the FIGS. 6A-6D are simplified for illustrative purposes and do not show these features to scale.

Figure 6B:
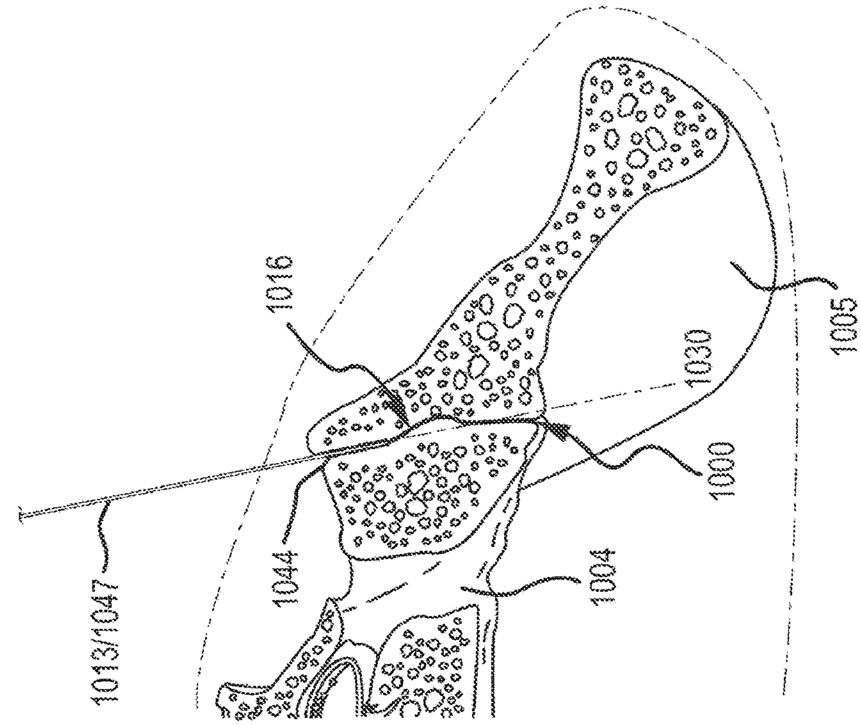
FIGS. 6A-6D are each a step in the methodology and illustrated as the same transverse cross section taken along a plane extending generally medial-lateral and generally anterior posterior.
Figure 6A:
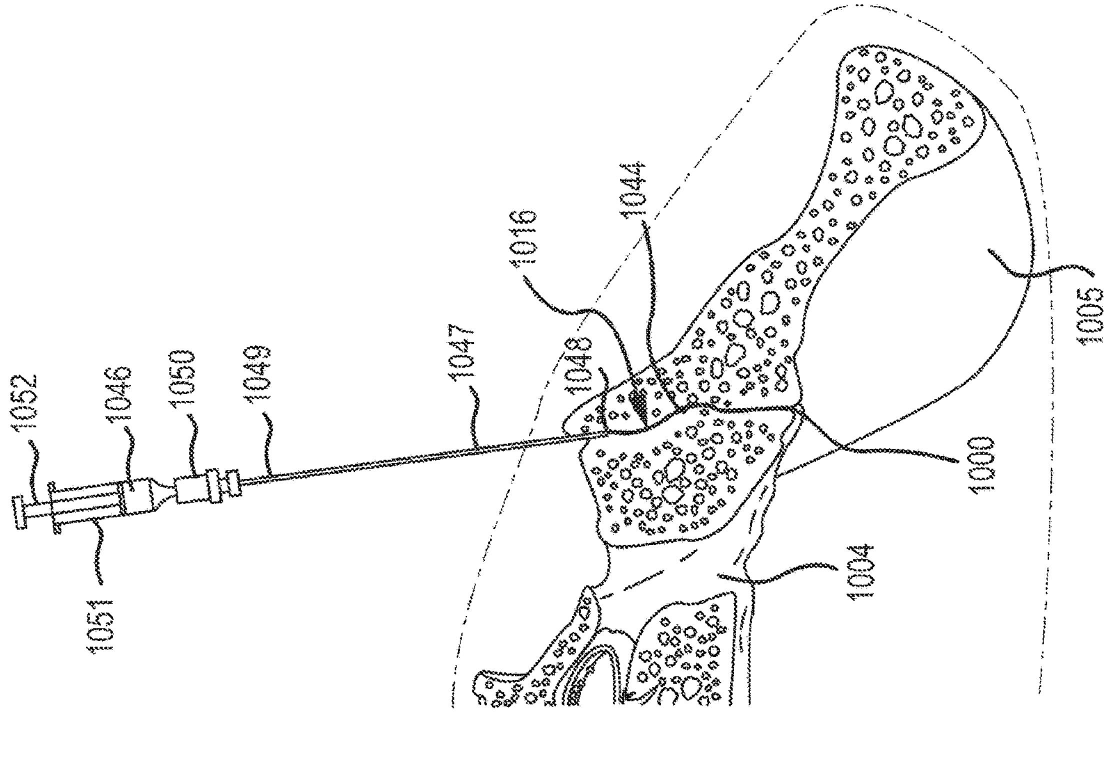

Now referring primarily to FIG. 6A, an embodiment of the method can include the step of placing a patient under sedation prone on a translucent operating table (or other suitable surface). The sacroiliac joint 1000 can be locally anesthetized to allow for injecting a radiographic contrast 1046 (as a non-limiting example, Isoview 300 radiographic contrast) under fluoroscopic guidance into the inferior aspect of the sacroiliac joint 1000 to outline the articular surfaces 1016 of the sacroiliac joint 1000) defined between the sacrum 1004 and ilium 1005, the sacroiliac joint 1000 having an interarticular region 1044. Injection of the radiographic contrast 1046 within the sacroiliac joint 1000 can be accomplished utilizing a tubular member 1047 (e.g., a syringe needle) having first tubular member end 1048 which can be advanced between the articulating surfaces 1016 of the sacroiliac joint 1000 and having a second tubular member end 1049 which removably couples to a hub 1050. The hub 1050 can be configured to removably couple to a syringe barrel 1051 or other device to contain and deliver an amount of radiographic contrast 1046. In the example of a syringe barrel 1051, the syringe barrel 1051 can have an internal volume capable of receiving an amount of the radiographic contrast 1046 sufficient for outlining the articular surfaces 1016 of the sacroiliac joint 1000, for example, under lateral fluoroscopy. A plunger 1052 can be slidingly received within the barrel 1051 to deliver the radiographic contrast 1046 through the tubular member 1047 into the sacroiliac joint 1000. The tubular member 1047 can have a gauge in the range of about 16 gauge and about 20 gauge and can further be incrementally marked on the external surface to allow determination of the depth at which the first needle end 1048 has advanced within the sacroiliac joint 1000. As the first needle end 1048 advances into the sacroiliac joint 1000 the radiographic dye 1046 can be delivered from within the syringe barrel 1051 into the sacroiliac joint 1000 to allow visualization of the sacroiliac joint 1000 and location of the tubular needle 1047 within the sacroiliac joint 1000.

Now referring primarily to FIG. 6B, once the first tubular member end 1048 has been sufficiently advanced into the sacroiliac joint 1000 and the articular surfaces 1016 of the sacroiliac joint 1000 have been sufficiently visualized, the hub 1050 can be removed from the tubular member 1047 leaving the tubular member 1047 fixed within the sacroiliac joint 1000 as an initial guide for tools subsequently used to locate or place the sacroiliac joint implant non-transversely between the articulating surfaces 1016 of the sacroiliac joint 1000 (e.g., locate the implant non-transversely to the joint plane 1030 generally defined by the articulating surfaces 1016 of the interarticular region 1044 of the sacroiliac joint 1000) or in removal of a portion of the sacroiliac joint 1000 within the region defined by the articular surfaces 1016 to generate an implant receiving space 1029. Alternately, one or more guide pins 1013 can be inserted along substantially the same path of the tubular member 1047 for fixed engagement within the sacroiliac joint 1000 and used in subsequent steps as a guide(s).

Figure 6D:
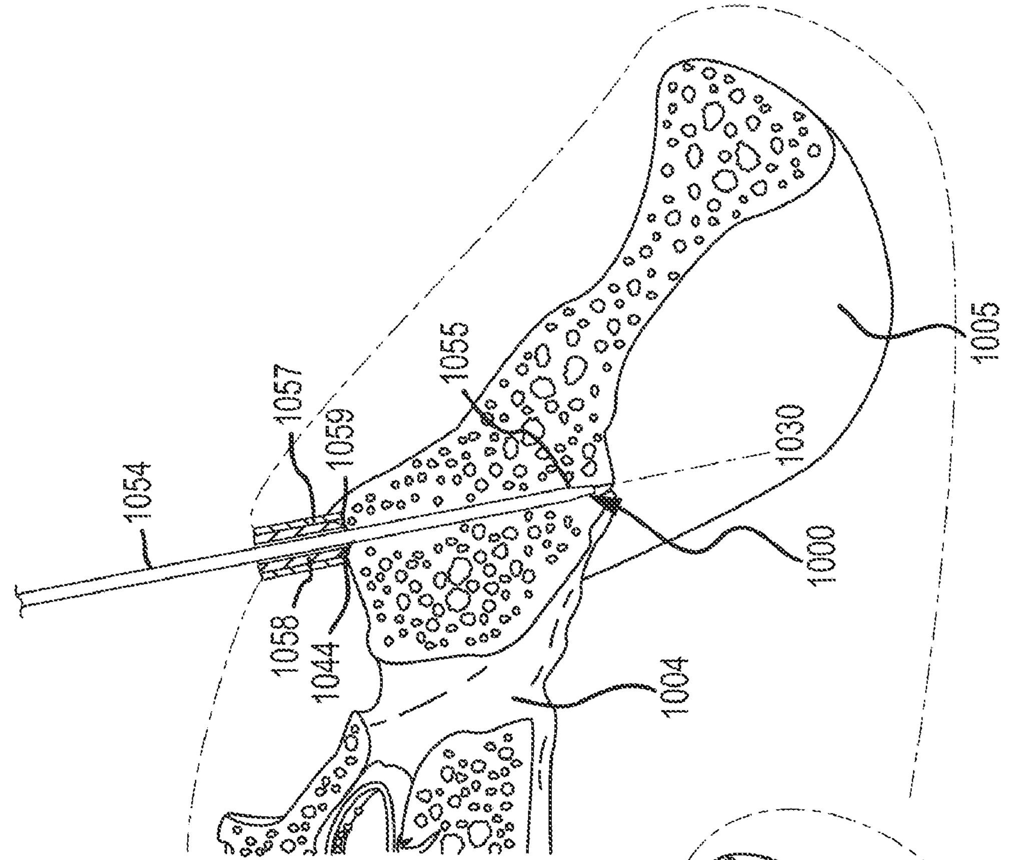
Figure 6C:
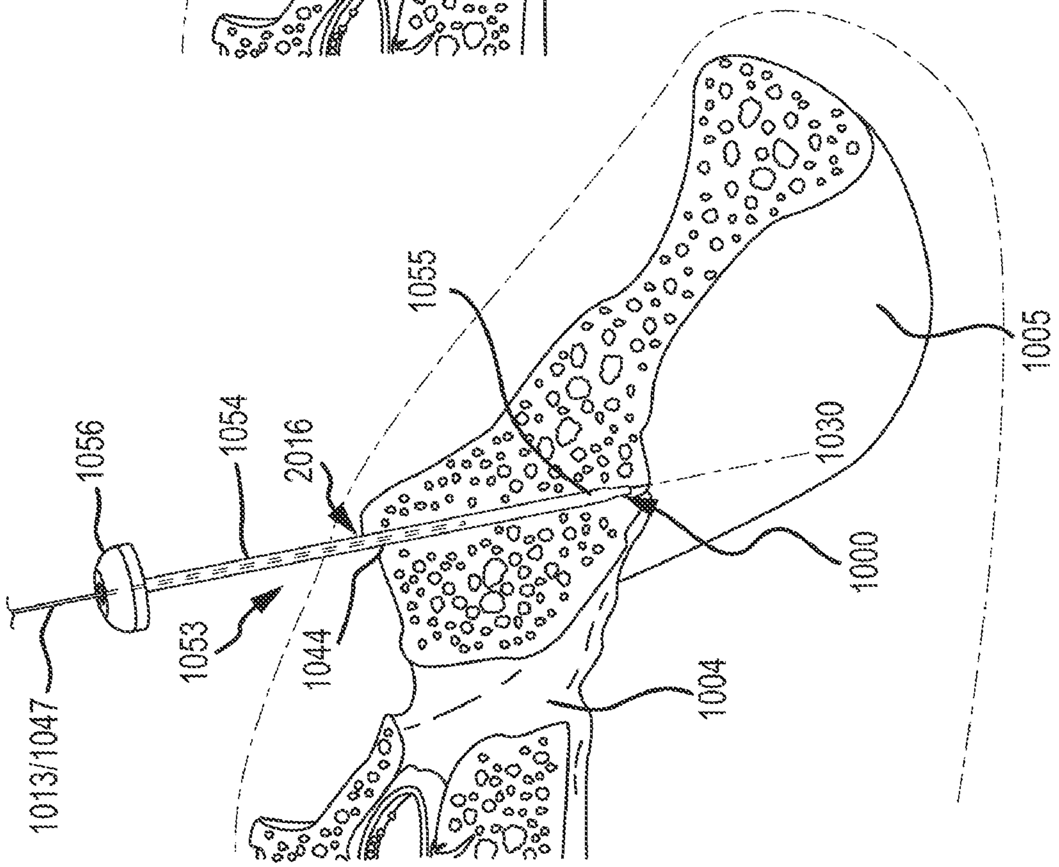

Now referring primarily to FIG. 6C, a small incision 1053 can be made in the skin at the posterior superior, or as to certain embodiments inferior, aspect of the sacroiliac joint 1000, extending proximal and distal to the tubular member 1047 along the line of the sacroiliac joint 1000 to provide a passage to access the interarticular space between the articulating surfaces 1016 (see FIG. 6B) of the sacroiliac joint 1000. More specifically, the small incision 1053 can be made along the joint line of the sacroiliac joint 1000 in the tissue covering the posterior inferior access region 2016 of the sacroiliac joint articular region 1044. A cannulated probe 1054 can be slidingly engaged with the tubular member 1047 (or guide pin 1013) extending outwardly from the sacroiliac joint 1000 (while the sacroiliac joint may be shown in the figures as being substantially linear for illustrative purposes, it is to be understood that the normal irregular features of the sacroiliac joint have not been removed). The cannulated probe 1054 can have a probe body 1054 of generally cylindrical shape terminating in a spatulate tip 1055 at the end advanced into the sacroiliac joint 1000. A removable cannulated probe handle 1056 couples to the opposed end of the probe body 1054. The spatulate tip 1055 can be guided along the tubular needle 1047 or guide wire 1013 into the posterior portion of the sacroiliac joint 1000 and advanced to the anterior portion of the sacroiliac joint 1000 under lateral fluoroscopic visualization. The cannulated probe handle 1056 can then be removed providing the generally cylindrical probe body 1054 extending outwardly from the sacroiliac joint 1000 through the incision 1053 made in the skin.

Alternatively, the probe 1054 can be used to guide, advance or place a needle, guide wire or other instrument up to, near, or into the joint.

Additionally, in particular embodiments, probe handle 1056 or the opposed end of the probe body 1054, or both, can be configured to have an interference fit or a luer lock hub to communicate with a syringe barrel 1051 in order to advance contrast, in situ curable biocompatible materials, stem cells, or etc. through the cannulated probe 1054 or cannulated probe handle 1056.

Now referring primarily to FIG. 6D, a passage from the incision 1053 (see FIG. 6C) to the sacroiliac joint 1000 can be generated by inserting a cannula 1057 into the incision. A soft tissue dilator 1058 having a blunt end 1059 can be advanced over the probe body 1054, or a plurality of soft tissue dilators of increasing size, until the blunt end 1059 of the soft tissue dilator 1058 and the corresponding cannula end contact the posterior aspect of the sacroiliac joint 1000. More specifically, in one embodiment, the ends of the dilator 1058 and cannula 1057 contact the joint line 2019 of the sacroiliac joint 1000 at the posterior inferior access region 2016 of the sacroiliac joint articular region 1044. The soft tissue dilator 1058 can be removed from within the cannula 1057. The external surface of the cannula 1057 can be sufficiently engaged with the surrounding tissue to avoid having the tissue locate within the hollow inside of the cannula 1057. A non-limiting embodiment of the cannula 1057 provides a tubular body having substantially parallel opposed side walls which terminate in a radius at both ends (lozenge shape) into which a plurality of different jigs can be inserted. Alternatively, as a non-limiting example, according to particular embodiments, cannula 1057 and corresponding dilators 1058 and alignment jigs 1060 can be configured to have tubular bodies with an elliptical or circular cross section.

In some embodiments, the cannula 1057 may be additionally configured to have within or near its walls a light source such as, for example, a fiberoptic or a LED light source to assist in visualization of the working area. Also, in some embodiments, irrigation and suction tubing may communicate with the inside passage of cannula 1057.

At this stage, additional tools and methods may be employed to provide access to the sacroiliac joint 1000 as described in U.S. patent application Ser. No. 13/475,695 filed May 18, 2012 entitled "SYSTEMS FOR AND METHODS OF FUSING A SACROILIAC JOINT", Ser. No. 14/514,221 filed Oct. 15, 2015 entitled "SYSTEMS FOR AND METHODS OF PREPARING A SACROILIAC JOINT FOR FUSION," and Ser. No. 16/133,605, filed Sep. 17, 2018, entitled "SYSTEMS FOR AND METHODS OF PREPARING AND FUSING A SACROILIAC JOINT", all of which are hereby incorporated by reference in their entireties. For example, drill jigs may be further advanced over the probe body 1054 to align a drill or other joint preparation tool. Accordingly, the discussion will now focus on employing the tools and devices described in previous sections of this application.

In certain embodiments of the method, an amount of articular cartilage or other tissues from between the articular surfaces of the sacroiliac joint 1000 can be removed sufficient to allow embodiments of the sacroiliac joint implant to be implanted in replacement of the removed articular cartilage or tissue. Because the method removes the degenerative articular cartilage or tissue between the articular surfaces of the sacroiliac joint 1000, the articular surfaces of the sacroiliac joint 1000 can remain intact or substantially intact allowing the sacroiliac joint implant to be non-transversely located between the articular surfaces of the sacroiliac joint 1000.

Understandably, other instruments can be utilized separately or in combination during the course of any of the steps of the methodology, e.g., for the removal of articular cartilage or tissue between articular surfaces, such as any of the tools previously described or any of: endoscopy tools, box chisels, side cutting router bits, burs, flexible burs and bits, hole saws, key hole saw, medical bone chainsaw osteotome, curettes, lasers (e.g., CO2, Neodymium/Y AG (yttrium-aluminum-garnet), argon, and ruby), electrosurgical equipment employing electromagnetic energy (the cutting electrode can be a fine micro-needle, a lancet, a knife, a wire or band loop, a snare, an energized scalpel, or the like) where the energy transmitted can be either monopolar or bipolar and operate with high frequency currents, for example, in the range of about 300 kHz and about 1000 kHz whether as pure sinusoidal current waveform where the "crest factor" can be constant at about 1.4 for every sinus waveform, and a voltage peak of approximately 300 V to enable a "pure" cutting effect with the smallest possible coagulation effect or as amplitude modulated current waveforms where the crest factor varies between 1.5 and 8, with decreasing crest factors providing less of a coagulation effect. Electrosurgical waveforms may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advance into the joint without grossly penetrating much beyond the cartilage.

III. Tools, Systems, and Methods for Diagnosing and Treating the Sacroiliac Joint The following discussion will focus on various tools, systems, and methods of diagnosing and treating a sacroiliac joint ailment or disorder. The tools, systems, and methods may be useful in determining if fusion of the sacroiliac joint may be beneficial to a patient by, for example, alleviating pain. The tools and systems may be used to isolate the bones in the pelvic region such that manipulation of the bones (e.g., sacrum, ilium) can more easily, accurately, and efficiently diagnose the sacroiliac joint as a source of pain and discomfort. Upon diagnosing the sacroiliac joint as a source of pain and fusion as a possible solution, the joint may be temporarily or permanently fixated. The following discussion will focus on the tools, systems and methods of diagnosing and treating a sacroiliac joint disorder or ailment.

A. Diagnostic Pins, Rods, or Bars

FIGS. 7A-7F illustrate diagnostic pins, rods, or bars 50 for use in diagnosing an ailment of a sacroiliac joint of a patient. The diagnostic pins 50 may be manipulated to cause movement of the sacrum and/or ilium, which may reproduce the pain in the patient or alleviate the pain in the patient (e.g., may realign the sacroiliac joint). In either scenario and depending on the particular manipulation, reproducing or alleviating the pain may suggest a need for fusing the joint via, for example, an implant. If the movement induced in the joint does not reproduce the pain in the patient, the diagnostics may suggest that the pain may come from areas other than the sacroiliac joint, such that fusion of the sacroiliac joint may not help to reduce the patient's pain. For these reasons, among others, the diagnostic method described herein may eliminate unnecessary implantation and trauma to the sacroiliac joint.

The diagnostic pins 50 may be caused to rotate or translate, which may cause movement of the sacrum and ilium about the joint. For example, one pin 50 may be placed in the sacrum while the other pin 50 may be placed in the ilium. The movement of the sacrum and ilium may vary depending upon the locations of the diagnostic pins or bars 50 and direction of the force. If the pin 50 is positioned on (or in) the caudal region of the sacrum and pushed anteriorly, the cephalad portion sacrum may rotate toward the posterior direction. If the pin is placed near the first sacral body (i.e., a cephalad portion of the sacrum) and a force is directed anteriorly, the cephalad portion of the sacrum may rotate toward the posterior direction. One pin may be placed in the ilium near the intra-articular region or extra-articular region of the joint.

Referring to FIGS. 7A-7D, which are respective isometric, front, back, and side views of the pin 50, the pin 50 may include an elongated body 52 extending between a distal end 54 and a proximal end 56. In some embodiments, the distal end 54 may be tapered and include threads 60 that terminate at a point 58 such that the pin 50 may be rotationally driven into the bone. In certain embodiments, the threads 60 may be self-tapping threads. The distal end 54 may have a smaller cross-section than the proximal end 56. It will be appreciated by those skilled in the art that the cross-section of pins or bars 50 may be generally circular, oval, square, rectangular or triangular in shape.

As seen in the figures, the elongated body 52 includes longitudinally extending and radially projecting ridges 62 that extend from the proximal end 56 to the threads 60 near the distal end 54 of the pins 50. The ridges 60 provide grip for the pins 50 when grasped by a medical professional or a mechanical device. Alternatively, the pins may be configured with a high-friction surface.

As one non-limiting example, the elongate body 52 may have a diameter of in the range of about 3 millimeters ("mm") to about 8 mm (e.g., 6 mm) and a length disposed between the proximal and distal ends 56, 54 in the range of about 2 centimeters ("cm") and about 20 cm. Pin length measurements may be marked along the length of the pin 50.

The pin 50 proximal end 56 may have a tool interface configured to permit, e.g., a handle or other tool to couple to the elongate body 52.

As to particular embodiments of the pin 50, the elongate body 52 can further include a cannulation which communicates between the distal end 54 and the proximal end 56. The cannulation allows for placement within the cannulation a guide pin (or other guide member) about which embodiments of the pins 50 can be guided for insertion and placement in the bones of the sacrum 1004 or ilium 1005, or allow injection of analgesics.

Figures 7A, 7B, 7C:
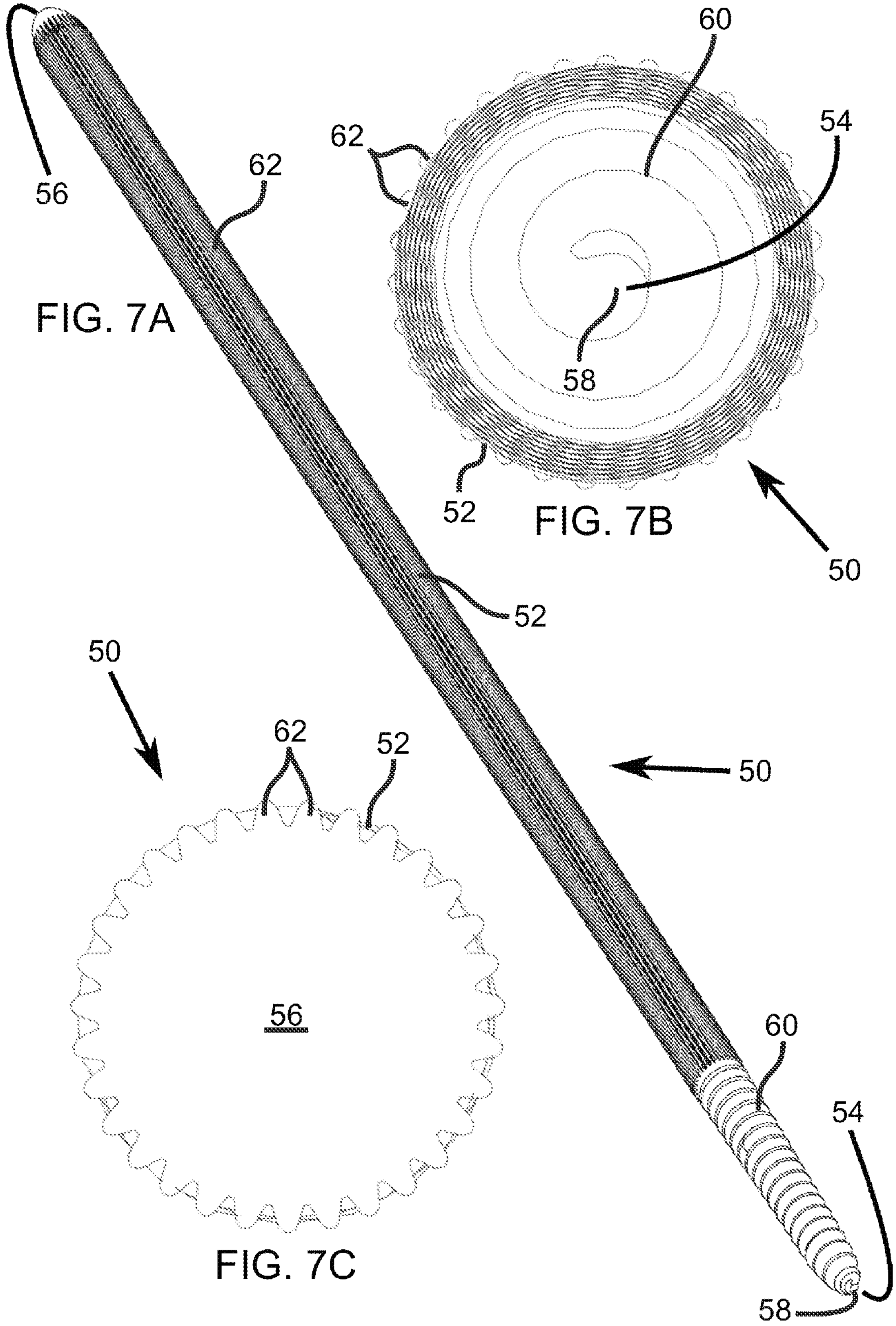
FIG. 7A is an isometric view of a diagnostic pin.
FIG. 7B is a bottom view of the diagnostic pin of FIG. 7A.
FIG. 7C is a top view of the diagnostic pin of FIG. 7A.
Figure 7D:
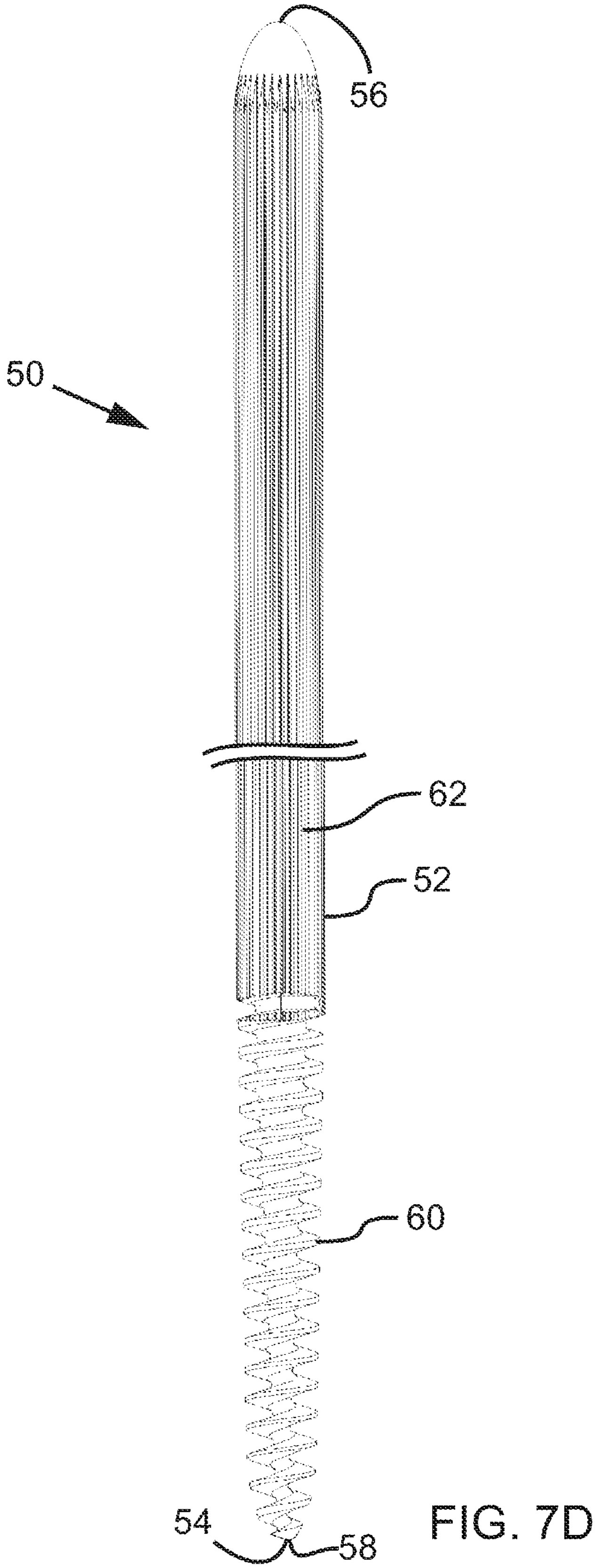
FIG. 7D is a side view of the diagnostic pin of FIG. 7A.
Figure 7E:
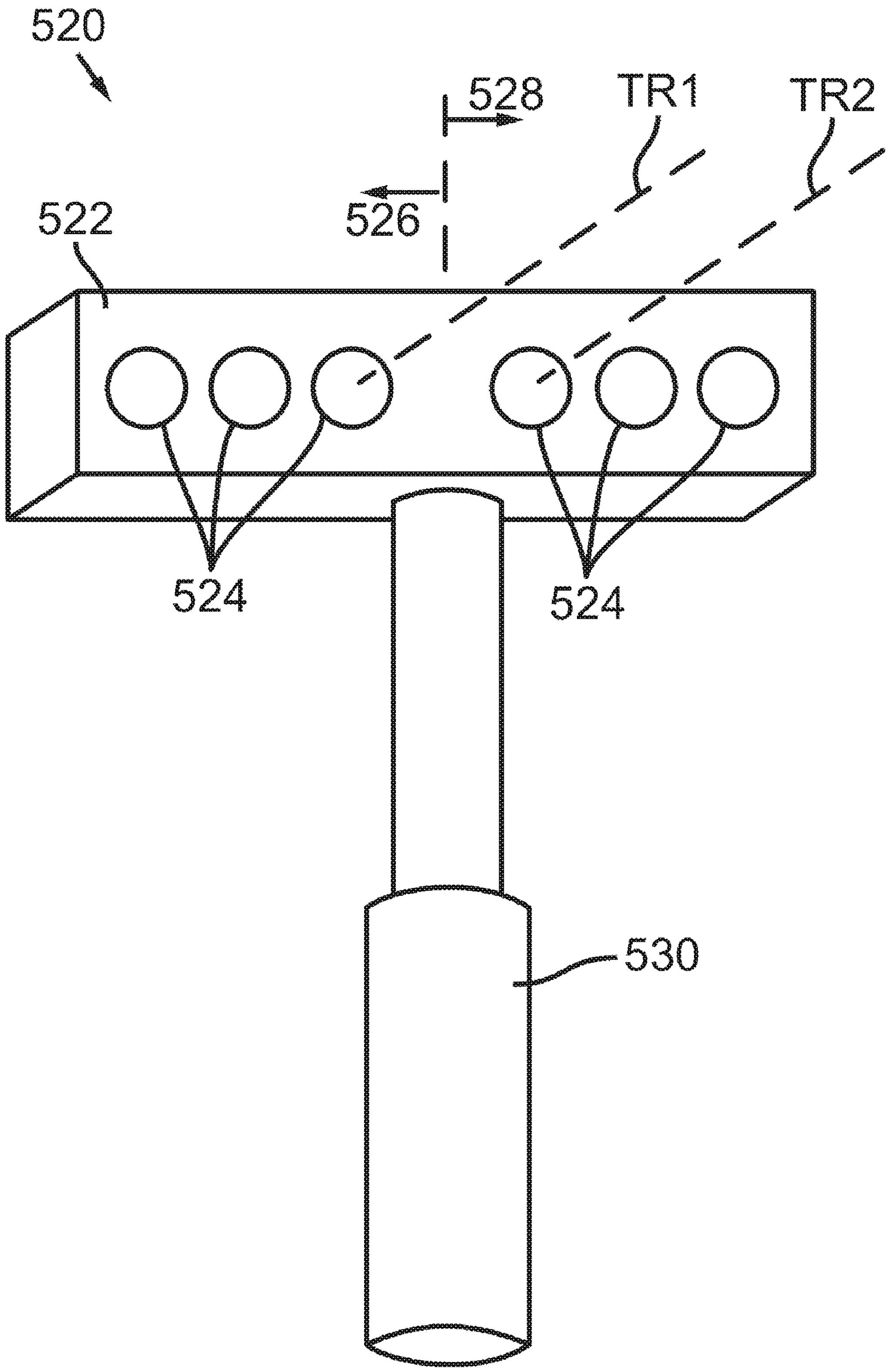
FIG. 7E is an isometric view of a diagnostic pin guidance tool.

Reference is made to FIG. 7E, which is an isometric view of a pin guidance tool 520 for guiding the placement of the pins 50 within the sacrum and ilium, respectively. The tool 520 includes a guidance head 522 with three cylindrical openings 524 on a left side 526 of the head 522 and three cylindrical openings 524 on a right side 528 of the head 522. The tool 520 further includes a handle 530 coupled and extending from the guidance head 522. The tool 520 is configured to guide one or more pins 50 within the openings 524 into the sacrum or ilium. When used to guide multiple pins 50, the pins will be delivered parallel to each other and with a pre-determined amount of space or distance between the placements. For example, a first pin may be guided along trajectory TR1 into the sacrum and a second pin may be guided along another trajectory TR2 into the ilium. The doctor or medical professional can be assured that the pins are parallel to each other and spaced apart a certain, known, distance. While this example and the figure shows the trajectories TR1, TR2 utilizing the most inner openings 524, the tool 520 may be used with other combinations of openings 524 without limitation.

Figure 8A:
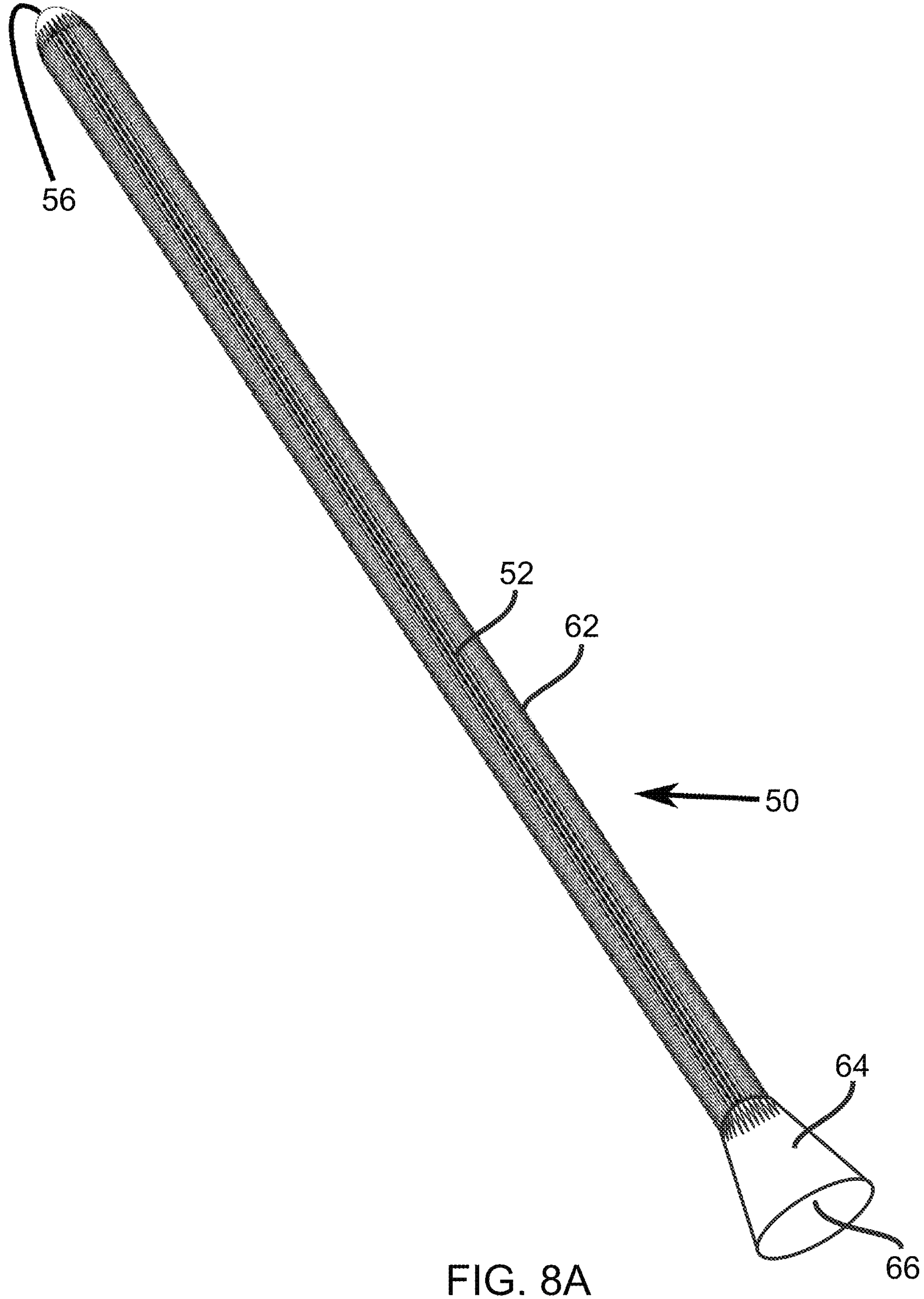
FIG. 8A is an isometric view of a diagnostic pin with a blunt distal end.
Figure 8B:
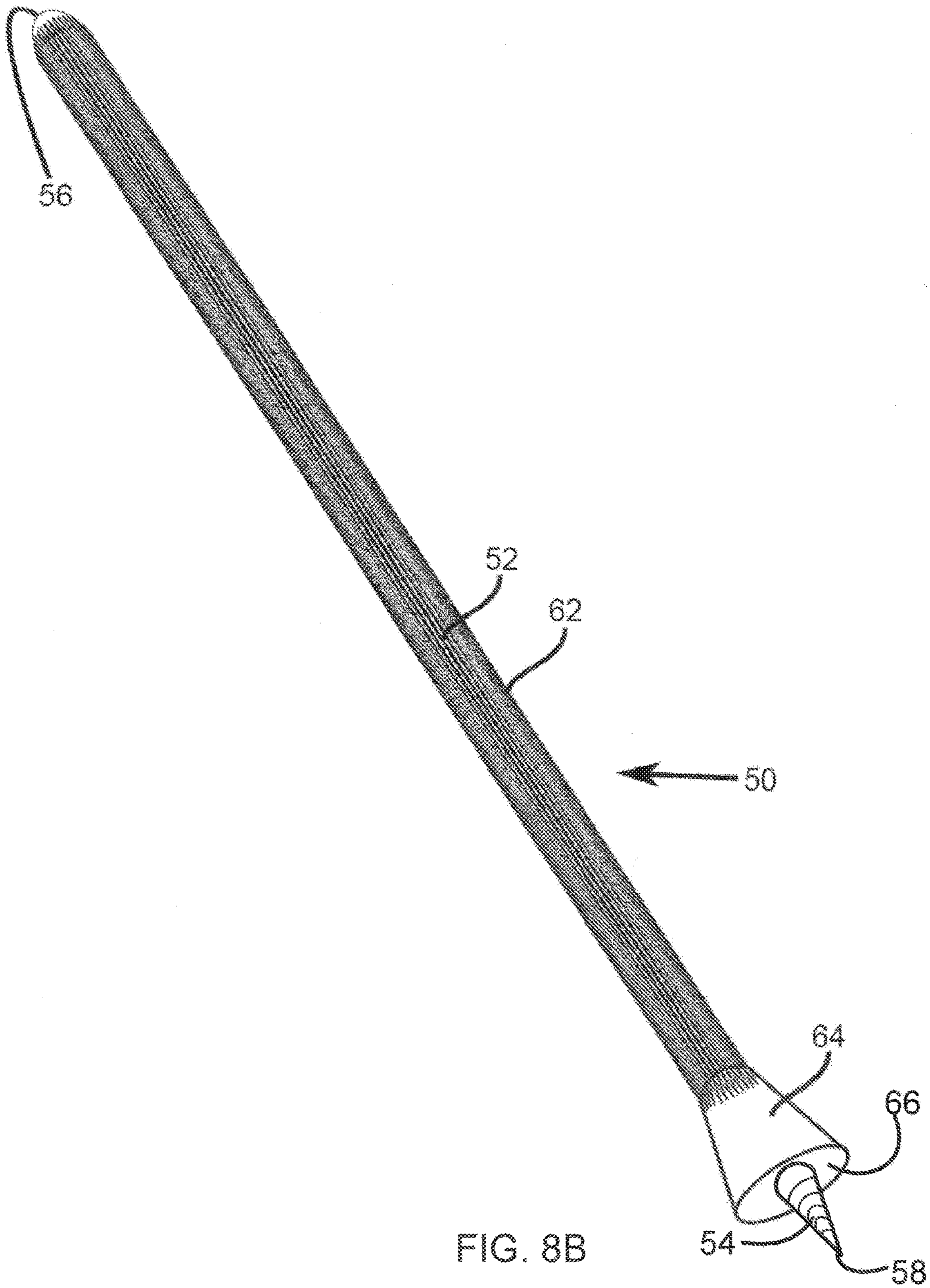
FIG. 8B is an isometric view of a diagnostic pin with a blunt distal surface and a tapered tip extending distally of the blunt distal surface.

Referring to FIG. 8A, which is an isometric view of another embodiment of the pin 50, the pin 50 may include a similar proximal end 56 and elongated body 52 with ridges 62 that was previously described in reference to FIGS. 7A-7D. The pin 50 of FIG. 8A may, however, include a blunt distal end 64 instead of a threaded 60 distal end 54 that terminates at a point 58. The blunt distal end 64 may include, for example, a planar distal surface 66 that may conform to the surface features of the bone or may simply be configured to not penetrate or minimally penetrate into the boney surfaces of the sacrum or ilium upon contact. The planar distal surface 66 may include surface features such as ridges or points that are configured to grip the bone surfaces upon contact. For example, as seen in FIG. 8B, the planar distal surface 66 may include a threaded distal end 54 that extends through the planar distal surface 66 and distally terminates at a point 58. Other variations to the pin 50 are contemplated herein and may include any type and kind of blunt distal end that is not designed to extend into the patient's bone upon application of a force. Alternatively, the distal end 64 may include surface contours that match the bones of the ilium and sacrum so as to provide a mating surface with which to apply force against.

With the blunt distal end 64, the medical professional may position the pin 50 in various orientations and on various boney landmarks to manipulate the sacrum and ilium without boring multiple holes into the patient's bone. Thus, the medical professional can attempt multiple different kinds and styles of manipulation prior to or instead of boring holes into the patient's bone.

Figure 9:
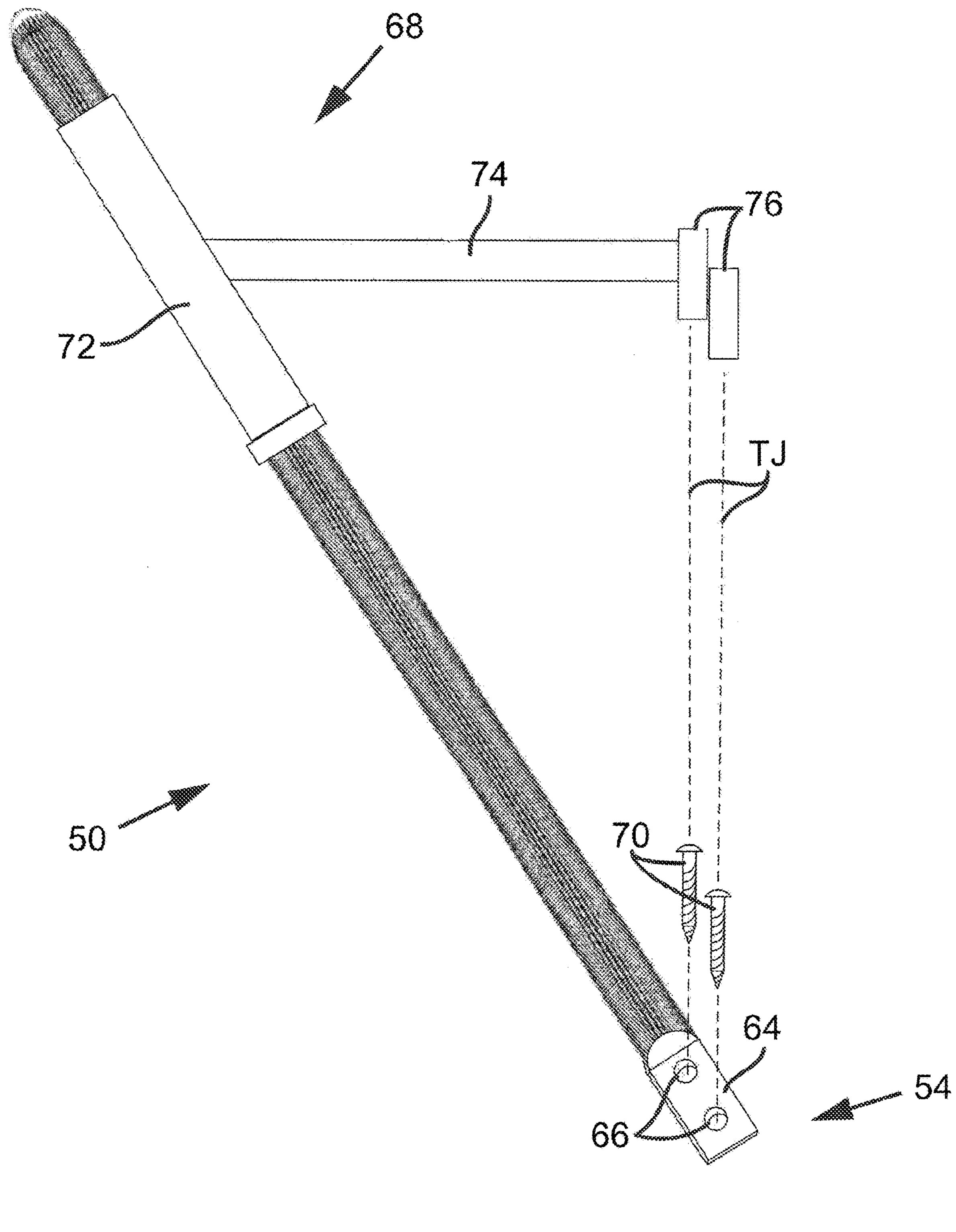
FIG. 9 is an isometric view of a diagnostic pin having a distal end with a pair of openings, the diagnostic pin coupled with an anchor guide.

Another embodiment of the pin 50 is shown in FIG. 9. As seen in the figure, the pin 50 includes a planar, plate member 64 at the distal end 54 with a pair of openings 66 extending transversely or across the plate member 64. The pin 50 may be used in conjunction with an anchor guide 68 that may guide anchors 70, such as bone screws, into the openings 66 of the plate member 64 when a sleeve 72 of the anchor guide 68 extends over the elongated body 52 of the pin 50. The anchor guide 68 may further include an extension member 74 extending from the sleeve 72 to a pair of guides 76 that are configured to align a trajectory TJ of the anchors 70 across the plate member 64 and into the openings 66 when the sleeve 72 is positioned on the elongated body 52. A shaft of a delivery tool (not shown) may be guided by the guides 76 to deliver the anchors 70 into the openings 66.

The pin 50 and anchor guide 68 shown in FIG. 9 may be delivered into a patient's pelvic region and positioned such that the plate member 64 lies generally parallel with a posterior lateral surface of the ilium, for example. The openings 66 of the plate member 64 may be oriented on the ilium such that a trajectory of the anchors 70 is across either the intra-articular region or the extra-articular region of the sacroiliac joint and into the sacrum. Once positioned adjacent the ilium, the anchors 70 may be delivered via the anchor guide 68 into the openings 66 and into the ilium. At this point, the pin 50 may be manually manipulated by a medical professional with his or her hands or with the aid of a diagnostic tool that grasps the pin 50. The pin 50 may, for example, facilitate nutation and counternutation of the ilium and sacrum, flexing and compression of the joint, or other manipulations of the bones and joint.

Upon determining that the joint requires fusion, the anchors 70 may be threadably released from the ilium and the pin 50 may be removed from the patient's pelvic region. If fusion by the anchors 70 is suitable for the particular patient and the ailment, the anchors 70 may be re-inserted into the ilium and further advanced across the sacroiliac joint and into the sacrum.

The plate member 64 may include a releasable feature (not shown) that releases the anchors 70 from being positioned within the openings 66 such that the anchors 70 do not need to be threadably released from the ilium prior to re-inserting them back into the ilium and, then, across the joint and into the sacrum. The releasable feature may be that the plate member 64 includes two longitudinally extending members that come together at the openings 66 in a scissor-like fashion. In a deployed state, the plate member 64 may close such that the member 64 appears as shown in FIG. 9. In a non-deployed state, the plate member 64 may open in the scissor-like fashion such that two longitudinally extending members separate and, thus, the pin 50 and the plate member 64 may be retracted from the anchors 70 without removing the anchors 70 from the bone.

While the pin 50 in FIG. 9 is shown as having a plate member 64 at a distal end 54 of the pin 50, the pin 50 may be differently configured. For example, the pin 50 may be as described with reference to FIGS. 7A-7D and further include one or more openings 66 extending through a distal end 54 of the pin 50. That is, the openings 66 would extend through a cylindrical portion of the pin 50, either through the tapered threaded portion or the elongated body portion having the ridges 62.

Alternatively, the plate may be releasably coupled to the pin 50 and left in place after the diagnostic procedure.

The pins 50 may be used individually, in pairs, or in other combinations. The following discussion will focus on the placement of the previously described pins 50 in the sacrum and ilium. Then, there will be a discussion of manipulating the pins to diagnose an ailment of the joint.

B. Positioning and Delivery of the Pins in the Sacrum and Ilium

Reference is now made to FIGS. 10A-10E, which show multiple views of positioning and delivery the pins into the sacrum and ilium.

In certain instances, such as when the pins 50 may be used to guide a temporary implant into the extra-articular region 3007, it may be beneficial to deliver the pins 50 into the sacrum and ilium in regions of the respective bone that are medial or lateral (i.e., immediately adjacent) of the extra-articular region 3007 of the sacroiliac joint. That is, the pins may be delivered into the sacrum and ilium superior of the intra-articular region 1044. In other instances and possibly depending on the configuration of the temporary implant, it may be beneficial to deliver the pins 50 into the sacrum and ilium in regions of the bone that are immediately adjacent the intra-articular region 1044. The ilium is generally harder in the region of the intra-articular region, so there may be advantages in certain instances to delivering the pins 50 in this region.

Figure 10A:
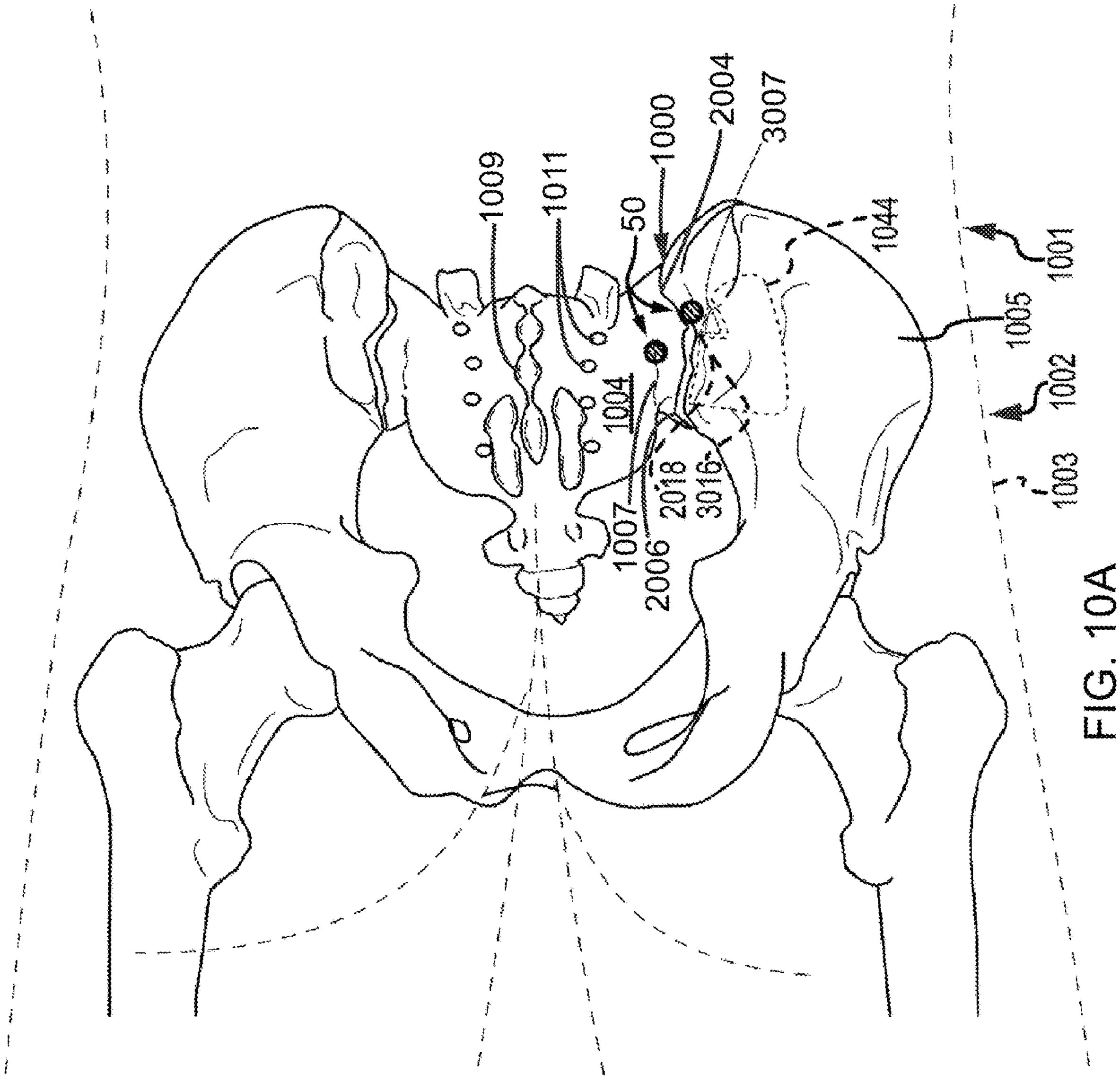
FIG. 10A is a posterior view of a hip region of a patient showing a diagnostic pin positioned in the sacrum and another diagnostic pin positioned in the ilium.

To begin, reference is made to FIG. 10A, which is a posterior view of the hip region 1002 of the patient 1001 with a pin 50 in each of the sacrum 1004 and the ilium 1005. As seen in the figure, the pin 50 may be posteriorly delivered into a patient 1001 with a generally anterior trajectory. In doing so, the pin 50 may extend through the soft tissue 1003 of the patient 1001 and extend into the hip region 1002 via tissue penetration in a superior region of the patient's buttock. The pin 50 in the ilium may be oriented immediately lateral of the posterior inferior access region of the extra-articular region 3007 of the joint 1000. The pin 50 in the sacrum may be oriented inferior and lateral of the superior articular facet and lateral of the median sacral crest.

Figure 10B:
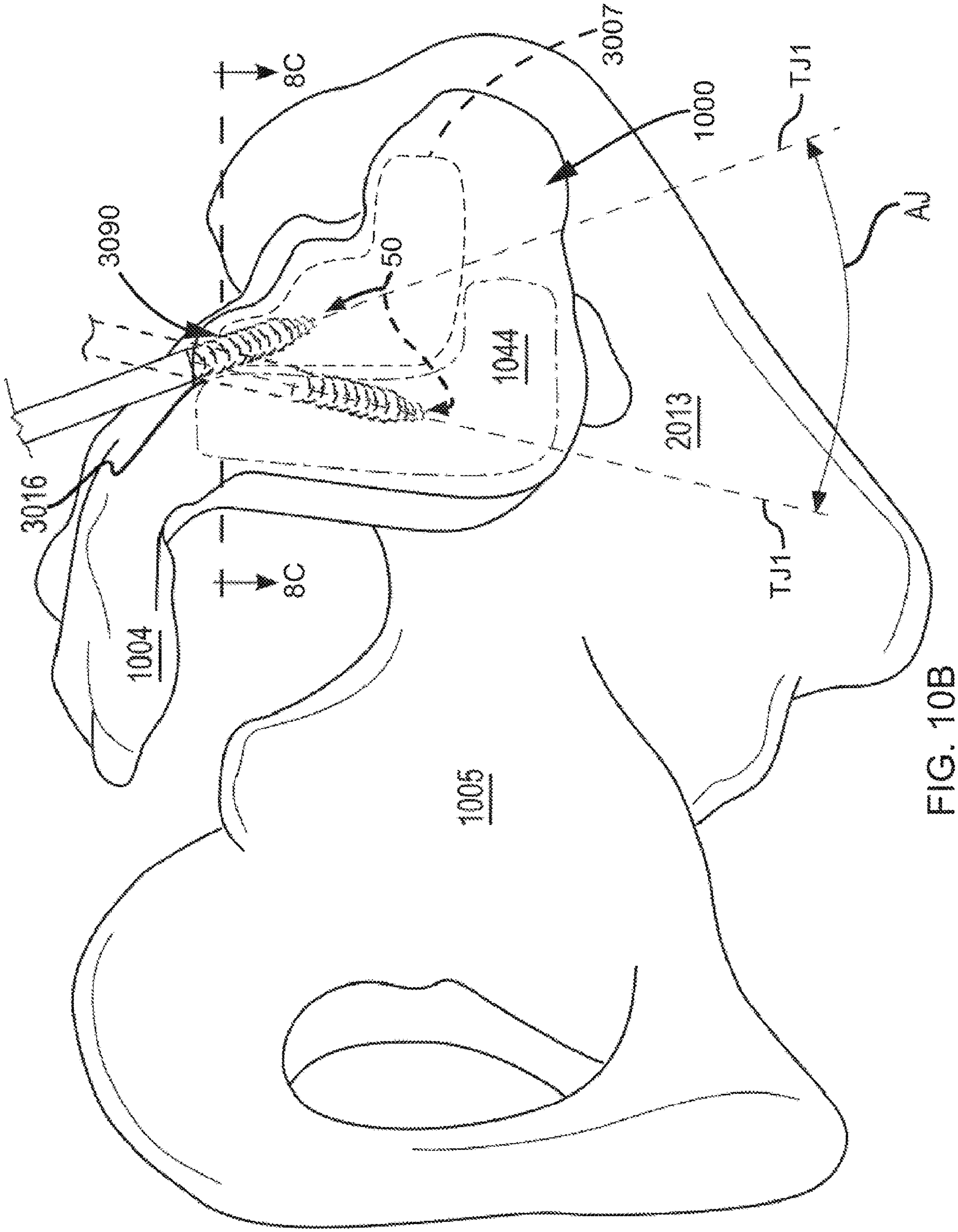
FIG. 10B is a lateral side view of the hip region of the patient with a nearest ilium removed and a diagnostic pin positioned in the sacroiliac joint region.

Turning to FIG. 10B, which is a lateral side view of the hip region 1002 with a nearest ilium removed from view to more clearly see the intra-articular region 1044 and the extra-articular region 3077, the pin 50 may be delivered into the sacrum 1004 or ilium 1005 immediately adjacent the posterior inferior access region 3090 of the extra-articular region of the joint 1000. As seen in the figure, the pin may include a trajectory TJ1 within a range of degrees AJ while still penetrating the bone immediately adjacent the posterior inferior access region 3090. In certain embodiments, the range of degrees AJ may be 20 degrees, 30 degrees, 50 degrees, or 60 degrees, among others.

Figure 10C:
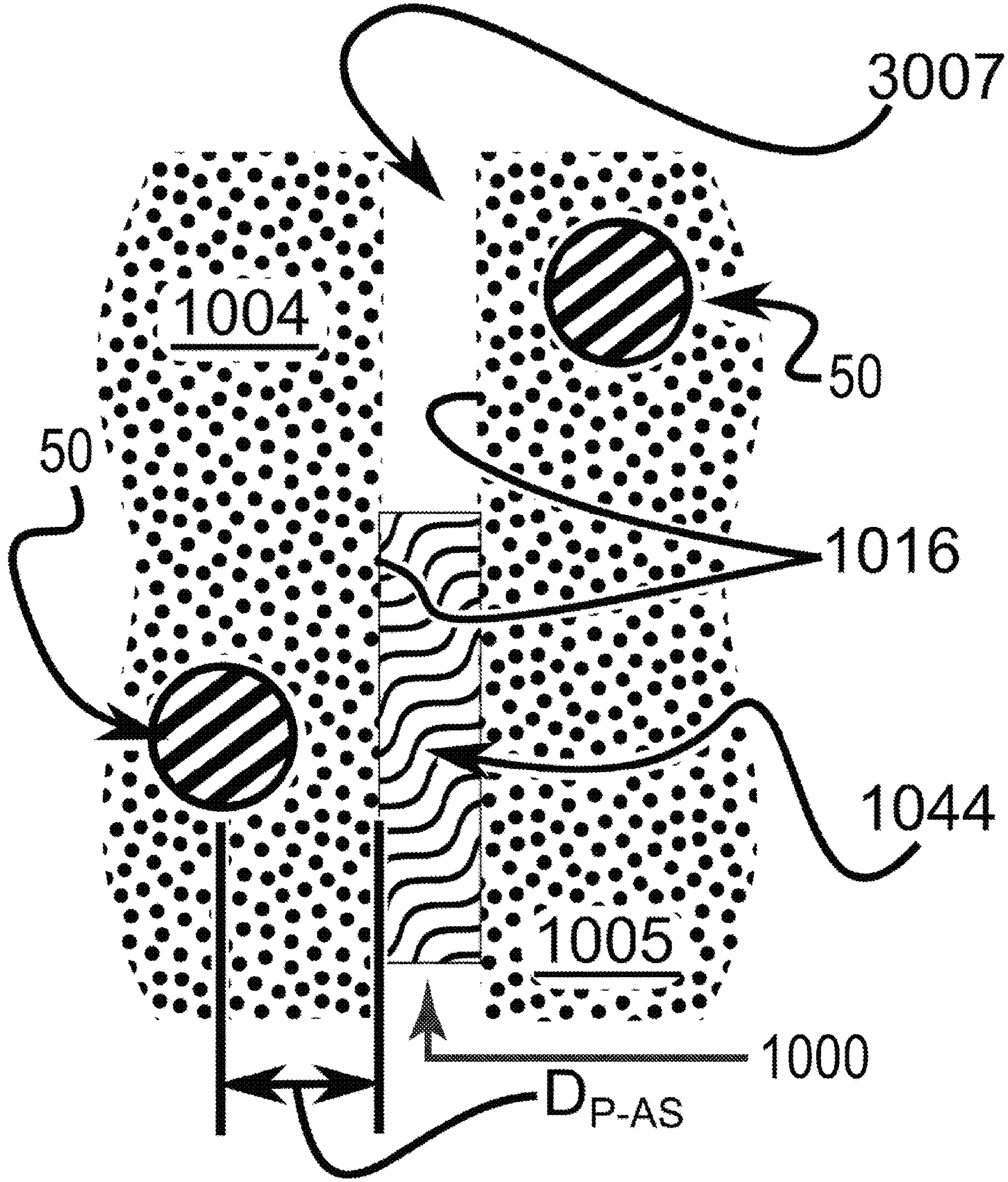
FIG. 10C is a posterior cross-sectional view of the sacroiliac joint with one pin positioned in the sacrum and one pin positioned in the ilium.

As seen in FIG. 10C, which is a cross-sectional view, generally in a coronal plane, of the extra-articular region 3007 and the intra-articular region 1044 of the sacroiliac joint, one pin 50 is positioned in the ilium 1005 immediately adjacent the extra-articular region 3007 and one pin 50 is positioned in the sacrum 1004 immediately adjacent the intra-articular region 1044. The pin 50 in the sacrum 1004 may also be positioned superiorly such that it would be parallel with the pin 50 in the ilium 1005 and a line connecting the pins would be generally perpendicular to a plane of the sacroiliac joint 1000. Additionally, the pin 50 in the ilium 1005 may also be positioned inferiorly such that it would be parallel with the pin 50 in the sacrum 1004 and a line connecting the pins would be generally perpendicular to a plane of the sacroiliac joint 1000.

Figure 10D:
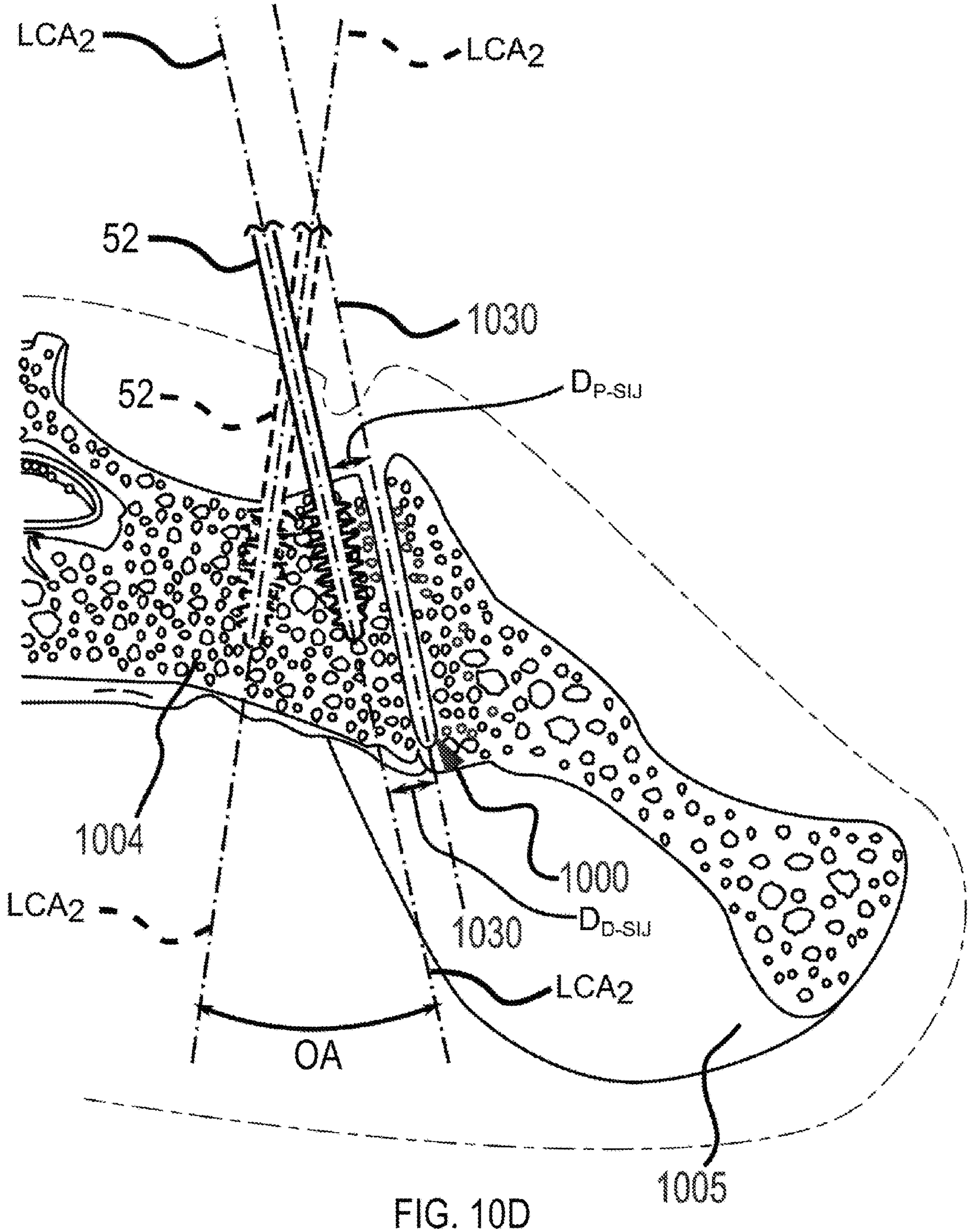
FIGS. 10D-10E are transverse cross-sectional views of the sacrum and ilium showing various pin placements in the sacrum.

Reference is now made to FIG. 10D, which is a transverse cross-section of the sacrum 1004 and ilium 1005 viewed superiorly showing a pin 50 positioned in the sacrum 1004. As seen in the figure, the longitudinal axis LCA2 of the elongate body 52 of the pin 50 may be generally parallel to the joint line 1030 of the sacroiliac joint 1000. In this embodiment, the longitudinal axis LCA2 may be offset from the joint line 1030 by a distance at a proximal portion of the joint DP-SIJ. In certain embodiments, the distance DP-SIJ may be about 0.5 centimeter ("cm"), 1 cm, 1.5 cm, 2 cm, 3 cm, 4 cm, 5 cm, or 6 cm, among others. And the distance DP-SIJ may be within a range of about 0.5 cm to about 6 cm. In this embodiment, the longitudinal axis LCA2 may be offset from the joint line 1030 by a distance at a distal portion of the joint DD-SIJ. In certain embodiments, the distance DD-SIJ may be about 0.5 centimeter ("cm"), 1 cm, 1.5 cm, 2 cm, 3 cm, 4 cm, 5 cm, or 6 cm, among others. And the distance DD-SIJ may be within a range of about 0.5 cm to about 6 cm.

Alternatively and as seen in the dashed line pin 50, the longitudinal axis LCA2 of the elongate body 52 of the pin 50 may be generally offset to the joint line 1030 of the sacroiliac joint 1000 by a certain degree OA. The certain degree may be between about 5 degrees and about 50 degrees, in certain embodiments. In other embodiments the certain degree may be about 5 degrees, 10 degrees, 15 degrees, 20 degrees, 25 degrees, 30 degrees, 35 degrees, 40 degrees, 45 degrees, or 50 degrees, among others and may include being directed medially (as shown in the figures) or laterally (while not crossing the sacroiliac joint).

Figure 10E:
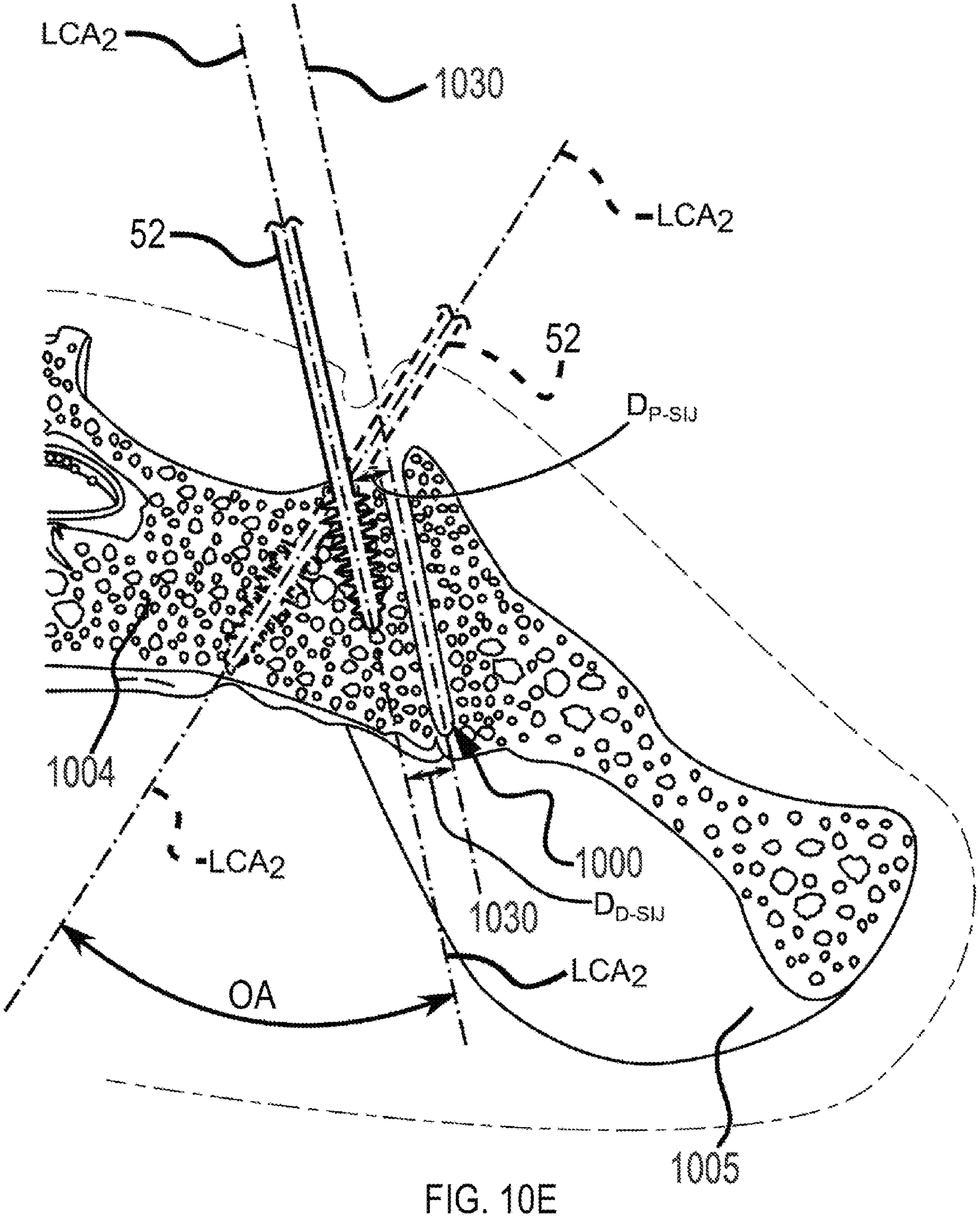

As another alternative of an angled placement of the pin 50 relative to the joint line 1030, as seen in FIG. 10E, which is the same view of the sacrum 1004 and ilium 1005 as in FIG. 10C, the pin 50 in dashed line may penetrate the sacrum 1004 such that the longitudinal axis LCA2 of the elongate body 52 extends a greater angle relative to the pin 50 that is positioned parallel to the joint line 1030.

Although not shown in FIGS. 10D and 10E, the pin 50 in the ilium may be parallel to the joint line, directed laterally or even medially, or generally parallel to an ilium outer cortex.

As an example of possible pin placements in the pelvic region, a first pin having a tapered and threaded distal end may be posteriorly delivered into the ilium just lateral of the extra-articular region of the sacroiliac joint (i.e., an upper or superior region defined between the posterior inferior iliac spine 2006 and the posterior superior iliac spine 2004, as seen in FIG. 10A). A second pin having a tapered and threaded distal end may be posteriorly delivered into the sacrum, between the lateral sacral crest (1007 in FIG. 10A) and the joint line of the joint.

As another possible example of pin placements in the pelvic region, a first pin having a tapered and threaded distal end may be posteriorly delivered into the ilium just lateral of the intra-articular region of the sacroiliac joint (i.e., a lower or inferior region defined between the posterior inferior iliac spine 2006 and the posterior superior iliac spine 2004, as seen in FIG. 10A). A second pin having a tapered and threaded distal end may be posteriorly delivered into the sacrum, between the lateral sacral crest (1007 in FIG. 10A) and the median sacral crest (1009 in FIG. 10A).

As another possible example of pin placements in the pelvic region, a first pin having a tapered and threaded distal end may be posteriorly delivered into the ilium just lateral of the intra-articular region of the sacroiliac joint (i.e., a lower or inferior region defined between the posterior inferior iliac spine 2006 and the posterior superior iliac spine 2004, as seen in FIG. 10A). A second pin having a blunt distal end may be posteriorly positioned against the sacrum, between the lateral sacral crest (1007 in FIG. 10A) and the posterior sacral foramina (1011 in FIG. 10A). Or, the second pin may be positioned against the lateral sacral crest.

Figure 10F:
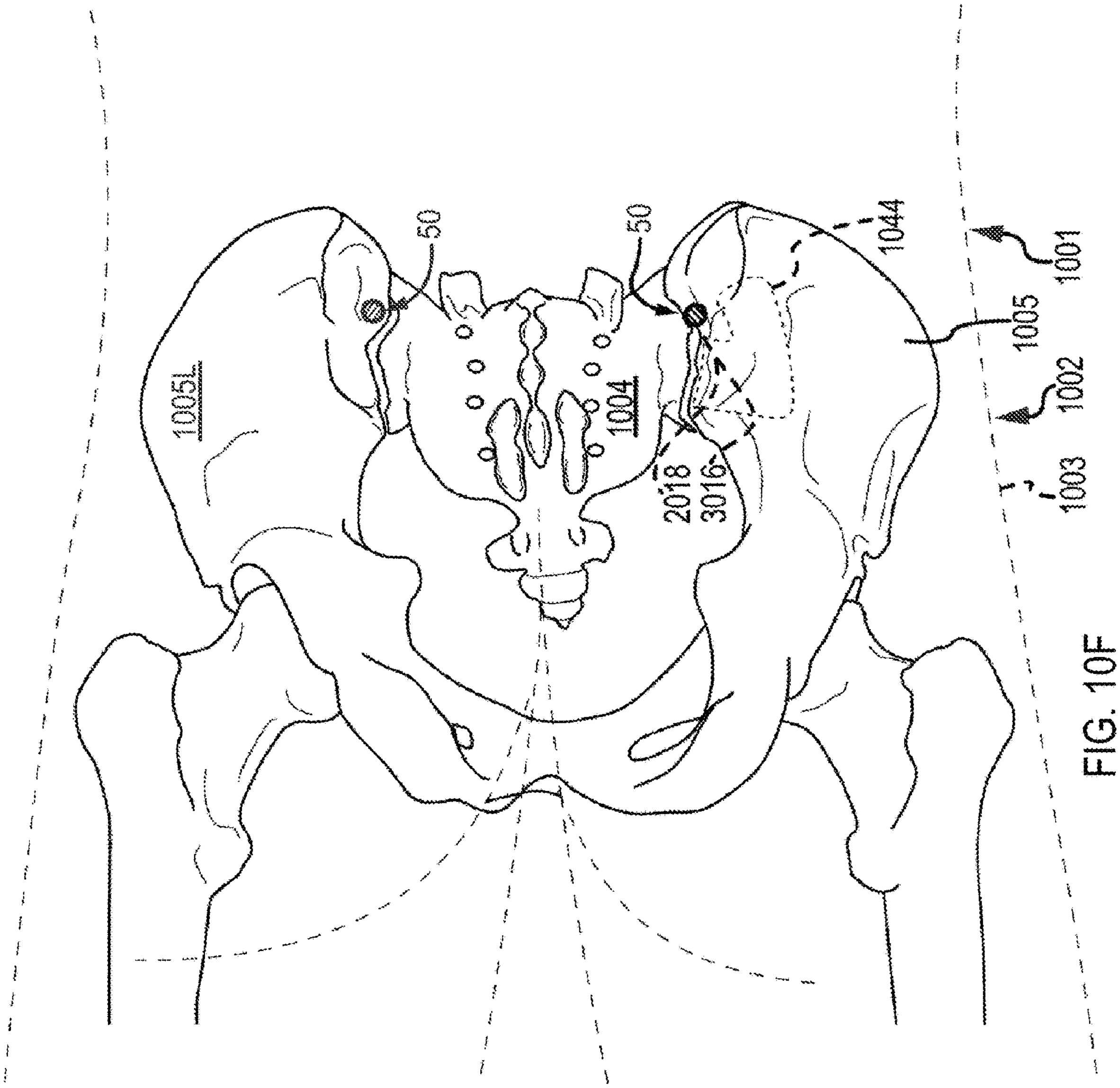
FIG. 10F is a posterior view of the hip region of the patient showing pins in a right ilium and a left ilium.

As another possible example of pin placements in the pelvic region, as seen in FIG. 10F, which is a posterior view of the hip region 1002 of the patient 1001, a first pin 50 having a tapered and threaded distal end may be posteriorly delivered into a right side ilium 1005R just lateral of the extra-articular region of the sacroiliac joint (i.e., an upper or superior region defined between the posterior inferior iliac spine 2006 and the posterior superior iliac spine 2004, as seen in FIG. 10A). A second pin 50 having a tapered and threaded distal end may be posteriorly delivered into a left side ilium 1005L just lateral of the extra-articular region of the sacroiliac joint (i.e., an upper or superior region defined between the posterior inferior iliac spine 2006 and the posterior superior iliac spine 2004, as seen in FIG. 10A). In this example, the two pins 50 are delivered into opposite iliums 1005R, 1005L. Thus, the joints may be manipulated without delivering a pin 50 into the sacrum 1004. Since the sacrum 1004 is a softer bone than the ilium 1005R, 1005L, this example of pin 50 placement may be useful in certain patients with an especially soft or brittle sacrum 1004.

Figure 10G:
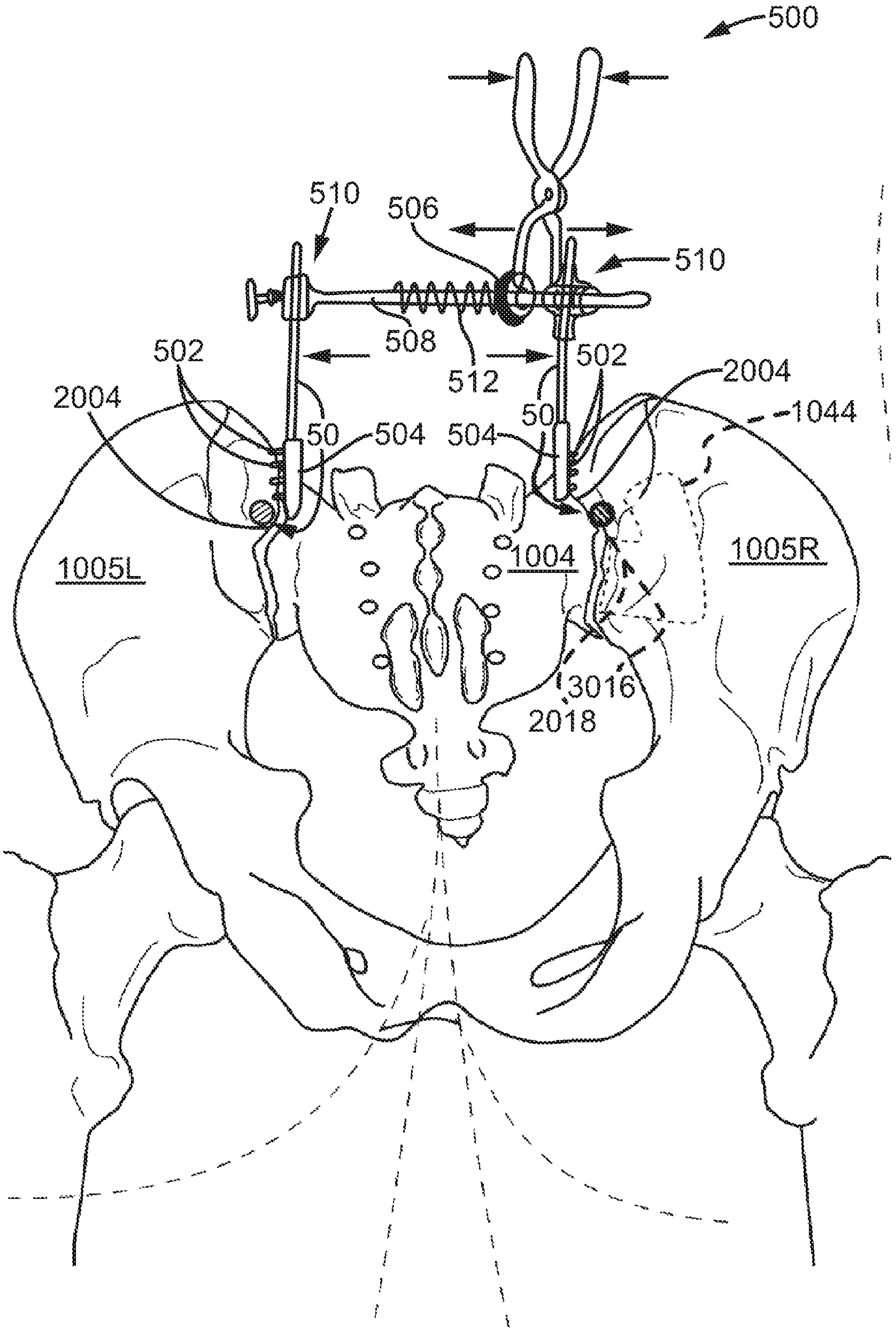
FIG. 10G is a posterior view of the hip region of the patient showing pins positioned in a right ilium and a left ilium for distracting the joint.

Reference is now made to FIG. 10G, which is a posterior view of a pelvic region of a patient with a distractor 500 positioned between a pair of pins 50 positioned in opposing iliums 1005L, 1005R. As seen in the figure, the pins 50 may include anchors 502 extending through a plate member 504 at a distal end of the pins 50. The pins 50 may be positioned such that the anchors 502 extend through openings in the plate member 504 and extend into an inner cortex of the ilium near the posterior superior iliac spine 2004. The pins 50 may couple with an extension rod 508 spanning the sacrum 1004 via adjustable couplers 510 that may be variably fixed on the length of the pins 50. The extension rod 508 may be a cylindrical rod having a spring 512 engaged with a thumb-wheel 506 that may be movably adjusted along the extension n rod 508. The spring 512 may bias the thumb-wheel 506 to the right. One of the couplers 510 (on right ilium 1005R) may slidably couple the extension rod 508 and the pin 50 such that as the distractor 500 is positioned between the coupler 510 on the right and the thumb-wheel 506, outward distraction of the arms of the distractor 500 causes a distance between the thumb-wheel 506 and the coupler 510 on the right to increase so as to also increase a distance between the pins 50 (i.e., and the opposing ilium).

Figure 10H:
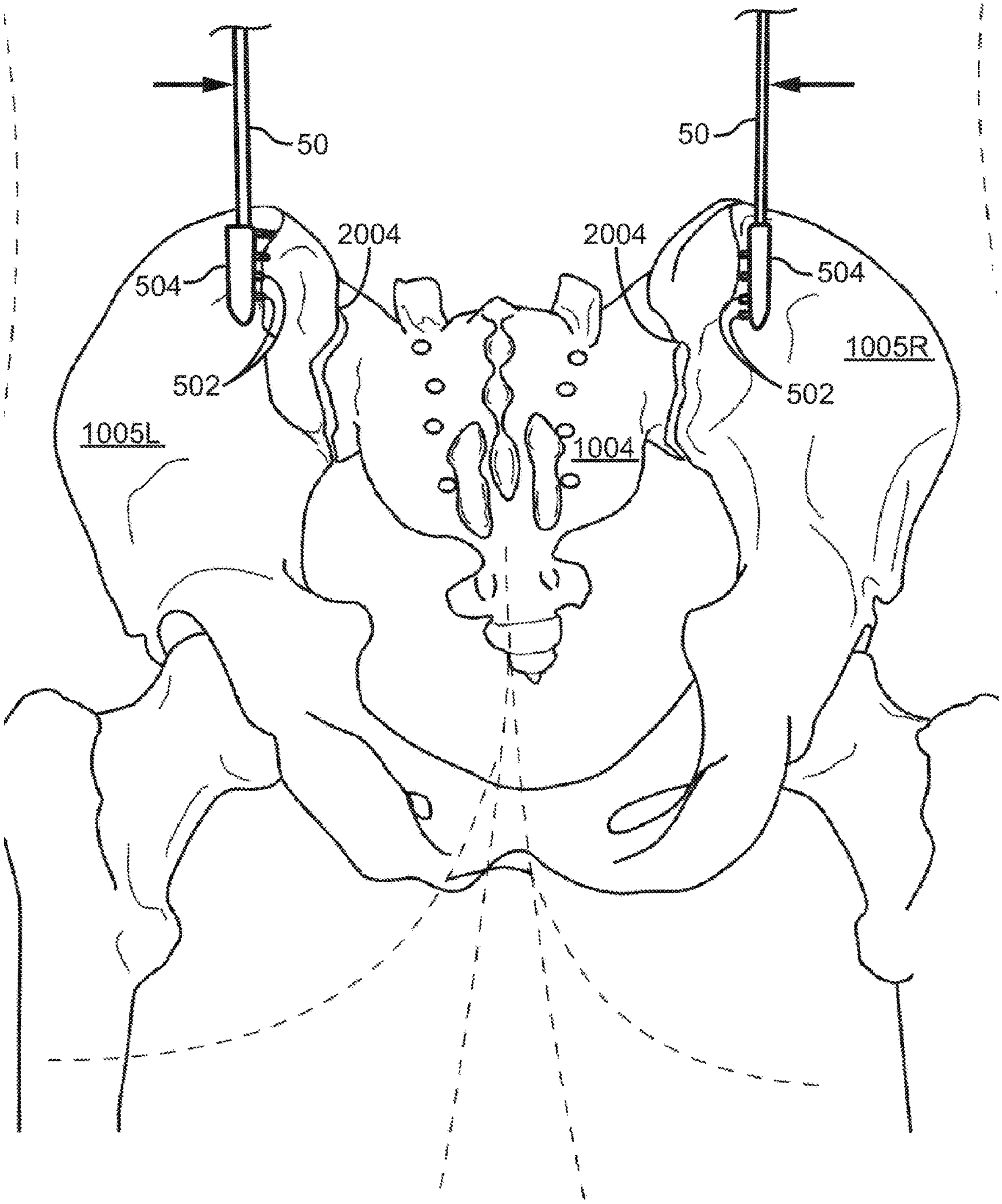
FIG. 10H is a posterior view of the hip region of the patient showing pins positioned in a right ilium and a left ilium for compressing the joint.

As opposed to distracting the joints via pins 50 positioned in the ilium 1005, the pins 50 may be used to compress the joint. As seen in FIG. 10H, which is a posterior view of a pelvic region of a patient with a pair of pins 50 positioned in opposing ilium 1005R, 1005L, the sacroiliac joint may be compressed with similar tools and methods as described with reference to FIG. 10G, except the pins 50 may be positioned against the outer cortex of the ilium 1005R, 1005L or against both the inner and outer cortex ("sandwich PSIS"). As seen in FIG. 10H, the pins 50 are similar to those described in reference to FIG. 10G. That is, the pins 50 include the plate member 504 at a distal end and are secured to the ilium via anchors 502 extending through openings in the plate member 504 and into the bone. As seen in the figure, the anchors 502 extend into the ilium on the outer cortex. A device for compressing the joint is not shown in this figure, but may be similar to that shown in FIG. 10G, except the tool may be configured to compress the joint, as opposed to distract the joint.

While not depicted in the figures, the system and methods described in reference to FIGS. 10G-10H can be combined to sandwich the posterior superior iliac spine 2004 and provide for distraction or compression, as desired for the particular diagnosis.

Figure 10I:
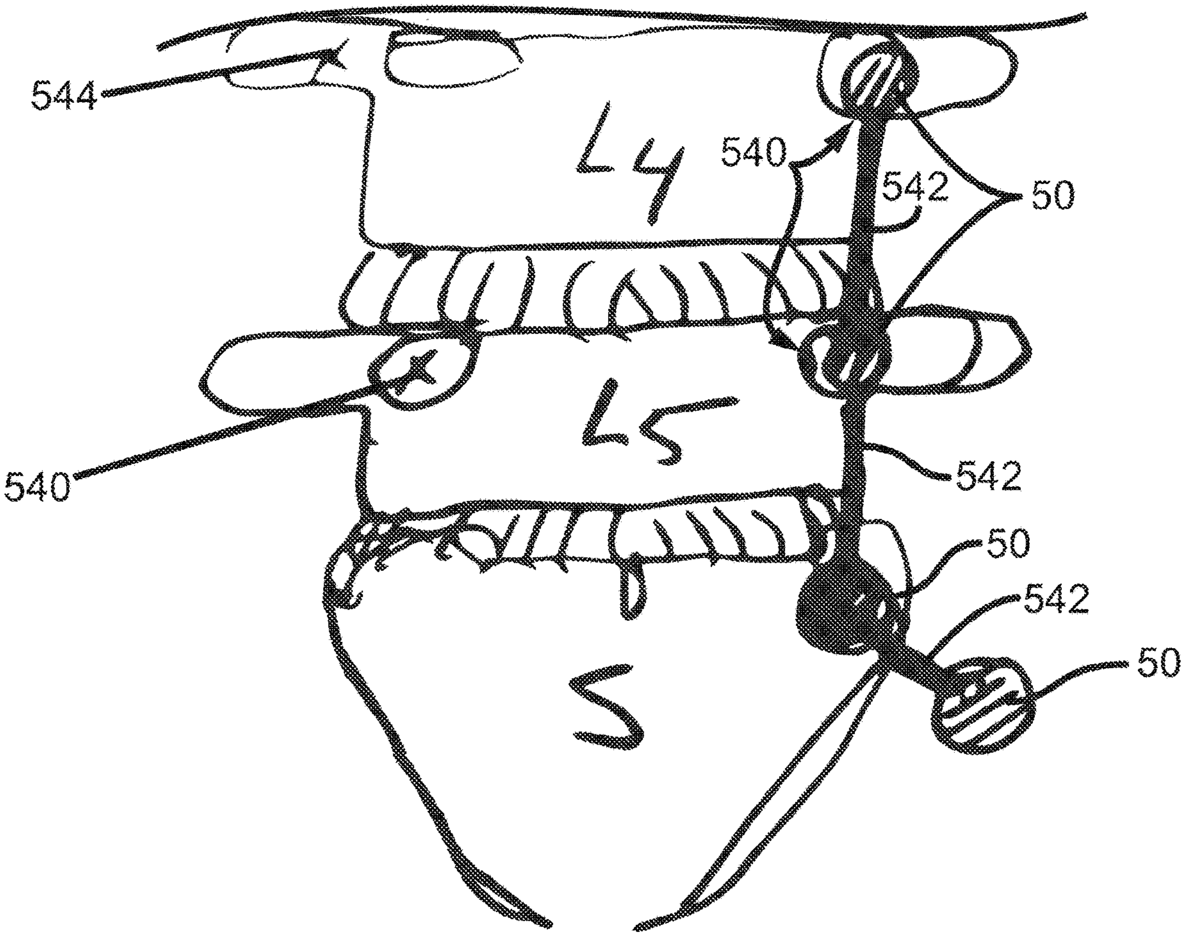
FIG. 10I is a posterior view of the lumbar spine showing pins to either stabilize or selectively allow motion between segments of the spine.

Reference is now made to FIG. 10I, which is a posterior view of the lumbar spine showing pins 50 to either stabilize or selectively allow motion between segments L4, L5 of the spine. As seen in the figure, pins 50 or anchors may be delivered into the spinal segments at, for example, the pedicles 540, which are medial of the transverse process 544. Further, an extension member 542 may be coupled with the pins 50 via a coupler (not shown) to link the segments of the spine. In this way, upon manipulation of the patient's sacrum and ilium, the segments of the spine will be linked to either: stabilize the segments of the spine; or allow relative motion between certain segments of the spine. In stabilizing the spine, the pins 50 and extension members 542 may be rigidly coupled via the couplers such forces transferred via manipulation of the sacroiliac joint are not concentrated on any one spinal segment. Rather, the forces are distributed in order to further isolate the movements of the sacrum and ilium, respectively, for diagnosing purposes. Alternatively, certain segments of the spine may be allowed certain movements relative to each other.

As seen with the most inferiorly placed pin 50, the pin 50 and extension member 542 construct may link with the a pin positioned in the ilium (not shown) for further manipulation of the sacroiliac joint.

C. Using the Pins to Mobilize the Sacroiliac Joint for Diagnostic Purposes

The sacroiliac joint or, more particularly, the sacrum and the ilium may be difficult to manipulate because of the vast array of ligaments surrounding the sacrum and ilium. Additionally, the joint may be difficult to diagnose as a source of pain since manual manipulating the joint may cause movement and pain or discomfort in other areas of the body.

With the diagnostic system described herein, the movements of the ilium and sacrum may be isolated from movement of other parts of the body (e.g., the spinal column) to provide for a more accurate diagnosis of a sacroiliac joint ailment. Additionally, the present disclosure provides a diagnostic system that may be effective in mobilizing the joint to determine if pain can be activated or alleviated, depending on the joint condition. The diagnostic system may include the use of the pins, previously described. The diagnostic system may also include one or more mechanical assemblies that assist in the movements of the pins or bars, including translational movements, rotational movements or combination of translational and rotational movements. The rotation of the diagnostic system may be controlled or limited to within a few degrees. The translational displacement or linear movement of the diagnostic system may be limited to within a few millimeters.

In some embodiments, the pins or bars described above may be inserted into the bones to cause the movement of the sacroiliac joint. In some embodiments, the pins may include a blunt distal end that is not inserted into the bones, but, rather, is pushed against the bones to cause the movement. In some embodiments, the screws may be used to cause the movement of the joint. In some embodiments, a combination of pins or screws may be used to cause the movement of the joint.

In some embodiments, opposing portions of a right and left ilium may be pushed or pulled against each other such that the joint is under tension or compression or rotation.

In some embodiments, the diagnostic system may also be used to cause movement of the sacroiliac joint to return to its natural position to release the pain of the patient.

Figure 11:
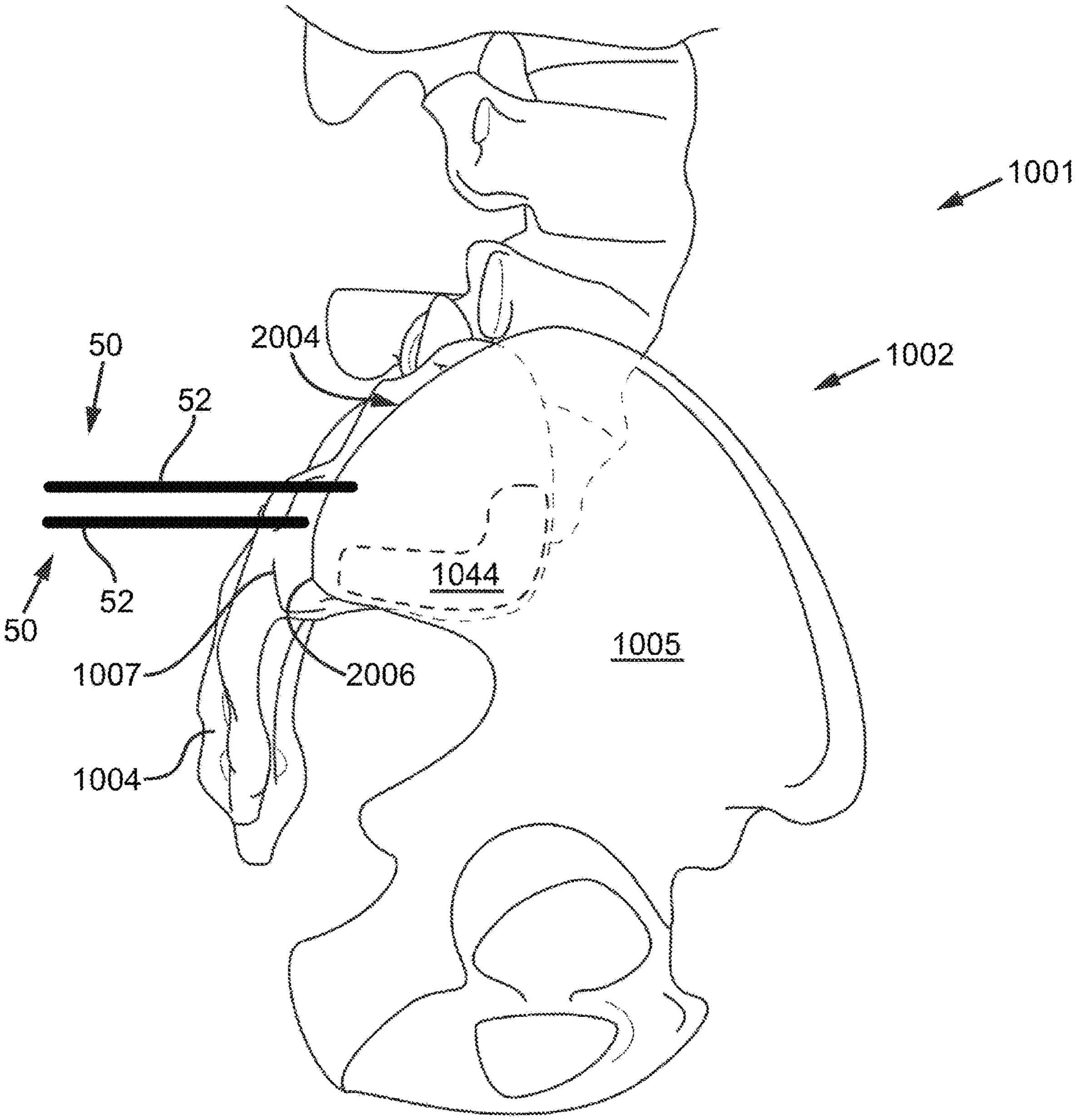
FIG. 11 is a lateral side view of the hip region of the patient in a neutral position with one pin in the sacrum and one pin in the ilium.
Figure 12A:
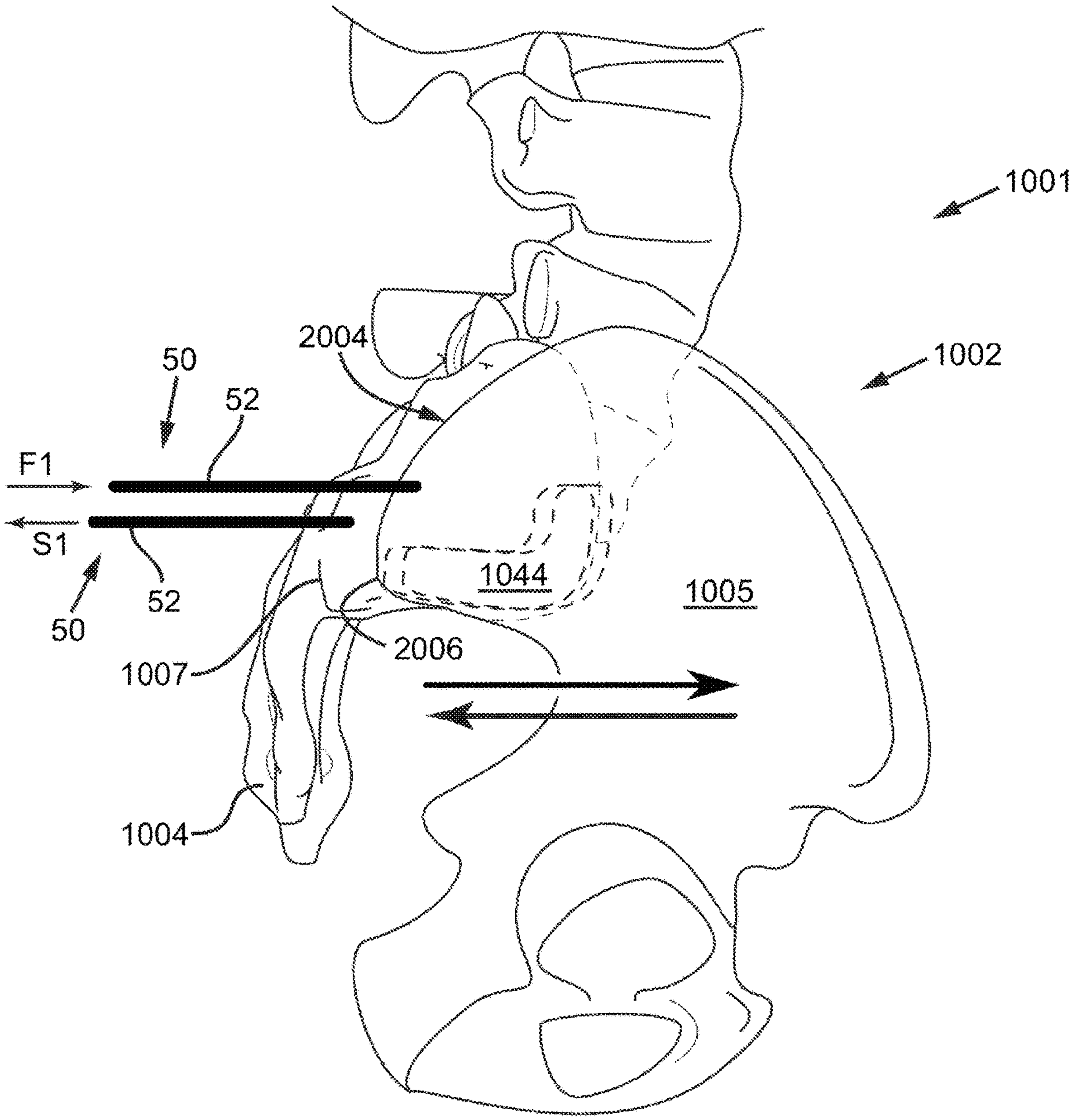
FIG. 12A is a lateral side view of the hip region of the patient showing anterior-posterior movement of the ilium via the pins positioned in the sacrum and ilium.
Figure 12B:
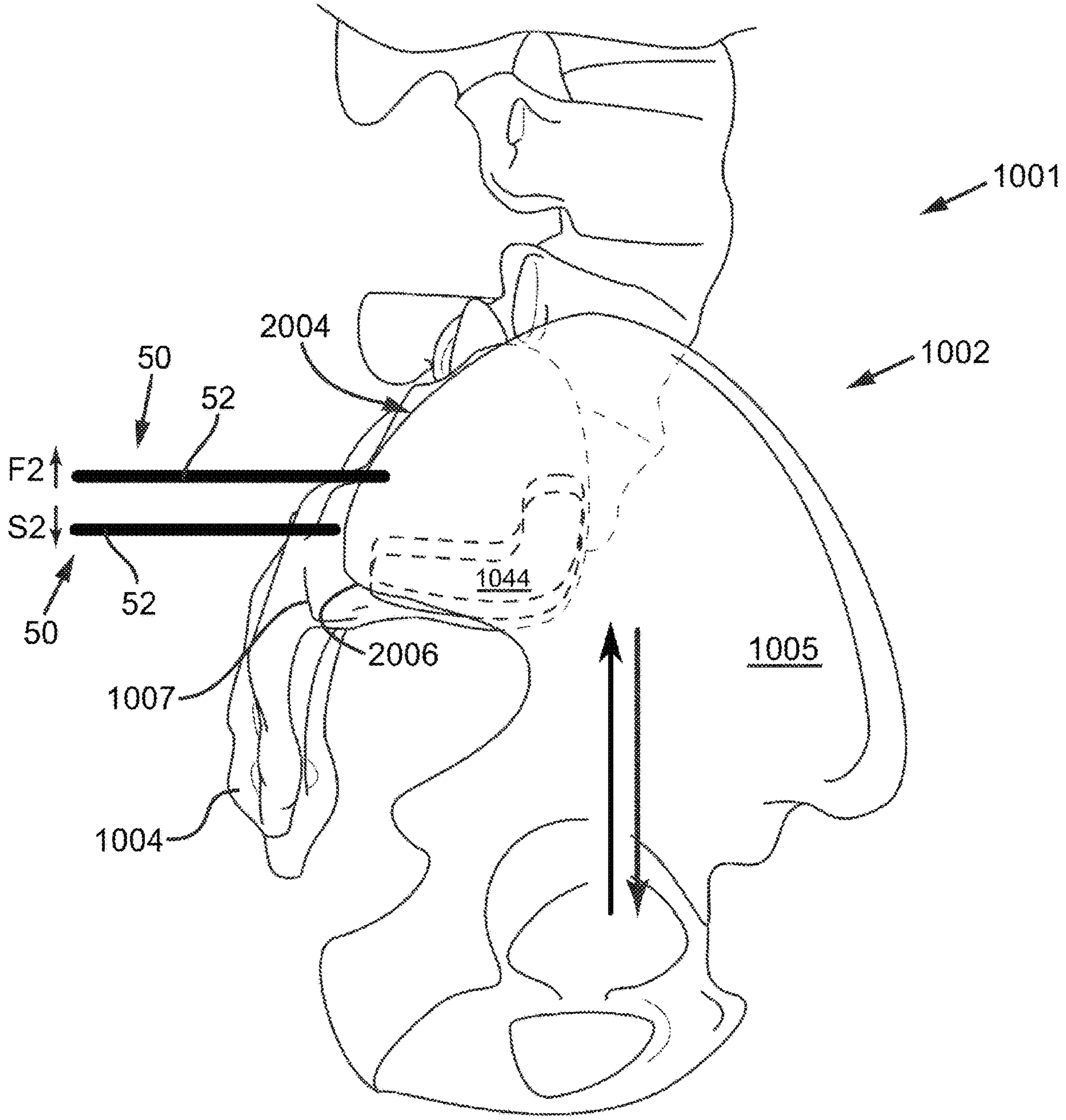
FIG. 12B is a lateral side view of the hip region of the patient showing cranial-caudal movement of the ilium via the pins positioned in the sacrum and ilium.
Figure 12C:
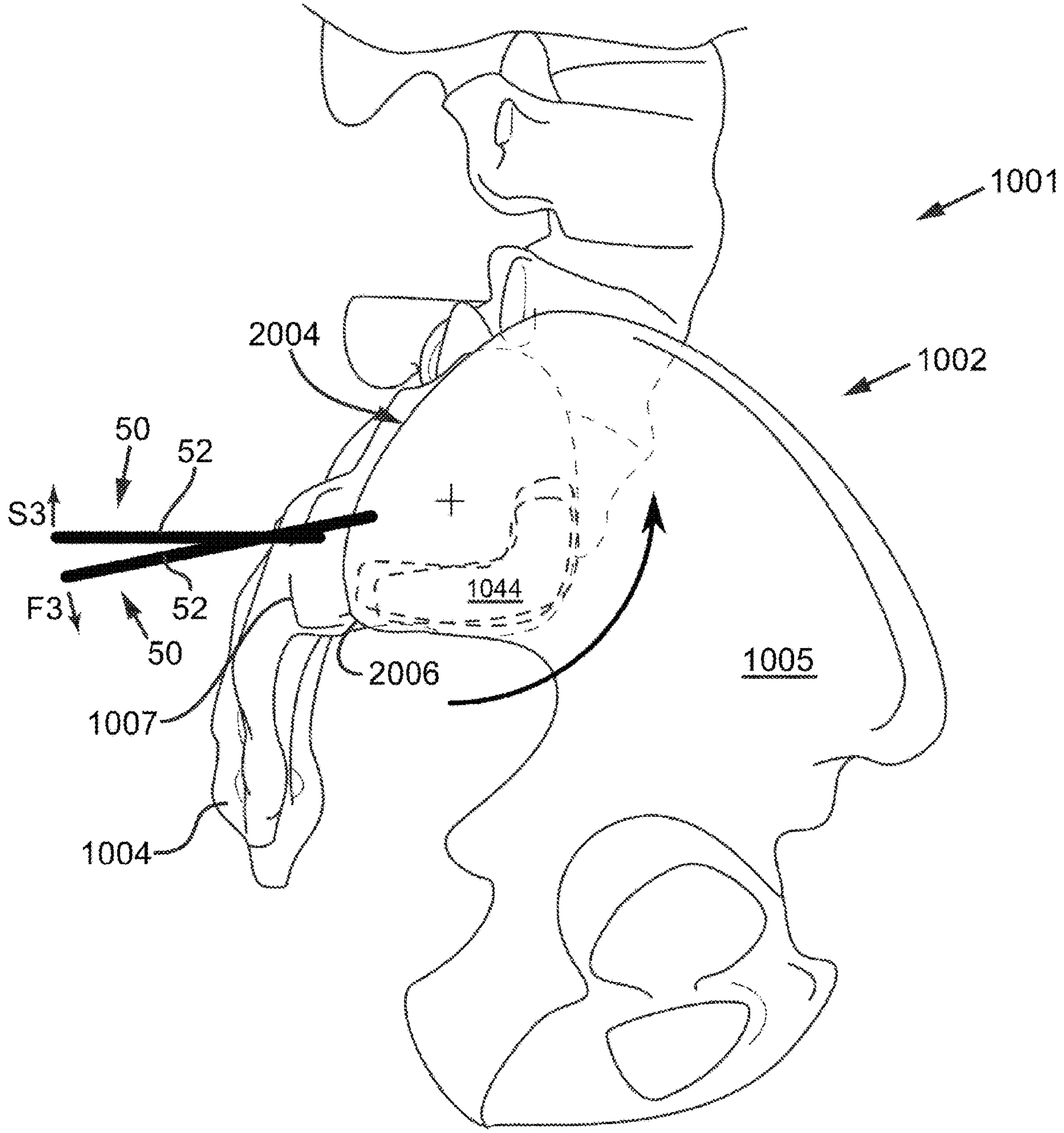
FIGS. 12C-12D are lateral side views of the hip region of the patient showing rotational movement of the ilium via the pins positioned in the sacrum and ilium.
Figure 12D:
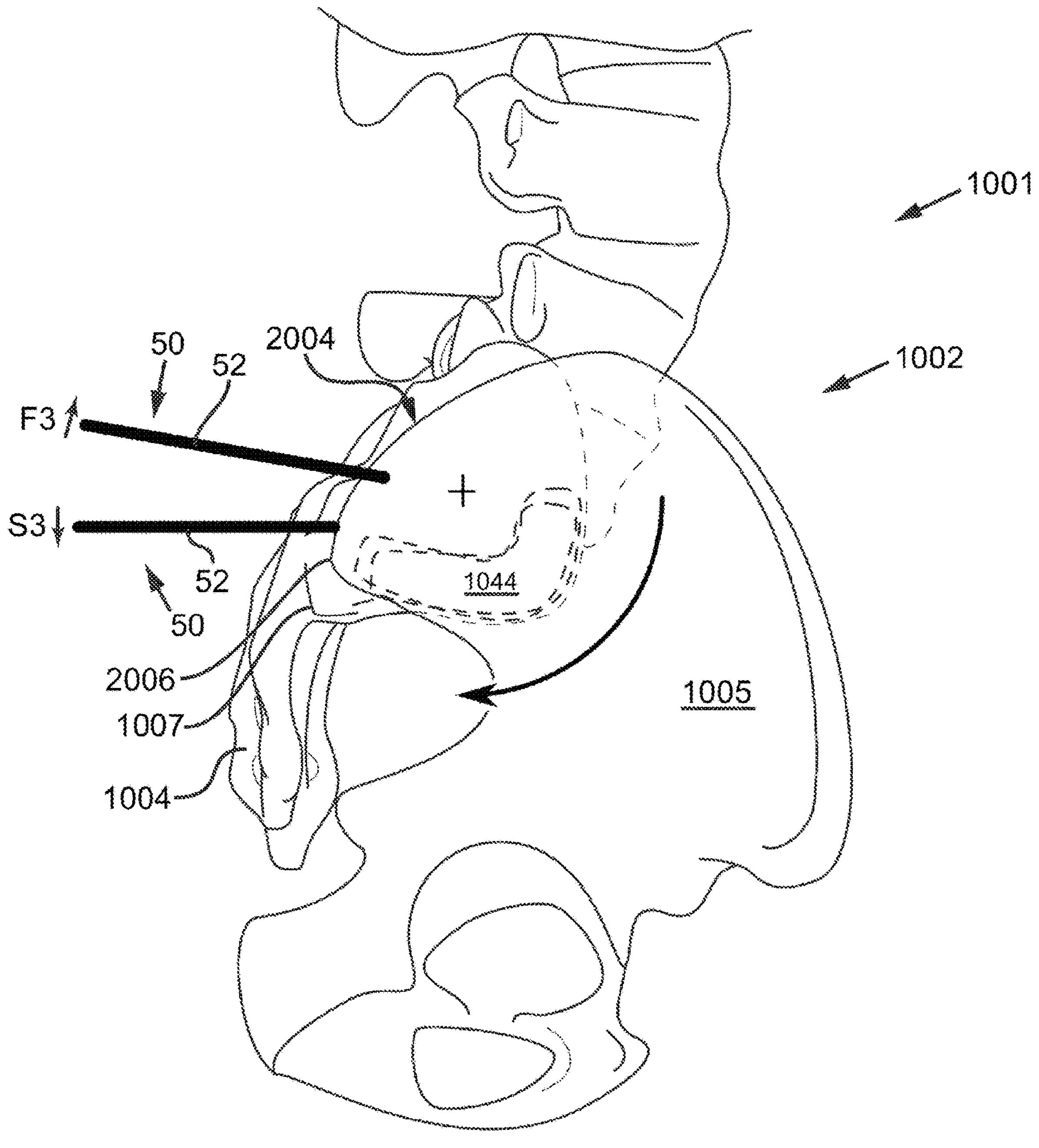

Reference is made to FIGS. 11-12D, which depict lateral side views of a hip region 1002 of a patient 1001 with a pin 50 positioned lateral of the lateral sacral crest 1007 of the sacrum 1004 and another pin 50 positioned in the ilium 1005 just lateral of and in an upper region of the iliac spine between the posterior superior iliac spine 2004 and the posterior inferior iliac spine 2006. FIG. 11 depicts a neutral position of the pins 50, just after delivery into the sacrum 1004 and ilium 1005 and before any manipulation has taken place. In this particular embodiment, the pins 50 are delivered parallel to each other, although the pin 50 in the sacrum 1004 is positioned slightly inferior to the pin 50 in the ilium. In this neutral position, the pins 50 may be manipulated in a variety of ways to determine if the patient's pain can be alleviated or reproduced.

As an example of how manipulation of the pins may alleviate pain while indicating that fusion of the joint may be helpful in reducing pain, a patient may have a compressed joint that is causing pain during normal activities (e.g., standing, walking). Upon inserting the pins into the patient's bones, the neutral position may be the compressed state of the joint. Thereby, when the doctor applies a force (e.g., distractive force) to relieve the compressive force on the joint, the pain may be alleviated. In that case, fusing the joint may alleviate the compression on the joint and, thus, alleviate the patient's pain.

As an example of how manipulation of the pins may reproduce a patient's pain while indicating that fusion of the joint may be helpful in reducing pain long term, the patient may only experience pain the in joint upon certain movements (e.g., flexing at the hips, decubital, prone, and standing positions). Upon inserting the pins into the patient's bones with the patient lying prone on an examining table, for example, the patient may not experience a significant amount of pain. When the doctor manipulates the joint, however, the doctor may be able to manipulate the joint in such a way that causes the same pain in the patient that is experienced upon doing those certain movements (e.g., flexing at the hips, decubital, prone, and standing positions). Thus, the doctor was able to manipulate the joint in order to reproduce the pain and diagnose that a fusion procedure may be helpful in alleviating the patient's pain.

Turning again to FIG. 11, in the neutral state, the joint has not yet been manipulated by the doctor or medical professional. Upon manipulation of the sacrum or ilium, the joint will have a tendency to revert back to or spring back to the neutral state.

From the neutral state, the joint may be manipulated in a number of ways to either reproduce the patient's pain or alleviate the patient's pain. As seen in FIG. 12A, which is the same view as FIG. 11, except the ilium 1005 is caused to move or translate anteriorly, a force F1 is applied to the pin 50 in the ilium 1005. The force F1 could be applied by the medical professional with his or her hands or with the aid of a diagnostic tool. Alternatively, the force F1 could be applied via a surgical robot. In order to isolate the force F1 to the pin 50 in the ilium 1005, a stabilizing or holding force S1, acting counter to the force F1, may be exerted on the pin 50 in the sacrum 1004. The stabilizing force S1 need not be actively pulled posteriorly, but be held at a constant force so as to isolate the movement of the ilium 1005 with respect to the sacrum 1004 and the rest of the upper body (e.g., spine). In certain instances, translating or moving the ilium anteriorly from the neutral state may reproduce or alleviate a patient's pain and indicate to the medical professional that fusion of the joint may be helpful in alleviating or lowering the patient's pain long-term.

In certain instances, for example, the ilium 1005 may have been posteriorly jammed or knocked out of a natural alignment. Thus, moving the ilium 1005 anteriorly may reduce the patient's pain as such movement would restore the natural alignment.

The force F1 may be applied in the opposite, posterior direction, as well and as similarly described with reference to applying the force F1 in an anterior direction. Applying the force F1 in a posterior direction by pulling on the pin 50 in the ilium 1005 may be helpful in reducing or reproducing pain in the joint.

Turning to FIG. 12B, which is the same view as FIG. 11, except the ilium 1005 is caused to move or translate in a cranial direction, a force F2 is applied to the pin 50 in the ilium 1005. The force F2 could be applied by the medical professional with his or her hands or with the aid of a diagnostic tool. Alternatively, the force F2 could be applied via a surgical robot. In order to isolate the force F2 to the pin 50 in the ilium 1005, a stabilizing or holding force S2, acting counter to the force F2, may be exerted on the pin 50 in the sacrum 1004. The stabilizing force S2 need not be actively pulled in a caudal direction, but be held at a constant force so as to isolate the movement of the ilium 1005 with respect to the sacrum 1004 and the rest of the upper body (e.g., spine). In certain instances, translating or moving the ilium 1005 in a cranial direction from the neutral state may reproduce or alleviate a patient's pain and indicate to the medical professional that fusion of the joint may be helpful in alleviating or lowering the patient's pain long-term.

In certain instances, for example, the ilium 1005 may have been jammed in a caudal direction so as to be out of a natural alignment. Thus, moving the ilium 1005 in a cranial direction may reduce the patient's pain as such movement would restore the natural alignment.

The force F2 may be applied in the opposite, caudal direction, as well and as similarly described with reference to applying the force F2 in the cranial direction. Applying the force F2 in a caudal direction by pushing on the pin 50 in the ilium 1005 may be helpful in reducing or reproducing pain in the joint.

The pins 50 may be moved or translated apart while keeping them parallel by, for example, using a tool that grasps the pins at multiple points along the elongated body 52. That is, the multiple contact points on each arm of the tool would counteract the bending moment caused by the joint resisting the movement.

Referring now to FIGS. 12C-12D, the ilium 1005 may be pivoted or rotated relative to sacrum 1004 via the pins 50 placed in the ilium 1005 and sacrum 1004. As seen in FIG. 12C, which is the same view as FIG. 11, except the ilium 1005 is caused to pivot or rotate in a posterior direction (i.e., nutation of sacrum 1004), a force F3 is applied to the pin 50 in the ilium 1005. The force F3 could be applied by the medical professional with his or her hands or with the aid of a diagnostic tool. Alternatively, the force F3 could be applied via a surgical robot. In order to isolate the force F3 to the pin 50 in the ilium 1005, a stabilizing or holding force S3, acting counter to the force F3, may be exerted on the pin 50 in the sacrum 1004. The stabilizing force S3 need not be actively pulled or pushed in a cranial direction, but be held at a constant force so as to isolate the movement of the ilium 1005 with respect to the sacrum 1004 and the rest of the upper body (e.g., spine). In certain instances, pivoting or rotating the ilium 1005 in a posterior direction from the neutral state may reproduce or alleviate a patient's pain and indicate to the medical professional that fusion of the joint may be helpful in alleviating or lowering the patient's pain long-term.

In certain instances, for example, the ilium 1005 may have been jammed or damaged so as to be out of a natural alignment. Pivoting or rotating the ilium 1005 in a posterior direction may reduce the patient's pain as such movement would restore the natural alignment.

The force F3 may be applied in the opposite, anterior direction (i.e., counternutation of sacrum 1004), as seen in FIG. 12D, as similarly described with reference to applying the force F3 so as to rotate the joint in a posterior direction. Applying the force F3 in an anterior direction by pushing on the pin 50 in the ilium 1005 may be helpful in reducing or reproducing pain in the joint.

Figure 13A:
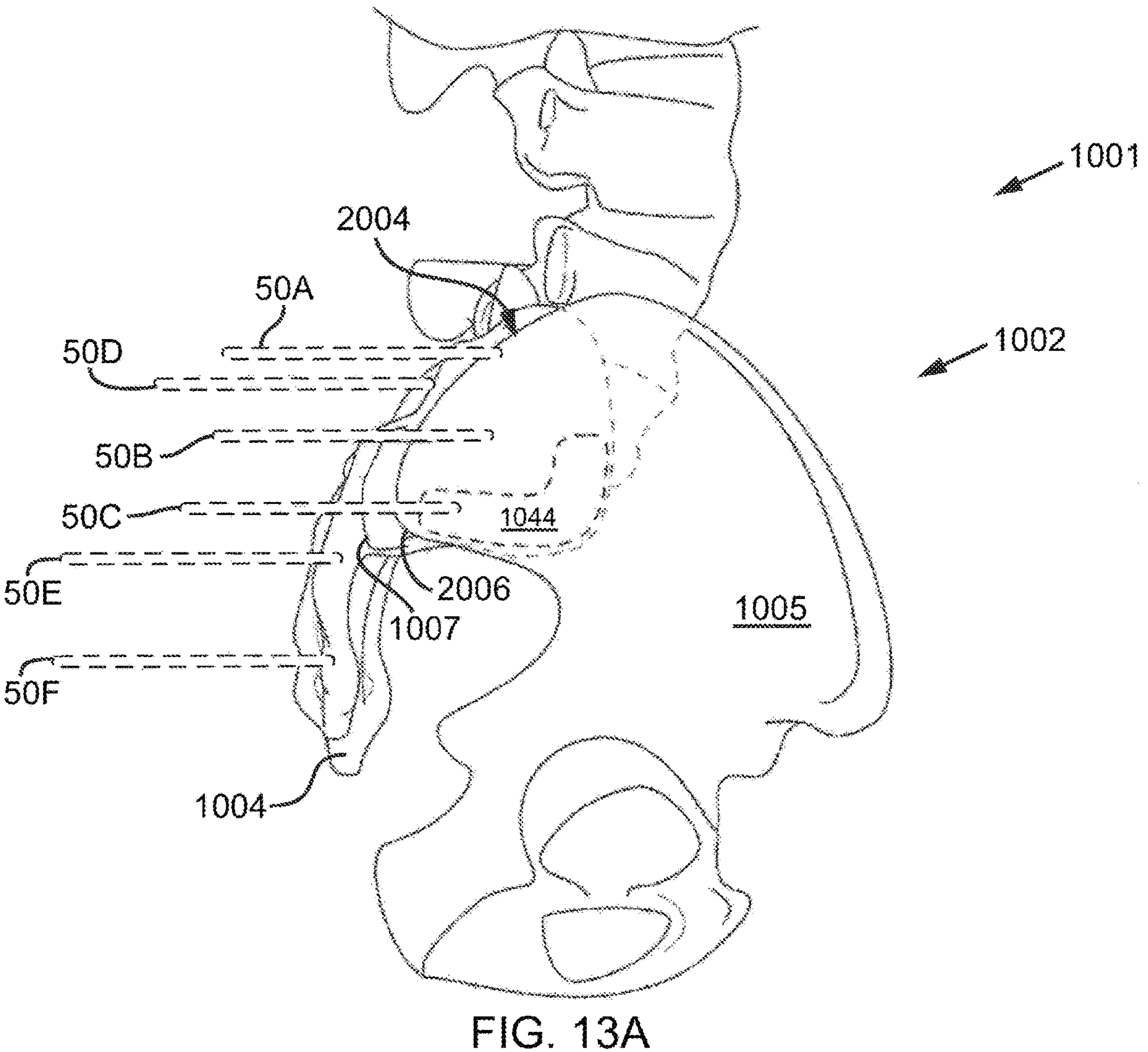
FIG. 13A is a lateral side view of the hip region of the patient showing possible pin placements in the ilium and sacrum.

The particular manipulations of the joint via the pins 50 described above in reference to FIGS. 11-12D are merely exemplary of pin placements in the sacrum 1004 and ilium 1005 and are merely exemplary of possible manipulations to the joint. Other pin placements and manipulations are possible and contemplated herein. As seen in FIG. 13A, which is the same view as FIG. 11, except multiple possible pin placement locations are depicted, the pins 50 may be placed in a number of locations on the sacrum 1004 and ilium 1005 to manipulate the joint. As seen in the figure and referring first to the ilium 1005, a pin 50A may be positioned near the posterior superior iliac spine 2004, a pin 50B may be positioned prominently in the wing of the ilium (gluteal surface), or a pin 50C may be positioned near the posterior inferior iliac spine 2006, among other possible placements of the pin 50.

Referring to placements of the pin 50 in the sacrum 1004, a pin 50D may be positioned near a superior region of the lateral sacral crest 1007 near the sacral tuberosity, a pin 50E may be positioned near a middle region of the lateral sacral crest 1007, or a pin 50F may be positioned near an inferior region of the lateral sacral crest 1007. It is noted that in regions of the sacrum 1004 with softer and/or thinner bone, it may be advantageous to use a pin 50 with a blunt distal end.

It is noted that the manipulations of the joint described in reference to FIGS. 11-12D may be accomplished using any of the previously described pins 50 in FIGS. 7-9.

D. Using the Pins to Stabilize the Sacroiliac Joint

Upon diagnosing the sacroiliac joint as a source of pain and determining that fusing the joint may be helpful in alleviating the pain, the doctor has a number of choices for the fusion procedure. A temporary or permanent implant may be implanted into the joint with or without the use of the pins as a guide. Another approach is to use the pins or a portion thereof as a temporary implant to assist in determining if the implant helps release the pain of the patient.

In some embodiments, the pins or merely a distal portion of the pins may be mechanically coupled together by a mechanical assembly to help stabilize the joint. The pins may be short enough such that they are less disturbing to the patient's activities, as the pins are not used for causing movements of the joint. The patient may monitor his or her reaction to pain with the temporary pins or implants. When the patient's pain is reduced, this may suggest that the joint movement may be a root cause for the pain and stabilization of the joint by using an implant may help to permanently reduce the pain.

Figure 13B:
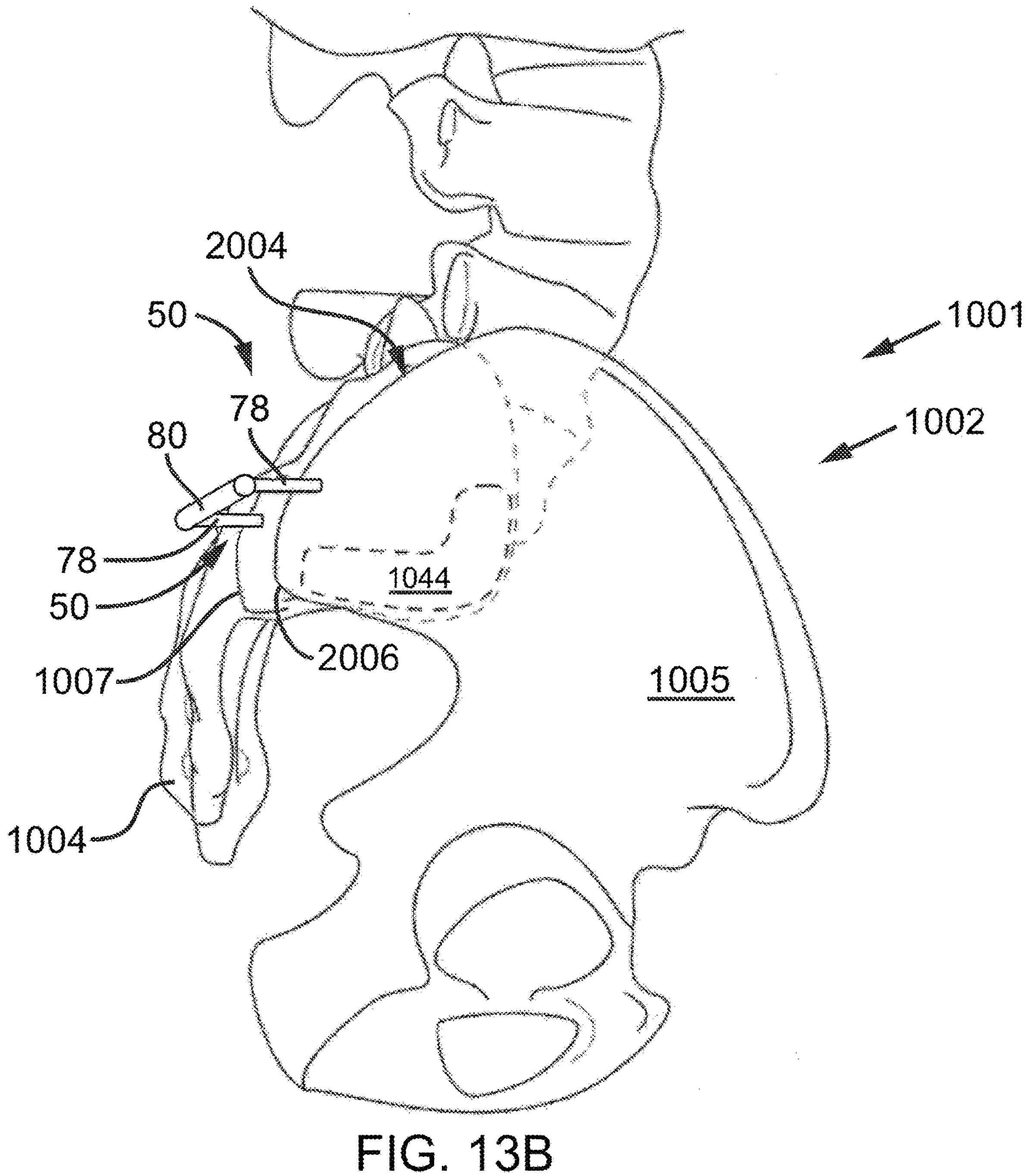
FIG. 13B is a lateral side view of the hip region of the patient showing releasable distal portions of the pins being coupled with a coupling member.

Reference is made to FIG. 13B, which is a lateral view of the hip region 1002 of the patient 1001 with a distal portion 78 of the pins 50 coupled together with a coupling member 80. The proximal portion (not shown) of the pins 50 may be releasable or detachable from the distal portion 78 of the pins 50 such that after manipulation of the joint with both the distal and proximal portions of the pins 50, the proximal portions may be removed from the pins 50 leaving the distal portion 78 still implanted in the sacrum 1004 and ilium 1005. The distal portion 78 may release from attachment with the proximal portion via a threaded connection or other mechanisms. The coupling member 80 may couple the distal portions 78 together close to the patient's bones so that the pins 50 do not extend out of the patient's skin.

Temporarily stabilizing the joint in this way allows for a determination if permanent stabilization is likely to be effective in reducing pain in the long-term. Since this method does not destroy or otherwise alter the capsule or cartilage of the sacroiliac joint, the distal portion 78 of the pins 50 and the coupling member 80 can be utilized and later removed without damage to the joint.

E. Diagnostic Tools Utilizing the Pins, Rods, or Bars

1. Diagnostic Tools and Systems for Causing and Controlling Translational Movement A diagnostic system may include a first elongated member and a second elongated member extending along a longitudinal axis. The elongate members may be the pins or bars, described previously. Each of the members has a distal end that can be delivered into the sacrum and the ilium via a posterior approach, as described above. The diagnostic system may also include a mechanical coupling assembly coupled between the elongated members. The mechanical coupling assembly may be configured to allow one of the elongated members to translate or rotate relative to the other elongated member, such that forces and directions of the forces applied by the elongated members to the sacrum and the ilium can be manipulated to determine a treatment plan.

The diagnostic system isolates manipulations of the sacrum and ilium such that a doctor can more accurately determine if the pain in a patient originates from the sacroiliac joint. If the joint causes the pain in the patient, the treatment plan or method may include inserting an implant into the joint to help temporarily stabilize the joint. The treatment plan or method may also include injecting a bio-based fusion material in the joint to aid in the fusion of the joint.

Figure 14:
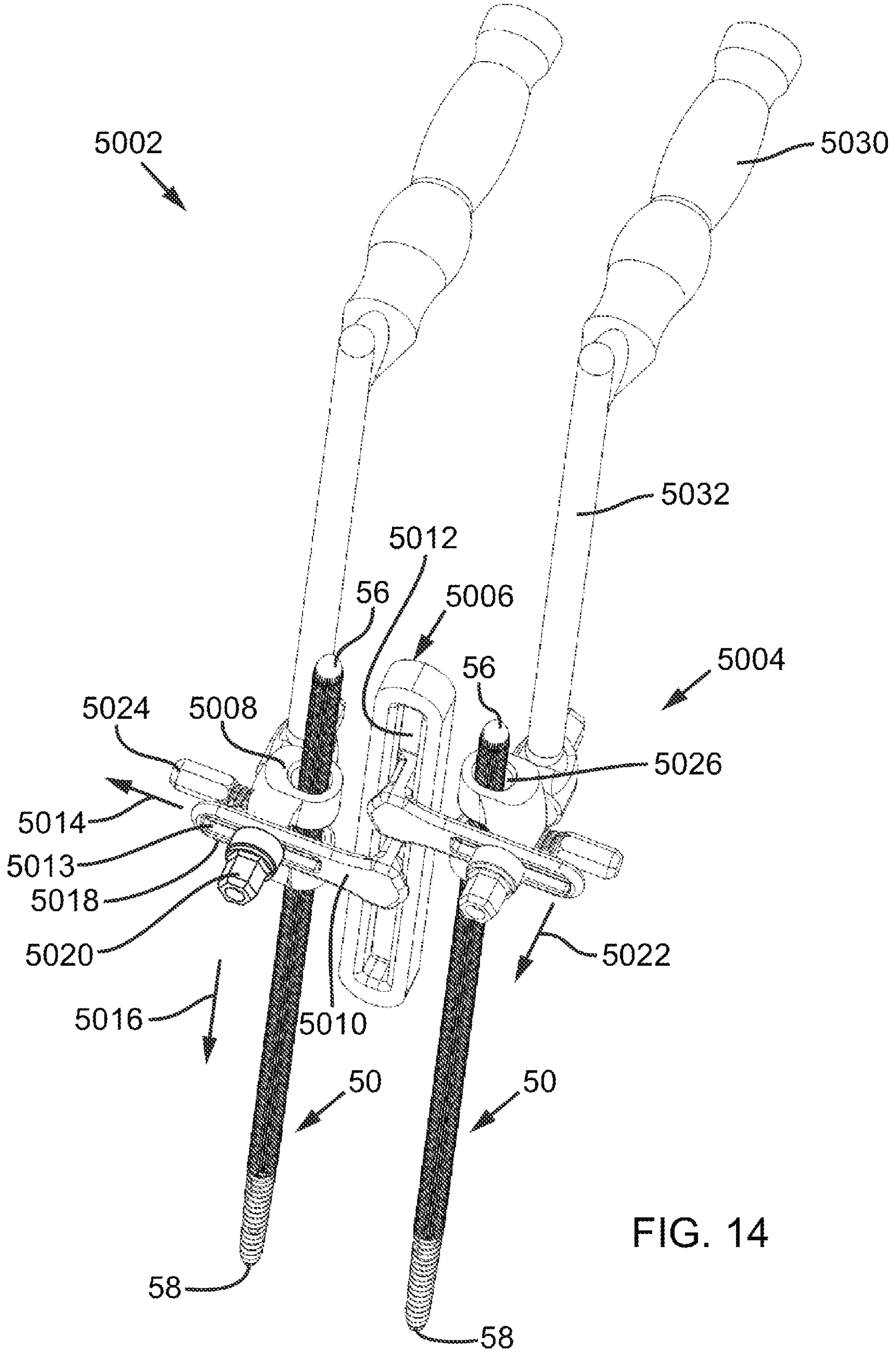
FIG. 14 is a front isometric view of a diagnostic system including a mechanical coupling assembly coupled between a pair of diagnostic pins in accordance with embodiments of the present disclosure.

FIG. 14 is a front isometric view of a diagnostic system including a mechanical coupling assembly coupled between a pair of diagnostic pins in accordance with embodiments of the present disclosure. This diagnostic system can cause the diagnostic pins to move linearly within a plane defined by the pins by applying forces to the pins using the handles, as shown in FIGS. 12A-12B. More particularly, the diagnostic system may be configured to move a pin linearly relative to the other pin, in a longitudinal direction of the pins. And, the diagnostic system may be configured to move a pin laterally away from the other pin while maintaining an orientation (e.g., parallel) with the other pin. The diagnostic system may control the forces of the pins and thus control the movement of the joint.

As shown in FIG. 14, a diagnostic system 5002 may include a pair of elongated members or pins 50, which were previously described with reference to FIGS. 7-9. Each elongated member 50 may include a distal end 58 that can be inserted into the sacrum 1004 or ilium 1005 near the sacroiliac joint. Each elongated member 50 may also include a proximal end 56 where a mechanical coupling assembly 5004 may be coupled to the elongated member 50. The elongated member 50 extends between the distal end 58 and the proximal end 56 along a longitudinal axis 5016. The mechanical coupling assembly 5004 can be used to manipulate the translational movement of the elongated members 50 along the longitudinal axis 5016. The mechanical coupling assembly 5004 may also be configured to align one elongated member 50 to be generally parallel to another elongated member 50.

Figure 15:
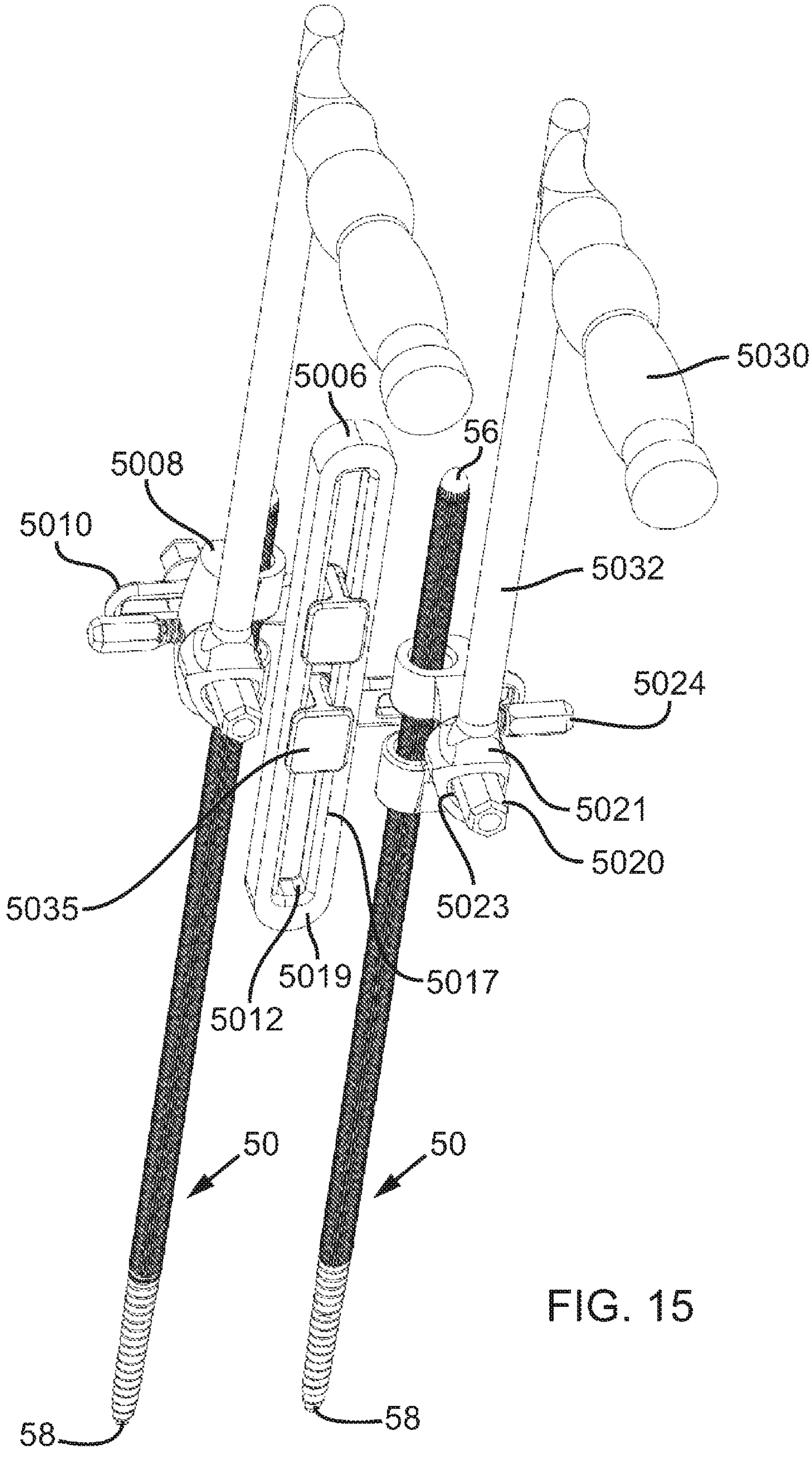
FIG. 15 is a back isometric view of the diagnostic system of FIG. 14.

As shown in FIG. 14, the mechanical coupling assembly 5004 may include a first coupling member 5006 positioned between the two elongated members 50, a second coupling member 5008 that couples to the respective elongated member 50, and a third coupling member 5010 that couples between the first coupling member 5006 and the respective second coupling member 5008. The first coupling member 5006 may include a longitudinal slot 5012 that is elongated along the longitudinal axis 5016. Each third coupling member 5010 may include an engagement element 5035, as seen in FIG. 15, which is configured to slidably engage with the slot 5012 of the first coupling member 5006, such that the respective elongated member 50 may move up or down. In the example shown in FIG. 14, the elongated member 50 on the right side may move up while the elongated member 50 on the left side may move down. The slot size may affect the translational displacement or movement of the elongated members 50.

The third coupling members 5010 may include transverse slots 5013 that extend along a transverse axis that is perpendicular to the longitudinal axis 5016, such that the third coupling member 5010 may be coupled to the second coupling members 5008. The transverse slots 5013 in the third coupling members 5010 enable adjustment of the distance between the two elongated members 50. The third coupling member 5010 may be fixedly attached to the second coupling member 5008 via a fastener 5020. A washer 5018 may also be used between the fastener 5020 and the third coupling member 5010 to help tighten against the third coupling member 5010. The fastener 5020 is attached to the elongated member 50 along a second transverse axis 5022, which is generally perpendicular to the longitudinal axis 5016 and also generally perpendicular to the transverse axis 5014.

The second coupling member 5008 may be fixedly attached to the elongated member 50 by a side screw 5024, which may be generally parallel to the transverse slot 5013 of the third coupling member 5010 along the transverse axis 5014. The second coupling member 5008 may include a hollow portion 5026 that is configured to allow the elongated member 50 to pass through to fixedly attach to the elongated member 50 by the side screw 5024. The second coupling member 5008 may also include a side extension 5042 that may have a threaded end configured to be fastened to the fastener 5020. The side extension 5042 may be perpendicular to the side screw 5024 for easily adjusting the third coupling member 5010 or the second coupling member 5008 independently without interference. The second coupling member 5008 may also include an opposite side extension 5042 that may be coupled to an extension bar 5032 extending away from the proximal end 56 of the elongated member 50 along the longitudinal axis 5016. The extension bar 5032 may connect to a handle 5030 at an opposite end. The handle 5030 may be at an angle from the extension bar 5032 for easy manipulation by hand. The handle 5030 may vary in shape or geometry or size to be comfortable for user to grasp.

FIG. 15 is a back isometric view of the diagnostic system of FIG. 14. As shown in this view, the engagement element 5035 extends beyond the slot 5012 toward sidewalls 5017 that surrounds the slot 5012. The engagement element 5035 overlaps with portions of the sidewalls 5017 of the first coupling member 5006. The engagement element 5035 may have a square shape, a circular shape, an oval shape, or a rectangular shape, among other shapes. This figure also illustrates that the extension bar 5032 has a coupling end portion or connector 5021 that includes a hollow portion 5023 that allows the side extension 5042 to pass through. A fastener 5020 including an inner threaded hole may be fastened to the side extension 5042. The engagement element 5035 may move within the slot 5012 toward one or two ends walls 5019. The end walls 5019 are connected between the sidewalls 5017 to surround the slot 5012.

Figure 16A:
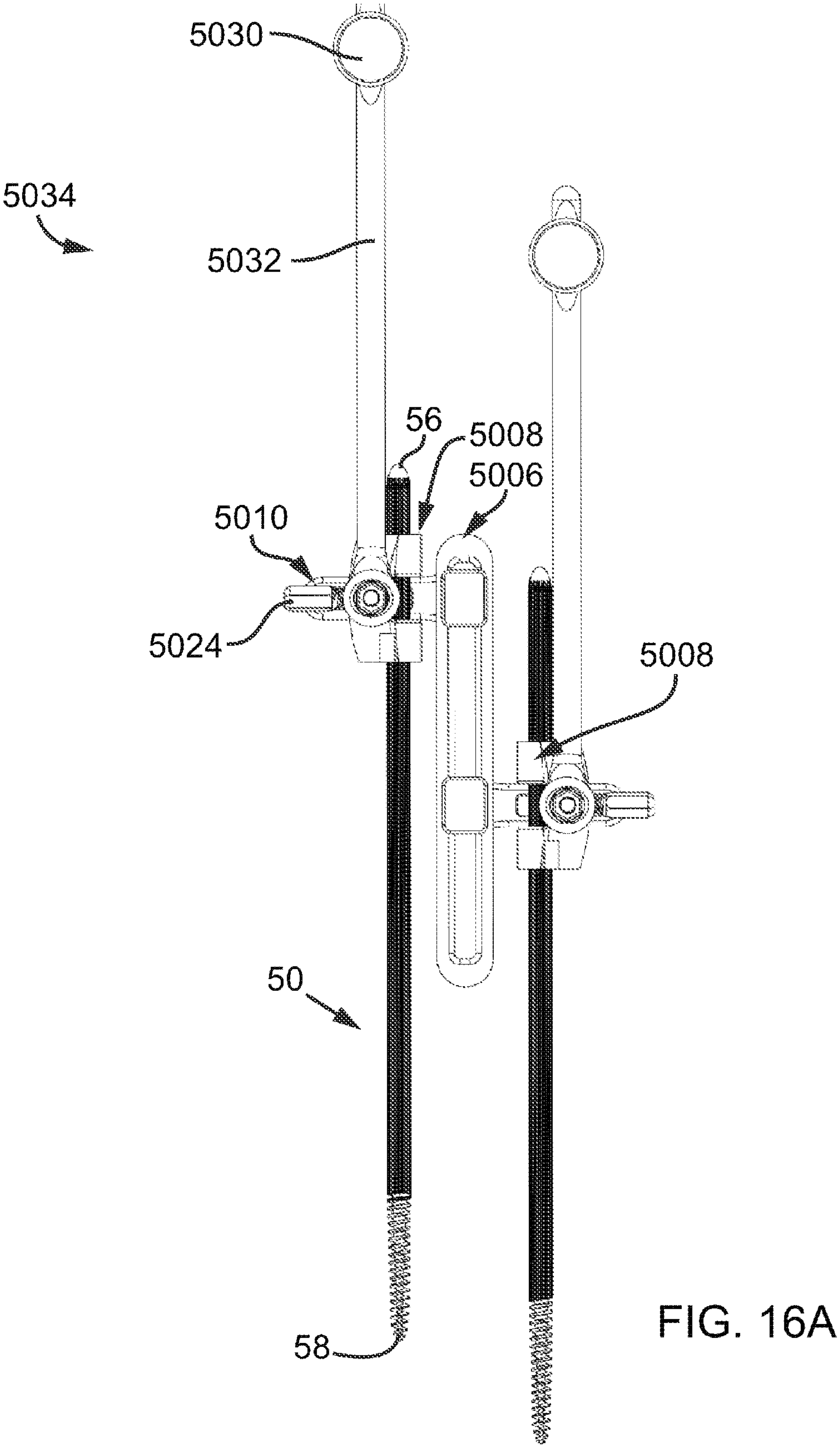
FIG. 16A-16C are back views of the diagnostic system of FIG. 15.
Figure 16B:
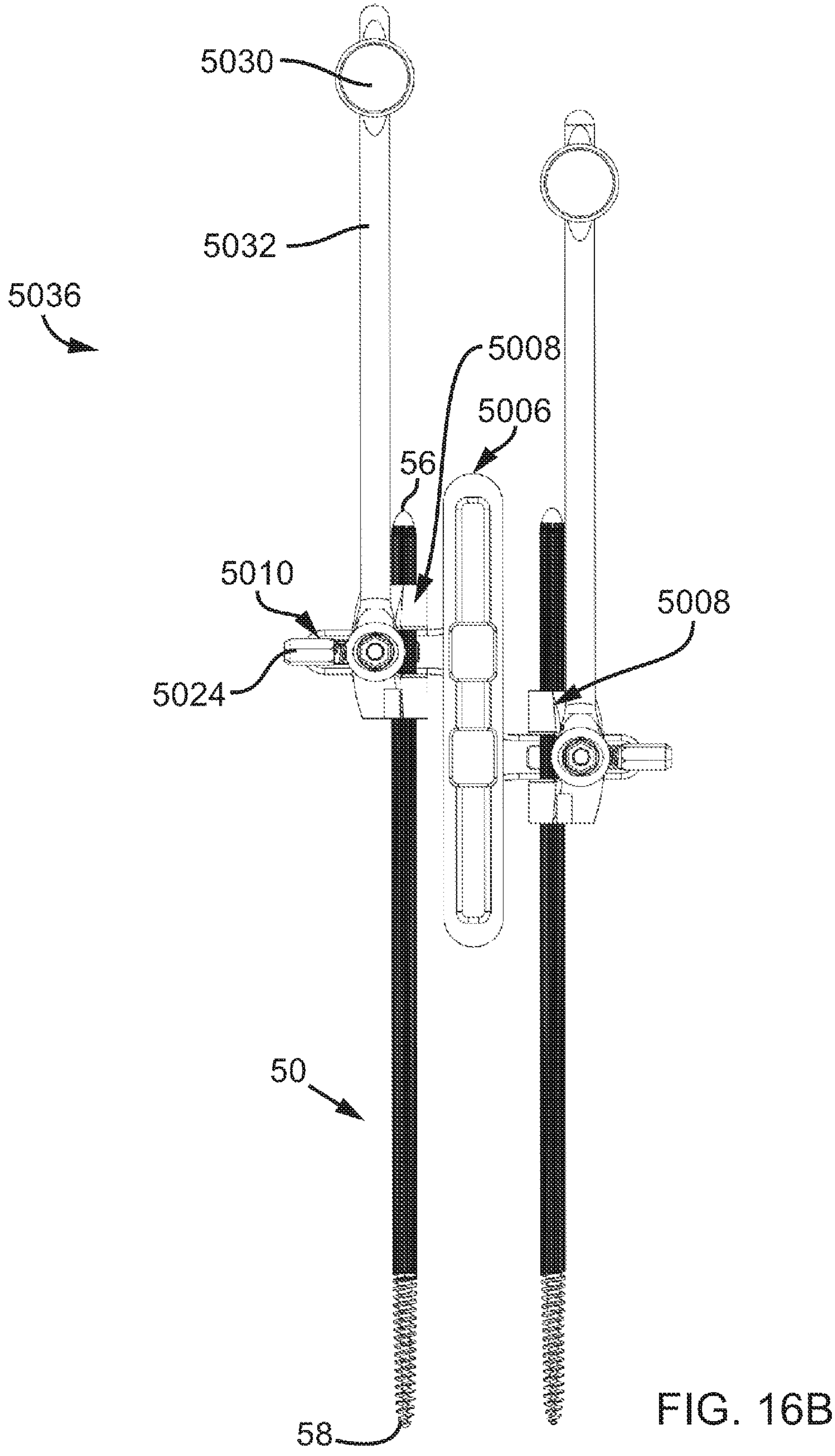
Figure 16C:
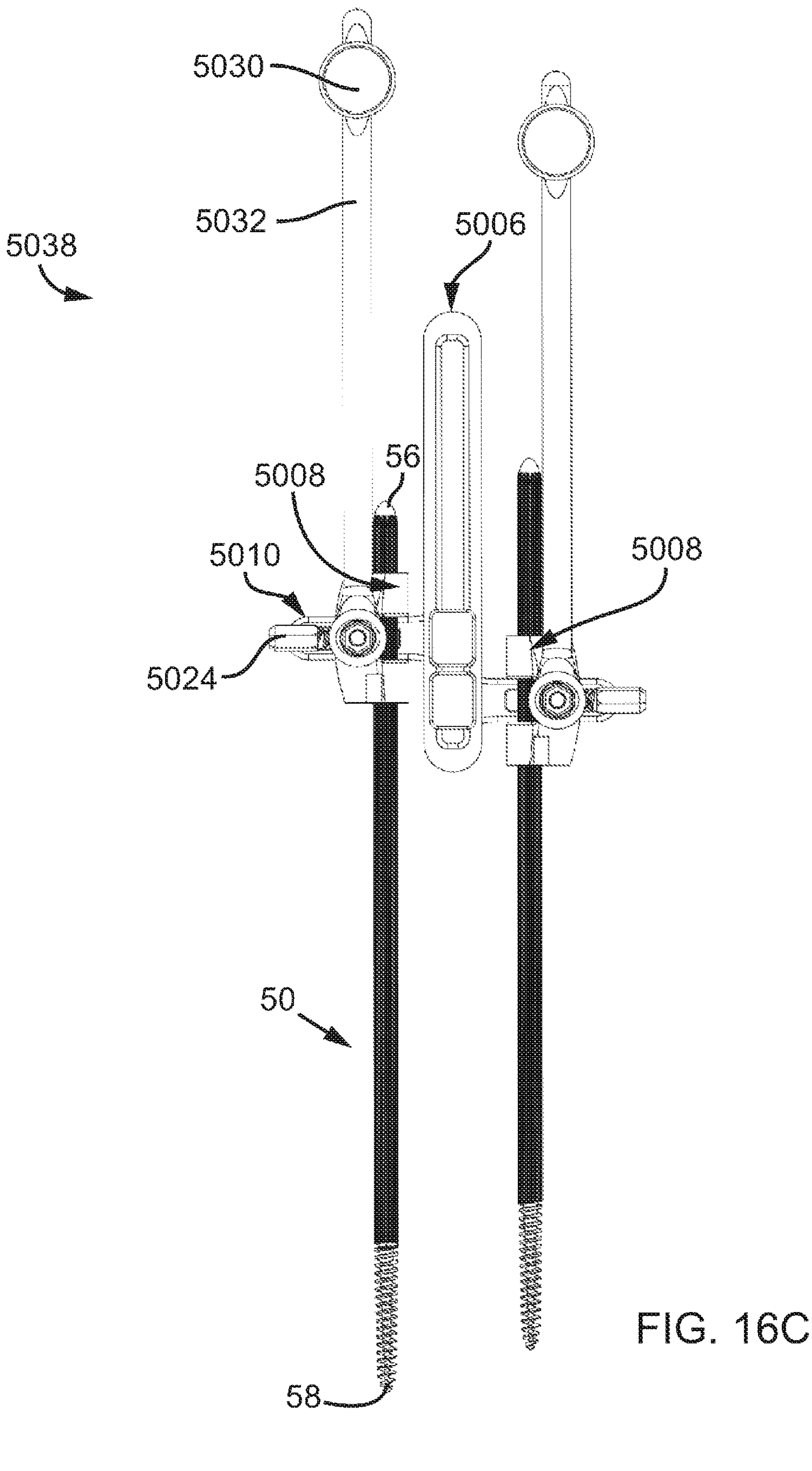

FIGS. 16A-16C depict side views of the diagnostic system of FIG. 15 with the second coupling members 5008 on the right and left at different translational positions. As shown in the figures, the second coupling member 5008 on the right side is attached to the elongated member 50 at a lower position than the second coupling member 5008 on the left side.

Figure 17:
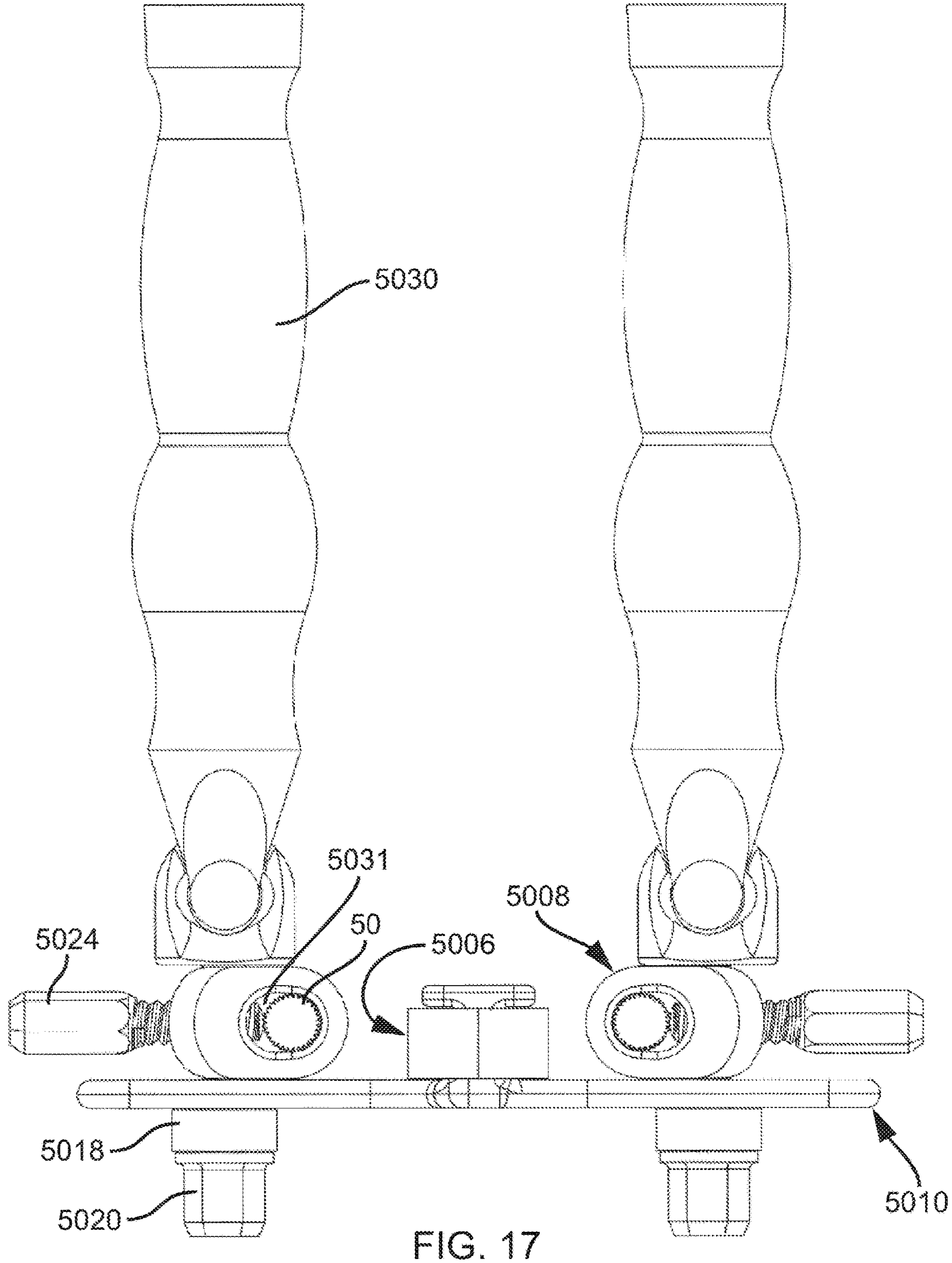
FIG. 17 is a top view of the diagnostic system of FIG. 14.
Figure 18:
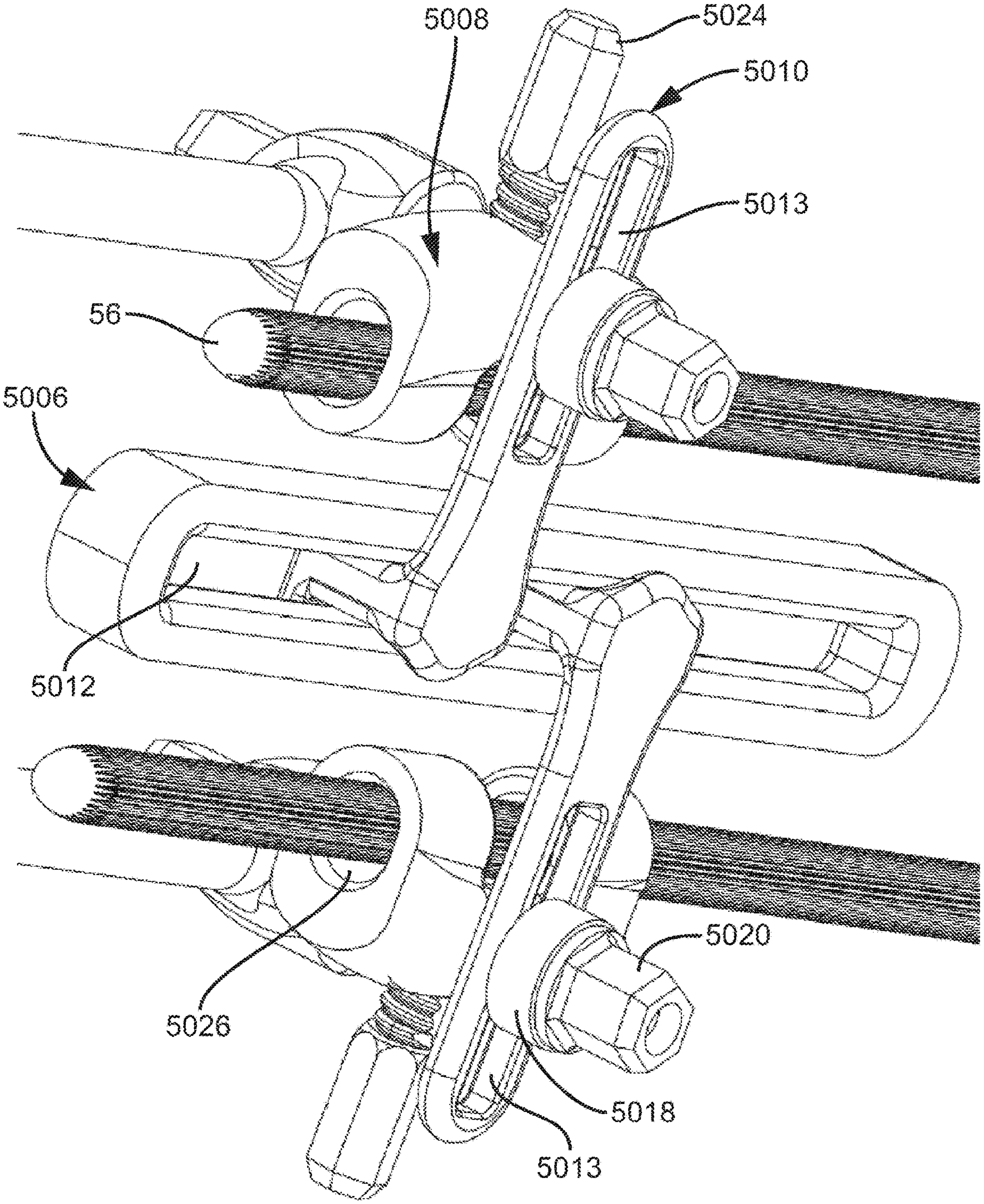
FIG. 18 is an enlarged view of the mechanical coupling assembly of FIG. 14.

FIG. 17 is a top view of the diagnostic system of FIG. 14. As shown, the side screw 5024 is pressed against the elongated member 50 so as to fixedly attach the tool to the elongated member 50. The second coupling member 5008 may have a hollow portion 5031 that is configured to conform to the elongated member 50 and to allow the side screw 5024 to extend into the hollow portion 5031 to tighten against the elongated member 50. FIG. 18 is an enlarged view of the mechanical coupling assembly of FIG. 14. The hollow portion may be generally oval shaped as shown, "pear" shaped or other shapes (not shown).

Figure 19:
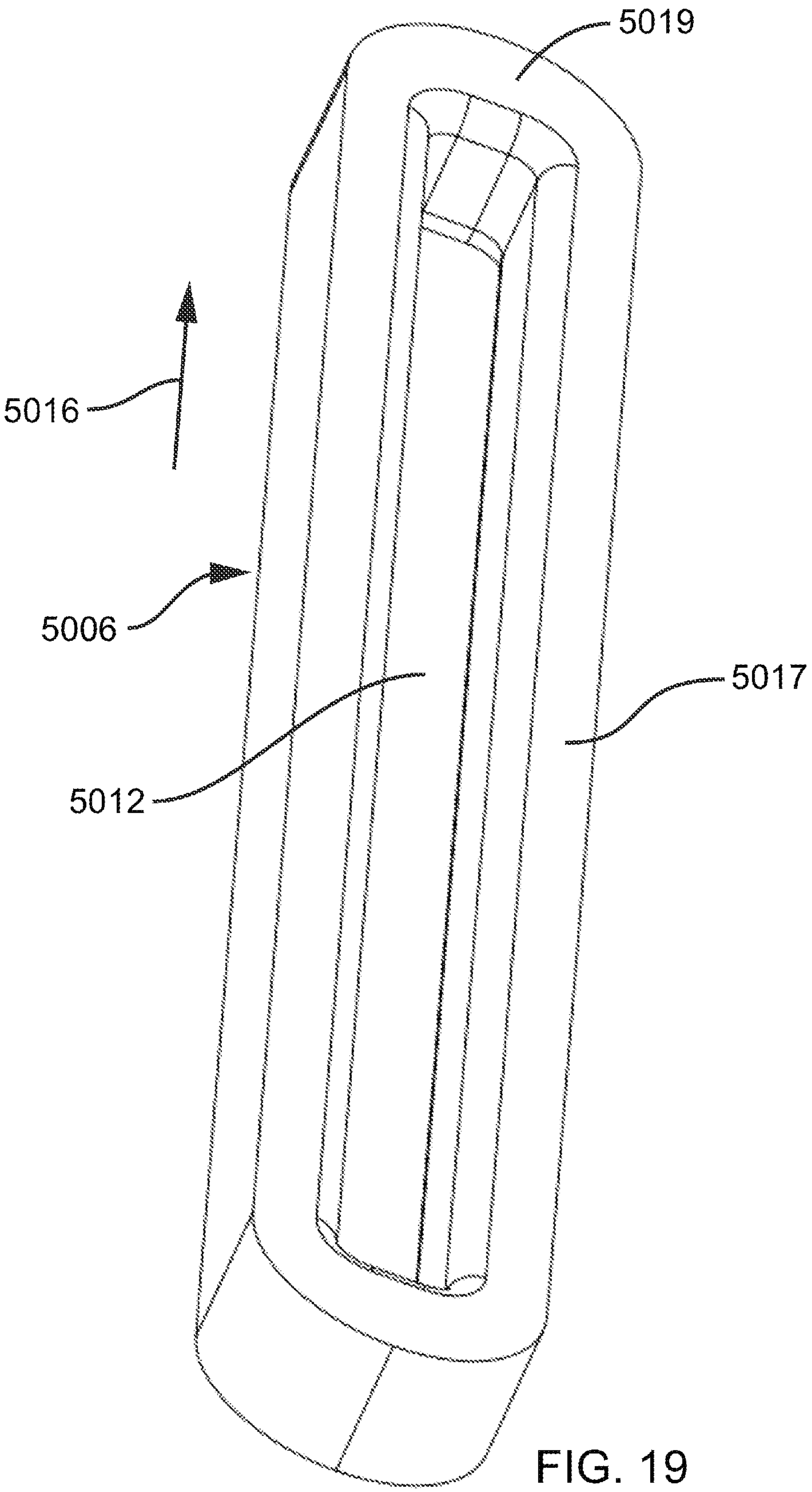
FIG. 19 is an isometric view of the first coupling member of the diagnostic system of FIG. 14.

FIG. 19 is an isometric view of the first coupling member of the diagnostic system of FIG. 14. As shown, the slot 5012 is enclosed by surrounding two opposing side walls 5017 along the longitudinal axis 5016 and two opposing end walls 5019 that connect between the two opposing side walls 5017. In certain instances, the length of the slot 5012 may be configured to correspond to an amount of possible translational movement of the ilium relative to the sacrum. That is, the length of the slot 5012 may be limited so that a medical professional utilizing the tool will not injure the patient by forcing the ilium to move past a certain point relative to the sacrum. In certain instances, the length of the slot 5012 may be about 0.075 cm, 0.1 cm, 0.2 cm, 0.25 cm, 0.3 cm, 0.4 cm, 0.5 cm, 0.6 cm, 0.7 cm, 0.8 cm, 0.9 cm, or 1 cm. In certain instances, the length of the slot 5012 may be within a range of about 0.075 cm to about 1 cm.

Figure 20A:
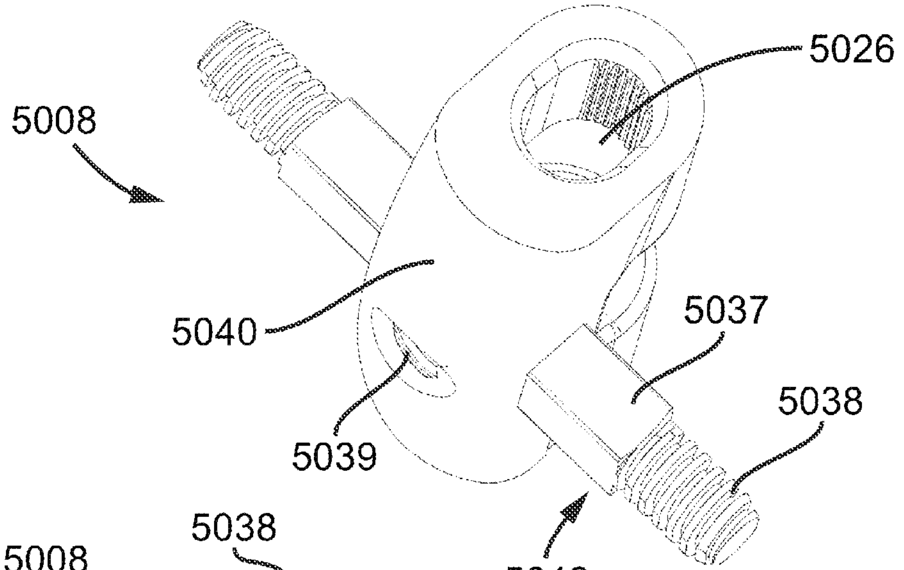
FIG. 20A is one isometric view from the side of the second coupling member 5008 of the diagnostic system of FIG. 14.
Figure 20B:
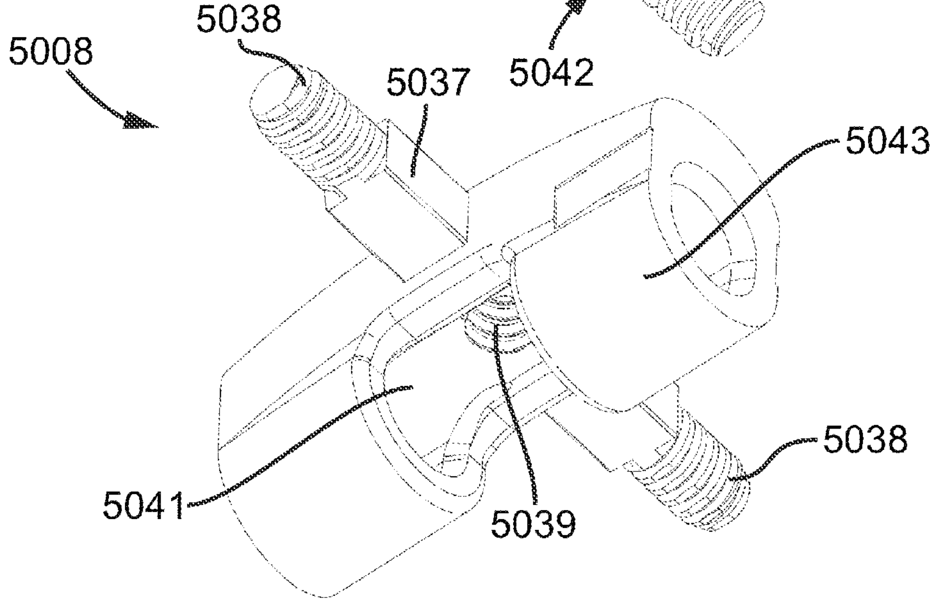
FIG. 20B is one isometric view from the bottom of the coupling member of the diagnostic system of FIG. 14.
Figure 20C:
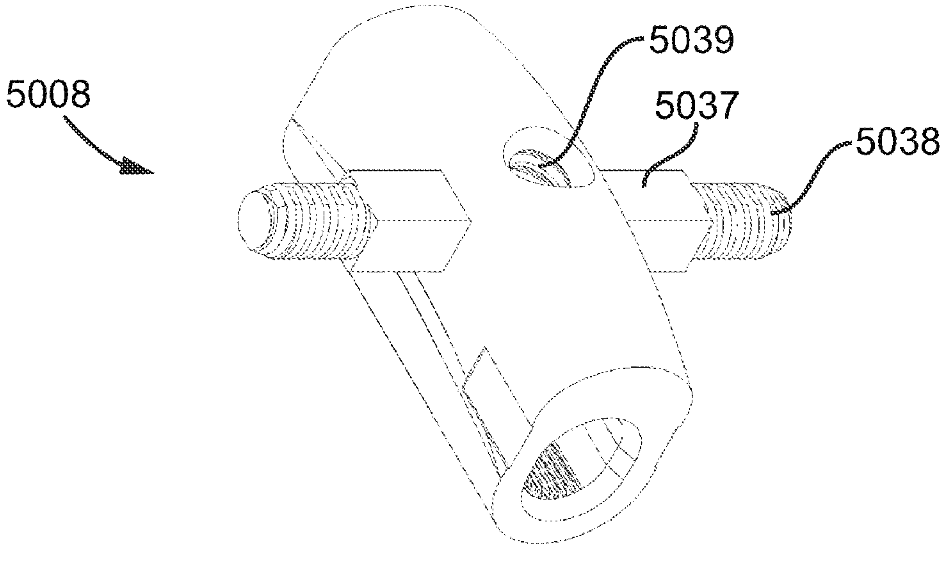
FIG. 20C is one isometric view from the top of the coupling member of the diagnostic system of FIG. 14.

FIG. 20A is an isometric view from the side of the second coupling member 5008 of the diagnostic system of FIG. 14. FIG. 20B is another isometric view from the bottom of the second coupling member of the diagnostic system of FIG. 14. FIG. 20C is yet another isometric view from the top of the second coupling member of the diagnostic system in an alternative embodiment.

As shown in FIG. 20A, the second coupling member 5008 may also include a non-threaded spacer 5037 between the main body 5040 and the threaded end 5038. The non-threaded spacer 5037 may be configured to slide within the transverse slot 5013 of the third coupling member 5010. In this particular embodiment, the non-threaded spacer 5037 has generally planar opposing surfaces that can slide within the slot of the third coupling member 5010. The threaded end 5038 may include outer threads configured to be received in a matched fastener 5020. According to other embodiments e.g., in FIGS. 26-30B, the non-threaded spacer 5037 may be cylindrical.

As shown in FIG. 20B, the second coupling member 5008 may include an inner threaded hole 5039 configured to receive the side screw 5024. Although the main body 5040 includes an opening 5041 between two opposing end portions 5043 in this particular embodiment, a different embodiment may not have the opening 5041. Instead, the opening may be solid side wall that connects the two end portions, as shown in FIG. 20C.

Figure 21:
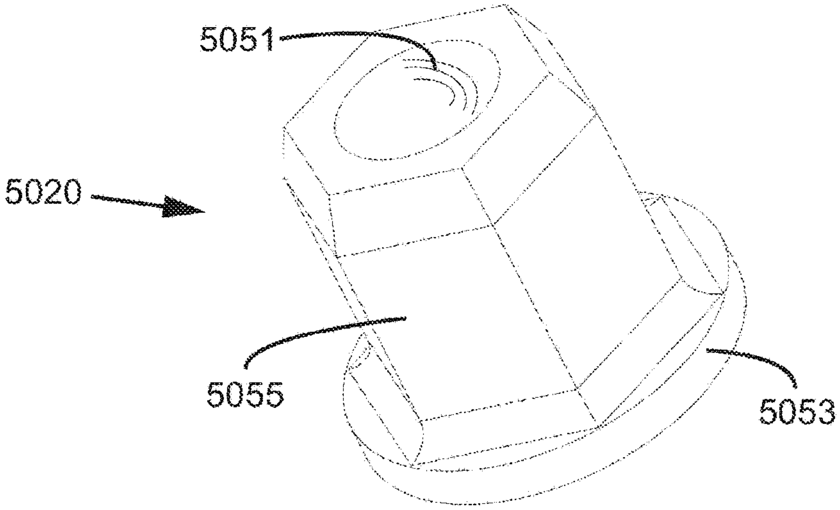
FIG. 21 is an isometric view of the fastener of the diagnostic system of FIG. 14.

FIG. 21 is an isometric view of the fastener 5020 of the diagnostic system of FIG. 14. As shown, the fastener 5020 includes inner threaded hole 5051 that is configured to receive the threaded end 5038 of the side extension 5042 of the second coupling member 5008. The fastener 5020 may also include a flange end portion 5053 that extends sideway from the main body 5055 of the fastener 5020.

Figure 22:
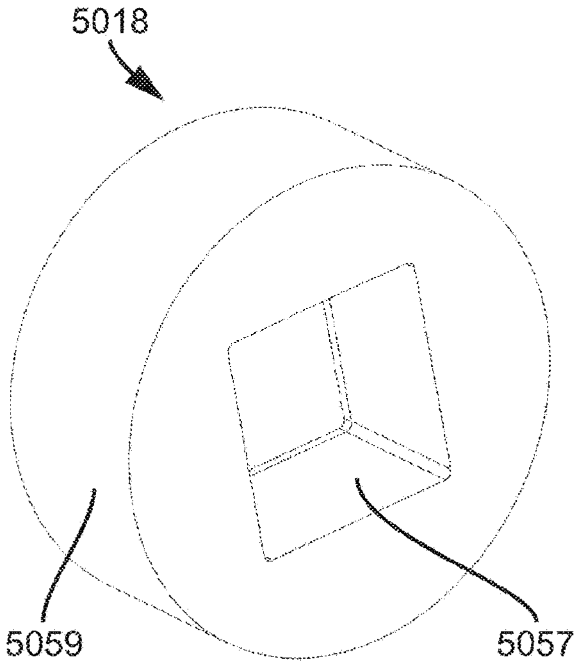
FIG. 22 is an isometric view of the washer of the diagnostic system of FIG. 14.

FIG. 22 is an isometric view of the washer of the diagnostic system of FIG. 14. As shown in FIG. 22, the washer 5018 may include a hollow portion 5057 that is shaped and sized to match to the spacer 5037 of the second coupling member 5008 as shown in FIG. 20A. The hollow portion 5057 may have cross-section that is a square shape, among others. The washer 5018 may include an outer surface, which may be in a cylindrical shape.

Figure 23:
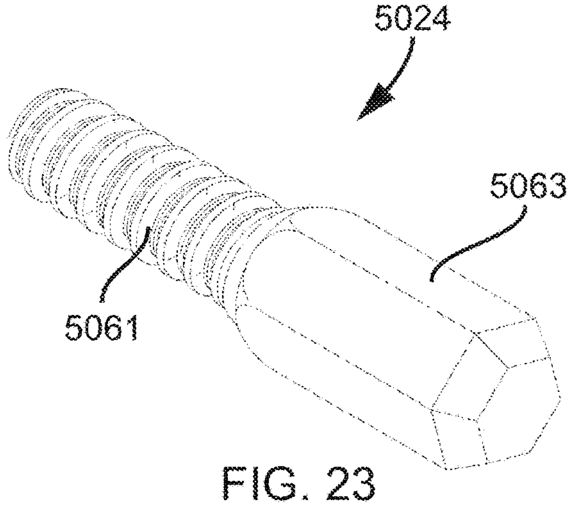
FIG. 23 is an isometric view of the side screw of the diagnostic system of FIG. 14.

FIG. 23 is an isometric view of the side screw 5024 of the diagnostic system of FIG. 14. The side screw 5024 includes an end portion 5061 with outer threads and a non-threaded grasping portion 5063 that connects to the threaded end portion.

Figure 24A:
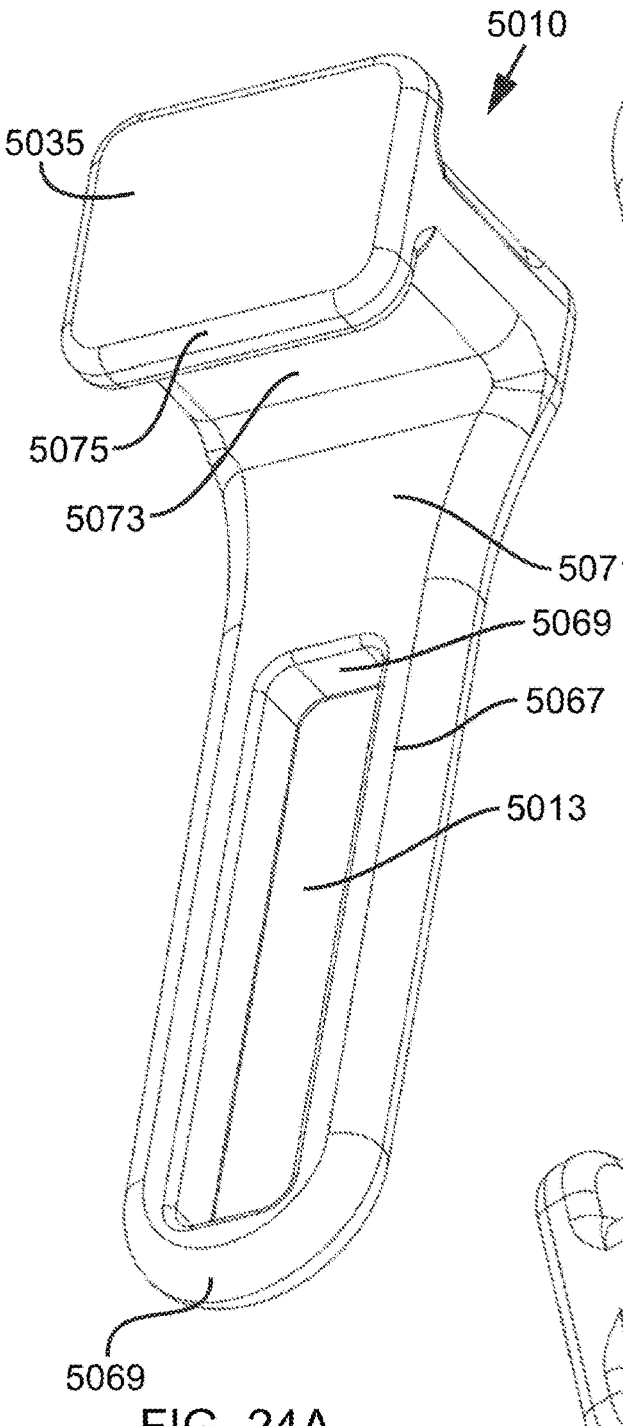
FIG. 24A is an isometric view from the back of the third coupling member 5010 of the diagnostic system of FIG. 14.
Figure 24B:
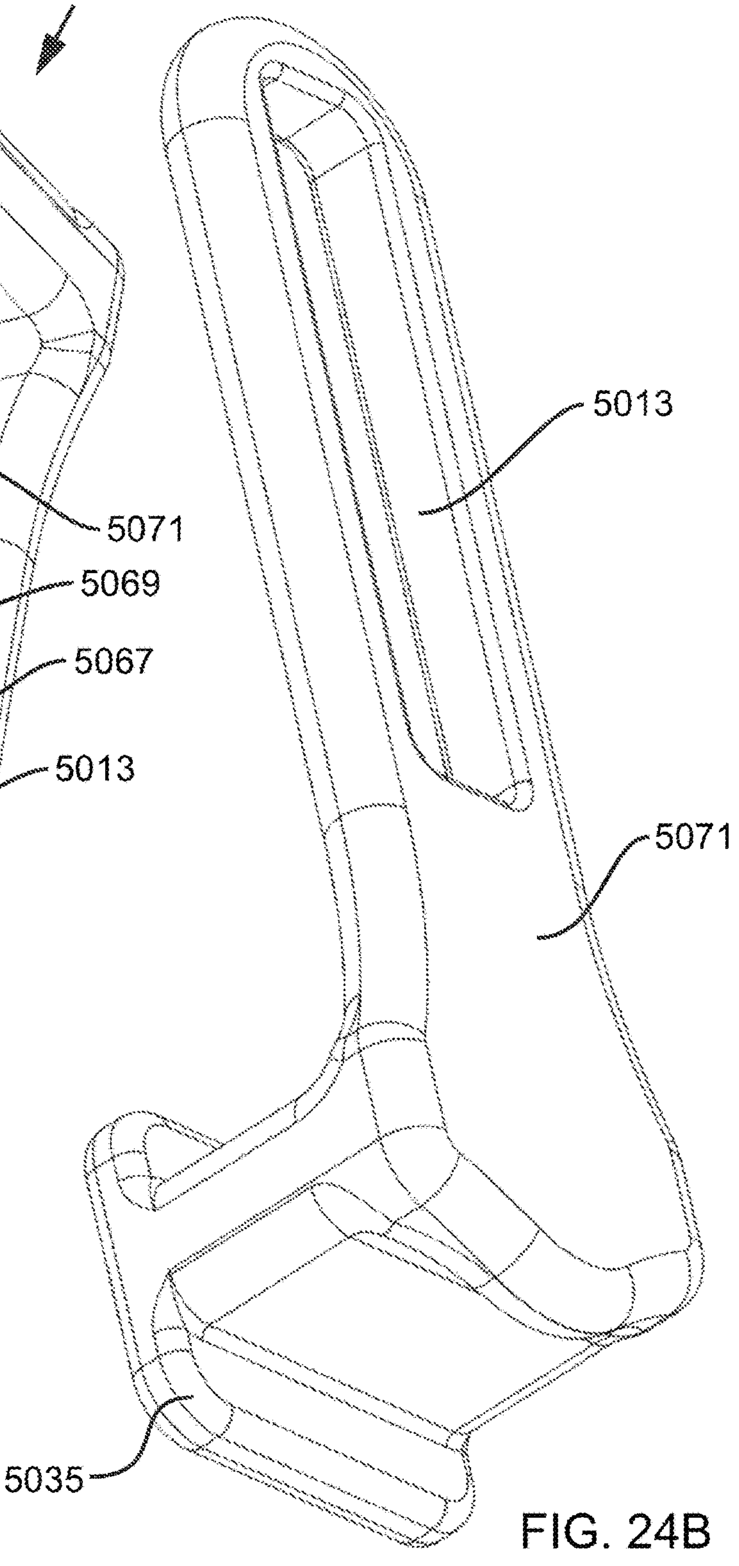
FIG. 24B is an isometric view from the front of the third coupling member 5010 of the diagnostic system of FIG. 14.

FIG. 24A is an isometric view from the back of the third coupling member 5010 of the diagnostic system of FIG. 14. As shown in FIGS. 24A-24B, the third coupling member 5010 may include a generally planar main body connected to the engagement element 5035 at a first end. The planar main body includes two opposing side walls 5067 connected to two opposing end walls 5069. The side walls 5067 and end walls 5069 are sandwiched between two generally planar opposing surfaces 5071. The second end wall 5069 is at an opposing end to the first end wall 5069 near the engagement element 5035. The planar main body also includes an elongated slot 5013 enclosed by the sidewalls 5067 and the end walls 5069. The elongated slot 5013 allows adjustment of the distance between the two elongated members 50. In certain instances, the length of the slot 5013 may be about 1 cm, 2 cm, 3 cm, 4 cm, 5 cm, 6 cm, 7 cm, 8 cm, 9 cm, 10 cm, 11 cm, 12 cm, 13 cm, 14 cm, or 15 cm. In certain instances, the length of the slot 5013 may be within a range of about 1 cm to about 15 cm.

The engagement element 5035 includes an extended portion that extends above one of the planar surfaces 5071 near the first end wall 5069 of the planar main body. The extended portion 5073 can fit within the slot 5012 of the first coupling member 5006. The engagement element 5035 also includes an end flange portion 5075 extending sideway from the extended portion 5073, such that the end flange portion can extend on sidewall of the first coupling member 5006 to hold the third coupling member 5010 within the slot 5012 of the first coupling member 5006.

Figure 25B:
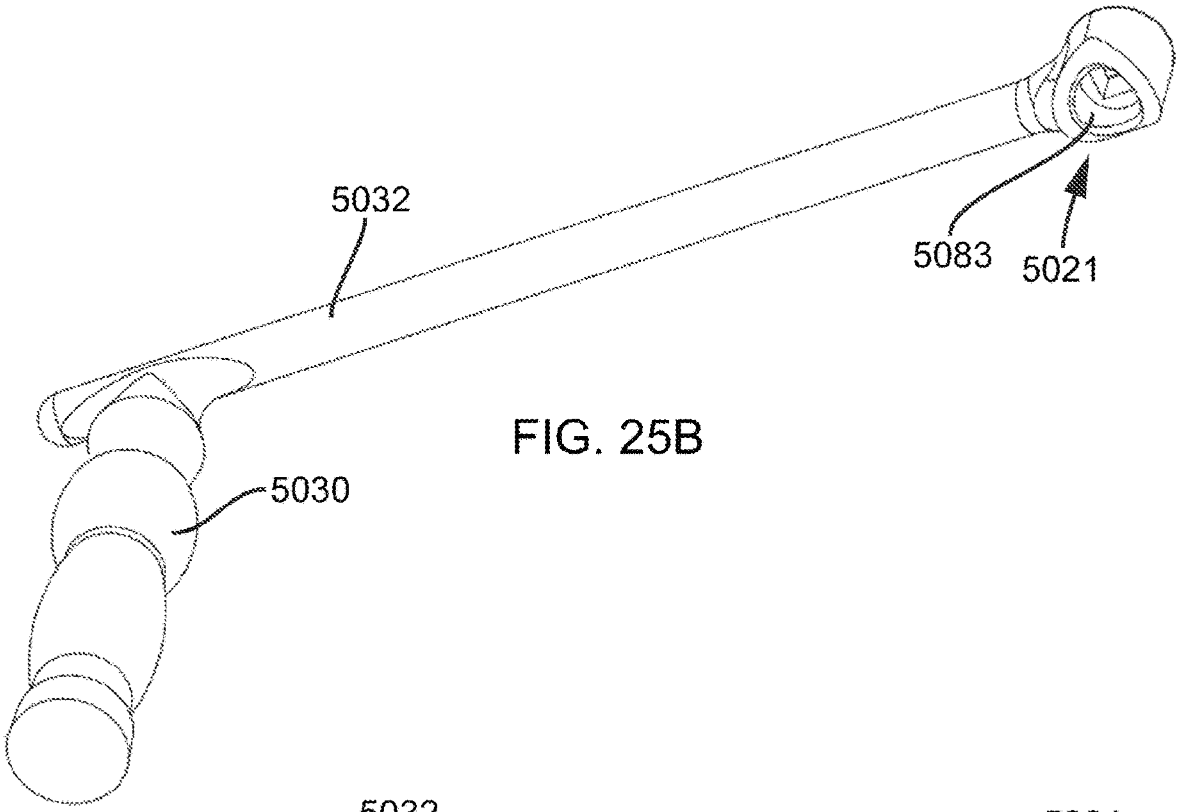
FIG. 25B is an isometric view from the top of the connector at the end of the extension bar connected to the handle of the diagnostic system of FIG. 14.
Figure 25A:
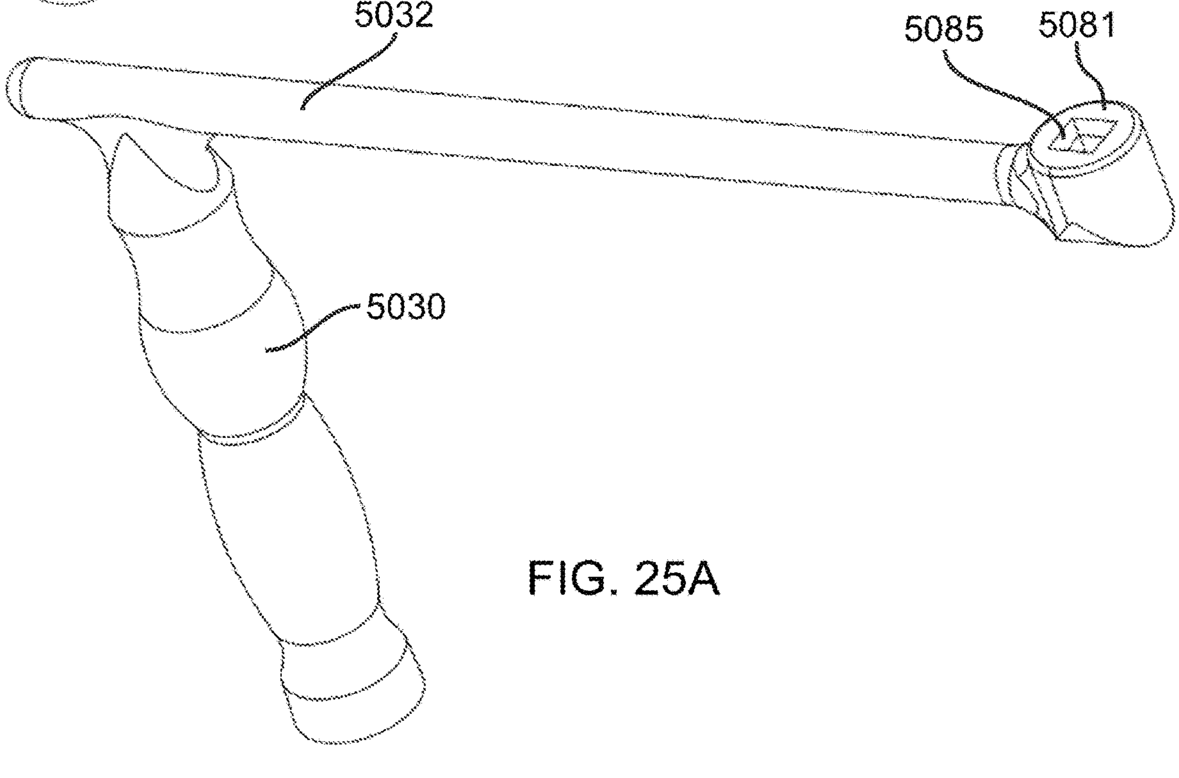
FIG. 25A is an isometric view from the bottom of the connector at the end of the extension bar connected to the handle of the diagnostic system of FIG. 14.

FIG. 25A is an isometric view from the bottom of the connector 5021 at the end of the extension bar 5032 connected to the handle 5030 of the diagnostic system of FIG. 14. FIG. 25B is an isometric view from the top of the connector 5021 at the end of the extension bar 5032 connected to the handle 5030 of the diagnostic system of FIG. 14. The handle 5030 is coupled to the second coupling member 5008, and configured to ergonomically force the third coupling member 5010 to slide within the first coupling member 5006 to move one of the first or second members relative to the other of first or second member along the longitudinal axis 5016.

As shown in FIGS. 25A-25B, the handle 5030 is at one end of the extension bar 5032 and the connector 5021 is at an opposing end of the extension bar 5032. The connector 5021 is configured to connect to the second coupling member 5008. Specifically, the connector 5021 includes a first surface 5081 having a square shape opening 5085 and a second surface 5082 with a generally circular opening 5083. The square shape opening 5085 is configured to fit to the spacer of the second coupling member 5008. The circular opening 5083 is configured to be large enough to allow the fastener 5020 as shown in FIG. 21 to fasten against the threaded portion 5038 of the second coupling member 5008 as shown in FIG. 20A. Again, the shapes of the opening may vary with the extension 5042 of the second coupling member 5008.

The amount of movement of the ilium relative to the sacrum may depend on the particular ailment of the sacroiliac joint. When used to manipulate the sacroiliac joint, as shown in FIGS. 11-12A, the ilium may have a small, moderate, or large amount of translational movement relative to the sacrum. In some embodiments, the translational movement may be less than 5 mm. In some embodiments, the translational movement may be less than 4 mm. In some embodiments, the translational movement may be less than 3 mm. In some embodiments, the translational movement may be less than 2 mm. In some embodiments, the translational movement may be less than 1 mm.

2. Diagnostic Tools and Systems for Causing and Controlling Translational and Rotational Movement An alternative mechanical coupling assembly may be used to cause translational movement and/or rotational movement. The mechanical coupling assembly may include a pivot subassembly, which may be attached to one diagnostic pin and used to cause translational movement or rotational movement of another diagnostic pin.

Figure 26:
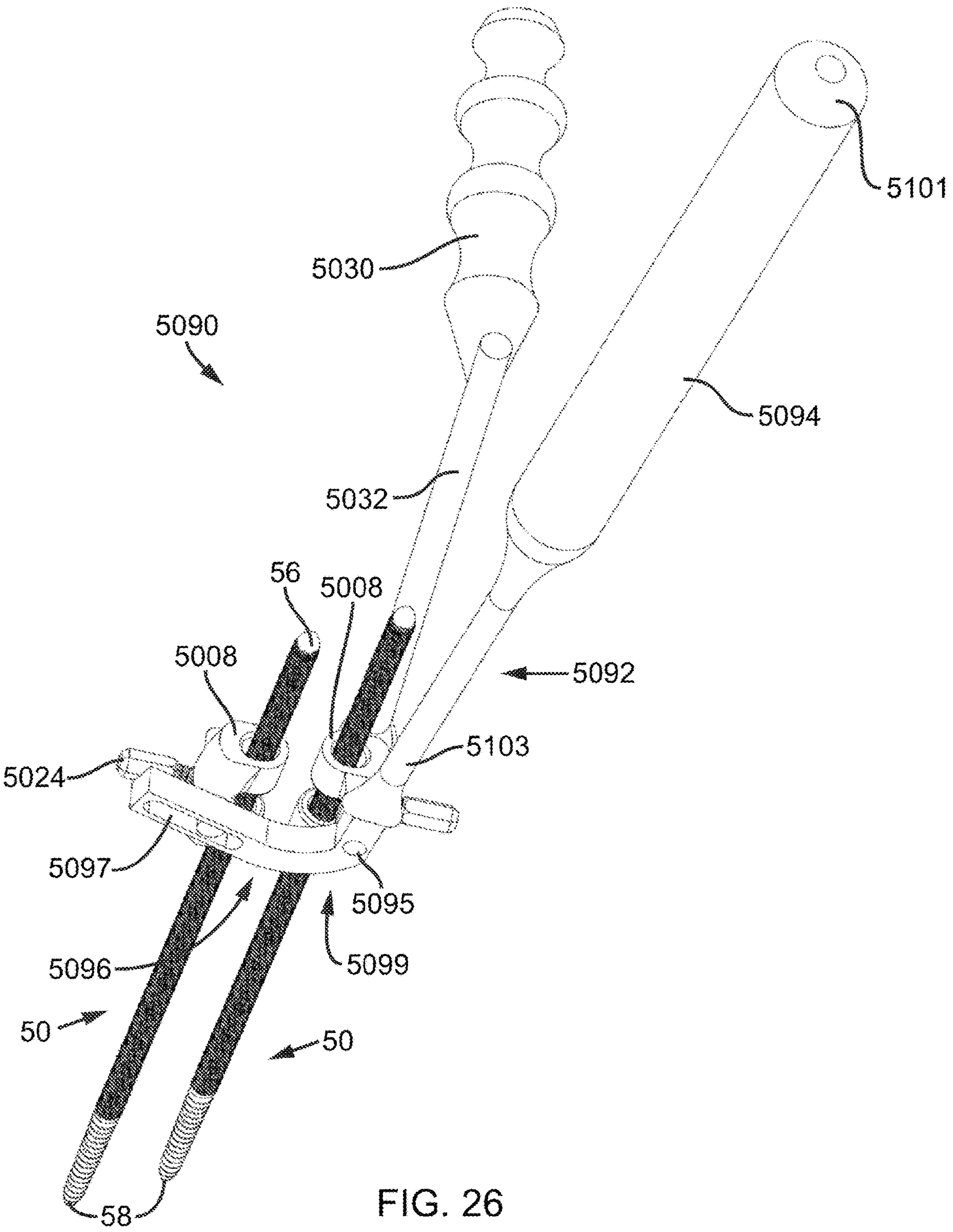
FIG. 26 is an isometric view of a diagnostic system including a pivot type mechanical coupling assembly for causing translational movements of the pins in accordance with embodiments of the present disclosure.

FIG. 26 is an isometric view of a diagnostic system including a pivot type mechanical coupling assembly in accordance with embodiments of the present disclosure. As shown, a mechanical coupling assembly 5090 may include a first coupling component 5008 attached to a first elongated member 50, such as a pin or bar described with reference to FIGS. 7A-9, a handle 5030 coupled to the first coupling component 5008 attached to the first elongated member 50 by using a side screw 5024, such as shown in FIG. 23. The mechanical coupling assembly 5090 may also include a second coupling component 5008 attached to a second elongated member 50 by using the side screw 5024, such as shown in FIG. 23. The first and second coupling components 5008 may be similar to the second coupling member 5008 as shown in FIGS. 20A-20C.

The mechanical coupling assembly 5090 may also include a pivot subassembly 5092, which may include a handle bar 5094 with a free end 5101 and an opposite end 5103, and a middle portion 5099 being pivotally attached to the first elongated member 50 and connected to the end 5103 of the handle bar 5094. The middle portion 5099 is connected to an arm portion 5096, which may be angled from the handle bar

5094. The middle portion 5099 is a curved transition portion between the handle bar 5094 and an arm portion 5096. The arm portion 5096 may extend from the transition portion and may be at an angle from the handle bar 5094. This angle may vary for different pivot subassemblies. In some embodiments, the angle is less than 90°. In some embodiments, the angle is less than 80°. In some embodiments, the angle is less than 70°. In some embodiments, the angle is less than 60°. In some embodiments, the angle is less than 50°. In some embodiments, the angle is greater than 40°. In some embodiments, the angle is greater than 50°. In some embodiments, the angle is greater than 60°. In some embodiments, the angle is greater than 70°. In some embodiments, the angle is greater than 80°.

The arm portion may include an elongated slot 5097, such that the position of the arm portion 5096 with respect to the second elongated member 50 can be adjusted with respect to the first elongated member 50. The slot size and configuration may vary to allow translational movement of the second elongated member 50 or diagnostic pin. The arm portion 5096 may be slidably attached to the second elongated member 50 to cause translational movement of the second member.

Figure 27:
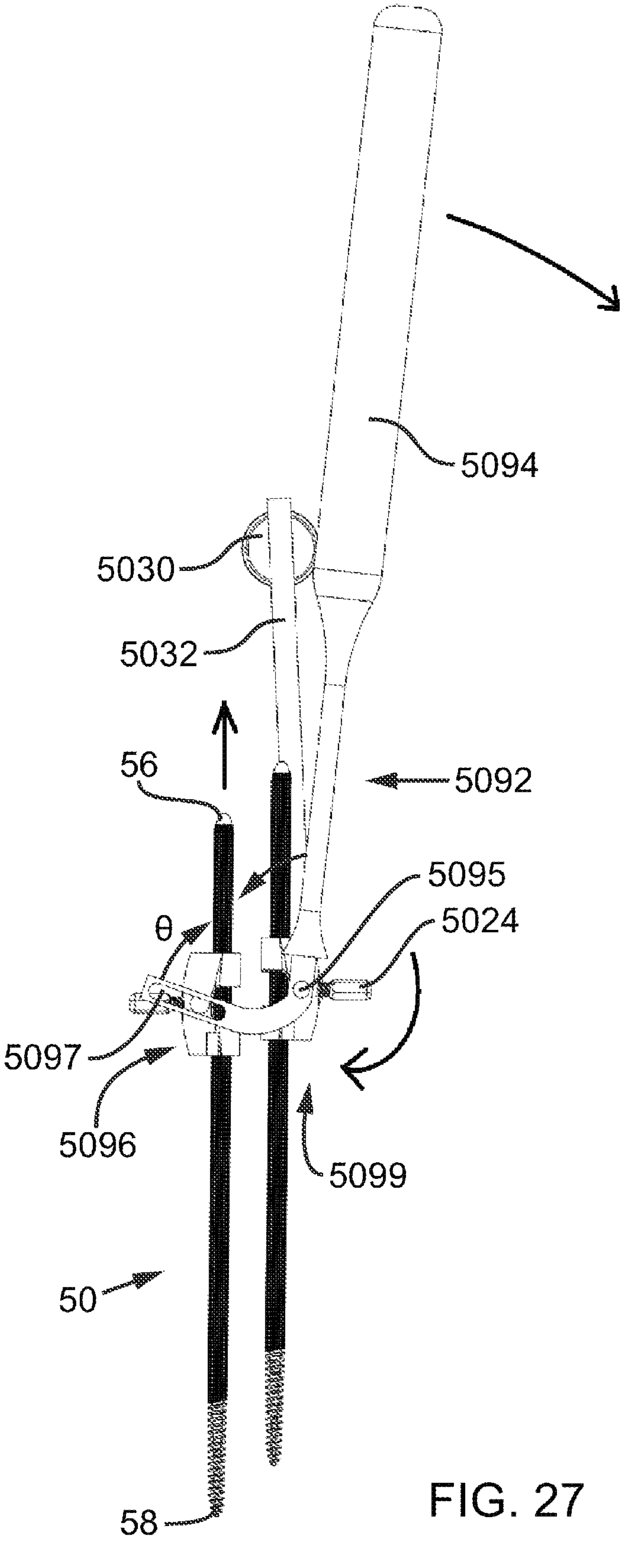
FIG. 27 is an isometric view of the diagnostic system of FIG. 26 in a position that one of the diagnostic pin moving upward in accordance with embodiments of the present disclosure.

FIG. 27 is an isometric view of the diagnostic system of FIG. 26 in a position such that one of the diagnostic pins is moving upward. As shown in FIG. 27, the handle bar 5094 is rotated clockwise about the pivot joint 5095, as indicated by the arrow, such that the pin 50 on the left moves upward. The arm portion 5096 may be caused to move relative to the slot 5097 toward a right end of the slot 5097. The arm portion 5096 may now be slidably attached to the second elongated member 50 near the right end position of the slot 5097.

Figure 28:
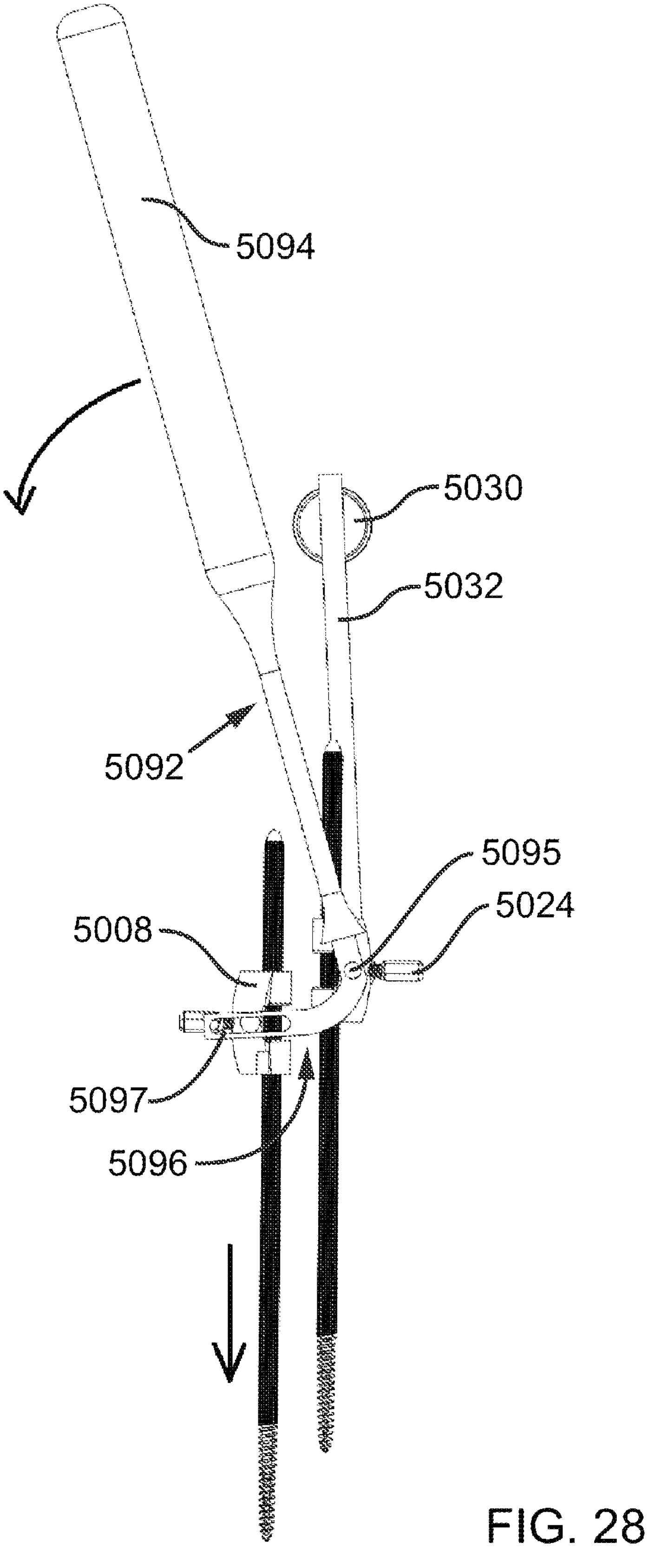
FIG. 28 is an isometric view of the diagnostic system of FIG. 26 in a position that one of the diagnostic pin moving downward in accordance with embodiments of the present disclosure.

FIG. 28 is an isometric view of the diagnostic system of FIG. 26 in a position such that one of the diagnostic pins is caused to move downward. As shown in FIG. 28, the handle bar is rotated counterclockwise about the pivot joint 5095, as indicated by the arrow, such that the second pin 50 moves downward. During this movement, the arm portion 5096 may move within the slot toward a left end of the slot 5097. The arm portion 5096 may be slidably attached to the second elongated member 50 near the left end of the slot 5097.

Figure 29:
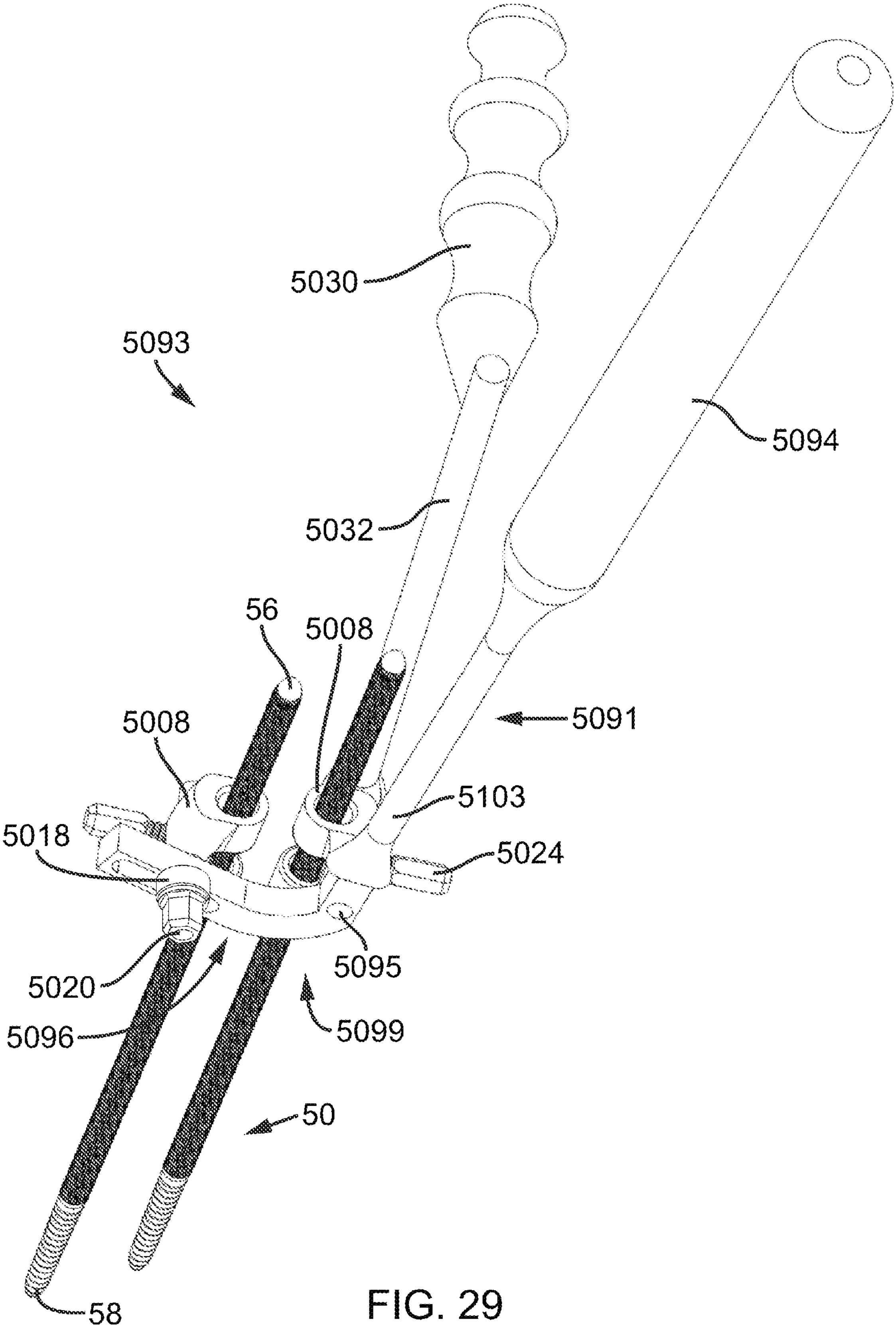
FIG. 29 is an isometric view of a diagnostic system including a pivot type mechanical coupling assembly for causing rotational movements of the pins in accordance with embodiments of the present disclosure.

In some embodiments, the arm portion 5096 may be fixedly attached to the second member 50 by affixing the arm portion 5096 within the slot 5097. For example, a fastener may be used affix the arm portion 5096 at a certain position within the slot. In this case, rotation of the handle bar 5094 about the pivot joint 5095 may cause rotational movement of the pins 50 relative to each other. FIG. 29 is an isometric view of a diagnostic system that is configured to rotate one of the diagnostic pins with respect to another diagnostic pin. As shown in FIG. 29, the diagnostic system includes a first coupling component 5008 and a second coupling component 5008 that are respectively coupled to the first and second elongated members 50, as similarly described above, with respect to FIG. 28. The diagnostic system may also include a pivot subassembly 5091 including an arm portion 5096 that is fixedly attached to the second elongated member 50, for example, by using the fastener 5020 such as shown in FIG. 21.

The pivot subassembly 5091 may also include a middle portion that is pivotally joined to the first elongated member 50 around a pivot joint 5095 that may be cylindrically shaped. The pivot joint 5095 allows the middle portion 5099 or transition portion 5099 to rotate about such that the arm portion 5096 can cause rotation of the second elongated member 50 when the handle bar 5096 is rotated.

The transition portion 5099 may be attached to the end 5103 of the handle bar 5094. The transition portion 5099 and the arm portion 5096 may be integrated together. Alternatively, the handle bar 5094 may be integrated with the transition portion 5099, which may be integrated with the arm portion 5096. The transition portion 5099 may include an opening that is configured to rotatably join to the pivot joint 5095. The opening may be cylindrically shaped and sized to match to the pivot joint 5095.

Still referring to FIG. 29, the arm portion 5096 may be fixedly attached to the second member 50 by a fastener 5020. The arm portion 5096 may include a slot 5097 for adjusting position of the fastener 5020 within the slot 5097, which may vary the angle of the rotation of the second elongated member 50. The other handle 5030 may be used to hold the first elongated member 50 in position such that the first elongated member 50 does not need to rotate or move while only the second elongated member 50 rotates, in this example.

In use and in one embodiment, the distal end of the first elongated member 50 may be inserted into the ilium 1005, while the distal end of the second elongated member 50 may be inserted into the sacrum 1004. In another embodiment, the first elongated member 50 may be inserted into the sacrum 1004, while the second elongated member 50 may be inserted into the ilium 1005.

Figure 30A:
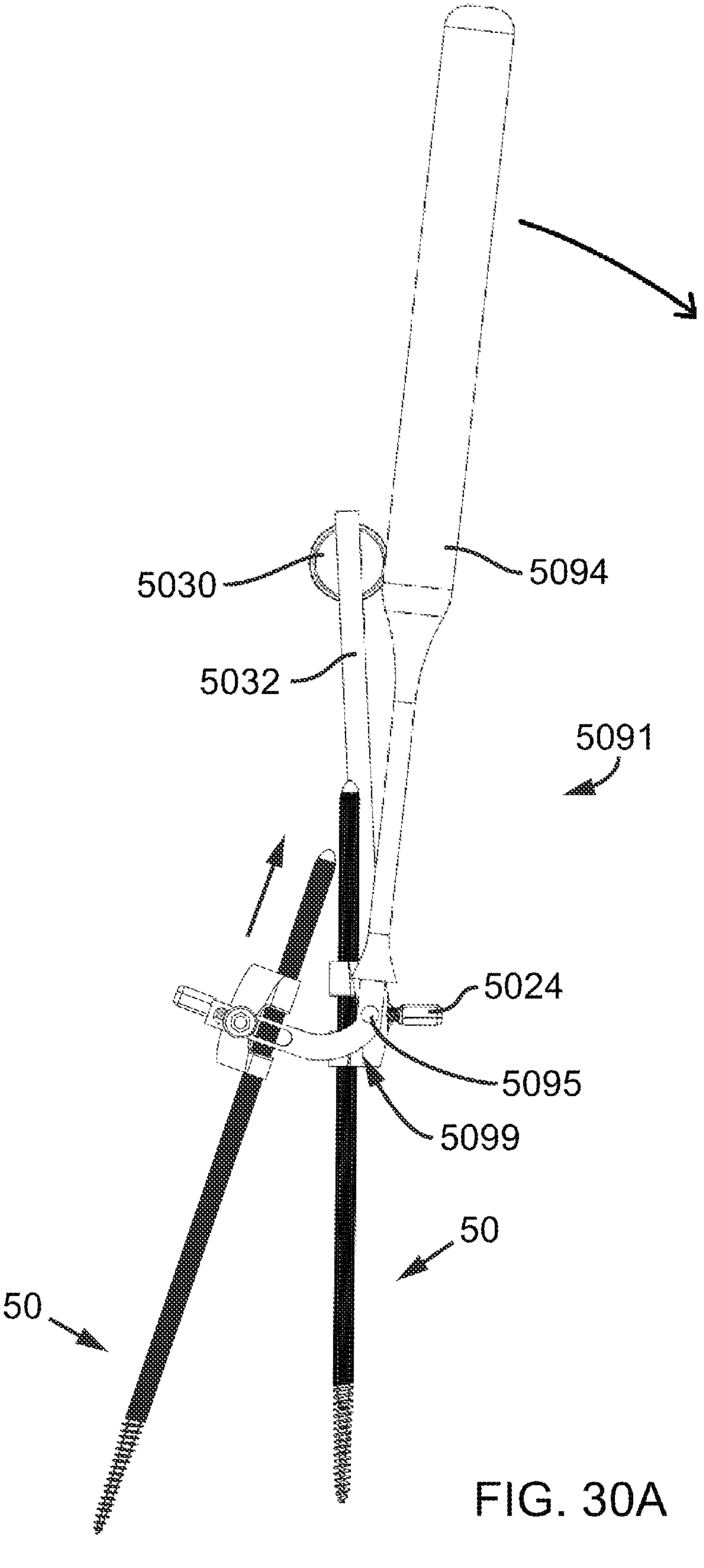
FIG. 30A is an isometric view of the diagnostic system that rotates one diagnostic pin clockwise with respect to another diagnostic pin.

FIG. 30A is an isometric view of the diagnostic system that rotates one diagnostic pins 50 clockwise with respect to the other diagnostic pin 50. As shown in FIG. 30A, the second elongated member 50 is caused to rotate clockwise by rotating the handle bar 5094 clockwise. The position of the fastener 5020 within the slot 5097 remains the same as shown in FIG. 29.

Figure 30B:
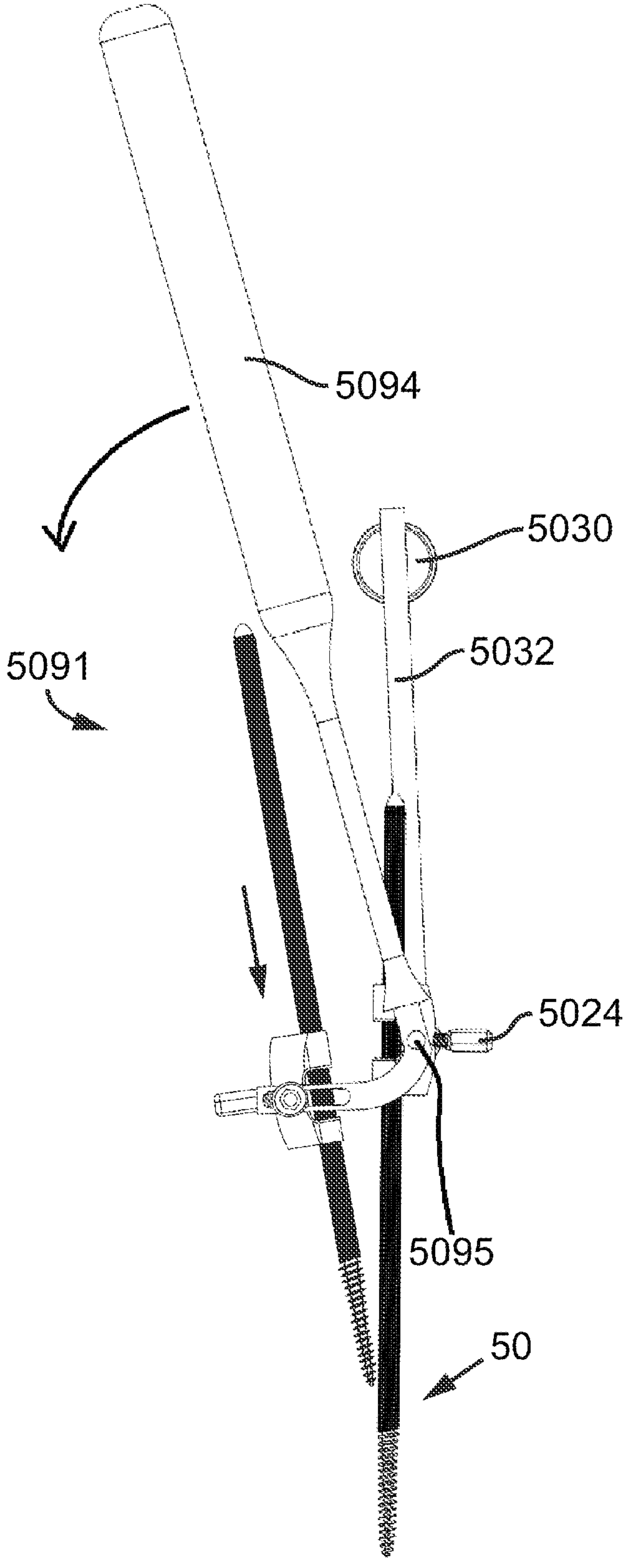
FIG. 30B is an isometric view of the diagnostic system that rotates one diagnostic pin counterclockwise with respect to another diagnostic pin.

FIG. 30B is an isometric view of the diagnostic system that rotates one diagnostic pin 50 counterclockwise with respect to the other diagnostic pin 50. As shown in FIG. 30B, the second elongated member 50 is caused to rotate counterclockwise by rotating the handle bar 5094 counterclockwise. The position of the fastener 5020 within the slot 5097 remains the same as shown in FIG. 29.

In some embodiments, the ilium 1005 or sacrum 1004 may be caused to rotate by using the mechanical coupling including the pivot subassembly shown in FIGS. 29 and 30A-B. In some embodiments, the rotation may be limited to less than 10°. In some embodiments, the rotation may be less than 5°. In some embodiments, the rotation may be less than 4°. In some embodiments, the rotation may be less than 3°. In some embodiments, the rotation may be less than 2°. In some embodiments, the rotation may be less than 1°.

Figure 30C:
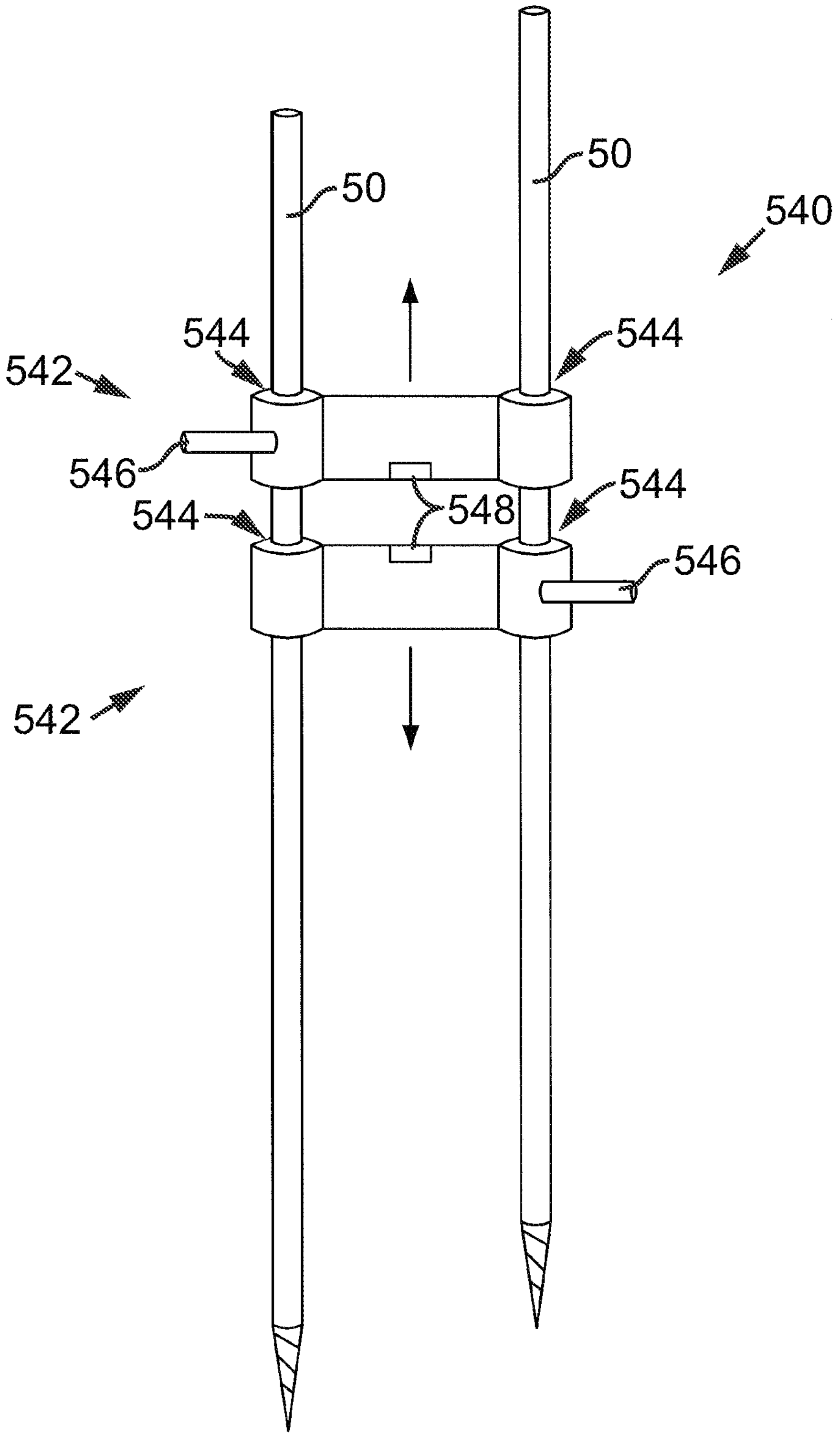
FIG. 30C is a front view of a diagnostic system that allows selective sliding of one pin relative to another pin.

Reference is now made to FIG. 30C, which is a front view of another diagnostic system 540 for controlled manipulation of pins 50. As seen in the figure, the system 540 includes a pair of coupling members 542 coupled between the pins 50. The coupling members 542 are identical. A bottom coupling member 542 is merely flipped relative to the top coupling member 542.

Each coupling member 542 includes a pair of through hole openings 544 that are configured to allow the pins 50 to slide through. One side of each coupling member 542 includes a set screw 546 extending into the opening to selectively affix a position of the pin 50 such that the pin 50 cannot slide within the opening 544. The opposite side of the coupling member 542 does not include a set screw such that the pin within that side can freely slide. The coupling members 542 include a notch or void 548 for engaging a distractor (not shown), which can drive the coupling members 542 longitudinally away from each other (as seen by the arrows in FIG. 30C).

In operation, a left side pin 50 can be affixed in a position via the set screw 546 relative to the top coupling member 542 and a right side pin 50 can be affixed in a position via the other set screw 546 relative to the bottom coupling member 542. A distractor may be positioned within the notch 548 and engaged to drive apart the coupling members 542. If, for example, the left pin 50 is in the sacrum and the right pin 50 in in the ilium, the distractor would drive the left pin 50 posteriorly and the right pin 50 anteriorly.

While reference is made to the previously described tools to manipulate the patient's bones, a physician may also manipulate the pins with his or her hands without the aid of the tools. Alternatively, a surgical robot may also manipulate the pins. Additionally, features of the various tools described herein may be incorporated into different and other embodiments without limitation.

F. Implant Delivery Device Utilizing the Pins, Rods, or Bars as a Guide

After diagnosing the patient's sacroiliac joint as a source of pain and diagnosing fusion of the joint as a possible solution to alleviate the pain, the diagnostic pins, described herein, may be used as a guide for the subsequent delivery of an implant (temporary or permanent) into or near the sacroiliac joint. The implant may be delivered by using a delivery tool that includes a shaft having an end configured to couple to a proximal end of the implant. The implant may also be delivered by using an implant delivery system as described below or as described in related U.S. patent applications incorporated by reference in this application. The implant delivery system may be configured to deliver the implant in a controlled manner (e.g., angle of delivery). The implant delivery system may include a pair of diagnostic pins connected by a guide coupling member, which guides the delivery of the implant.

Figure 31:
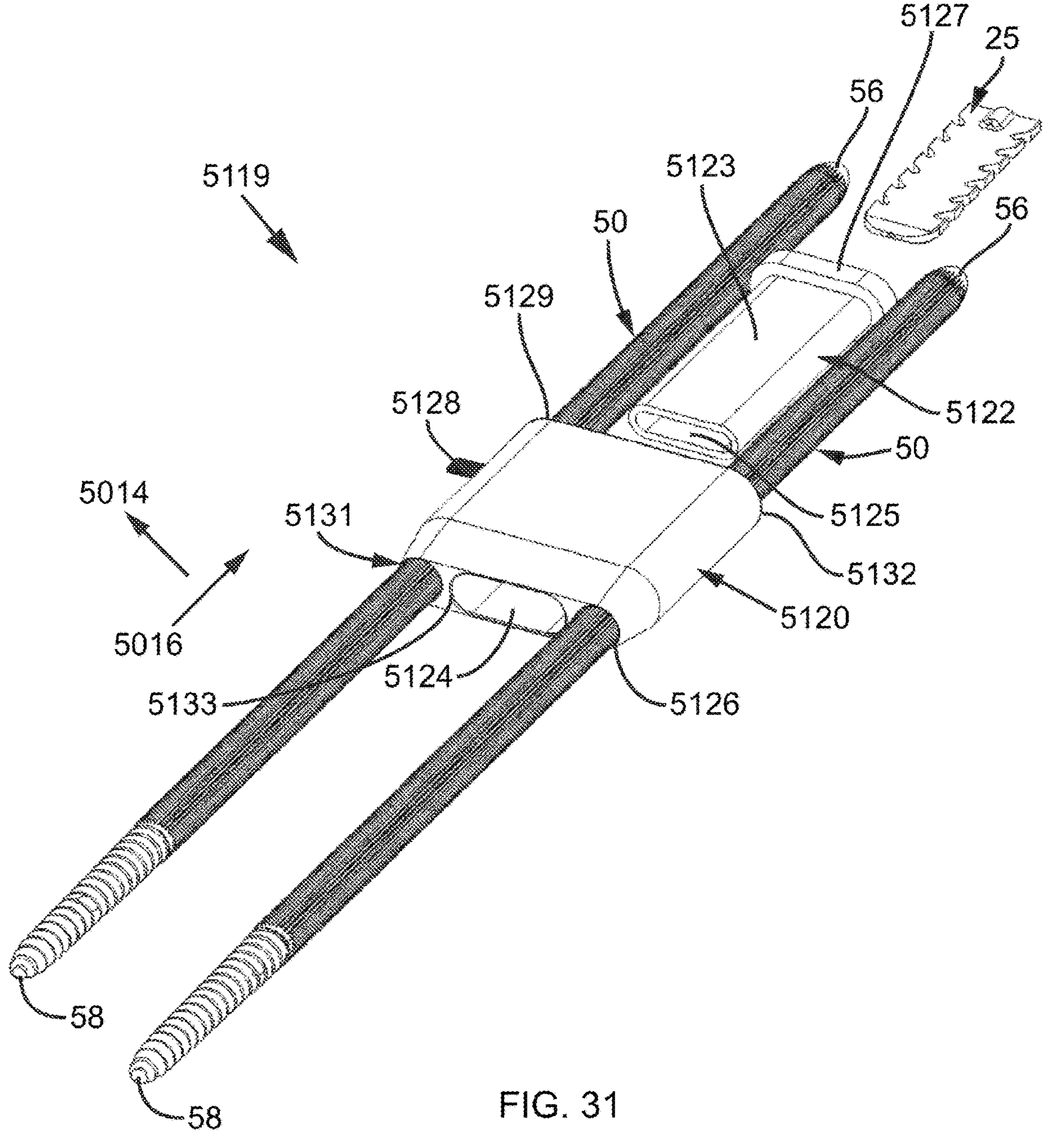
FIG. 31 is an isometric view from a bottom of a surgical system for delivering an implant in accordance with embodiments of the present disclosure.

To begin the discussion, reference is made to FIG. 31, which is an isometric view from a bottom of an implant delivery system or a surgical system for delivering an implant. As shown in the figure, an implant delivery system 5119 may include a first guide member 50 and a second guide member 50, as described previously, and a guide coupling member 5120 configured to be slidably positioned between the first and second guide members 50. The first guide member 50 extends along a first longitudinal axis 5016 and has a distal end 58 configured to be delivered into the sacrum 1004 or ilium 1005 via a posterior approach. The second guide member 50 extends along a second longitudinal axis generally parallel to the first longitudinal axis and has a distal end 58 configured to be delivered into the ilium 1005 or sacrum 1004 via the posterior approach.

The guide coupling member 5120 can slide onto the first and second guide members 50 and can receive an implant 25 from the top of the guide coupling member 5120 to deliver the implant 25 into the sacroiliac joint along a predetermined trajectory. The guide coupling member 5120 may have a general planar body with a proximal end 5132, a distal end 5131, and an inner opening 5124 configured to allow the implant 25 to be delivered therethrough. The inner opening 5124 may be located in a center of the guide coupling member 5120 and may extend from the proximal end 5132 to the distal end 5131 along the longitudinal axis 5016. The central opening 5124 may elongate along a transverse axis 5014, which is generally perpendicular to the first and second guide members 50 to match to the shape of the implant 25.

The guide coupling member 5120 may also include two opposite through-holes 5129 configured to attach to the first and second guide members 50. The two opposite through-holes 5129 are positioned on opposite ends 5133 of the central opening 5124. The through-holes 5129 may be sized to provide interference fitting to the first and second guide members 50. Alternatively, a side screw 5128 may be used to fasten the guide coupling member 5120 to the first or second guide members 50.

The implant delivery system 5119 may also include a guide spacer 5122 positioned between the guide coupling member 5120 and the implant 25 to accommodate various types of implants, which may vary in shape, geometry or dimension. The guide spacer 5122 may have an outer surface 5123 configured to fit inside the central opening 5124 of the guide coupling member 5120 from the proximal end 5132 to the distal end 5131. The guide spacer 5122 may have an inner opening 5125 configured to fit to a size or shape of the implant 25, such that the implant 25 can slide through the guide spacer 5122.

The guide spacer 5122 member may also include an end portion 5127 configured to stop by the top surface 5129 near the proximal end 5132 of the guide coupling member 5120. As shown in FIG. 31, the end portion 5127 extends circumferentially to contact the top surface 5129 of the guide coupling member 5120. The extended end portion 5127 still remains between the first and second guide members 50.

Figure 32:
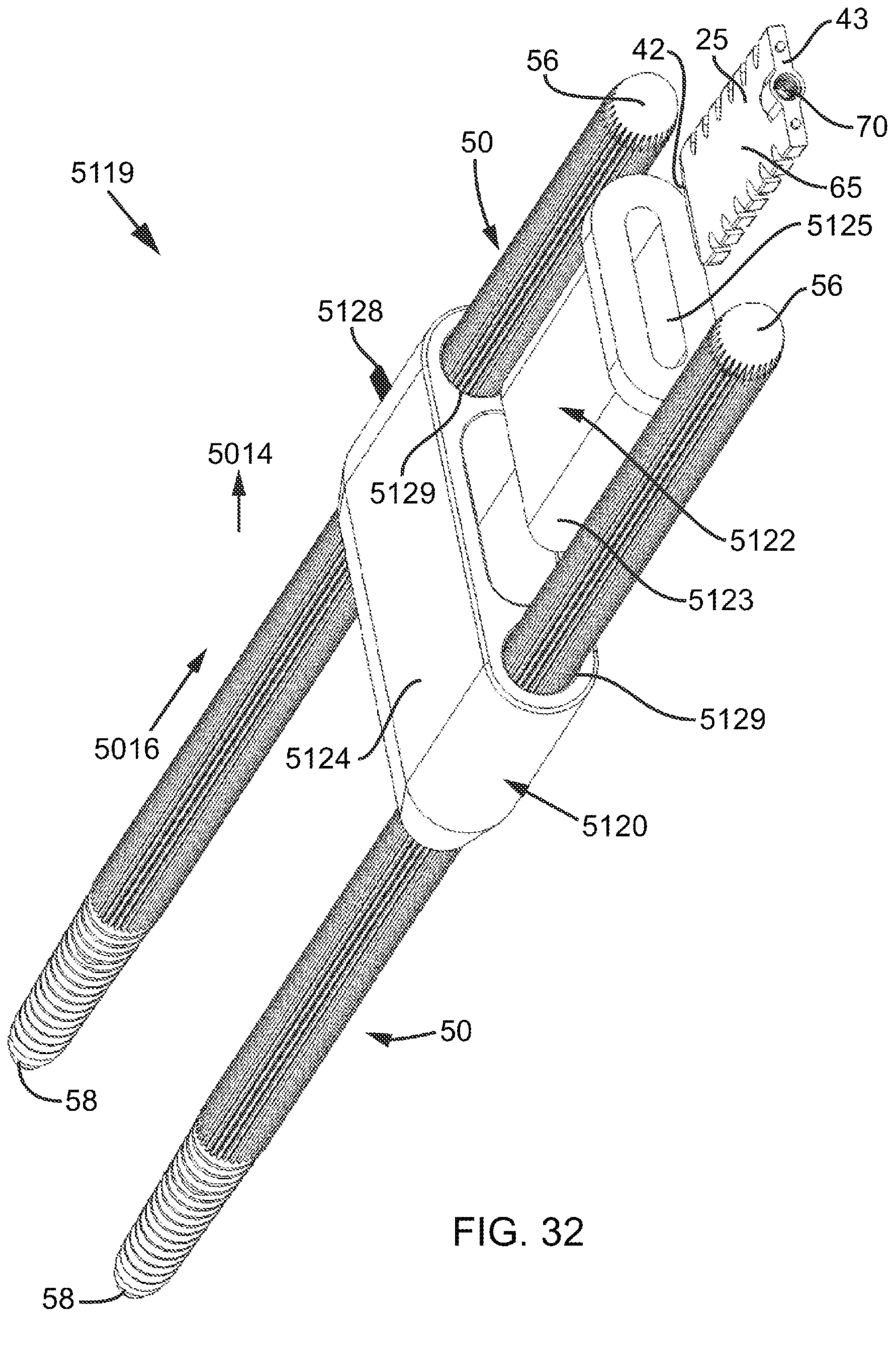
FIG. 32 is an isometric view from a top of the surgical system for delivering an implant of FIG. 31.

Reference is now made to FIG. 32, which is an isometric view from a top of the implant delivery system for delivering an implant of FIG. 31. As shown in FIG. 32, the implant 25 may include a generally planar body having a proximal end 43, a distal end 42 opposite the proximal end 43, and a pair of generally planar surfaces 65 extending between the proximal and distal ends 43, 42. The implant 25 may have a threaded opening 70 near the proximal end 43. A delivery tool may be coupled to the threaded opening 70 to push the implant 25 through the guide spacer 5122.

Figure 33:
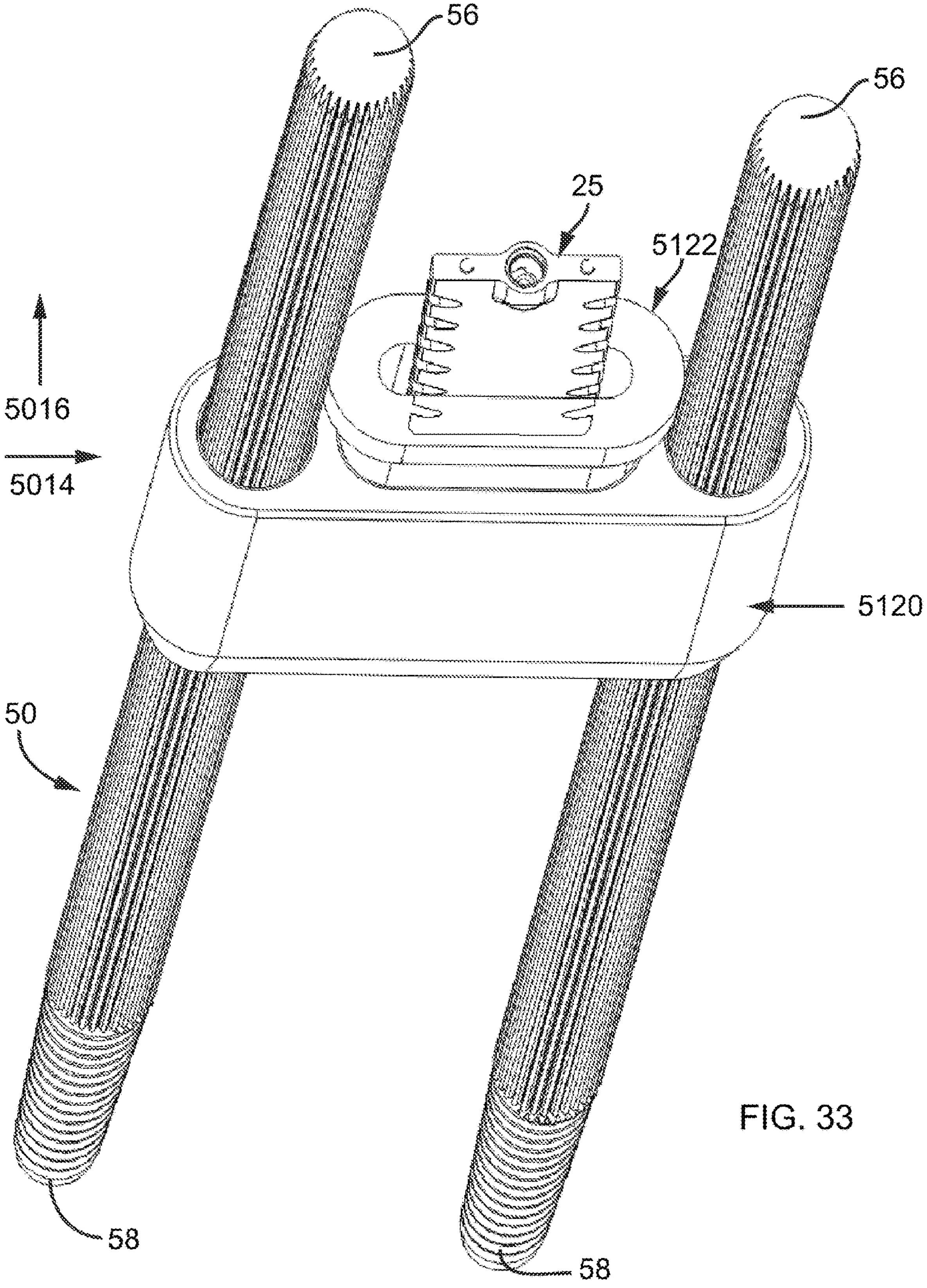
FIG. 33 is an isometric view of the surgical system of FIG. 31 with the implant inserted partially.

FIG. 33 is an isometric view of the implant delivery system of FIG. 31 with the implant 25 inserted partially. As shown, the implant 25 is pushed into the guide spacer 5122. The guide coupling member 5120, which may be distally driven in the patient's body until the distal end of the guide coupling member 5120 abuts the ilium 1005 and sacrum 1004, the implant 25 may be delivered into a region of the joint defined between the diagnostic pins 50, which may be in the intra-articular region or extra-articular region of the joint. That is, if the pins 50 are positioned such that they span the extra-articular region of the sacroiliac joint, the implant 25 will subsequently be delivered into the extra-articular region of the joint. On the other hand, if the pins 50 are positioned such that they span the intra-articular region of the sacroiliac joint, the implant 25 will subsequently be delivered into the intra-articular region of the joint. Accordingly, the physician may choose to position the pins 50 in a certain region of the sacrum 1004 and ilium 1005 during the diagnostic portion of the procedure while contemplating that, if an implant fusion procedure is necessary, the pins may be used to subsequently guide the implant into the joint.

As an example, a physician may choose to position a first pin 50 in a patient's ilium in a superior region of the iliac spine between the posterior superior iliac spine 2004 and the posterior inferior iliac spine 2006 (i.e., lateral of the extra-articular region of the joint). The physician may choose to position a second pin 50 in a patient's sacrum just medial of the first pin. Thus, after diagnosing the sacroiliac joint as a source of pain and fusion as a procedure for alleviating the pain, the physician may deliver the implant into the extra-articular region of the sacroiliac joint using the pins as a guide.

As another example, a physician may choose to position a first pin 50 in a patient's ilium in an inferior region of the iliac spine between the posterior superior iliac spine 2004 and the posterior inferior iliac spine 2006 (i.e., lateral of the intra-articular region of the joint). The physician may choose to position a second pin 50 in a patient's sacrum just medial of the first pin. Thus, after diagnosing the sacroiliac joint as a source of pain and fusion as a procedure for alleviating the pain, the physician may deliver the implant into the intra-articular region of the sacroiliac joint using the pins as a guide.

Figure 34:
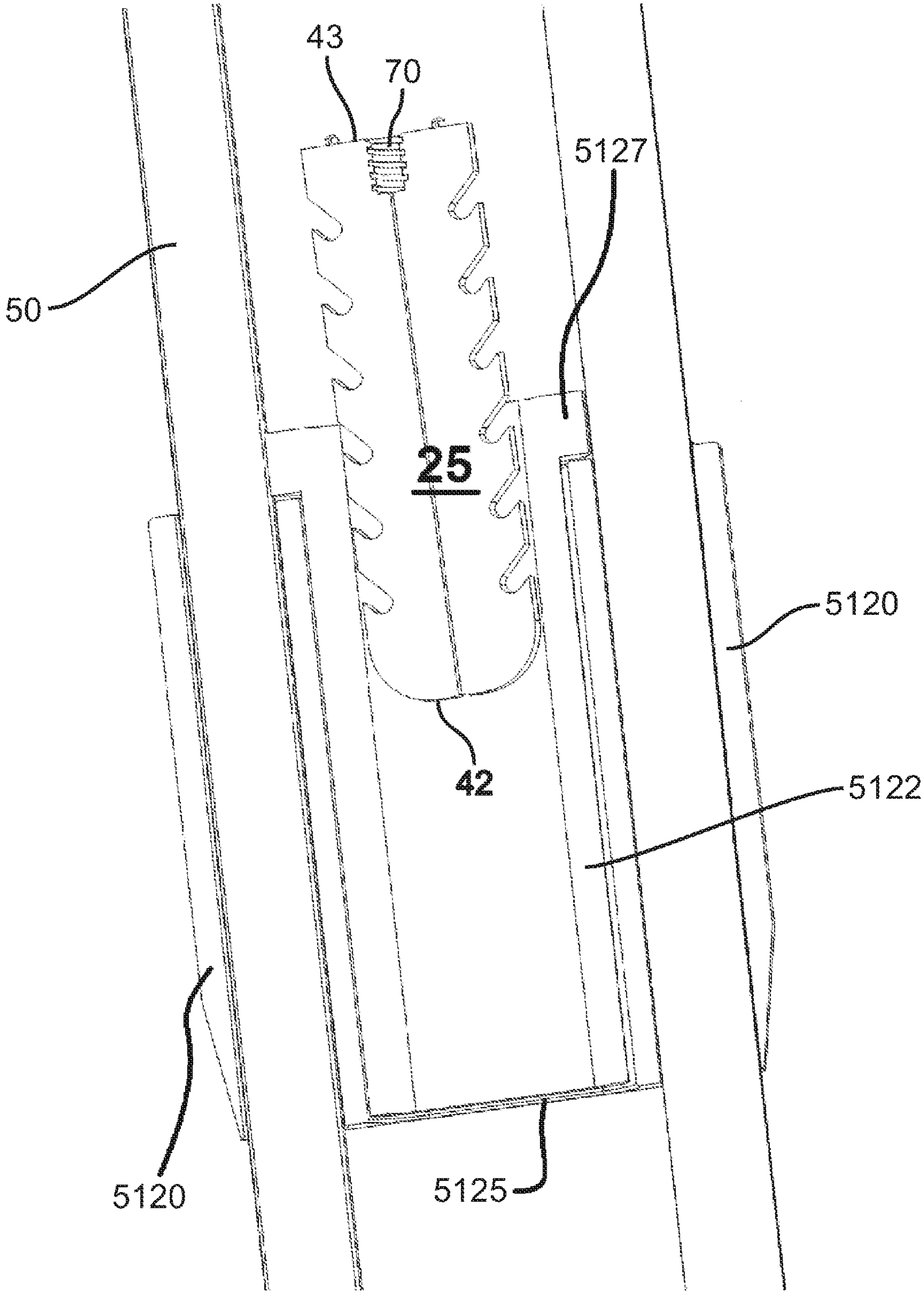
FIG. 34 is a sectional view of the surgical system of FIG. 33 with the implant inserted partially.

Moving on, reference is made to FIG. 34, which is a sectional view of the implant delivery system of FIG. 33 with the implant inserted partially. As shown, the implant 25 slides down from the proximal end toward the distal end. The tolerance between the outer surface of the implant 25 and the inner surface of the guide spacer 5122 may be large enough to allow the implant 25 to slide down without resistance or friction, but small enough such that the implant 25 can be guided down along the longitudinal axis.

The guide members 50 may have any shaped cross section, including circular, oval, triangular, rectangular, square, diamond, or the like. As one non-limiting example, the generally cylindrical elongated guide member 50 may have a diameter of in the range of about 3 mm to about 8 mm and a length between the distal end and the proximal end may be in the range of about 2 cm to about 20 cm.

G. Implant Delivery Locations

During an implantation procedure, the implant or insertion element 25 may be positioned into a pelvic region of a patient through an incision in the patient's skin. A retractor may be used to open the incision and a trocar or other device may be used to provide a passageway into the surgical site. A medical person may grasp a delivery tool with a mechanically attached insertion element and advance the distal end of the insertion element to a sacroiliac joint region. Alternatively, a surgical robot may conduct the implantation procedure. The distal end of the insertion element may further be advanced into the bones defining a sacroiliac joint. The insertion element may be positioned to substantially or generally avoid the intra-articular portion of the sacroiliac joint. Alternatively, in order to capture the dense bone surrounding the intra-articular portion of the joint, the insertion element may be advanced to be positioned generally or substantially within the intra-articular portion of the sacroiliac joint.

A medical personal may apply a force along the longitudinal axis of the insertion element or the delivery tool to advance the insertion element. The force may cause the insertion element to translate or advance into the joint in a generally anterior direction.

Figure 35:
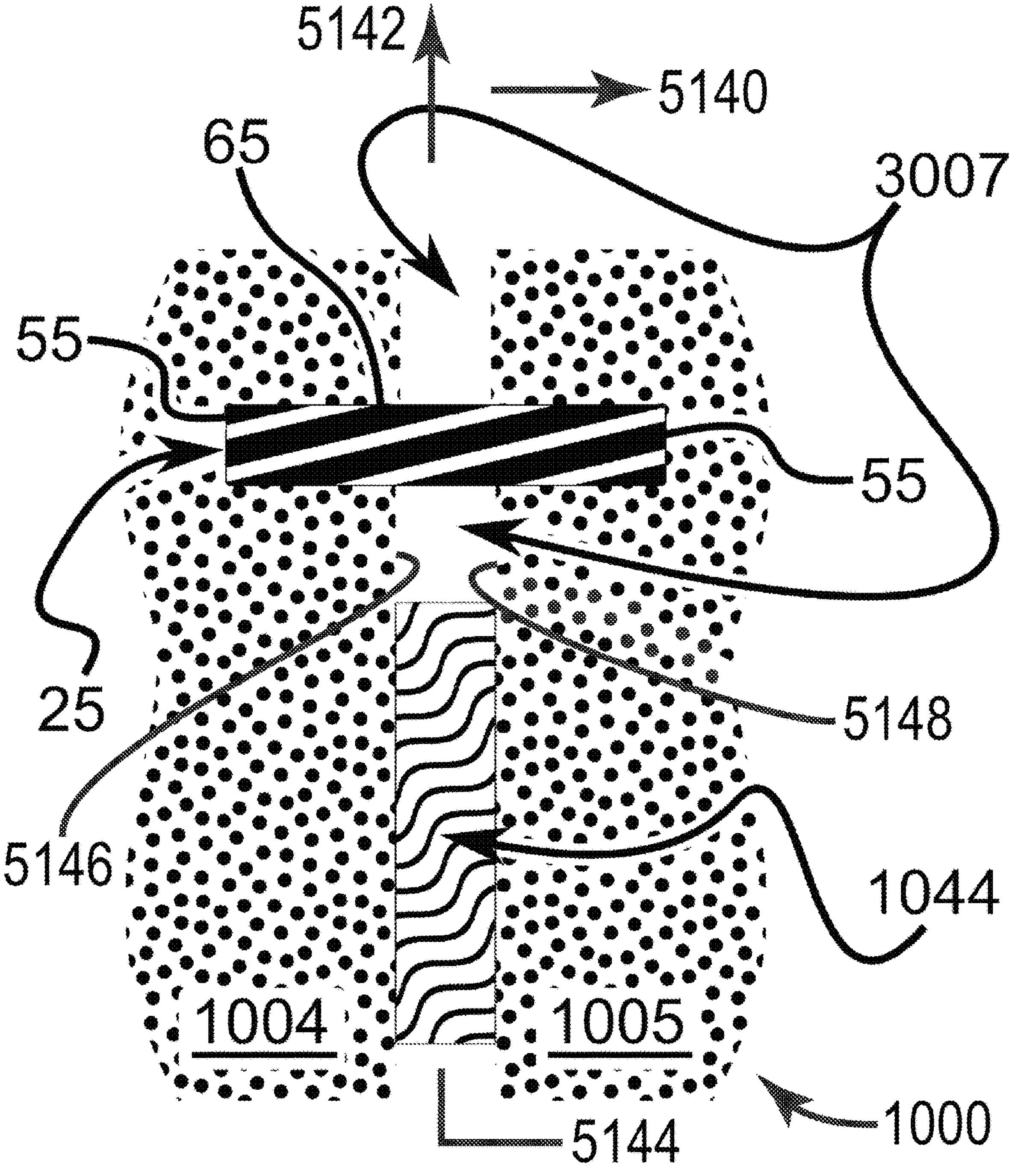
FIG. 35 is an enlarged sectional view illustrating that the implant is inserted in the extra-articular region.

FIG. 35 is an enlarged sectional view illustrating the implant being inserted in the extra-articular region 3007 of the sacroiliac joint. The sectional view is obtained from FIG. 50 as shown by arrows in that figure. As shown in FIG. 35, the implant 25 is in a generally transverse direction 5140 across the joint line 5144 defining the sacroiliac joint 1000 and the sacrum 1004 and the ilium 1005. As seen in the figure, the intra-articular region 1044 is shown inferior to the extra-articular region 3007 of the joint. The implant 25 may be positioned substantially perpendicular to the joint line 5144 of the ilium 1005 and sacrum 1004. The joint line 5144 is along a vertical axis 5142 generally perpendicular to the transverse axis 5140. The generally planar surface 65 of the implant 25 is generally perpendicular to the joint line 5144 along the vertical axis 5142, as shown in FIG. 35. The joint line 5144 is generally in a plane defined by an ilium plane 5148 and sacrum plane 5146. The implant 25 may also be positioned to be generally symmetric across the joint line 5144 such that the implant 25 may stabilize the joint evenly from both the ilium 1005 and sacrum 1004. Specifically, one edge 55 of the implant 25 may extend into the sacrum 1004 and one opposite edge 25 may extend into the ilium 1005. The distance from the edge 55 to the joint line 5144 may be about the same as the distance from the opposite edge 55.

In alternative embodiments, the implant 25 may be positioned non-symmetrically across the joint line 5144. For example, the distance of the edge 55 extending into the sacrum 1004 may be smaller or larger than the distance of the opposite edge 55 extending into the ilium 1005. The distance may vary in order to help temporarily stabilize the joint and to reduce the pain in a patient. In alternative embodiments, the implant 25 may be positioned across the joint line 5144 in a non-perpendicular manner. That is, the implant 25 may be positioned at an angle relative to the joint line 5144 that is less than or more than ninety degrees.

In some embodiments, two or more implants 25 may be used. For example, one fork type implant, such as shown in FIGS. 47A-B, may be used in the intra-articular region 1044, while another implant, such as shown in FIGS. 44-46 may be used in the extra-articular region.

Figure 36:
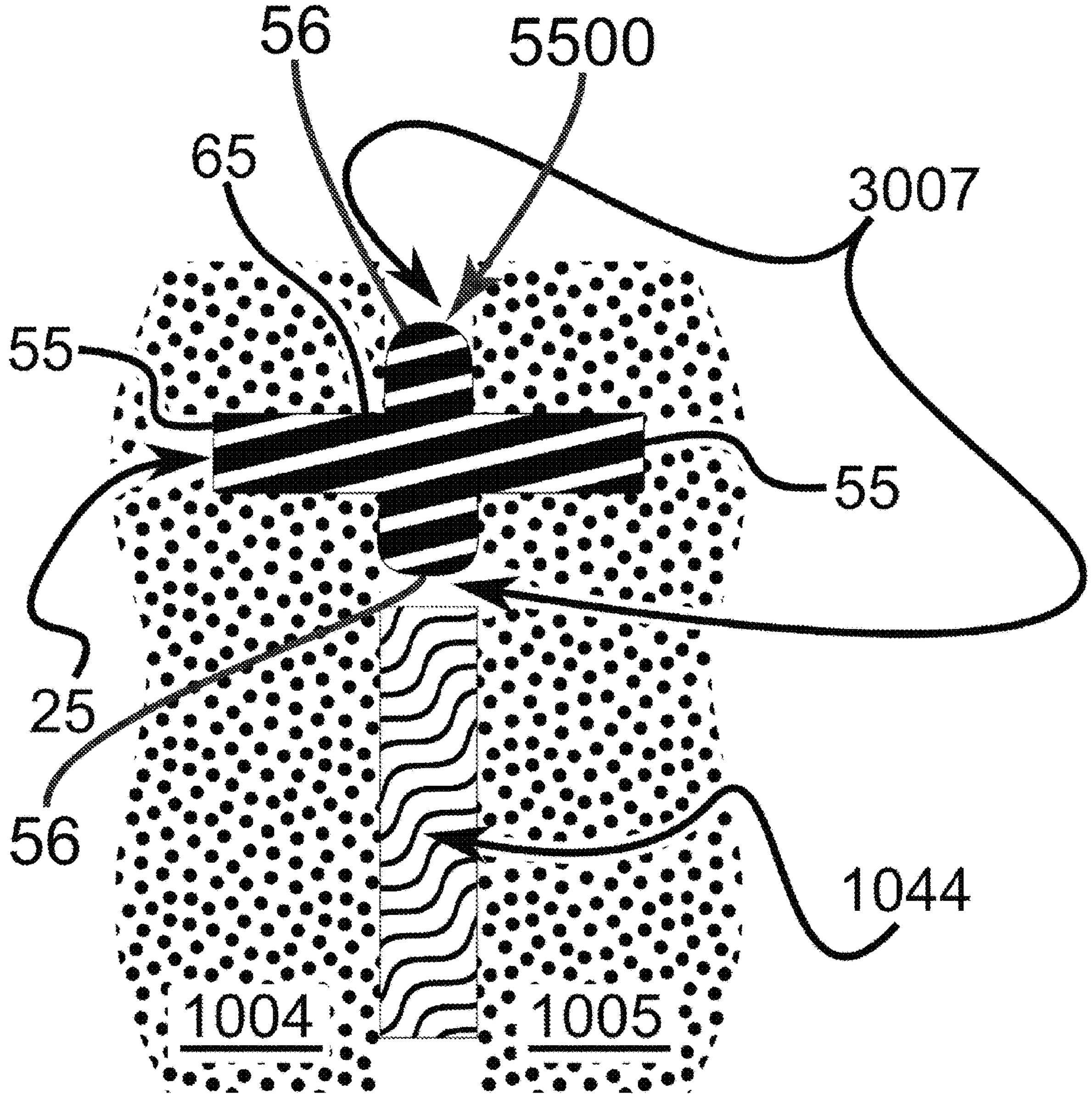
FIG. 36 is an enlarged sectional view illustrating that a cross type implant is inserted in the extra-articular region.

FIG. 36 is an enlarged sectional view illustrating another type of implant 25 inserted in the extra-articular region 3007. As shown in the figure, the implant 5500 may include a cross-shape cross-section with a pair of keels 55 extending into the sacrum 1004 and ilium 1005 and a pair of perpendicularly oriented keels 56 extending generally vertically or in-line with the joint line 5144 in a gap between the ilium 1005 and sacrum 1004 in the extra-articular region 3007. The additional implant 5500 may be similar to implant embodiments described in related U.S. patent applications that are previously identified as being incorporated by reference in this application.

Figure 37:
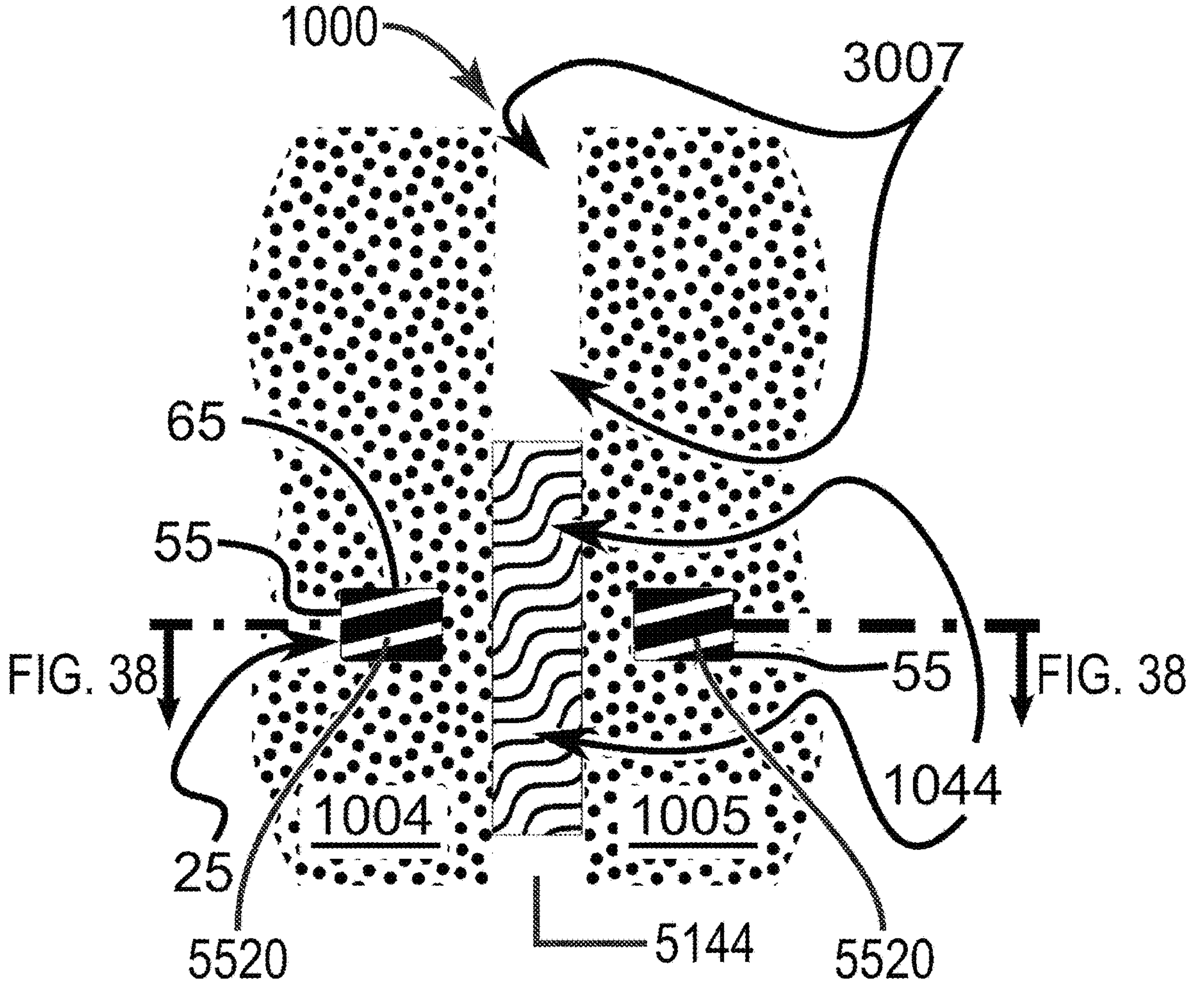
FIG. 37 is an enlarged sectional view illustrating that the fork-like shaped implant is inserted in the intra-articular region.
Figure 38:
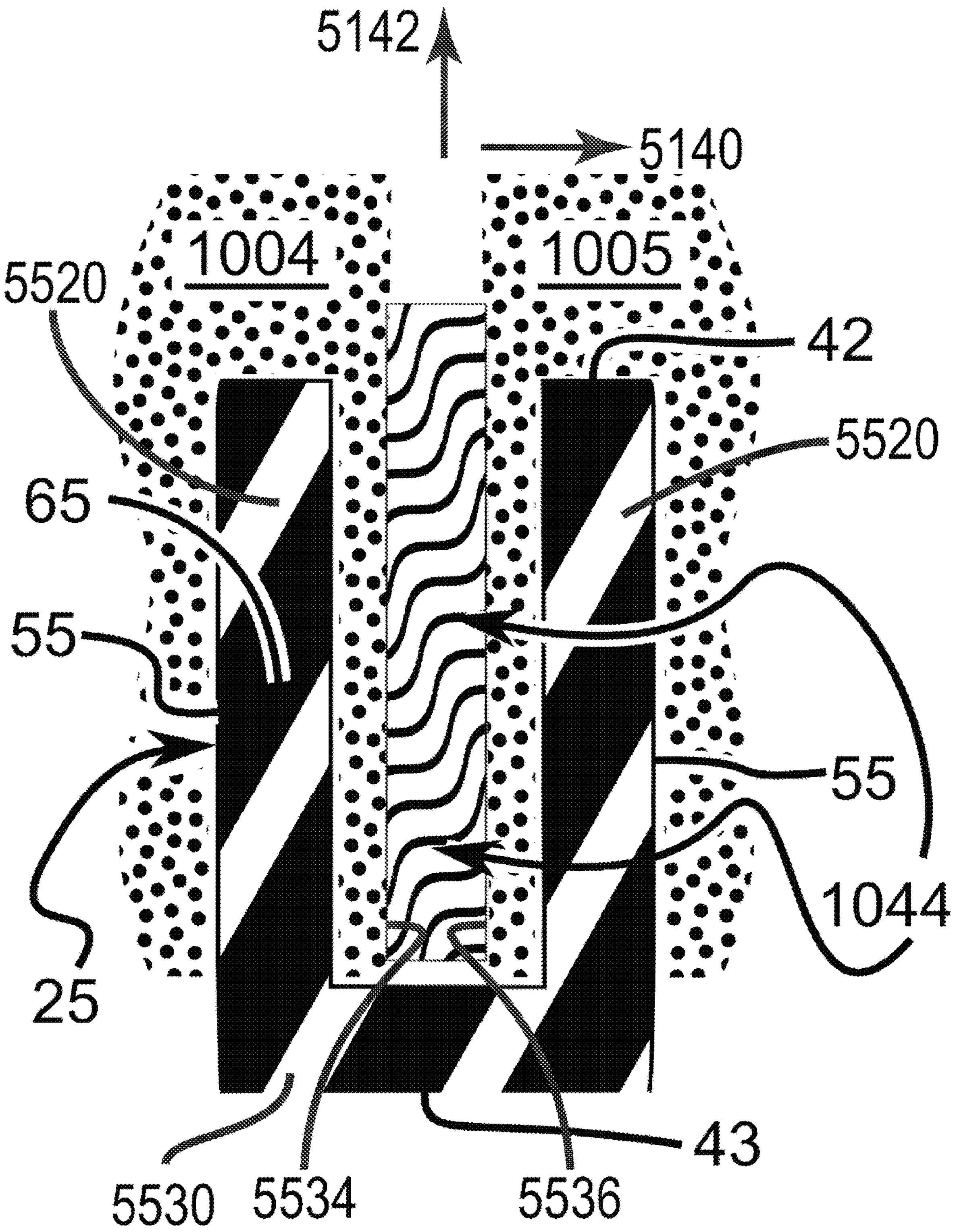
FIG. 38 is a sectional view of FIG. 37 as shown by arrows A-A.

Other embodiments of the implant 25 include a fork or U-shaped implant 25, as seen in FIGS. 37-38 and 48A-48B. FIG. 37 is a cross-sectional view of the implant 25 taken along the cross-section line shown in FIG. 50, except the implant 25 in FIGS. 37-38 depict the implant 25 spanning the intra-articular region 1044 instead of the extra-articular region of the sacroiliac joint 1000. As seen in FIG. 38, which is another cross-sectional view of the implant 25 taken along the cross-section line shown in FIG. 37, the implant 25 may include a first longitudinally extending member or finger 5520 and a second longitudinally extending member or finger 5520 that are coupled together at a proximal end of the implant 25 by a coupling member 5530.

In use, the first longitudinally extending member 5520 may be positioned in the sacrum 1004, the second longitudinally extending member 5520 may be positioned in the ilium 1005, and the coupling member 5530 may span the intra-articular region 1044 of the sacroiliac joint 1000. In this way, the implant 25 may be used in the intra-articular region 1044, which includes a harder portion of the ilium 1005 than in the extra-articular region 3007. Although not shown in FIGS. 37-38, the implant 25 may also be positioned such that the coupling member 5530 spans the extra-articular region 3007 of the joint 1000.

When implanted in the joint 1000, the fingers 5520 may be generally parallel to the joint line 5144. When implanted in this way, the first and second longitudinally extending members 5520 may be fully positioned within the sacrum 1004 and ilium 1005, respectively, such that an inner sacrum surface 5534 and an inner ilium surface 5536, on opposing surfaces of the intra-articular region 1044, are substantially or completely undisturbed by implantation and positioning of the implant 25. As seen in FIG. 38, the longitudinally extending member 5520 are aligned along a transverse axis 5141. The transverse axis 5141 and the horizontal axis are in a transverse plane to a human body. Also, when implanted in the region of the intra-articular region 1044, the coupling member 5530 does not contact the cartilage in the intra-articular region 1044; rather, the coupling member 5530 remains positioned outside the joint 1000. In some embodiments, the coupling portion 5530 may be outside within the patient's soft tissue, or inside a patient's body.

In some embodiments, a temporary implant may include two implant pins with a mechanical coupling that joins the two implant pins, as previously described with reference to FIG. 13B. The implant pins 50 may be inserted into the sacrum 1004 and ilium 1005 near intra-articular region 1044 or extra-articular region 3007 to help temporarily stabilize the joint for a patient. The patient may carry the temporary implant for a period of time to evaluate if the temporary implant helps reduce the pain. Then, the temporary implant may be removed. A long term implant may be placed in the joint where the temporary implant locates.

Figure 39A:
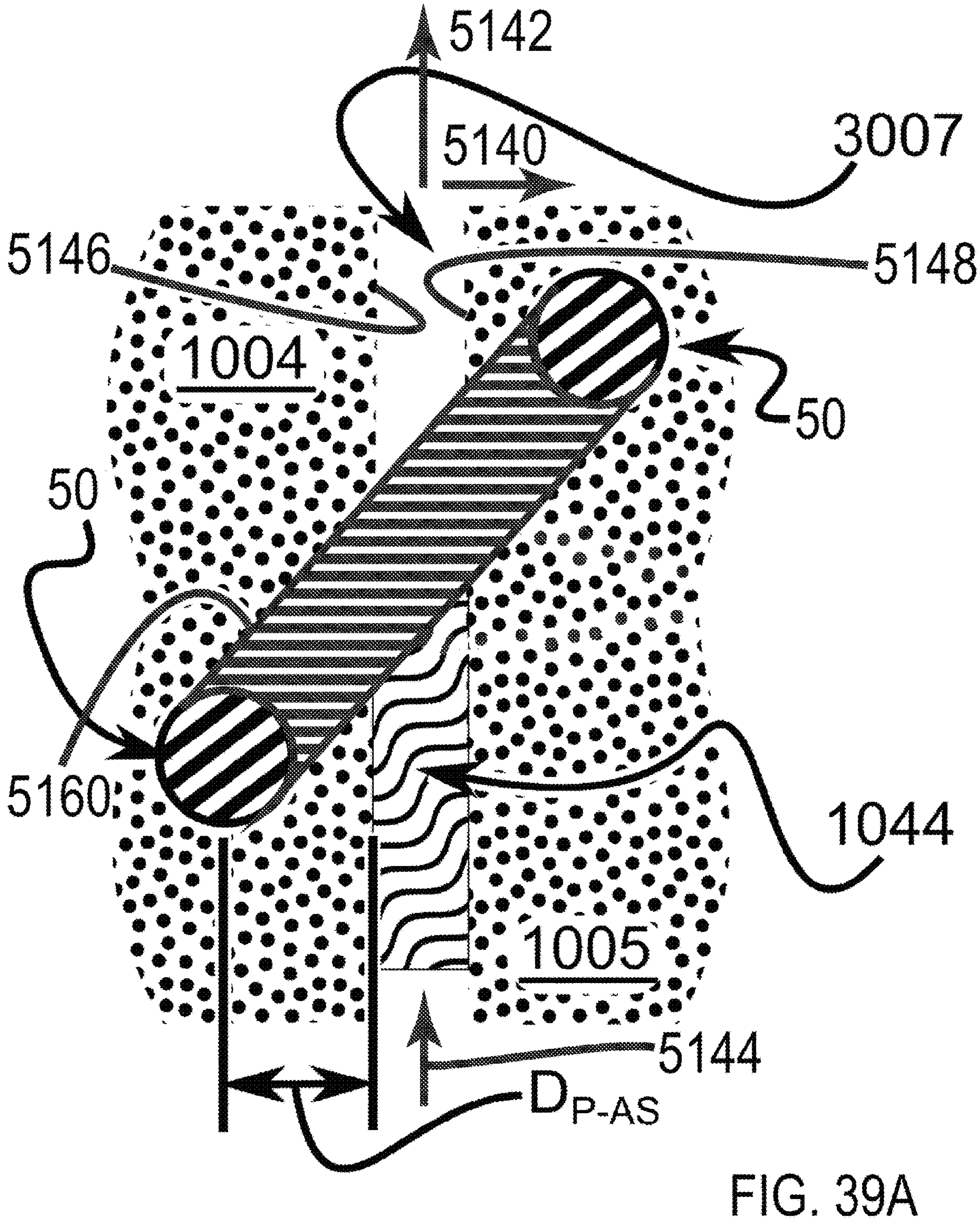
FIG. 39A is an enlarged sectional view illustrating that one pin is inserted in ilium near extra-articular region and one pin is inserted into the sacrum near the intra-articular region with coupling between the pins.

FIG. 39A is an enlarged posterior view of the sacroiliac joint 1000 illustrating that one implant pin is inserted in ilium 1005 near extra-articular region 3007 and one implant pin is inserted into the sacrum 1004 near the intra-articular region 1044. As shown in FIG. 39A, one implant pin 50 is inserted into the ilium 1005 near the extra-articular region, while another implant pin 50 is inserted into the sacrum 1004 near the intra-articular region. The pins 50 are respectively coupled together at a proximal end via a mechanical coupling 5160.

Figure 39B:
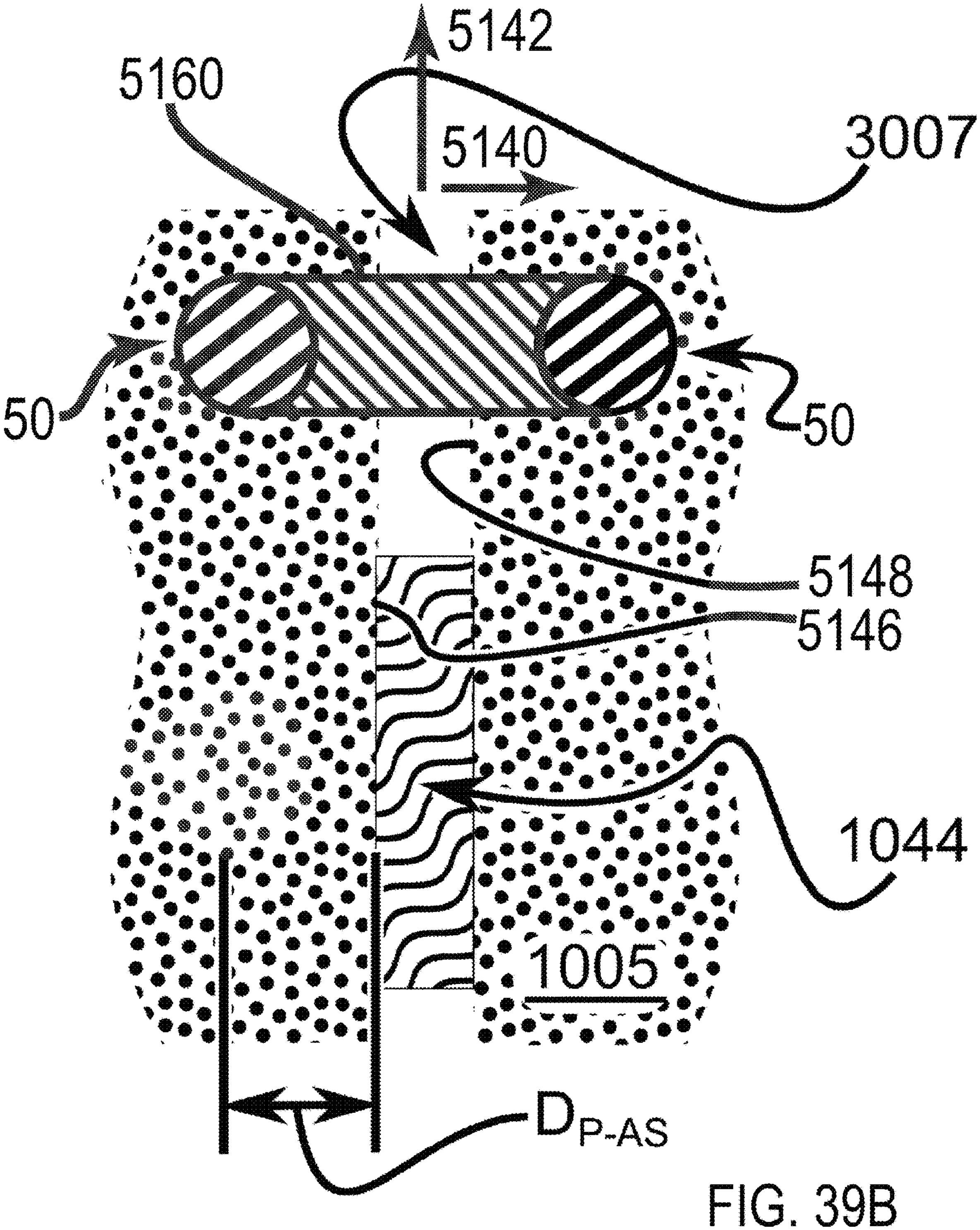
FIG. 39B is an enlarged sectional view illustrating that one pin is inserted in ilium near extra-articular region and one pin is inserted into the sacrum near the extra-articular region with coupling between the pins.

FIG. 39B is an enlarged posterior view of the sacroiliac joint 1000 illustrating that one pin is inserted in ilium 1005 near extra-articular region 3007 and one implant pin 50 is inserted into the sacrum 1004 near the extra-articular region 3007. As shown in FIG. 39B, one implant pin 50 is inserted into the ilium 1005 near the extra-articular region 3007, while another implant pin 50 is inserted into the sacrum 1004 also near the extra-articular region 3007. The pins 50 are respectively coupled together at a proximal end via a mechanical coupling 5160.

Figure 39C:
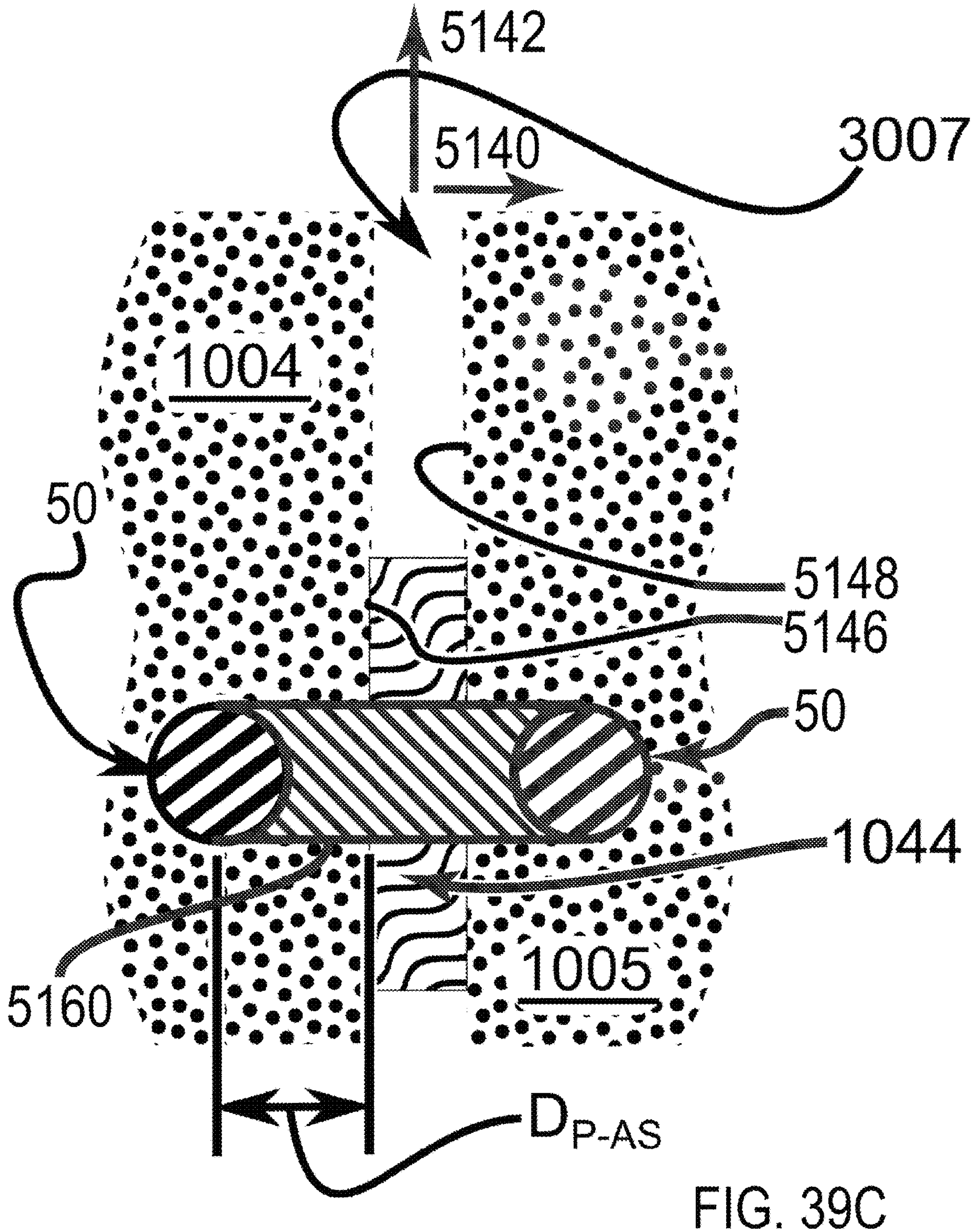
FIG. 39C is an enlarged sectional view illustrating that one pin is inserted in ilium near intra-articular region and one pin is inserted into the sacrum near the intra-articular region with coupling between the pins.

FIG. 39C is an enlarged posterior view of the sacroiliac joint 1000 illustrating that one pin is inserted in ilium 1005 near intra-articular region 1044 and one implant pin 50 is inserted into the sacrum 1004 near the intra-articular region 1044. As shown in FIG. 39C, one implant pin 50 is inserted into the ilium 1005 near the intra-articular region 1044, while another implant pin 50 is inserted into the sacrum 1004 also near the intra-articular region 1044. The pins 50 are respectively coupled together at a proximal end via a mechanical coupling 5160.

The implant pins 50 as shown in FIGS. 39A-C may be joined by a mechanical coupling 5160 to hold the two implant pins 50 in position, such that the coupling 5160 along with the two implant pins 50 can help stabilize the joint temporarily or permanently depending on the needs of the patient. The mechanical coupling 5160 may be like the guide coupling, as shown in FIG. 31, which is positioned between the two implant pins 50 to connect them together. The coupling 5160 can hold the implant pins 50 in their positions such that the joint is effectively stabilized.

Figure 40:
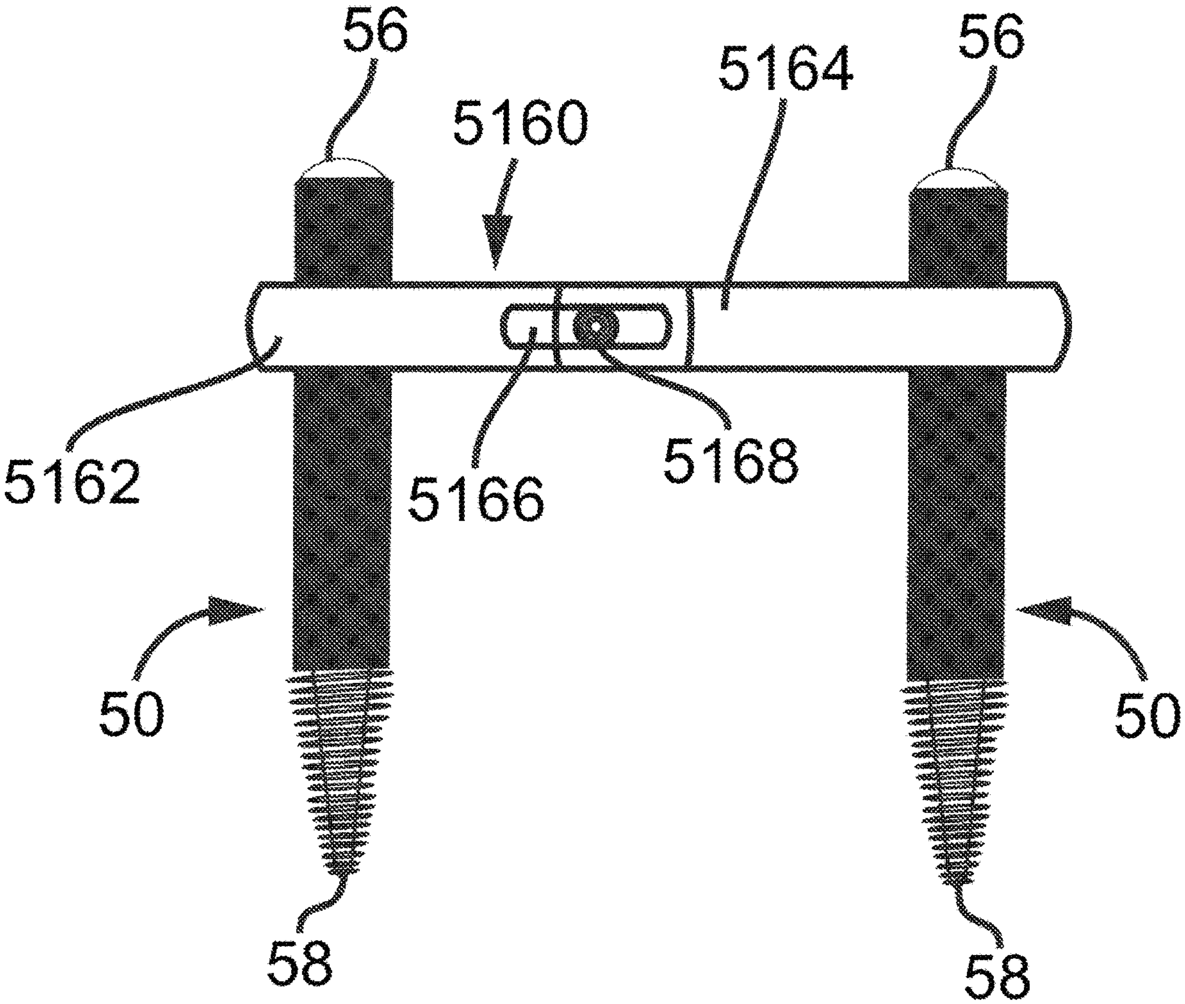
FIG. 40 is a simplified diagram illustrating an adjustable coupling member for the pins.

In some embodiments, the mechanical coupling 5160 may also be configured to adjust the distance between the two implant pins 50, such that the implant pins 50 may be placed in various locations as shown in FIGS. 39A-C. FIG. 40 illustrates a mechanical coupling 5160 that may include a first portion 5162 attached to the first implant pin 50 and a second portion 5164 attached to the second implant pin 50. The first portion 5162 may include an elongated slot 5166 configured to allow the distance between the two pins 50 to be adjustable, while the second portion 5164 may include a protruded screw 5168 such that the screw 5168 may be fastened within the slot 5166 by a fastener. The mechanical coupling 5160 may be located outside of a patient's body or inside a patient's body. The mechanical coupling 5160 may be configured to join the implant pins 50, fixedly or not fixed depending upon the need according to a medical person.

Figure 41:
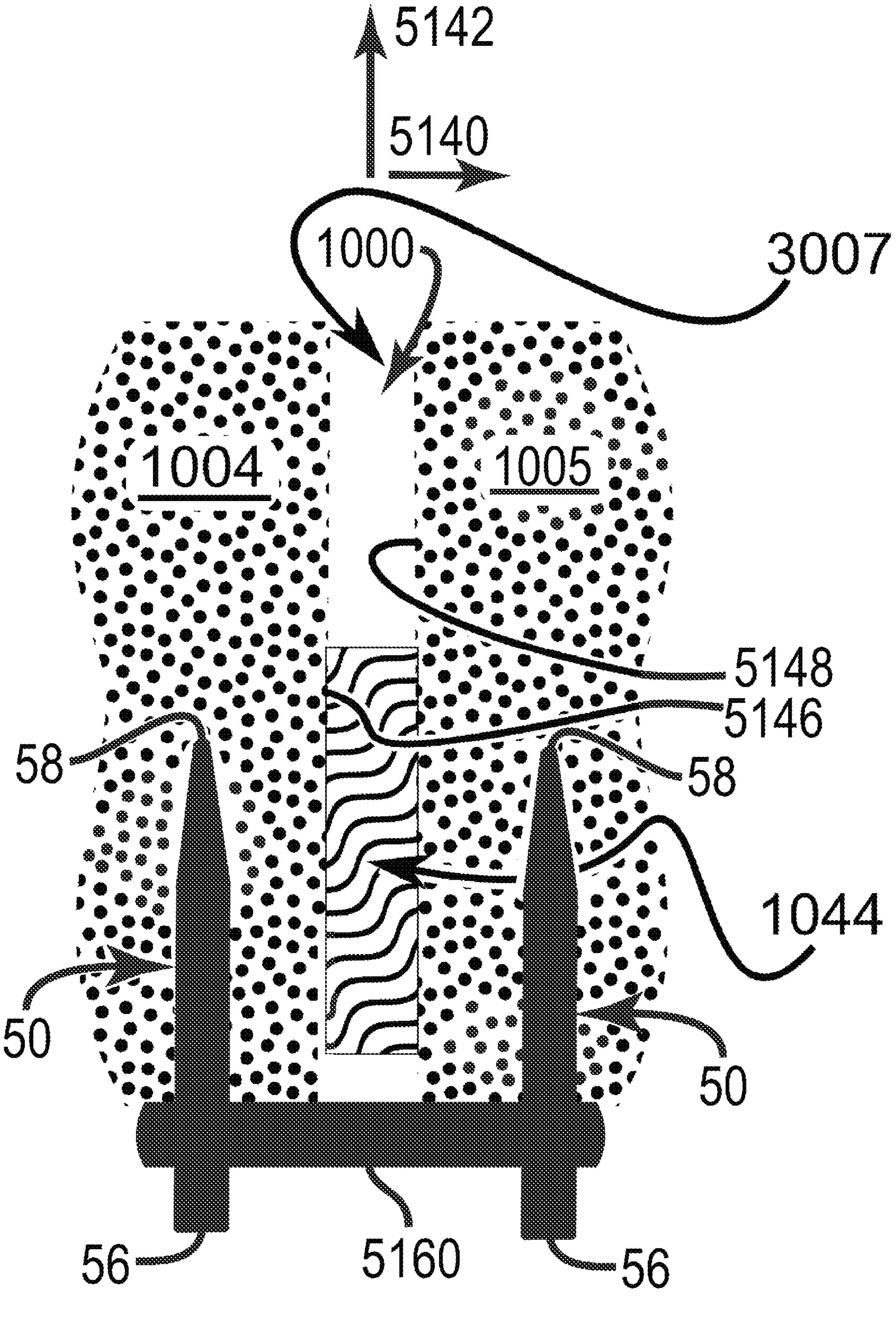
FIG. 41 is an enlarged sectional view illustrating that a temporary implant including coupled pins is inserted in the intra-articular region.

FIG. 41 is an enlarged sectional view illustrating that a temporary implant including coupled implant pins is inserted in the intra-articular region. As shown in FIG. 41, a distal end 58 of one implant pin 50 is inserted into the ilium 1005 and a distal end 58 of another implant pin 50 is inserted into the sacrum 1004. Both implant pins 50 are positioned near the intra-articular region 1044. One implant pin 50 is inside the sacrum joint surface 5146 and another implant pin 50 is inside the ilium joint surface 5148. Both proximal ends 56 of the implant pins 50 are outside the joint 1000, thus, not disturbing the cartilage, capsule, and fluid within the intra-articular region 1044 of the joint 1000. The implant pins 50 may be coupled together via the mechanical coupling 5160, which is also positioned outside of the joint 1000. The implant pins 50 are along a transverse axis 5141 which is generally perpendicular to the vertical axis 5142 as shown in FIG. 39C, and also perpendicular to the horizontal axis 5140. The transverse axis 5141 and the horizontal axis are in a transverse plane to a human body.

In some embodiments, the implant 25 may be inserted into the sacroiliac joint 1000 without using the guidance tool as shown in the previous figures.

H. Imaging and Radiographic Contrasting Agents

An imaging system may be used to assist in delivering the implant into the intra-articular region or extra-articular region of the sacroiliac joint. More particularly, the capsule of the intra-articular region of the sacroiliac joint, among other anatomical areas, may be injected with a radiographic contrasting agent such that delivery of the implant, in relation to the anatomical feature injected with the contrasting agent, may be viewed under X-ray or fluoroscopy, among other methods, to ensure proper implant placement. As an example, the intra-articular region of the joint may be injected with the radiographic contrasting agent. Then, the implant may be delivered into the extra-articular region of the joint while the joint is viewed under X-ray or fluoroscopy. In this way, with the intra-articular region of the joint clearly visible with the contrasting agent, the implant may be properly positioned and delivered into the extra-articular region.

Figure 42:
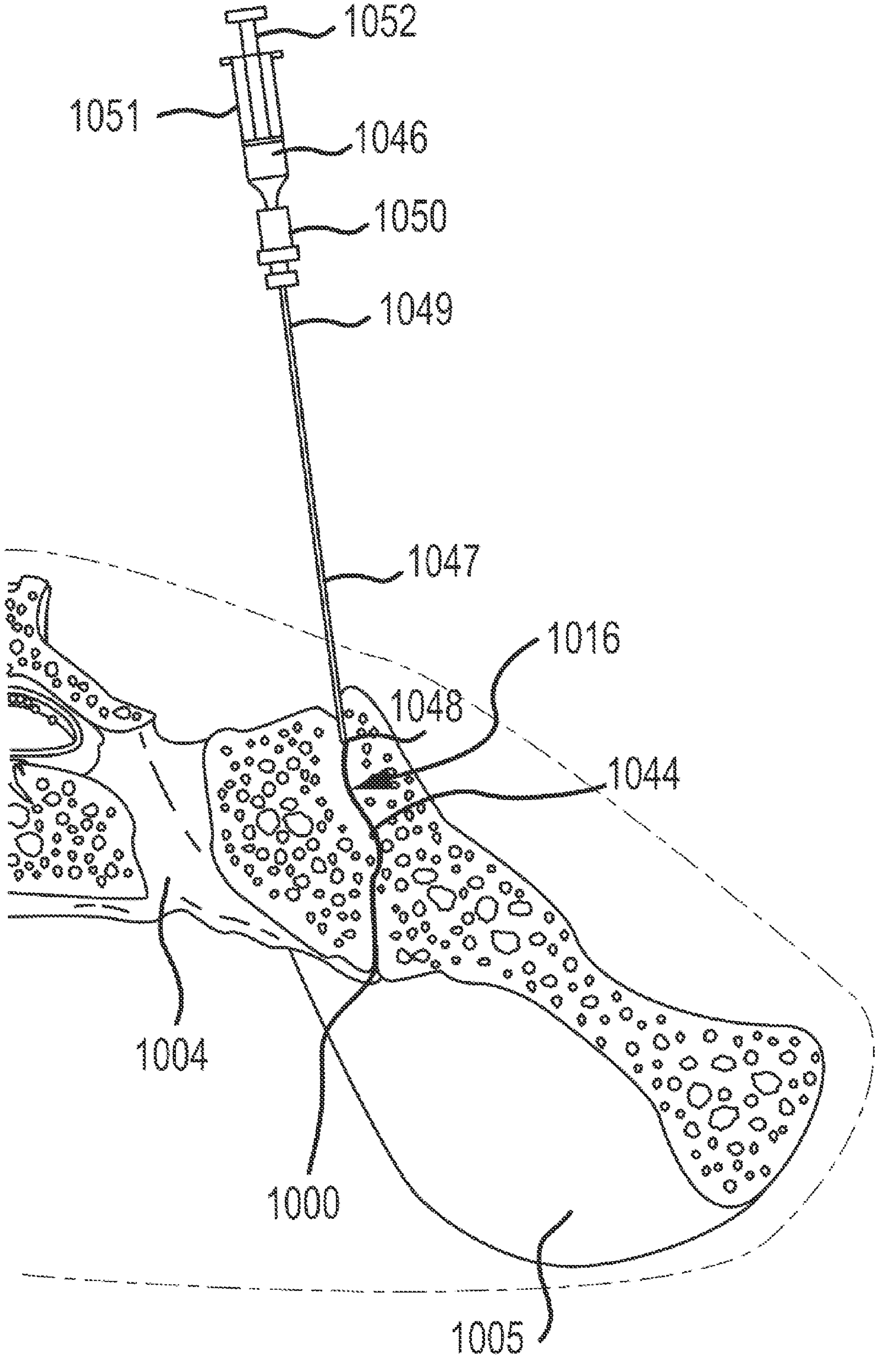
FIG. 42 illustrates a radiographic contrast tool that injects radiographic contrast under fluoroscopic guidance into the joint.

FIG. 42 illustrates a radiographic contrast tool that injects radiographic contrast under fluoroscopic guidance into the joint. As shown in FIG. 42, the sacroiliac joint 1000 can be locally anesthetized to allow for injecting a radiographic contrast 1046 (as a non-limiting example, ISOVIEW 300 radiographic contrast) under fluoroscopic guidance into the inferior aspect of the sacroiliac joint 1000 to outline the articular surfaces 1016 of the sacroiliac joint 1000) defined between the sacrum 1004 and ilium 1005, the sacroiliac joint 1000 having an interarticular region 1044. Injection of the radiographic contrast 1046 within the sacroiliac joint 1000 can be accomplished utilizing a tubular member 1047 (such as a syringe needle) having first tubular member end 1048 which can be advanced between the articulating surfaces 1016 of the sacroiliac joint 1000 and having a second tubular member end 1049 which removably couples to a hub 1050. The hub 1050 can be configured to removably couple to a syringe barrel 1051 (or other device to contain and deliver an amount of radiographic contrast 1046). In the example of a syringe barrel 1051, the syringe barrel 1051 can have an internal volume capable of receiving an amount of the radiographic contrast 1046 sufficient for outlining the articular surfaces 1016 of the sacroiliac joint 1000, for example, under lateral fluoroscopy.

A plunger 1052 can be slidingly received within the barrel 1051 to deliver the radiographic contrast 1046 through the tubular member 1047 into the sacroiliac joint 1000. The tubular member 1047 can have a gauge in the range of about 16 gauge and about 20 gauge and can further be incrementally marked on the external surface to allow determination of the depth at which the first needle end 1048 has advanced within the sacroiliac joint 1000. As the first needle end 1048 advances into the sacroiliac joint 1000 the radiographic dye 1046 can be delivered from within the syringe barrel 1051 into the sacroiliac joint 1000 to allow visualization of the sacroiliac joint 1000 and location of the tubular needle 1047 within the sacroiliac joint 1000.

By highlighting the intra-articular region 1044 of the sacroiliac joint 1000, important landmarks for subsequent steps of the for implanting an insertion element via the posterior inferior access region 3090 of the sacroiliac joint extra-articular region 3007 (as described in greater detail below) may be more easily identified, e.g., the posterior inferior corner 3091 of the sacroiliac joint extra-articular region boundary 3009, the inferior end 3092 of the posterior inferior access region 3090 of the sacroiliac joint extra-articular region 3007, the inferior boundary segment 3093 of the sacroiliac joint extra-articular region boundary 3009, the anterior boundary segment 3094 of the sacroiliac joint extra-articular region boundary 3009 or the superior-posterior corner 3016 and superior end 2018 of the posterior inferior access region 2016.

I. Insertion Element or Implant Configurations

FIGS. 43A-B-48A-B illustrate various embodiments of the insertion element or implant 25. Each implant or insertion element 25 may have a generally planar body having a proximal end, a distal end opposite to the proximal end. The implants may vary in shape, surface features, for example, main surfaces or side surfaces, which may provide variation in friction or resistance to movements. Also, the implants may vary in edges or surface features to provide better bonding to the bones of the sacrum and ilium.

The insertion elements may be formed of biocompatible materials including biocompatible metals, such as stainless steel, titanium, biocompatible ceramics, biocompatible polymers or composite materials. The insertion element may be manufactured by processes including machining, injection molding, among others.

Figure 43A:
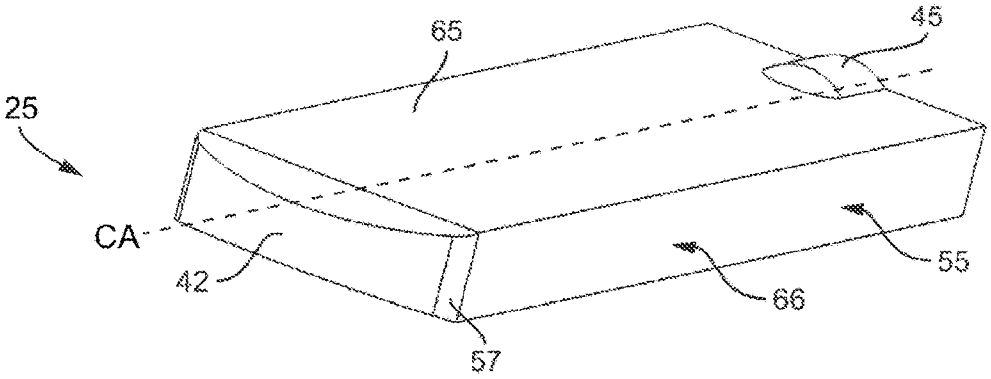
FIG. 43A is an isometric view from a distal end of an implant in accordance with a first embodiment of the present disclosure.
Figure 43B:
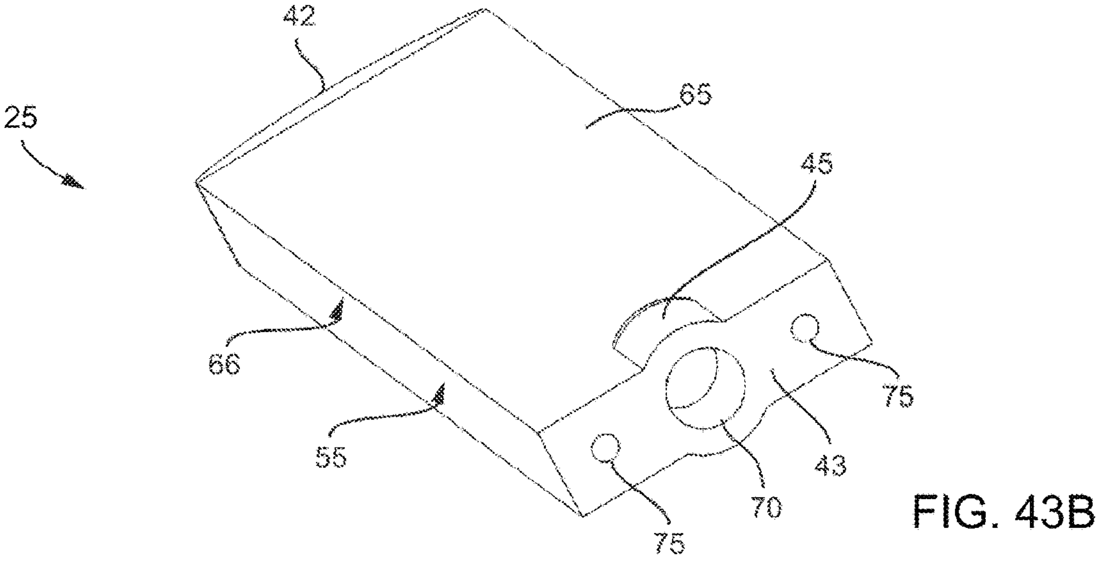
FIG. 43B is another isometric view from a proximal end of the implant of FIG. 43A.

To begin, reference is made to FIGS. 43A and 43B. FIG. 43A is an isometric view from a distal end of an implant 25, in accordance with a first embodiment of the present disclosure. FIG. 43B is another isometric view from a proximal end of the implant of FIG. 43A. As shown in the figures, an insertion element 25 includes a planar member 66, a distal or leading end 42, a proximal or trailing end 43. The planar member 66 has a length between the distal and proximal ends 42, 43 along a longitudinal center axis CA. The planar members 66 include a pair of generally opposed main surfaces 65 and side edge surfaces 55. The insertion element 25 also includes a longitudinally extending body 45. The planar members 66 that extend the length between the distal end 42 and proximal end 43. The planar members 66 may radially extend outwardly away from the body 45.

In one embodiment, the radially extending planar members 66 may be grouped into pairs of planar members 66 that are generally coplanar with each other. For example, planar members 66 that are opposite the body 45 from each other, or opposite the longitudinal center axis CA, generally exist in the same plane. More specifically, the planar faces 65 of a first planar member 66 are generally coplanar with the planar faces 65 of a second planar member 66 opposite the body 45 from the first planar member 66. The longitudinally extending body 45 can extend a greater distance outwardly or transversely from the longitudinal center axis CA than the planar faces 65 of the planar members 66 yet the body 45 does not extend beyond the side edge surfaces 55.

The cylindrical body 45 may include a threaded hole 70 configured to connect to an implant delivery tool. The threaded hole 70 may be large enough such that the outer surface of the body 45 near the threaded hole may radially extend beyond the two generally opposed main surfaces 65.

The distal end 42 may be rounded or tapered. For example, the distal end 42 may have a convex surface that may be less resistant when inserted into the sacroiliac joint. The distal end 42 may also be thinner than the general planar body 66 such that the distal end 42 may be easier to be placed into the sacroiliac joint.

The thickness of the planar member 66 may be between approximately 1 mm and approximately 10 mm. In a particular embodiment, the thickness may be approximately 3.5 mm. The length of the planar member may be between approximately 5 mm and approximately 30 mm. In a particular embodiment, the length of the planar member may be approximately 20 mm. The cylindrical body may have a radius between approximately 2 mm and approximately 4 mm. In a particular embodiment, the radius may be approximately 2.75 mm. The width of the planar member 66 may be between 1 cm and 5 cm.

Figure 44A:
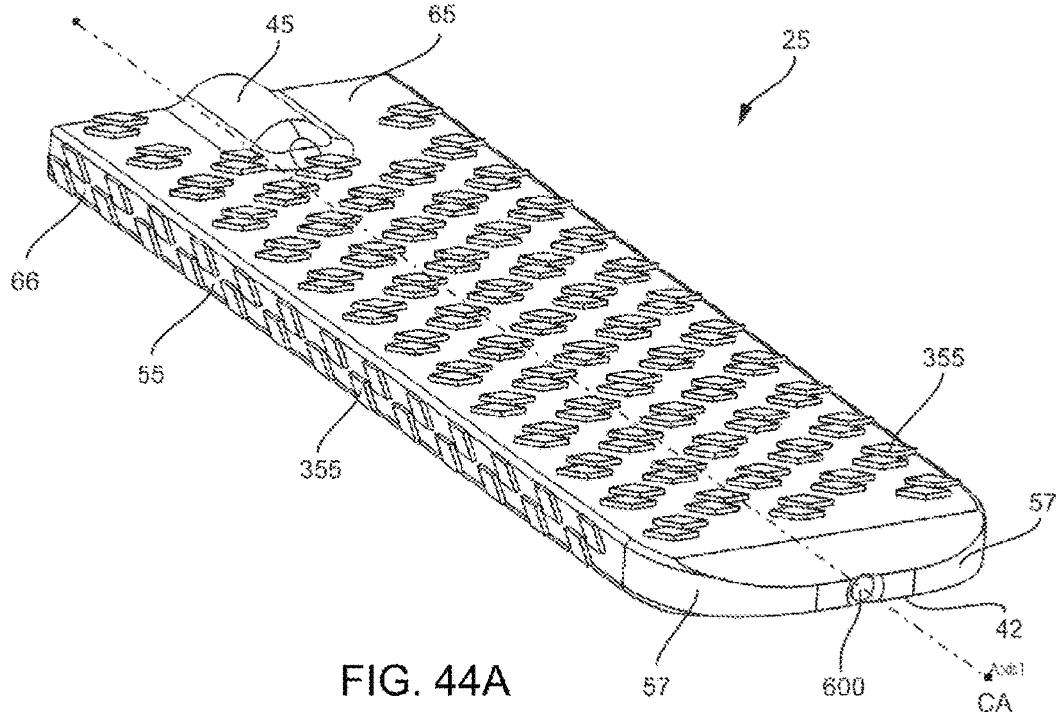
FIG. 44A is an isometric view from a distal end of an implant in accordance with a second embodiment of the present disclosure.
Figure 44B:
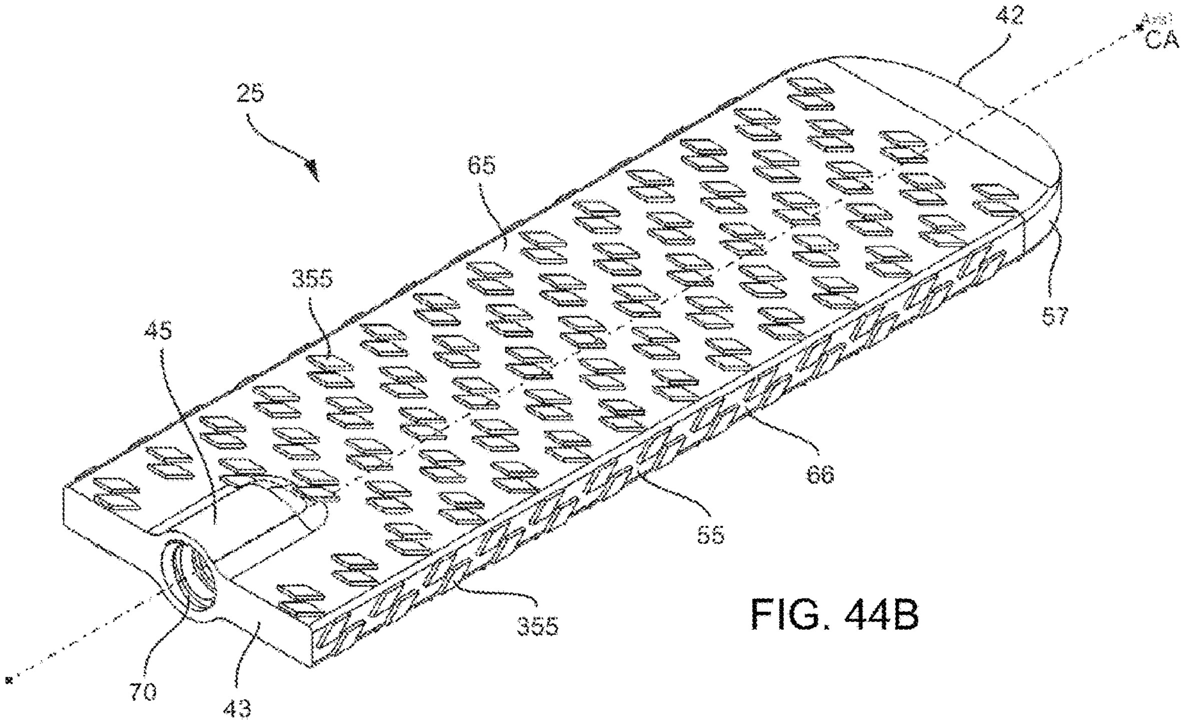
FIG. 44B is another isometric view from a proximal end of the implant of FIG. 44A.

FIG. 44A is an isometric view from a distal end of an implant in accordance with a second embodiment of the present disclosure. FIG. 44B is another isometric view from a proximal end of the implant of FIG. 44A. As shown in FIGS. 44A-44B, an insertion element 25 may include a generally planar body 66 with an anti-migration surface feature 355 on opposed main surfaces 65 and/or side edge surfaces 55. The anti-migration surface feature 355 may increase the resistance to the movement of sacroiliac joint. The surface feature 355 may include protruded portions from the planar surfaces 65. The protruded portions 355 may be spaced from each other.

The anti-migration features 355 are generally evenly distributed along the planar surfaces of the planar members in a rows and columns arrangement. The anti-migration features 355 may be in the form of trapezoids, squares, rectangles, etc. The anti-migration features 355 may have a rectangular cross sectional elevation with a thickness FT of between approximately 0.2 mm and approximately 5 mm, with one embodiment having a thickness FT of approximately 1 mm. The anti-migration features may be generally pyramidal.

Figure 45A:
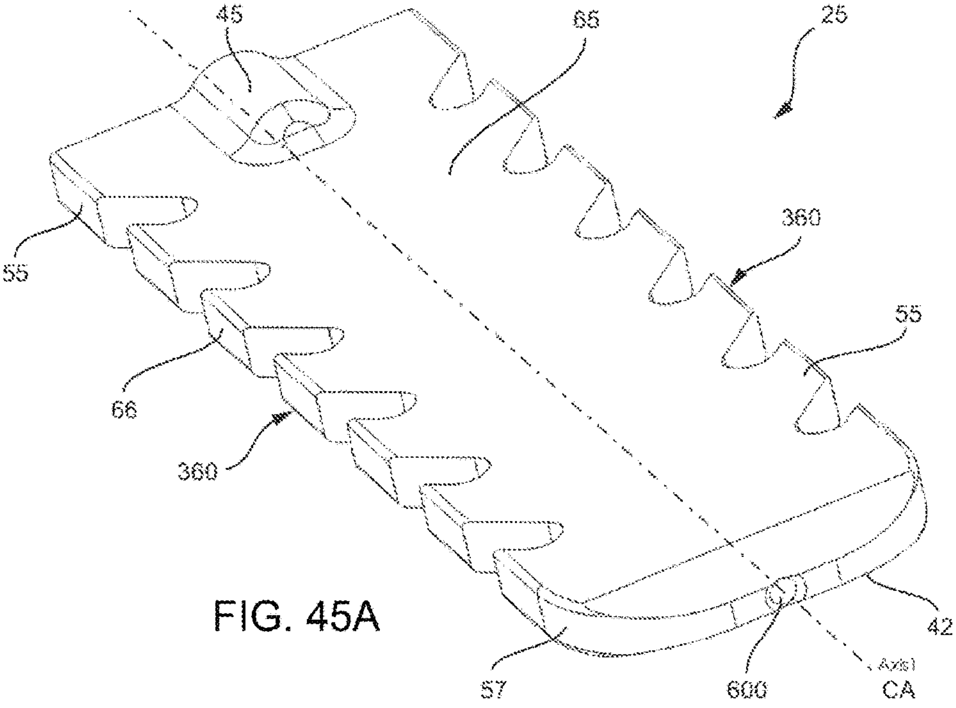
FIG. 45A is an isometric view from a distal end of an implant in accordance with a third embodiment of the present disclosure.
Figure 45B:
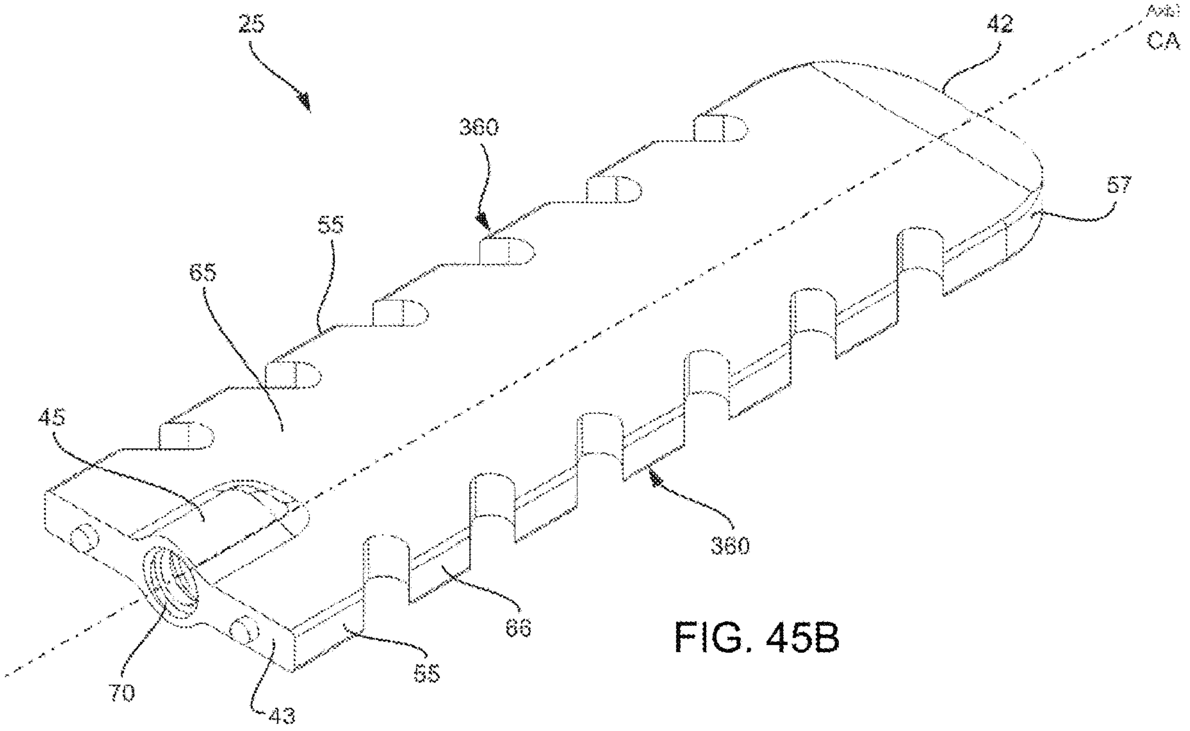
FIG. 45B is another isometric view from a proximal end of the implant of FIG. 45A.

FIG. 45A is an isometric view from a distal end of an implant 25 in accordance with a third embodiment of the present disclosure. FIG. 45B is another isometric view from a proximal end of the implant of FIG. 45A. As shown in FIGS. 45A-B, an insertion element 25 may include a generally planar body 66 having opposing planar surfaces 65. The planar body 66 may include side edges 55 that may have a teeth-type or notch type pattern 360, that are anti-migration edges. The teeth-type pattern 360 may include a number of protruded portions interleaved with a number of recessed regions. The teeth pattern or notches 360 may increase surface friction or resistance to movement of the sacroiliac joint. The notches 360 may generally be evenly distributed along longitudinally extending free edges or ends of the planar members 66. The orientation of each notch 365 may be such that the center line NL of the notch 360 forms an angle with the center axis CA of the insertion element 25 that is between approximately 90 degrees and approximately 15 degrees, with one embodiment having an angle NA of approximately 45 degrees. As indicated in FIG. 45A, each notch 365 may have a length LN between the extreme point on the arcuate end 375 and the outer edge boundary of the notch of between approximately 0.2 mm and approximately 10 mm, with one embodiment having a length LN of approximately 3 mm. Each notch 365 may have a width WN of between approximately 0.5 mm and approximately 20 mm, with one embodiment having a width WN of approximately 2 mm.

In some embodiments, the angles may be less than 80°. In some embodiments, the angles may be less than 70°. In some embodiments, the angles may be less than 60°. In some embodiments, the angles may be less than 50°. In some embodiments, the angles may be less than 40°. In some embodiments, the angles may be less than 50°. In some embodiments, the angles may be less than 30°. In some embodiments, the angles may be less than 20°. In some embodiments, the angles may be greater than 15°. The recessed regions may vary in the recessed depth from the outer edge surface. Similar to other insertion elements, this insert element 25 may also include a cylindrical body with a threaded hole at the proximal end.

Figure 46A:
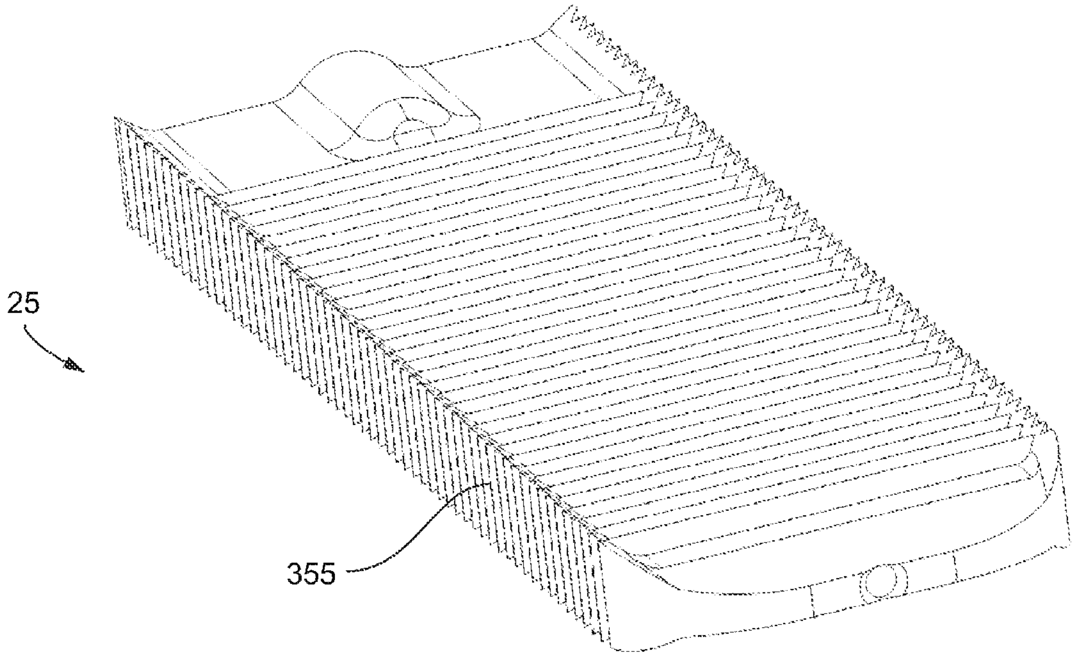
FIG. 46A is an isometric view from a distal end of an implant in accordance with a fourth embodiment of the present disclosure.
Figure 46B:
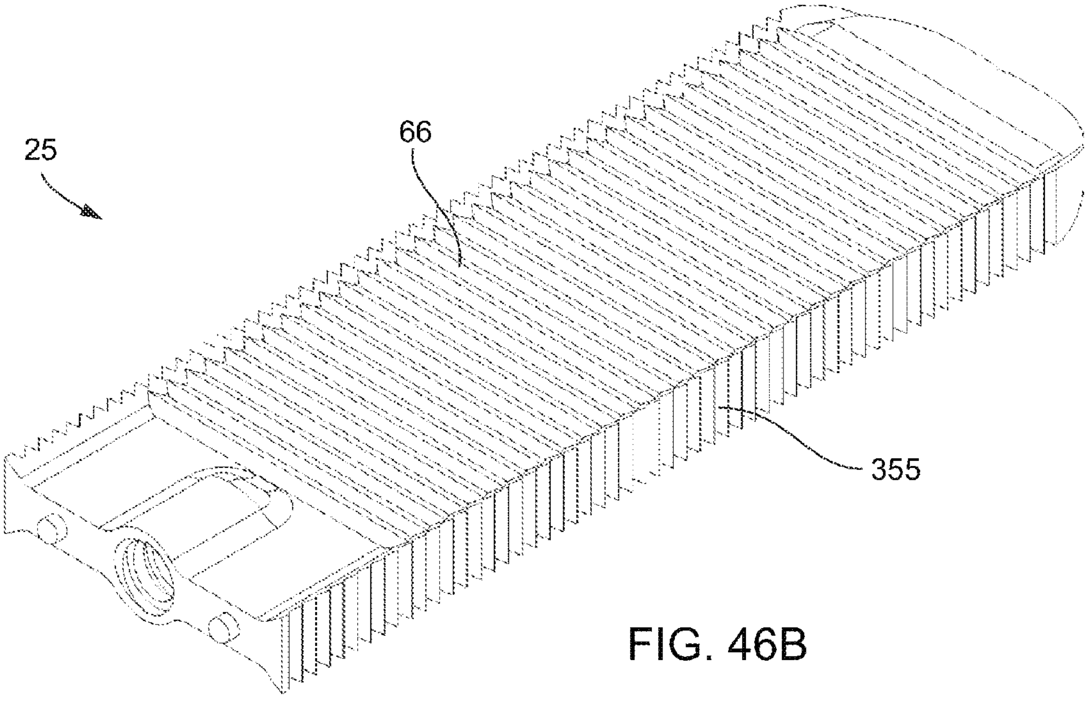
FIG. 46B is another isometric view from a proximal end of the implant of FIG. 46A.
Figure 47A:
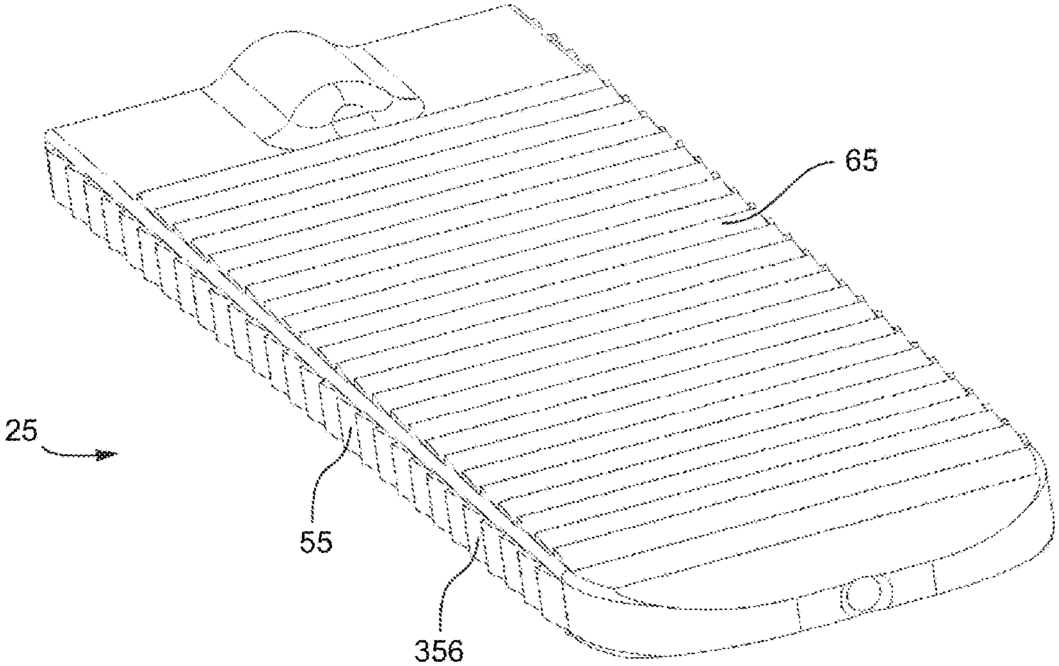
FIG. 47A is an isometric view from a distal end of an implant in accordance with a fifth embodiment of the present disclosure.
Figure 47B:
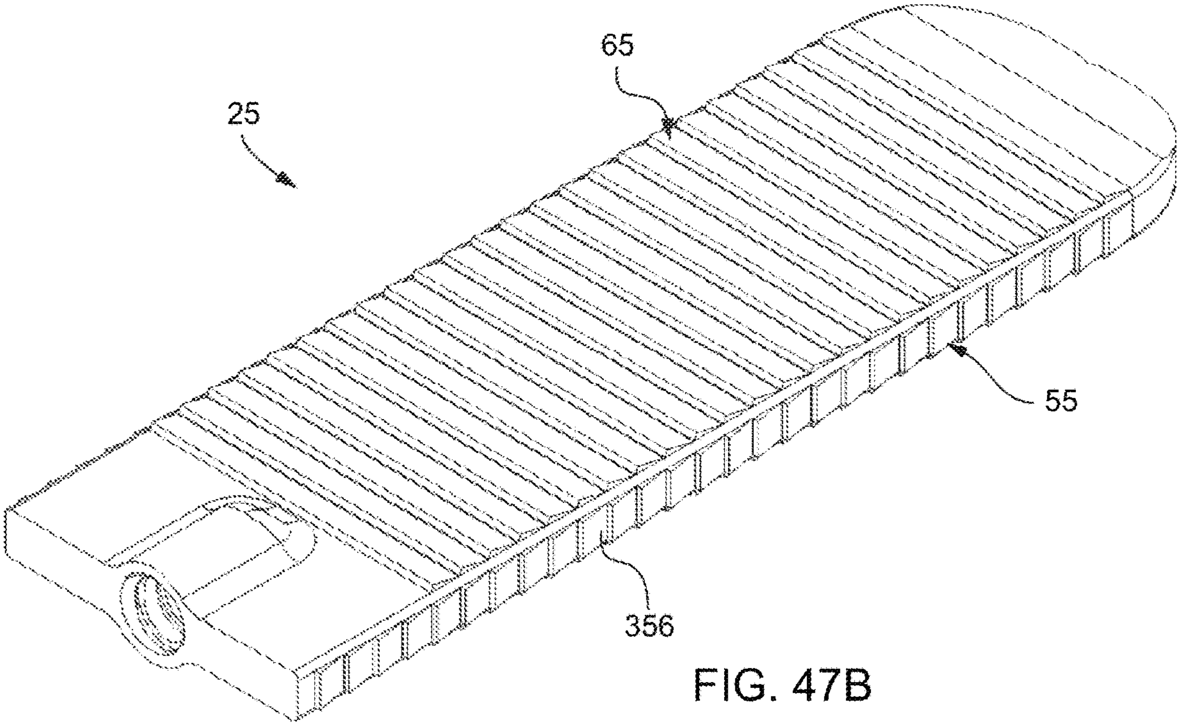
FIG. 47B is another isometric view from a proximal end of the implant of FIG. 47A.

FIG. 46A is an isometric view from a distal end of an implant in accordance with a fourth embodiment of the present disclosure. FIG. 46B is another isometric view from a proximal end of the implant of FIG. 46A. As shown in FIGS. 46A-46B, an insert element 25 may include anti-migration features that are in the form of unidirectional serrated triangular shaped teeth or ridges on opposed main surfaces and side surfaces. The ridges 355 may increase the resistance to movement of the implant when positioned in the sacroiliac joint. The triangular ridges 355 are generally evenly distributed along the planar surfaces 65 of the planar members 66 in ridges 355 that run transverse to the length of the insertion element 25. The anti-migration features 355 are generally similarly distributed along the planar surfaces of the edges of the planar members 66.

Although the anti-migration features 355 are depicted in the form of unidirectional serrated teeth or ridges 355 on each of the textured surfaces of the insertion device, the invention is not so limited and, as to particular embodiments, can be configured to have said features 355 arranged in multiple directions, unidirectional, or a combination of multiple direction on some surfaces of the insertion element and unidirectional on other surfaces of the insertion element. Accordingly, the features 355 can be so arranged on the various surfaces of the insertion element so as to prevent undesired migration in particular directions due to the forces present at the sacroiliac joint. Features 355 may be spike like or pyramidal.

FIG. 47A is an isometric view from a distal end of an implant in accordance with a fifth embodiment of the present disclosure. FIG. 47B is another isometric view from a proximal end of the implant of FIG. 47A. As shown in FIGS. 46A-46B, an insert element 25 may include anti-migration features that are in the form of unidirectional square shaped teeth or ridges 356 on opposed main surfaces 65 and side surfaces 55.

Figure 48A:
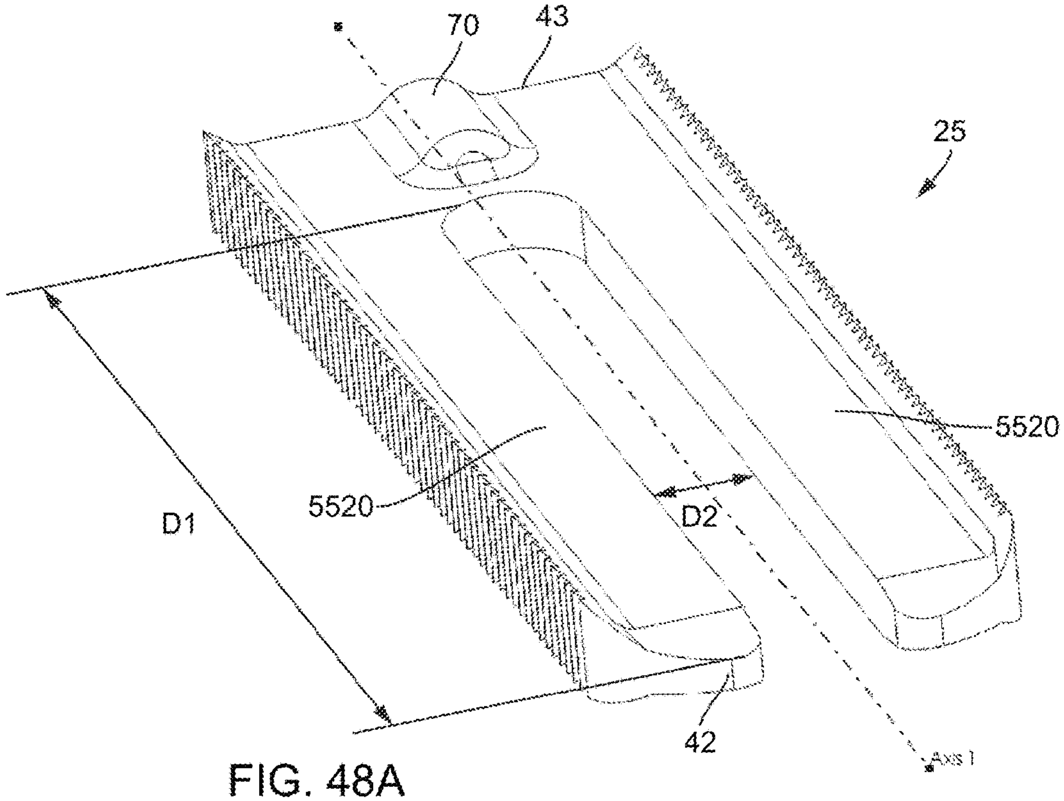
FIG. 48A is an isometric view from a distal end of an implant in accordance with a sixth embodiment of the present disclosure.
Figure 48B:
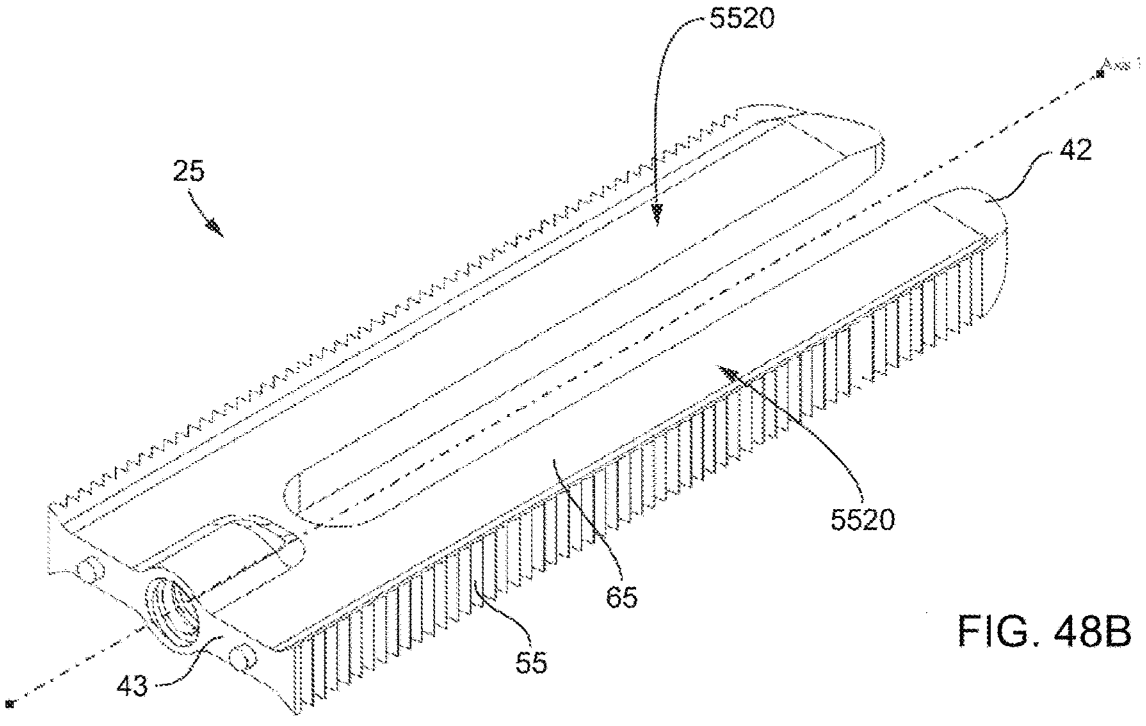
FIG. 48B is another isometric view from a proximal end of the implant of FIG. 48A.

FIG. 48A is an isometric view from a distal end of an implant in accordance with a sixth embodiment of the present disclosure. FIG. 48B is another isometric view from a proximal end of the implant of FIG. 48A. As seen in the figures, the insertion element 25 may include a U-shaped or fork-like generally planar member having a pair of longitudinally extending members or fingers that are coupled together by a proximal end member or portion, which may include a cylindrical body with a threaded hole and a planar portion surrounding the cylindrical body. The cylindrical body has a radius larger than the thickness of the planar member. In some embodiments, the side surfaces may include patterns that may increase resistance to movement of the sacroiliac joint. In some embodiments, the main surfaces of the fingers may also include surface features that may increase resistance to movement of the sacroiliac joint.

Referring still to FIGS. 48A and 48B, the insertion element 25 includes a distal or leading end 42, a proximal or trailing end 43, a length between the distal and proximal ends 42, 43, a longitudinal center axis CA, a longitudinally extending body 45, and two longitudinally extending members 5520 that extend the length between the distal end 42 and proximal end 43. The longitudinally extending members 5520 include a pair of generally opposed faces 65 and side edge surfaces 55. The longitudinally extending members 5520 may radially extend outwardly away from the body 45. From the longitudinal center axis CA of the insertion element 25, the longitudinally extending members 5520 project outwardly on opposite sides of the body 45 and extend distally beyond the most distal region of the body 45 forming the fork-like shape of planar finger members 5520. The longitudinally extending members 5520 define an opening 5521 between the members 5520. The width of the opening 5521 may correspond with a width of a portion of the sacroiliac joint. For example, a width of the opening 5521 may be slightly wider than a width of a widest portion of the intra-articular region of the joint. In this way, the implant 25 may be implanted in the joint 1000 in the intra-articular region such that the longitudinally extending members 5520 extend into the sacrum and ilium, respectively, while the opening 5521 spans the intra-articular region of the joint and, thus, avoids damaging the capsule, cartilage, and synovial fluid in the joint.

The distance D1 spanned by the longitudinally extending members 5520 is between approximately 5 mm and approximately 25 mm, with one embodiment having a distance D1 of approximately 14 mm. The distance D2 of the planar members that project outwardly on opposite sides of the fingers 5520 is between approximately 1 mm and 5 mm, with one embodiment having a distance D2 of approximately 4.5 mm. The distance D3 of the cylindrical threaded opening is between approximately 3 mm and 8 mm, with one embodiment having a distance D3 of 5 mm. Distance D3 may vary along the length of the implant. The cylindrical threaded opening 70 has a radius R of between approximately 2 mm and approximately 4 mm, with one embodiment having a radius R of approximately 2.75 mm.

In one embodiment, the implant 25 has a length L of between approximately 5 mm and approximately 30 mm, with one embodiment having a length L of approximately 20 mm.

Figure 48C:
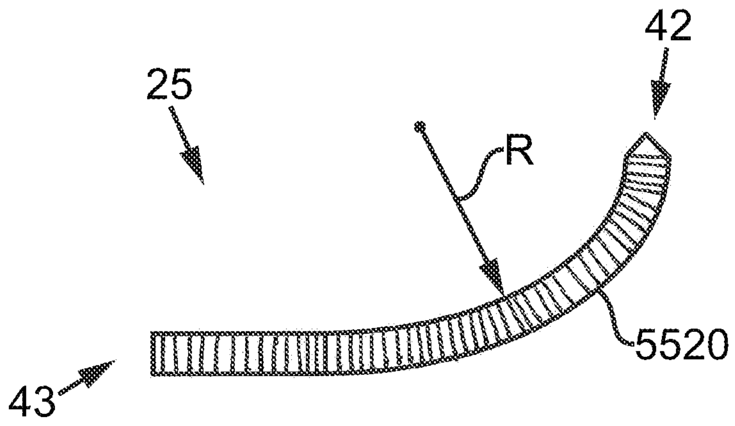
FIG. 48C is a side view of a curved implant in accordance with a seventh embodiment of the present disclosure.
Figure 48D:
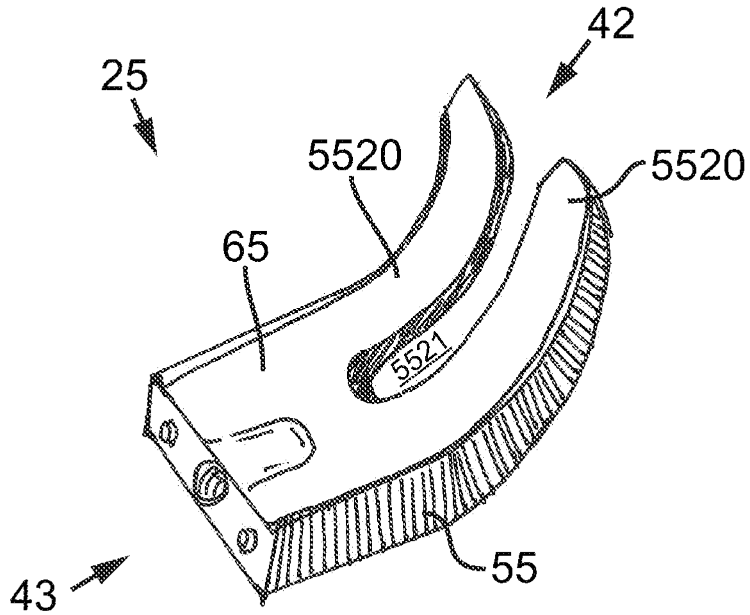
FIG. 48D is an isometric view from a proximal end of the implant of FIG. 48C.

Reference is now made to FIGS. 48C-48D, which are, respective, side and isometric views of the implant of FIG. 48A-48B, except the longitudinally extending members 5520 of the implant 25 in FIGS. 48C-48D is curved as it extends from the proximal end 43 to the distal end 42. The curve of the members 5520 defines a radius R, which may be about 20 mm to about 60 mm. In certain embodiments the radius R may be about 60 mm. In certain embodiments the radius R may be about 55 mm. In certain embodiments the radius R may be about 50 mm. In certain embodiments the radius R may be about 45 mm. In certain embodiments the radius R may be about 40 mm. In certain embodiments the radius R may be about 35 mm. In certain embodiments the radius R may be about 30 mm. In certain embodiments the radius R may be about 25 mm. In certain embodiments the radius R may be about 20 mm. In certain embodiments, an arc of the curved portion of the implant 25 may be about 40, 50, 60, 70, 80, 90, 100, 110, or 120 degrees. In certain embodiments, the implant 25 has a length L that is similar to that of the implant 25 in FIGS. 48A-48B. The implant 25 may include a ratio of length L to radius of curvature R or a ratio of radius of curvature R to length L as defined by the measurements given herein.

The implant 25 of FIGS. 48C-48D would look similar to the cross-sectional views shown in FIGS. 37-38, except the implant 25 would be curved along a longitudinal extension of the implant 25. This type of implant 25 may be useful when implanted in the region of the intra-articular region of the sacroiliac joint because the opening 5521 in the implant 25 could span the articular region and follow the contour of intra-articular region as it transitions from the caudal region to the cranial region (i.e., because of the curved nature of the longitudinally extending members 5520).

This type of implant may be used in the intra-articular region or extra-articular region. The intra-articular region has a higher bone density than the extra-articular region. This may make the intra-articular region a better implant location, for implants that can avoid damaging the intra-articular region, because the implant can anchor into stronger bone.

J. Materials, Coatings, and Agents

Embodiments of the sacroiliac joint insertion element can further include a coat coupled, generated or integral to all or a part of the external surface of the sacroiliac joint insertion element, elongate bodies, or pins. The coat can be of any composition that can be coupled to the sacroiliac joint insertion element capable of biocompatible osseointegration with the bone of the ilium 1005 and sacrum 1004, such as pure alumina, titanium-dioxide, hydroxyapatite, calcium triphosphate, or the like. As a non-limiting example, the coat can be applied by plasma spraying with a plasma torch, plasmatron or a plasma gun. Alternately, the coat can be achieved by producing a surface roughness, porosity, or irregularity of the sacroiliac joint insertion element by sand blasting, bead blasting, molding, or the like. The coat can have a thickness in the range of about 40 micrometers and about 100 micrometers. Again, embodiments of the sacroiliac joint insertion element can be configured as a material having interconnecting pores throughout such as TRABECULAR METAL available from Zimmer, P.O. Box 708, 1800 West Center Street, Warsaw, Ind. 46581-0708 or a metallic foam such as a titanium foam available from the National Research Council Canada, 1200 Montreal Road, Bldg. M-58, Ottawa, Ontario, Canada or fully-engineered, porous, titanium structures such as TRABECULITE available from Tecomet, 115 Eames Street, Wilmington, Mass. 01887.

One or more biologically active agent(s) can be applied directly to the external surface of the sacroiliac joint insertion element or can be mixed with a biocompatible material or biocompatible biodegradable material or biocompatible osseointegratable material which can be applied to the external surface of the sacroiliac joint insertion element or otherwise made a part of the sacroiliac joint insertion element. As to particular embodiments of the insertion element, the biologically active agent(s) can be mixed with an amount of a biocompatible or biodegradable material or osseointegratable material and located within one or more of the aperture elements.

Biocompatible means the ability of any material to perform the intended function of an embodiment of the invention without eliciting any undesirable local or systemic effects on the recipient and can include non-biodegradable materials such as: ceramic; metals or steels such as titanium alloys or rigid polymeric materials or rigid laminate materials or composites which include suitably dimensioned particles of metals or steels dispersed within rigid laminate materials, or suitably sized particles of biocompatible materials suitably bound or formed to provide configurations, polyurethanes, polyisobutylene, ethylene-alpha-olefin copolymers, acrylic polymers and copolymers, vinyl halide polymers and copolymers, polyvinyl esters, polyvinylidene chloride, polyacrylonitrile, polyvinyl ketones, polyvinyl aromatics such as polystyrene, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyesters, epoxy resins, rayon-triacetate, cellophane, polyether ether ketone (PEEK), polyetherketoneketone (PEKK), bone-from-wood available from the Istituto di Scienza e Tecnologia dei Mareriali Ceramici, Faenza, Italy, or the like, or biodegradable materials, as herein described.

Biodegradable means the ability of any biocompatible material to breakdown within the physiological environment of the sacroiliac joint by one or more physical, chemical, or cellular processes at a rate consistent with providing treatment of a condition of the sacroiliac joint at a therapeutic level controllable by selection of a polymer or mixture of polymers (also referred to as polymeric materials), including, but not limited to: polylactide polymers (PLA), copolymers of lactic and glycolic acids (PLGA), polylactic acid-polyethylene oxide copolymers, poly(.epsilon.-caprolactone-co-L-lactic acid (PCL-LA), glycine/PLA copolymers, PLA copolymers involving polyethylene oxides (PEO), acetylated polyvinyl alcohol (PVA)/polycaprolactone copolymers, hydroxybutyrate-hydroxyvalerate copolymers, polyesters such as, but not limited to, aspartic acid and different aliphatic diols, poly(alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA), aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biologically active agents are those agents or mixture of agents which can be varied in kind or amount to provide a therapeutic level effective to mediate the formation or healing of bone, cartilage, tendon, or to reduce, inhibit, or prevent a symptom of a condition of the sacroiliac joint subsequent to placement of an embodiment of the fixation fusion insertion element within the sacroiliac joint such as infection or pain and without limitation can include agents that influence the growth of bone, demineralized bone matrix, stem cells, allografts, autografts, xenografts, bone forming protein whether naturally occurring, synthetic, or recombinate, growth factors, cytokines, bone morphogenetic protein 2, bone morphogenetic protein 7, analgesics, anesthetics, anti-inflammatory agents, antibacterials, antivirals, antifungals, antiprotozoals, anti-infectives, antibiotics such as aminoglycosides such as gentamicin, kanamycin, neomycin, and vancomycin; amphenicols such as chloramphenicol; cephalosporins, such as cefazolin HCI; penicillins such as ampicillin, penicillin, carbenicillin, oxycillin, methicillin; lincosamides such as lincomycin; polypeptide antibiotics such as polymixin and bacitracin; tetracyclines such as tetracycline, minocycline, and doxycycline; quinolones such as ciprofloxacin, moxifloxacin, gatifloxacin, and levofloxacin; anti-viral drugs such as acyclovir, gancyclovir, vidarabine, azidothymidine, dideoxyinosine, dideoxycytosine; analgesics, such as codeine, morphine, ketorolac, naproxen, an anesthetic, lidocaine; cannabinoids; antifungal agents such as amphotericin; anti-angiogenesis compounds such as anecortave acetate; retinoids such as tazarotene, steroidal anti-inflammatory agents such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide; or allograft cellular matrix containing viable mesenchymal stem cells such as OSTEOCEL PLUS available from NuVasive, Inc., 7475 Lusk Blvd., San Diego, Calif. 92121 USA, and any of their derivatives, whether separately or in combinations thereof.

The biologically active agent(s) can be dispersed throughout a biocompatible or biocompatible biodegradable material (or mixture of biocompatible materials or mixture of biocompatible biodegradable materials) by mixing biologically active agent(s) into the melted biocompatible or biodegradable polymer and then solidifying the resulting material by cooling, having the biologically active agent(s) substantially uniformly dispersed throughout. The biodegradable material or biocompatible material or mixture thereof can be selected to have a melting point that is below the temperature at which the biologically active agent(s) becomes reactive or degrades. Alternatively, the biologically active agent(s) can be dispersed throughout the biocompatible or biodegradable material by solvent casting, in which the biocompatible or biodegradable material is dissolved in a solvent, and the biologically active agent(s) dissolved or dispersed in the solution. The solvent is then evaporated, leaving the biologically active agent(s) in the matrix of the biocompatible or biodegradable material. Solvent casting requires that the biocompatible or biodegradable material be soluble in organic solvents. Alternatively, the insertion element can be placed in a solvent having a concentration of the biologically active agent(s) dissolved and in which the insertion element or the biocompatible or biocompatible biodegradable material located in the aperture elements, or applied to the external surface, swells. Swelling of the insertion element or portions thereof draws in an amount of the biologically active agent(s). The solvent can then be evaporated leaving the biologically active agent(s) within the biocompatible or biocompatible biodegradable material. As to each method of dispersing the biologically active agent(s) throughout the biocompatible or biodegradable biocompatible material of or coupled to the insertion element, therapeutic levels of biologically active agent(s) can be included in biocompatible biodegradable material to provide therapeutically effective levels of the biologically active agent to the sacroiliac joint to treat a particular sacroiliac joint condition.

Other non-active agents may be included in the biocompatible biodegradable material for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA or other appropriate agencies in the United States or foreign countries, for the desired route of administration. Electrolytes such as sodium chloride and potassium chloride may also be included in the formulation.

K. Sensors and Display

The diagnostic system may include sensors for determining position changes from original positions of the pins or bars, which may give quantitative indication of the movement of the ilium 1005 or sacrum 1004 near the joint. The sensors may be placed near the joint. The pins or bars may be manipulated to cause either linear movement or angular movement of the joint. The pins or bars may be held at certain positions for a period of time to either reduce the pain or to cause or reproduce the pain in the patient. The system may include pressure sensors for measuring forces. The sensors may be placed near the joint. In particular, the sensor may be positioned in the plane of the joint, across the joint, or outside the joint.

If positioned in the plane of the joint, a portion of the joint may be removed for insertion of the sensor. In this instance, the sensor may be paddle shaped and may match a shape of a portion of the joint (e.g., intra-articular region). If positioned across the joint, a portion of the ilium and sacrum may be bored-out to provide a passageway for the sensor. If positioned outside the joint, the sensor may bridge the joint and be positioned partially on the ilium and partially on the sacrum. Or, the sensor may be positioned on the ligaments surrounding the joint.

The sensor may be a piezoelectric sensor or transducer. The sensor may sense and transmit measurements that correspond to movement (e.g., bending, twisting, elongation, compression) that may be further associated with pain or discomfort. The patient may, for example, log the points in time that correspond with pain and discomfort and the points may be correlated with the measurements of the sensor to diagnose the types of movements associated with the patient's pain. The sensor may transmit the measurements through an application on the patient's cell phone, for example. The movements associated with pain may be used by the doctor to diagnose an ailment of the sacroiliac joint.

The sensors or transducers may also be positioned on any of the devices described in this application. For example, the implant as shown in FIG. 13B may include a sensor positioned on the coupling member 80 that is positioned outside the joint. Alternatively, any of the implants, for example as shown in FIGS. 43A-48D may include a sensor or transducer on or integrated with the implant. In this way, the implant may be used, temporarily perhaps, while measurements of compression, distraction, and bending, among others, are taken during a period of time. The information associated with the measurements may be used by the doctor to further diagnose the need for a permanent fixation of the joint.

When used with the tools and systems described herein, the sensors and transducers may be useful in providing a vast amount of data across of a large span of time to the doctor for his or her use in diagnosing an ailment of the sacroiliac joint. Measuring distraction and compression, among other metrics, while in a doctor's office is certainly helpful, but obtaining more data over an extended period of time provides even more data that can be used in the diagnosis.

The system may also include a display that may reveal quantitative information, such as angle, displacement, or holding time. The sensors are in communication with the display to provide the quantitative information. The measured angles, displacements or holding time may be stored on a storage device.

Systems, devices and methods described herein may use oscillatory motion for the diagnosis of a sacroiliac joint ailment. In certain embodiments, a method of diagnosing a medical condition associated with a sacroiliac joint of a patient may include delivering a first member in close proximity to a sacroiliac joint region. The first member may be a pin as described herein an implant or anchor. Subsequently, a force may be applied to the first member. The force may include a periodic oscillation. The periodic oscillation may be applied through via an eccentric rotating mass actuator, a linear resonant actuator, a piezo module, or an electro-active polymer actuator, among others. The periodic oscillation may include a linear displacement comprising an amplitude within a range of about 0.25 mm to about 0.5 mm, about 0.4 mm to about 0.75 mm, about 0.6 mm to about 1 mm, about 0.8 mm to about 1.2 mm, or about 1 mm to about 2 mm. The periodic oscillation may include proportional amplitudes of displacement such that the periodic oscillation resembles a sinusoidal waveform. In certain instances, the displacement may occur in a direction along a longitudinal axis of the first member. In certain instances, the displacement may occur in a direction generally transverse to a longitudinal axis of the first member. And, in certain instances, the periodic oscillation is may be caused by an electrically or pneumatically driven motor comprising a drive shaft with an off-balanced mass coupled thereto.

Based on a patient's pain, discomfort, or alleviation of the pain or discomfort, a doctor may be able to diagnose a sacroiliac joint ailment based on the oscillatory vibrations delivered to the patient through the first member.

L. Delivery of the Implant

The following discussion will focus on delivering the implant into the sacroiliac joint region. The discussion will further focus on the implant and its relation to the various regions (e.g., intra-articular, extra-articular) of the sacroiliac joint. While the pins, described previously, are not shown in the following figures, it is intended that the implant may be delivered with or without the aid of the pins.

Figure 49A:
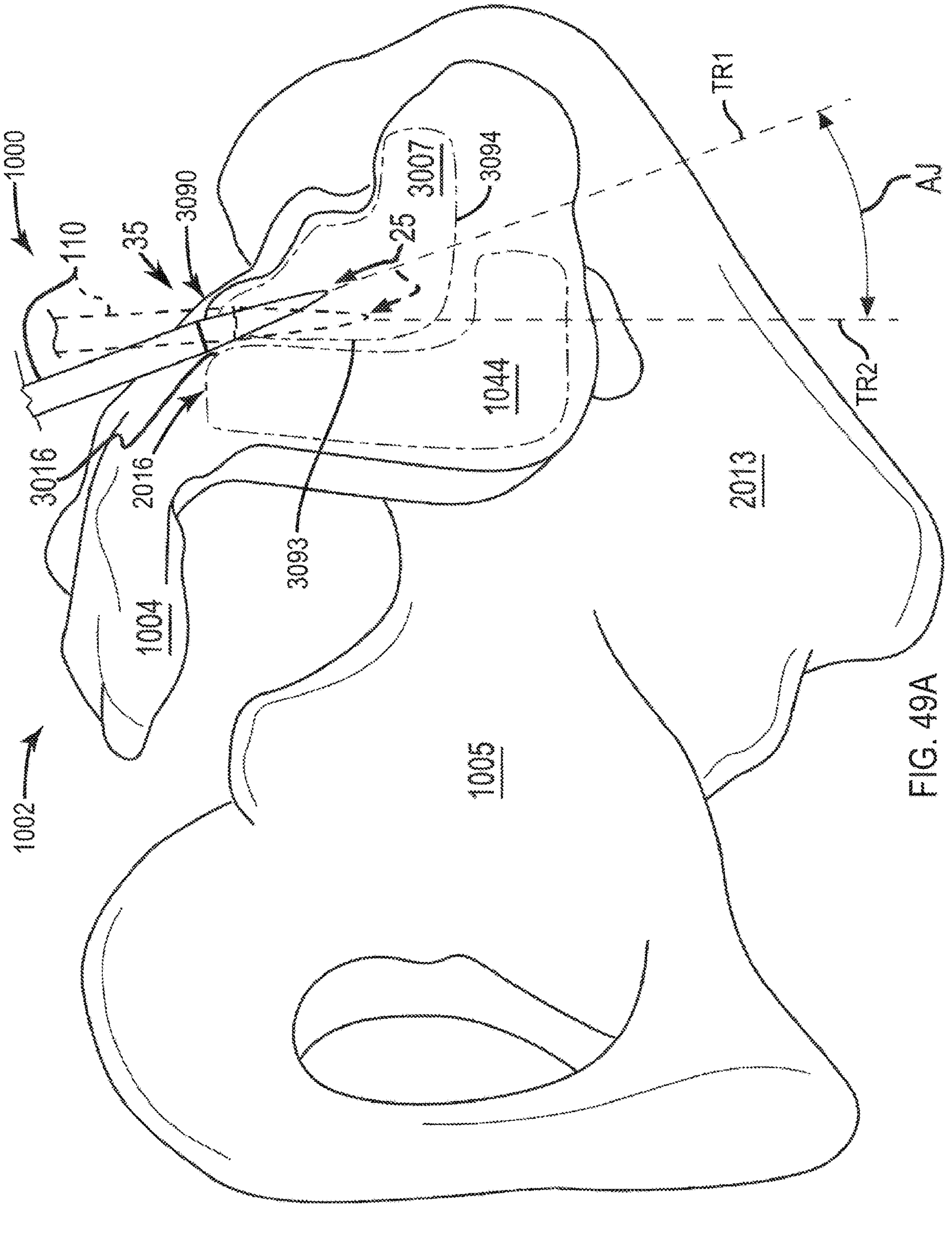
FIG. 49A is a lateral side view of the hip region of the patient with a nearest ilium removed and an implant positioned in the extra-articular region of the sacroiliac joint.

To begin, reference is made to FIG. 49A, which is a lateral side view of a hip region 1002 of a patient showing a sacrum 1004 and an ilium 1005 with a nearest ilium 1005 removed to more clearly depict the intra-articular region 1044 and the extra-articular region 3007 of the sacroiliac joint 1000. Preparing an access region from the patient's skin to the patient's bone is described in this and other applications, such as, U.S. patent application Ser. No. 12/998,712, filed May 23, 2011 entitled SACROILIAC JOINT FIXATION FUSION SYSTEM and Ser. No. 13/236,411, filed Sep. 19, 2011 entitled SYSTEMS FOR AND METHODS OF FUSING A SACROILIAC JOINT. These applications are hereby incorporated by reference in their entireties. As seen in FIG. 49A, the implant 25 may include a distal end and be coupled with a distal end 35 of an implant arm 110. The distal end of the implant 25 may be posteriorly delivered into the hip region 1002 with a general anterior trajectory. The implant in solid line is shown entering the posterior inferior access region 3090 of the extra-articular region 3007 of the sacroiliac joint 1000 along a trajectory TR1. Depending on the shape and configuration of the implant 25, it may penetrate into both the ilium (nearest ilium not shown) and the sacrum 1004 and extend across the joint 1000.

The dotted line depiction of the implant shows another trajectory TR2 of the implant as it extends into the posterior inferior access region 3090 of the extra-articular region 3007 of the joint 1000. In both trajectories TR1, TR2, the implant avoids penetration into the intra-articular region 1044 of the joint 1000. The intra-articular region 1044 of the joint includes a capsule containing cartilage and synovial fluid. For this reason, implanting an implant within the extra-articular region 3007, as opposed to the intra-articular region 1044, avoids damaging to the capsule in the event that a permanent fusion procedure is unnecessary. That is, it may be desirable to avoid damaging the intra-articular region 1044 of the joint 1000 until a permanent fusion procedure within the intra-articular region 1044 occurs.

Accordingly, the doctor or medical professional may deliver the implant along trajectories TR1, TR2 or at any points in between. Trajectory TR1 is generally parallel to the caudal boundary segment 3093. Trajectory TR2 extends an angle AJ cranial of trajectory TR1 towards a mid-section of the anterior boundary segment 3094. In certain embodiments, the angle AJ may be between 5 degrees and 35 degrees. In certain instances, the angle AJ may be about 5 degrees. In certain instances, the angle AJ may be about 10 degrees. In certain instances, the angle AJ may be about 15 degrees. In certain instances, the angle AJ may be about 20 degrees. In certain instances, the angle AJ may be about 25 degrees. In certain instances, the angle AJ may be about 30 degrees. In certain instances, the angle AJ may be about 55 degrees.

Still referring to FIG. 49A and in certain embodiments of the implant (shown in FIG. 48A-48B), the implant may be delivered into the sacrum 1004 and ilium (nearest is hidden) in the region of the intra-articular region 1044 without damaging the capsule, cartilage, and synovial fluid of the joint. In these configurations, the distal opening of the implant occupies the joint space such that the capsule of the joint is not damaged or disturbed by the body of the implant. That is, the implant may be delivered such that it is in-line with the posterior inferior access region 2016 of the intra-articular region 1044. A sacral side of the implant 25 may be delivered into the sacrum 1004 in the region just medial of the posterior inferior access region 2016 and an ilial side of the implant may be delivered into the ilium 1005 in the region just lateral of the posterior inferior access region 2016. On the ilium 1005, the ilial side of the implant may extend into the ilium between the posterior superior iliac spine 2004 and the posterior inferior iliac spine 2006.

Figure 49B:
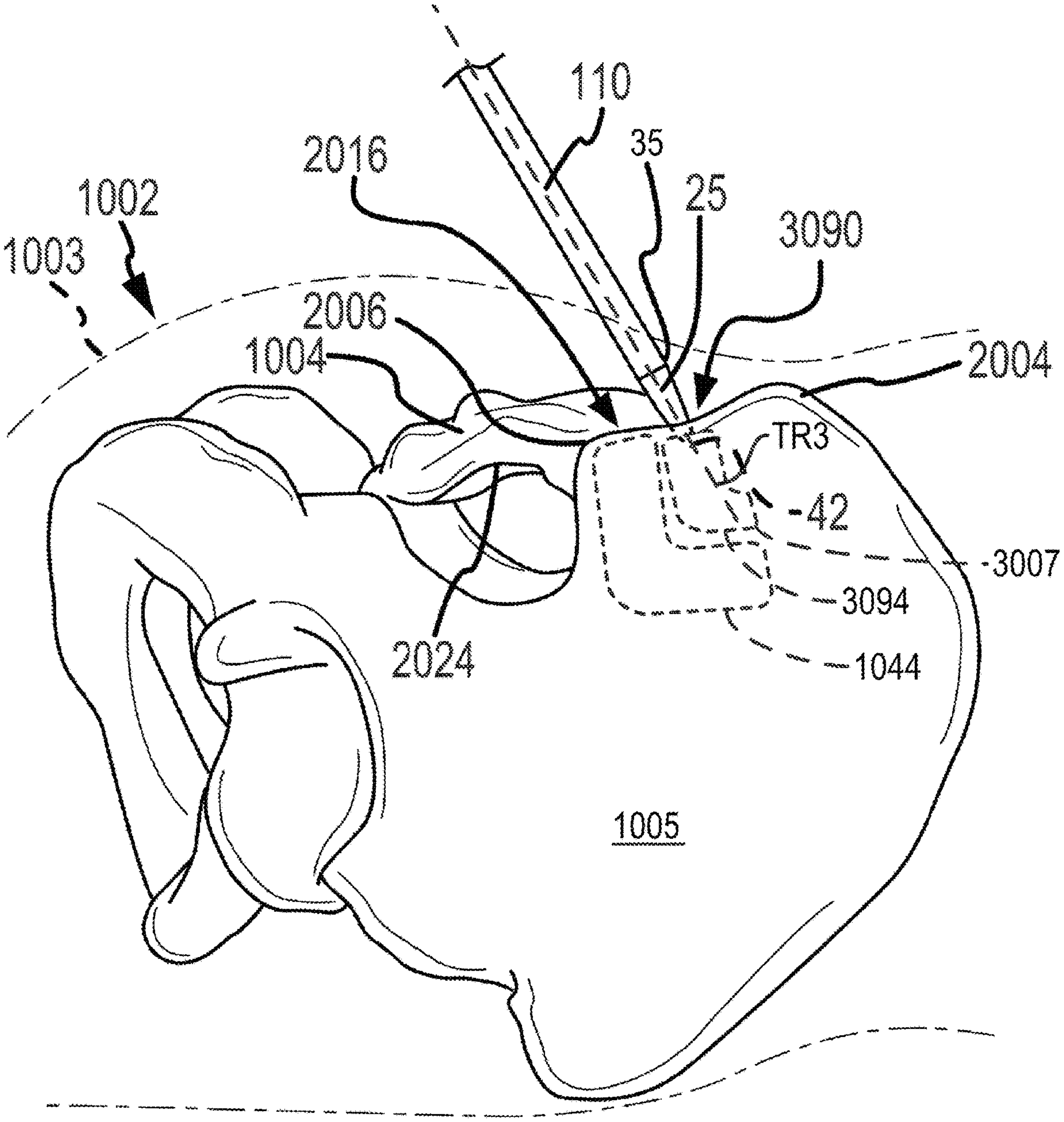
FIG. 49B is a lateral side view of the hip region of the patient showing an implant coupled with a delivery tool positioned for delivery into the sacroiliac joint.
Figure 49C:
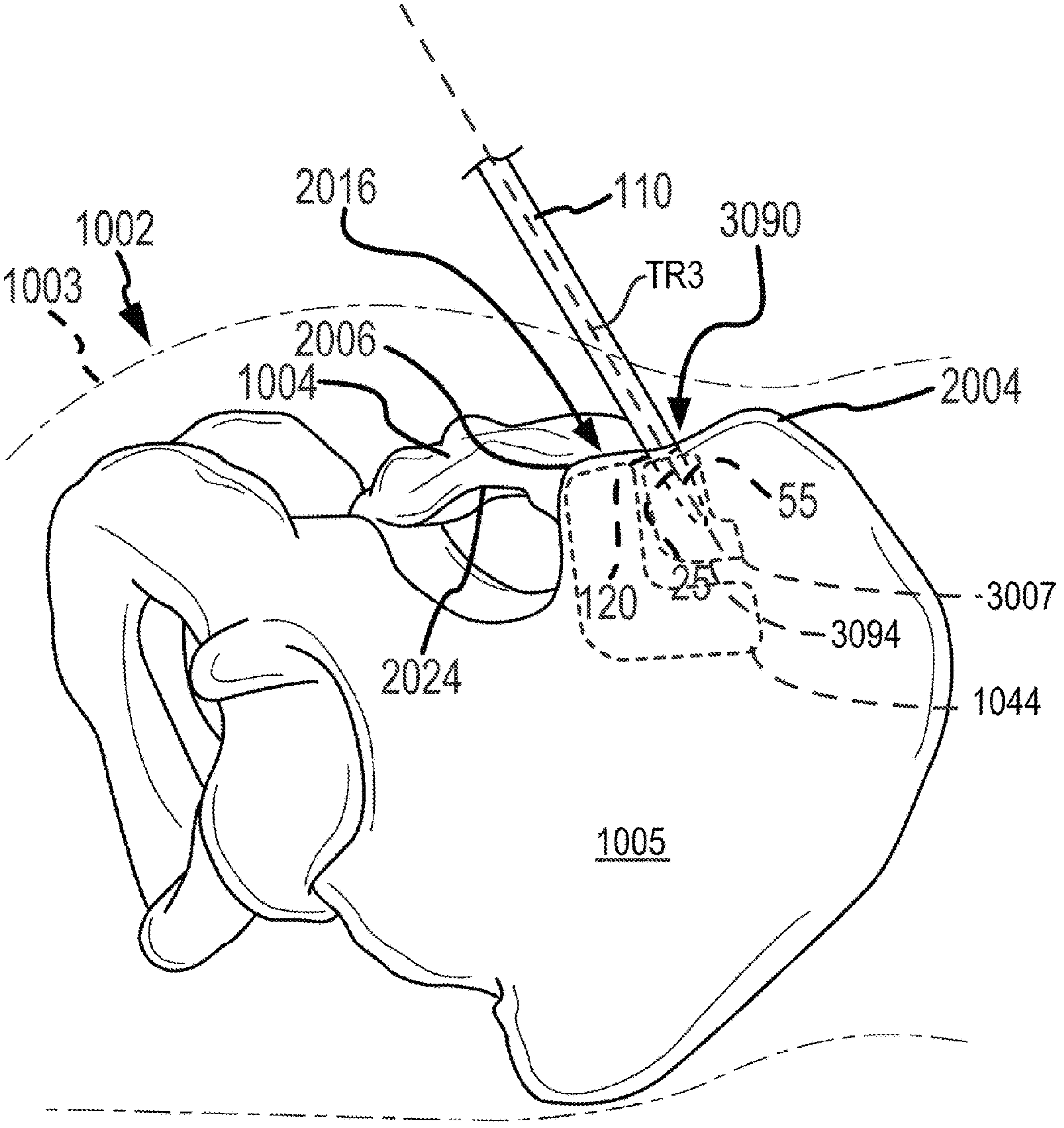
FIG. 49C is the same view as FIG. 48B, except the implant has been delivered into the extra-articular region of the sacroiliac joint.

Turning to FIGS. 49B-49C, which are lateral views of the hip region 1002 showing the patient's skin 1003 in dotted line, the implant 25, being coupled with a distal end 35 of the shaft 110 of a delivery tool, is being delivered into the extra-articular region of the sacroiliac joint via a posterior approach. FIG. 49B shows the distal end of the implant 25 entering the extra-articular region 3007 of the joint. A trajectory TR3 of the implant is oriented to extend through the posterior inferior access region 3090 and extend superior-anterior towards a mid-section of the anterior boundary segment 3094 of the extra-articular region 3007. FIG. 49C shows the implant 25 extending into the caudal region of the extra-articular region 3007 of the joint.

Figure 50:
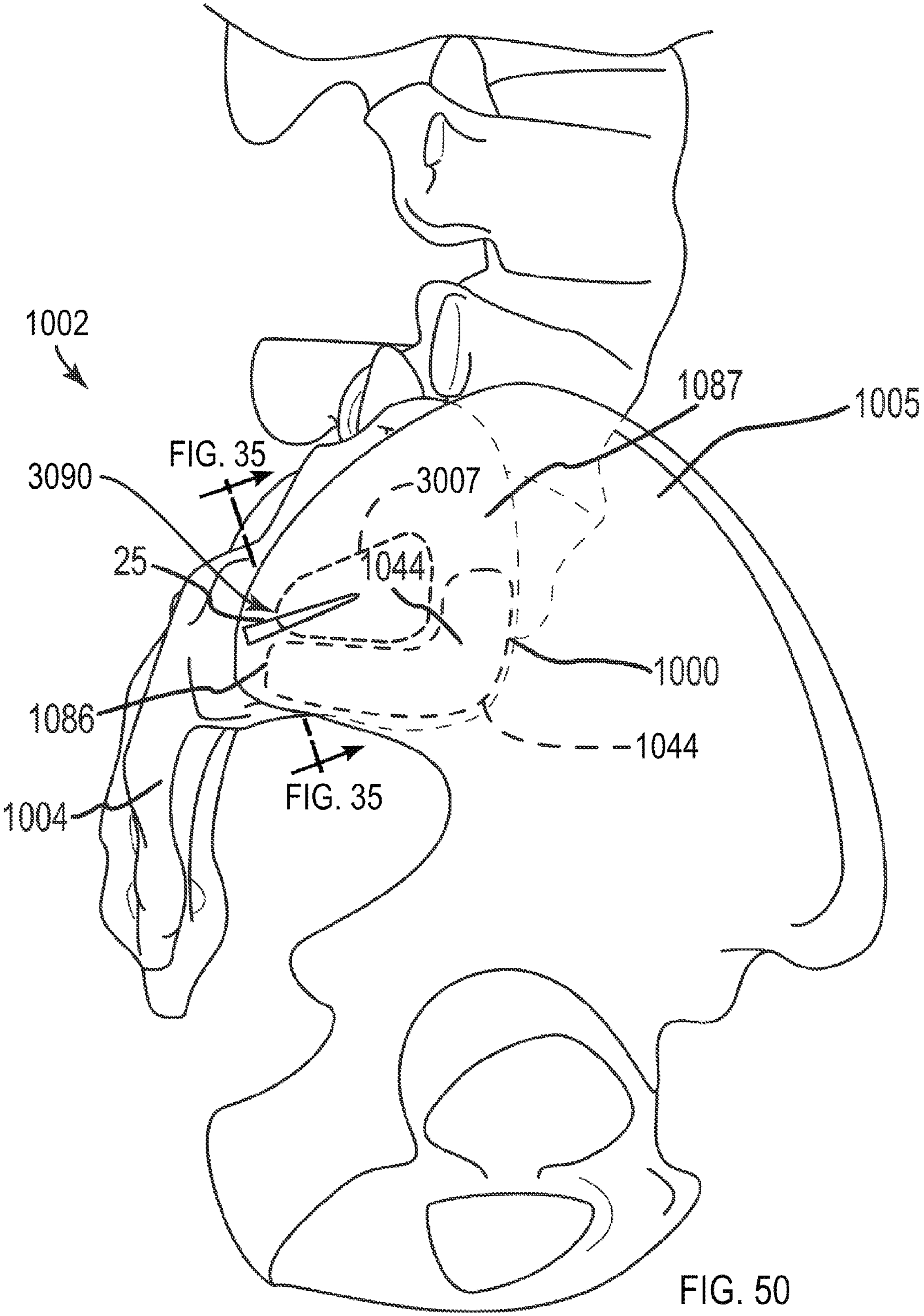
FIG. 50 is a lateral side view of the hip region of the patient showing positioning of the implant within the extra-articular region of the sacroiliac joint.

FIG. 50, which is a lateral side view of the hip region 1002 with a nearest ilium hidden from view to more clearly show the regions of the sacroiliac joint 1000, depicts the implant 25 positioned in the extra-articular region 3007 of the sacroiliac joint 1000. As seen in the figure, the implant is de-coupled from the shaft 110 of the delivery tool such that the implant 25 resides in the joint 1000, extending into the posterior inferior access region 3090 of the extra-articular region 3007. As stated previously, delivering the implant 25 in this region 3007 avoids disruption of the capsule, cartilage, and fluid within the intra-articular region 1044 of the joint 1000. In this way, if it is determined that a permanent implant is not needed, the implant (i.e., in the extra-articular region 3007) may be removed and the joint 1000 has not been irreparably damaged by, for example, removing the cartilage.

Figure 51:
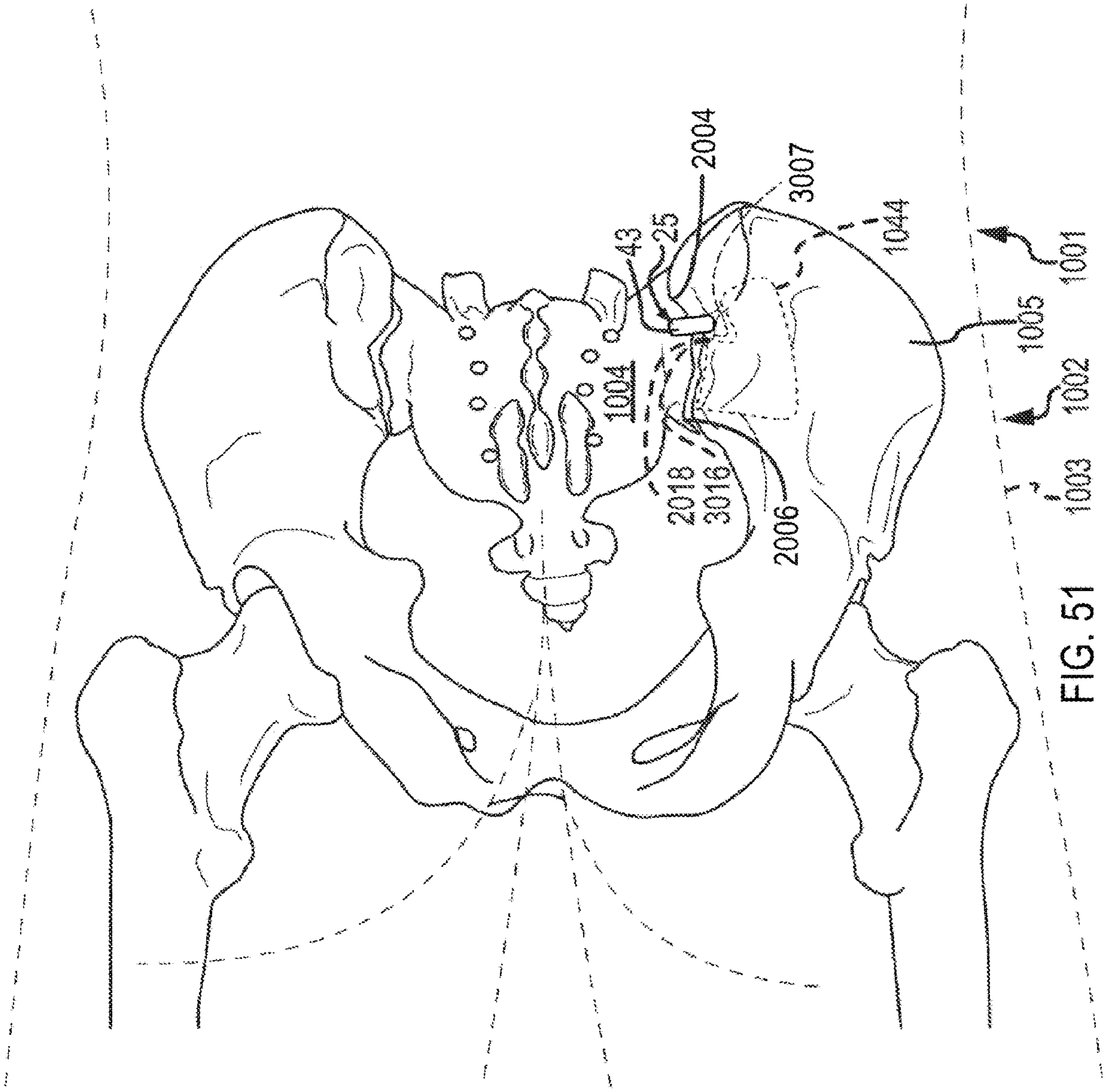
FIG. 51 is a posterior view of the hip region of the patient showing the implant within the extra-articular region of the sacroiliac joint.

Reference is now made to FIG. 51, which shows a posterior view of FIG. 50 showing the implant 25 positioned in the sacrum and ilium above the intra-articular region 1044. As seen in the figure and as described previously, the implant 25 extends across the extra-articular region 3007 of the joint and extends into the ilium 1005 between the posterior superior iliac spine 2004 and the posterior inferior iliac spine 2006.

Once the temporary implant is delivered into the patient and the delivery tool is removed from the implant, the various surgical tools may be removed from the incisions and the incision may be sterilized and closed. The patient may move about and simulate movements that would previously cause pain (e.g., flexing at hips). The implant may remain in the patient for a given period of time (e.g., minutes, hours, days) to determine if fusion of the joint is effective in eliminating or alleviating the pain. In certain patients, for example, a petite individual with a low activity level, if the temporary implant relieves the pain, it may be suitable to allow the implant to remain in the patient's body. Perhaps no other fusion procedure is necessary. Or, perhaps a subsequent implant may be delivered into the joint to permanently fuse the joint.

In certain instances, the temporary implant may be removed by coupling the shaft of the delivery tool with the implant and removing the implant from its position within the joint. This procedure may be done just prior to delivering a permanent implant into the joint in either the intra-articular region or the extra-articular region. If a permanent implant is to be delivered into the joint region, the joint may be prepped for the procedure according to U.S. patent application Ser. No. 14/514,221, filed Oct. 15, 2014, which is hereby incorporated by reference in its entirety. It is noted that the temporary implant positioned within the extra-articular region need not be removed prior to insertion of a permanent implant in the intra-articular region of the joint.

M. Tools, Systems, and Methods for Bone Pin Delivery and Manipulation

Figure 52A:
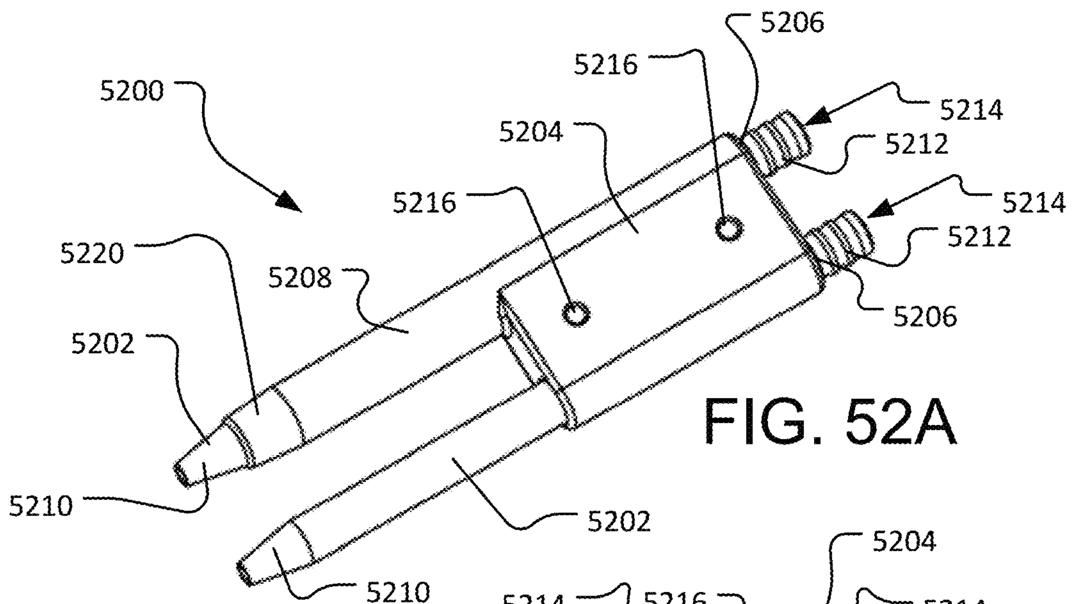
FIG. 52A is an isometric front view of a parallel pin guide supporting a pair of dilators.
Figure 52B:
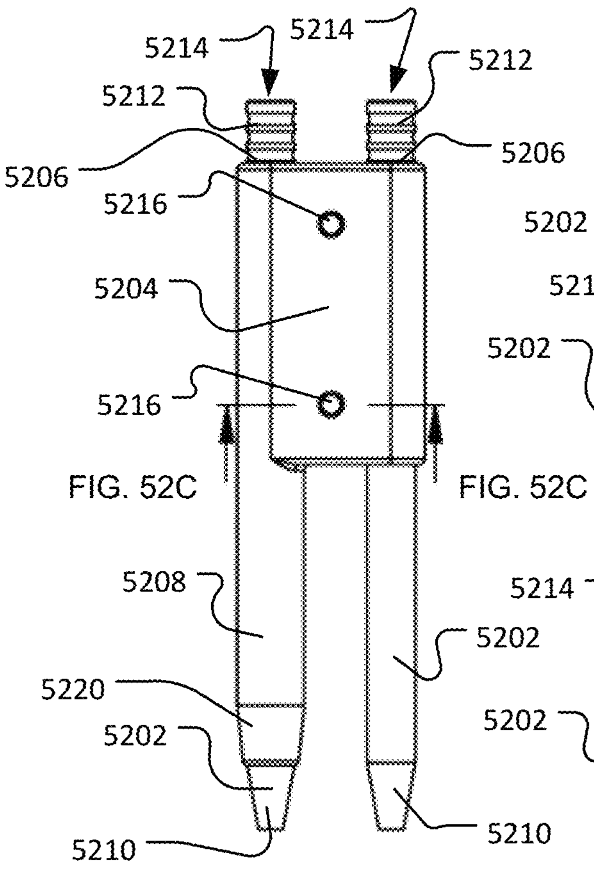
FIG. 52B is a front view of the parallel pin guide supporting the pair of dilators.
Figure 52C:
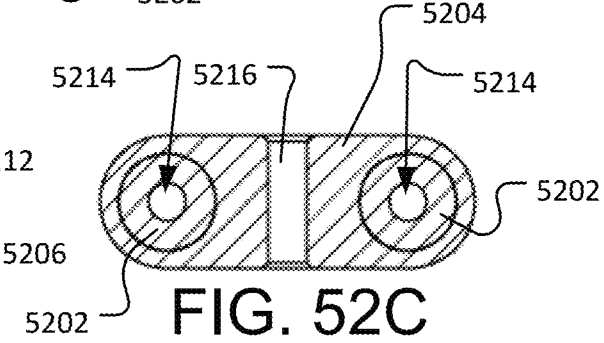
FIG. 52C is a cross-sectional view of the parallel pin guide supporting the pair of dilators.
Figure 52D:
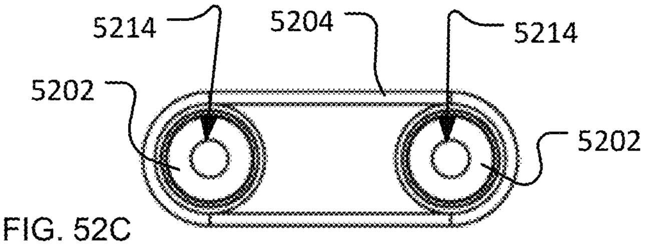
FIG. 52D is a top view of the parallel pin guide supporting the pair of dilators.
Figure 52E:
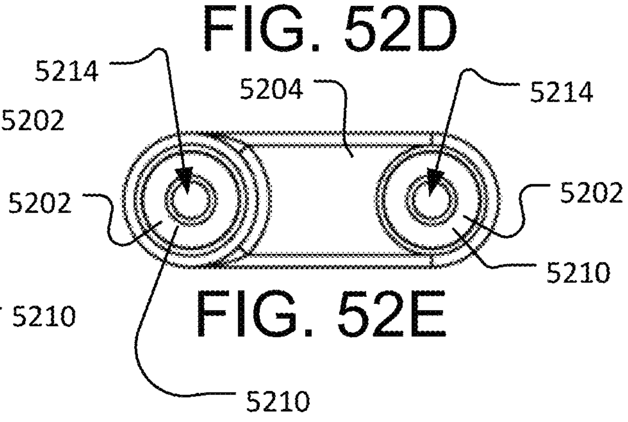
FIG. 52E is a bottom view of the parallel pin guide supporting the pair of dilators.
Figures 52F, 52G, 52H:
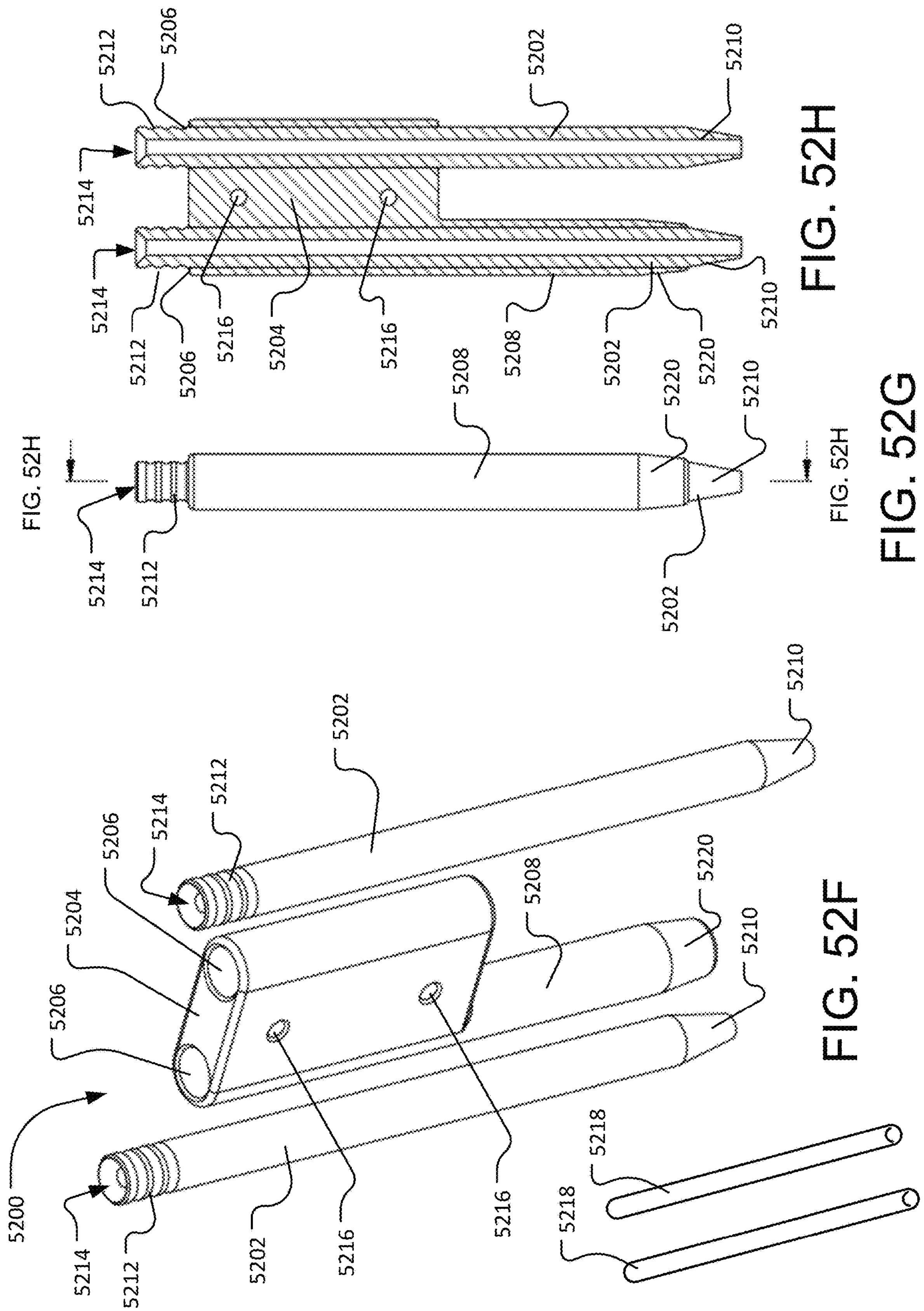
FIG. 52F is an isometric front view of the parallel pin guide separated from the pair of dilators.
FIG. 52G is a side view of the parallel pin guide supporting the pair of dilators.
FIG. 52H is a cross-sectional view of the parallel pin guide supporting the pair of dilators.

The following is a description of various tools, systems, and methods for bone pin delivery and manipulation. FIGS. 52A-52H depict various views of a parallel pin guide 5200. More particularly, FIG. 52A is an isometric front view of the parallel pin guide 5200 supporting a pair of dilators 5202. FIG. 52B is a front view of the parallel pin guide 5200 supporting the pair of dilators 5202. FIG. 52C is a cross-sectional view of the parallel pin guide 5200 supporting the pair of dilators 5202. FIG. 52D is a top view of the parallel pin guide 5200 supporting the pair of dilators 5202. FIG. 52E is a bottom view of the parallel pin guide 5200 supporting the pair of dilators 5202. FIG. 52F is an isometric front view of the parallel pin guide 5200 separated from the pair of dilators 5202. FIG. 52G is a side view of the parallel pin guide 5200 supporting the pair of dilators 5202. And, FIG. 52H is a cross-sectional view of the parallel pin guide 5200 supporting the pair of dilators 5202.

As best seen in FIG. 52F, among others, the parallel pin guide 5200 may include a guide body 5204 having a pair of spaced-apart guide holes 5206 extending in a distal-proximal direction. One of the guide holes 5206 may include a sleeve 5208 extending distally from the guide body 5204. A distal tip 5220 of the sleeve 5208 may include a conical taper. The guide holes 5206 may define a passageway there through for receiving a dilator 5202. The dilators 5202 may include a distal tip 5210 that may be conically tapered, a ribbed proximal end 5212 for grip, and passageway 5214 extending there through.

The guide body 5204 may additionally include a pair of radiographic guides or apertures 5216 extending transversely through the body 5204. An axis extending through the radiographic guides 5216 may be generally perpendicular to an axis extending through the guide holes 5206. The radiographic guides 5216 may receive radiographic contrasting cylinders 5218 therein for aligning relative to a joint line of the sacroiliac joint during the surgical procedure while under radiographic guidance (e.g., C-arm fluoroscopy). Alternatively or additionally, the guide body (or bone pins 5302, a handle coupled to the bone pins, or any other component of the system described here or throughout the present application) may be configured for a navigated stereotactic procedure. As an example, the system may be configured to be used with a Medtronic StealthStation™ Navigation System and TeraTrackers or similar system (e.g., any system comprising optical or electromagnetic tracking) in order to assist the physician in precisely locating anatomical structures and accurately placing certain components of the system (e.g., the bone pins, guide wires or any other tool or implant) into or onto the patient. As such the guide body or other tool may have an attachment site configured to support a tracking array comprising active (transmits its own infrared light, e.g., via light-emitting diodes) or passive (reflects infrared light supplied by an external illumination source) markers.

As seen in FIGS. 52A-52E and 52G-52H, when the first and second dilators 5202 are positioned in the guide holes 5206 of the guide body 5204, the ribbed proximal end 5212 of the dilators 5202 may extend from the proximal end of the guide body 5204, and the distal tip 5210 of the first dilator 5202 extends beyond the distal tapered tip 5220 of the sleeve 5208. The second dilator 5202 extends from the proximal end of the guide body 5204 in parallel alignment with the first dilator 5202.

Figure 53B:
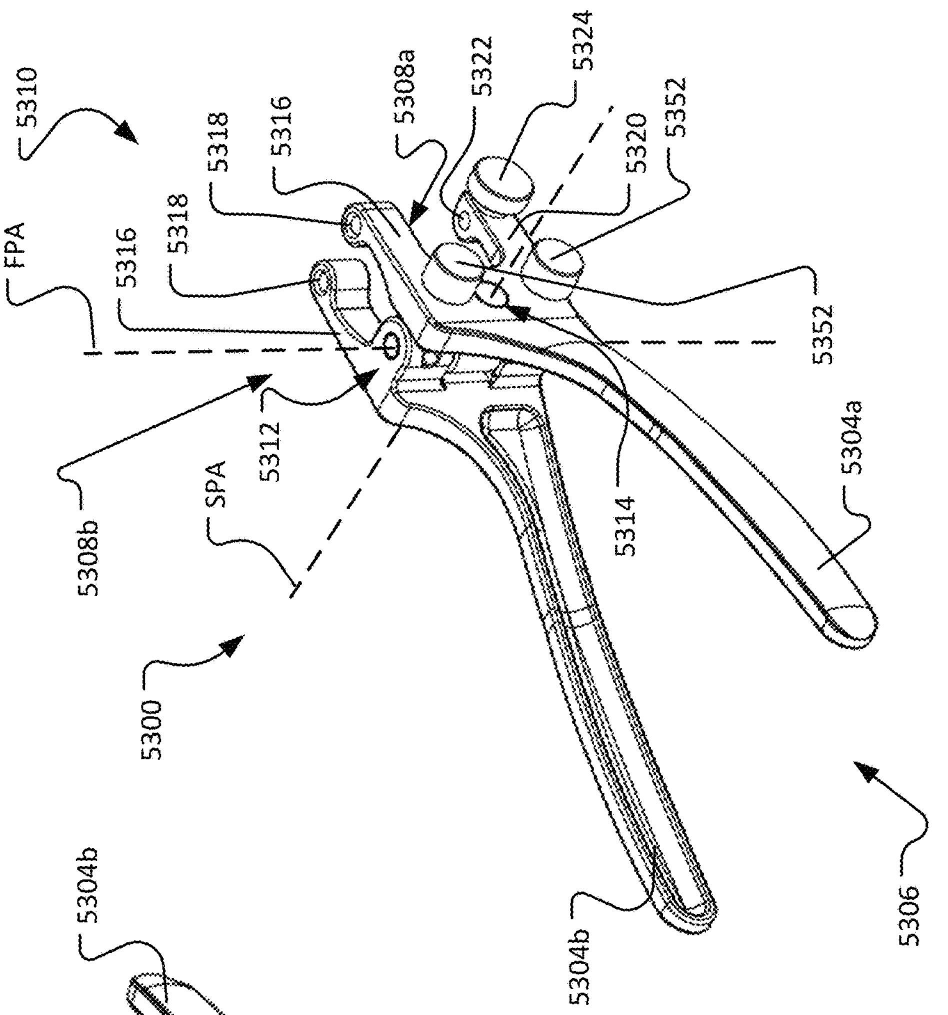
FIG. 53B is an isometric rear view of the dual-axis pliers.
Figure 53A:
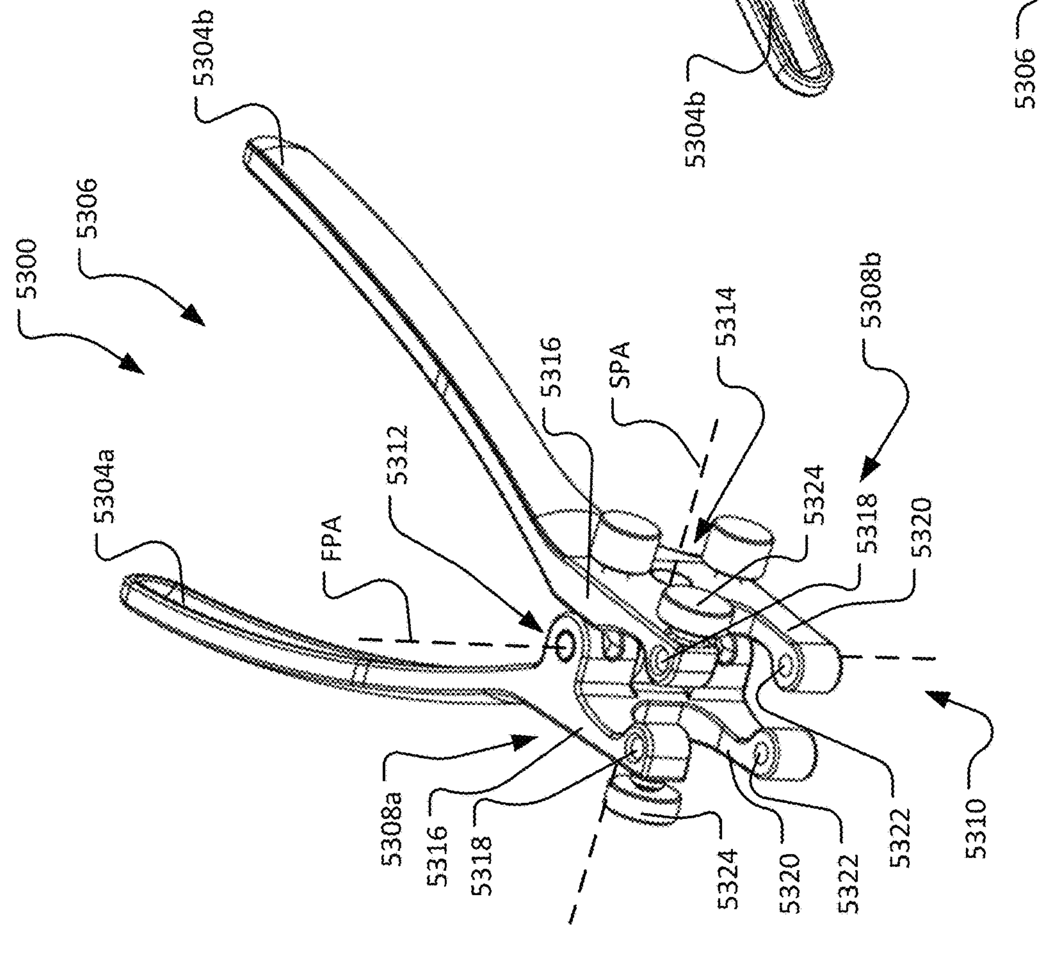
FIG. 53A is an isometric front view of a dual-axis pliers.
Figure 53D:
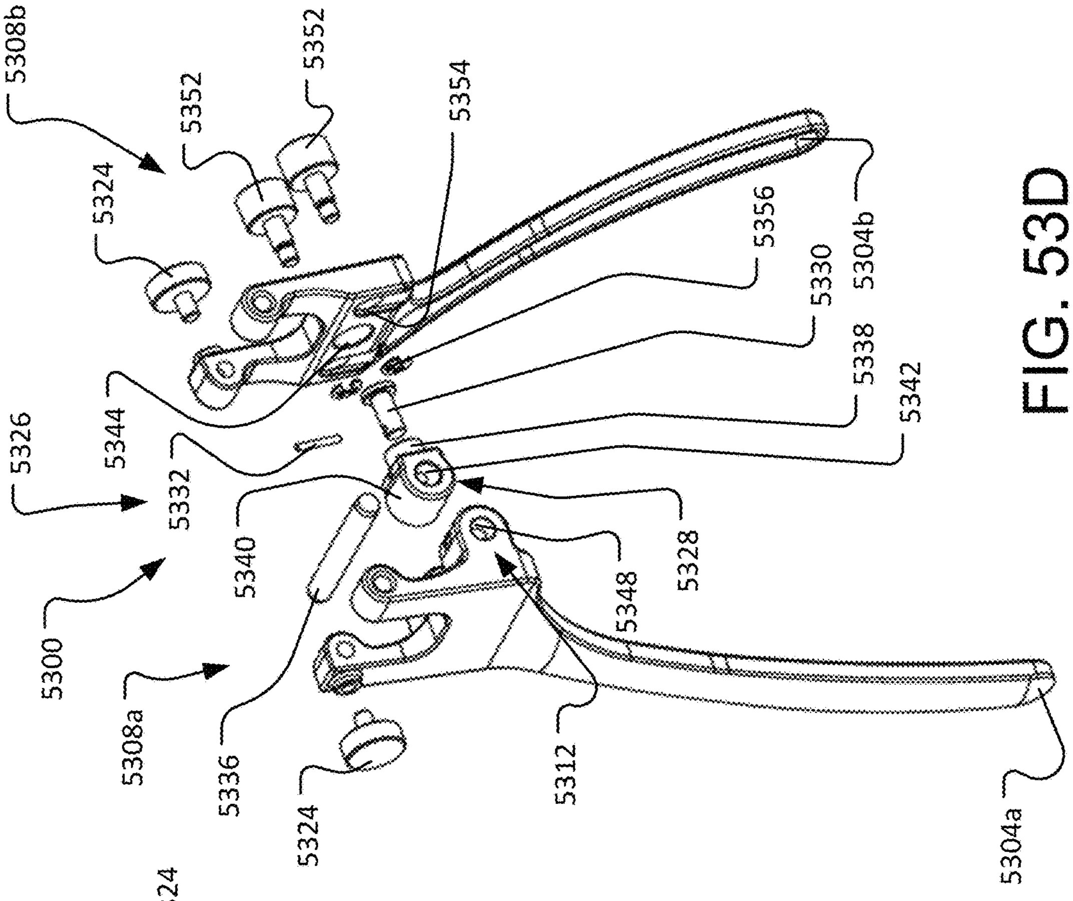
FIG. 53D is an isometric exploded view of the dual-axis pliers from a second side.
Figure 53C:
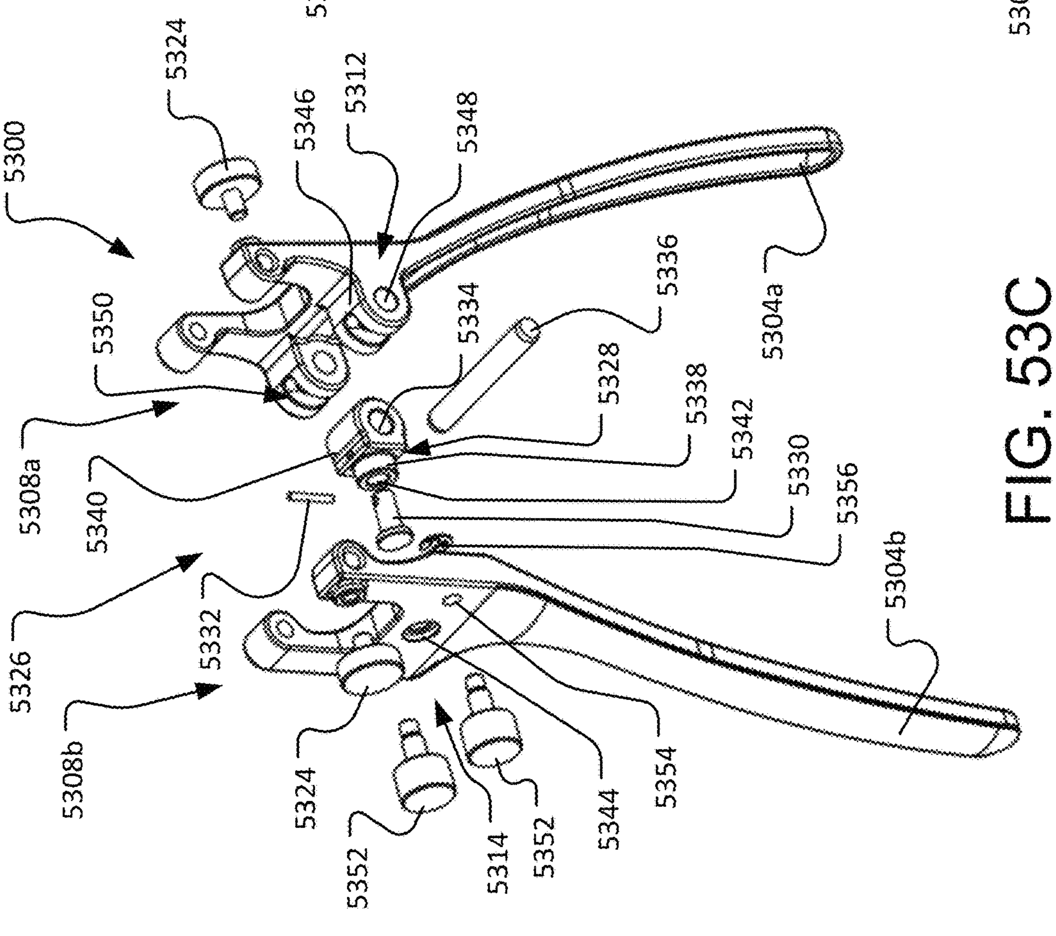
FIG. 53C is an isometric exploded view of the dual-axis pliers from a first side.
Figure 53E:
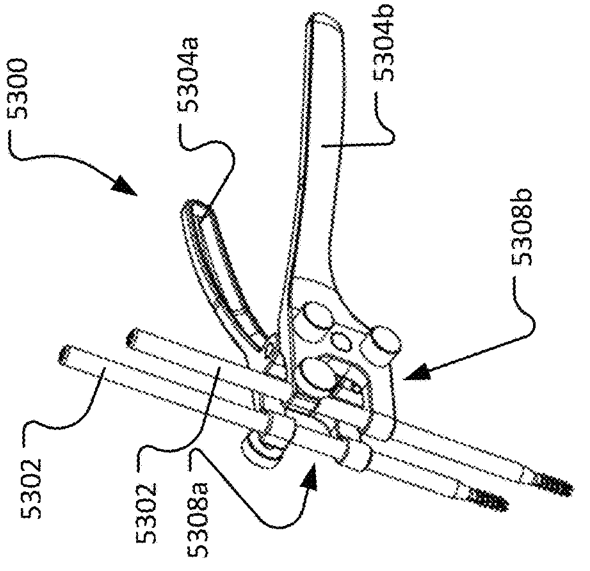
FIG. 53E is an isometric front view of the dual-axis pliers supporting a pair of bone pins in a first parallel orientation.
Figure 53F:
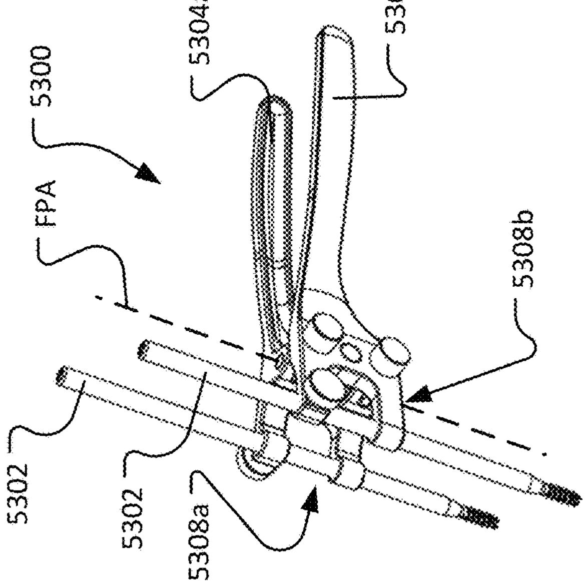
FIG. 53F is an isometric front view of the dual-axis pliers supporting a pair of bone pins in a second parallel orientation where the bone pins are spaced apart a farther distance than in the first parallel orientation.
Figure 53G:
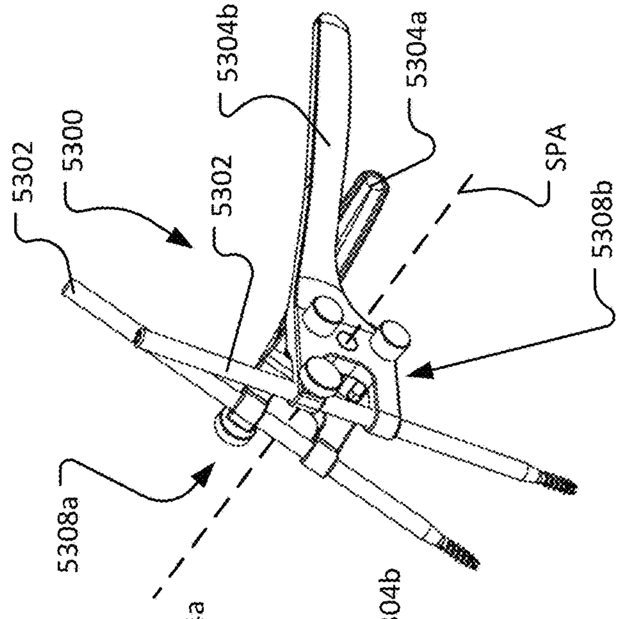
FIG. 53G is an isometric front view of the dual-axis pliers supporting a pair of bone pins in a third orientation where the pair of bone pins are angled relative to each other but within parallel planes.

FIGS. 53A-53G depict various views of a dual-axis pliers 5300. More particularly, FIG. 53A is an isometric front view of a dual-axis pliers 5300. FIG. 53B is an isometric rear view of the dual-axis pliers 5300. FIG. 53C is an isometric exploded view of the dual-axis pliers 5300 from a first side. FIG. 53D is an isometric exploded view of the dual-axis pliers 5300 from a second side. FIG. 53E is an isometric front view of the dual-axis pliers 5300 supporting a pair of bone pins 5302 in a first parallel orientation. FIG. 53F is an isometric front view of the dual-axis pliers 5300 supporting a pair of bone pins 5302 in a second parallel orientation where the bone pins 5302 are spaced apart a farther distance than in the first parallel orientation. FIG. 53G is an isometric front view of the dual-axis pliers 5300 supporting a pair of bone pins 5302 in a third orientation where the pair of bone pins 5302 are angled relative to each other but within parallel planes.

As seen in FIGS. 53A and 53B, the dual-axis pliers 5300 may include handles 5304 at a proximal end 5306, a head 5308 at a distal end 5310, and first and second pivot joints 5312, 5314 intermediate of the handles 5304 and head 5308. A first handle 5304*a* may be integrally formed with a first head portion 5308*a*, and a second handle 5304*b* may be integrally formed with a second head portion 5308*b*. The dual-axis pliers 5300 may function as expanding pliers where inward movement of the handles 5304*a*, 5304*b* relative to each other causes the head portions 5308*a*, 5308*b* to move away from each other, or expand, and thereby (depending on the arrangement of the bone pins to the sacroiliac joint) causing a distractive force at the sacroiliac joint, e.g., when a line drawn between the pins is substantially perpendicular to the sacroiliac joint line or when a line drawn between the pins forms an acute angle relative to the joint line such action may cause a shearing force or motion at the joint or a rotational force or motion at the joint. Conversely, outward movement of the handles 5304*a*, 5304*b* relative to each other causes the head portions 5308*a*, 5308*b* to move closer to each other, or to contract, and thereby (depending on the arrangement of the bone pins to the sacroiliac joint) causing a compressive force at the sacroiliac joint, e.g., when a line drawn between the pins is substantially perpendicular to the sacroiliac joint line or when a line drawn between the pins forms an acute angle relative to the joint line such action may cause a shearing force or motion at the joint or a rotational force or motion at the joint.

Each of the head portions 5308*a*, 5308*b* of the dual-axis pliers 5300 may include a proximal head member 5316 having a through-hole 5318 extending there through and a distal head member 5320 with a through-hole 5322 extending there through. The through-holes 5318, 5322 are coaxial with each other and sized to accept a bone pin (e.g., schanz screw/pin) therein. The proximal head members 5316 may each include a thumb-screw 5324 with a portion of the shaft extending into the through holes 5318 so as to contact and retain the bone pin in a desired position relative to the head portion 5308*a*, 5308*b*. While the thumb-screw 5324 is shown on the proximal head member 5316, the thumb-screw 5324 may additionally or alternatively be positioned on the distal head member 5320.

The pliers 5300 are referred to as dual-axis plier because the first and second pivot joints 5312, 5314 are oriented perpendicular to each other; the first pivot joint 5312 facilitates movement or rotation (e.g., expanding and contracting) of the head portions 5308*a*, 5308*b* about a first pivot axis FPA, and the second pivot joint 5314 facilitates movement or rotation (e.g., shearing) of the head portions 5308*a*, 5308*b* about a second pivot axis SPA. In this way, as seen in FIGS. 53E-53F, the pliers 5300 may be used to expand a pair of bone pins secured to the pliers 5300 away from each other or closer to each other via rotation about the first pivot axis FPA. And, as seen in FIG. 53G, the pliers 5300 may be used to rotation or shear a pair of bone pins secured to the pliers 5300 via rotation about the second pivot axis SPA.

Referring to FIGS. 53C and 53D, the first and second pivot joints 5312, 5314 will be described. As seen in the figures, the dual-axis pliers 5300 may include a pivot assembly 5326 including a dual-cylinder body 5328, a pivot pin 5330, and a retention pin 5332 (similar to a cotter pin). The dual-cylinder body 5328 includes a barreled body 5340 with a first through-hole 5334 for receiving the first pivot pin 5336 there through. The dual-cylinder body 5328 may also include cylinder flange 5338 extending perpendicular to the barreled body 5340. The cylinder flange 5338 may include a second through-hole 5342 perpendicular to the first through-hole 5334. The second through-hole 5342 may receive the shaft of the pivot pin 5330 therein, and the retention pin 5332 may extend through the barreled body 5340 and into an opening in the tip of the pivot pin 5330 such that the pivot pin 5330 and dual-cylinder body 5328 are coupled to the second head portion 5308*b* of the pliers 5300. As seen in FIG. 53C, the second head portion 5308*b* includes a through-bore 5344 for receiving the pivot pin 5330 therein.

When the pivot pin 5330 is retained in the through-bore 5344 of the second head portion 5308*b*, and when the pivot pin 5330 is also coupled to the dual-cylinder body 5328 via the retention pin 5332, the cylinder flange 5338 of the dual-cylinder body 5328 is received within an enlarged portion of the through-bore 5344 such that the dual-cylinder body 5328 can rotate about the pivot pin 5330, which defines the second pivot axis SPA.

As seen in FIG. 53C, the first head portion 5308*a* includes a pair of inwardly extending knuckles or barrels 5346 with through-holes 5348 for receiving the first pivot pin 5336 therein. Each of the pair of knuckles 5346 includes a slot 5350 jutting into the knuckle 5346.

The pliers 5300 may function so as to pivot only about the first pivot joint 5312, or function to pivot about both the first and second pivot joints 5312, 5314. To pivot about only the first pivot joint 5312, a pair of thumb-studs 5352 may be selectively engaged with the slots 5350 of the knuckles 5346 so as to prevent rotation about the second pivot joint 5314 (the pivot pin 5330). As seen in FIG. 53C, the thumb-studs 5352 may extend through openings 5354 (e.g., threaded) in the second head portion 5308*b*, and may be retained from removal from the second head portion 5308*b* via e-clips 5356. The thumb-studs 5352 may be pushed or threadedly advanced to contact the second head portion 5308*b*, and in doing so the unthreaded tips of the thumb-studs 5352 may enter the slots 5350 of the knuckles 5346 on the first head portion 5308*a*. With the tips of the thumb-studs 5352 within the slots 5350, the pliers 5300 are permitted to pivot about the first pivot pin 5336 extending through the knuckles 5346 and the dual-cylinder body 5328 of the pivot assembly 5326 as the tips of the thumb-studs 5352 may slide within the slots 5350; but, in this orientation, the pliers 5300 are prevented from rotating about the second pivot joint 5314 defined by the pivot pin 5330 by contact of the tips of the thumb-studs 5352 against the upper and lower walls defined by the slots 5350.

By pulling back on or unthreading the thumb-studs 5352, relative to the second head portion 5308*b*, the tips of the thumb-studs 5352 may disengage or pull-out from within the slots 5350 of the knuckles 5346. In this orientation, the second head portion 5308*b* is permitted to rotate relative to the first head portion 5308*a* via the pivot pin 5330 and the cylinder flange 5338 of the dual-cylinder body 5328 (about the second pivot axis). It is noted, the second head portion 5308*b* may still rotate relative to the first head portion 5308*a* about the first pivot pin 5336 when the thumb-studs 5352 are disengaged from the slots 5350 of the knuckles 5346.

As seen in FIG. 53E, the dual-axis pliers 5300 is coupled to a pair of bone pins 5302 such that the bone pins 5302 are parallel to each other. As seen in FIG. 53F, the handles 5304*a*, 5304*b* are moved closer to each other (rotated about the first pivot axis FPA of the first pivot joint 5312) so as to cause the first and second head portions 5308*a*, 5308*b* to move farther apart from each other while the bone pins 5302 are still parallel to each other. And in FIG. 53G, the thumb-studs 5352 are disengaged (pulled away from the second head portion 5308*b*) from the slots 5350 of the knuckles 5346 (not seen in FIG. 53G) such that the pliers 5300 are pivotable about the second pivot axis SPA of the second pivot joint 5314. As configured the dual-axis pliers allow the physician to selectively and reproducibly constrain manipulation or force delivery to certain desirable degrees of freedom.

Figure 54B:
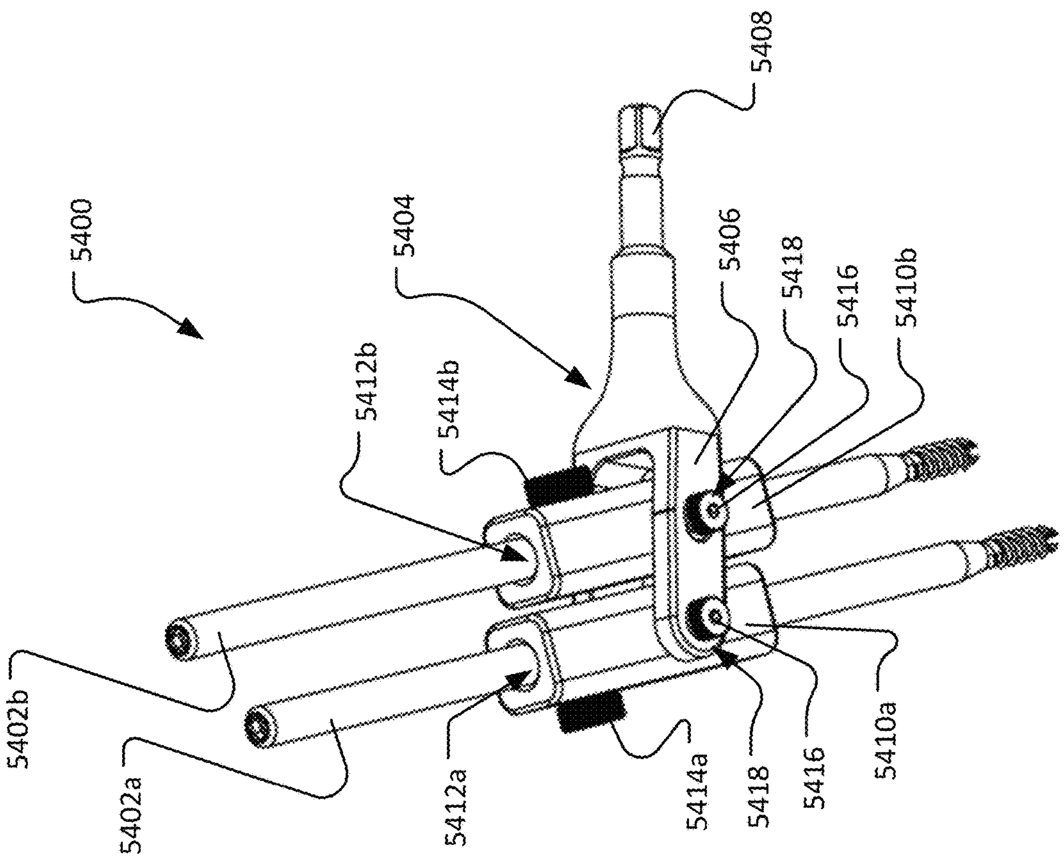
FIG. 54B is an isometric front view of the clevis guide supporting the pair of bone pins in a second parallel orientation where the bone pins are moved longitudinally relative to each other relative to their positions in the first parallel orientation.
Figure 54A:
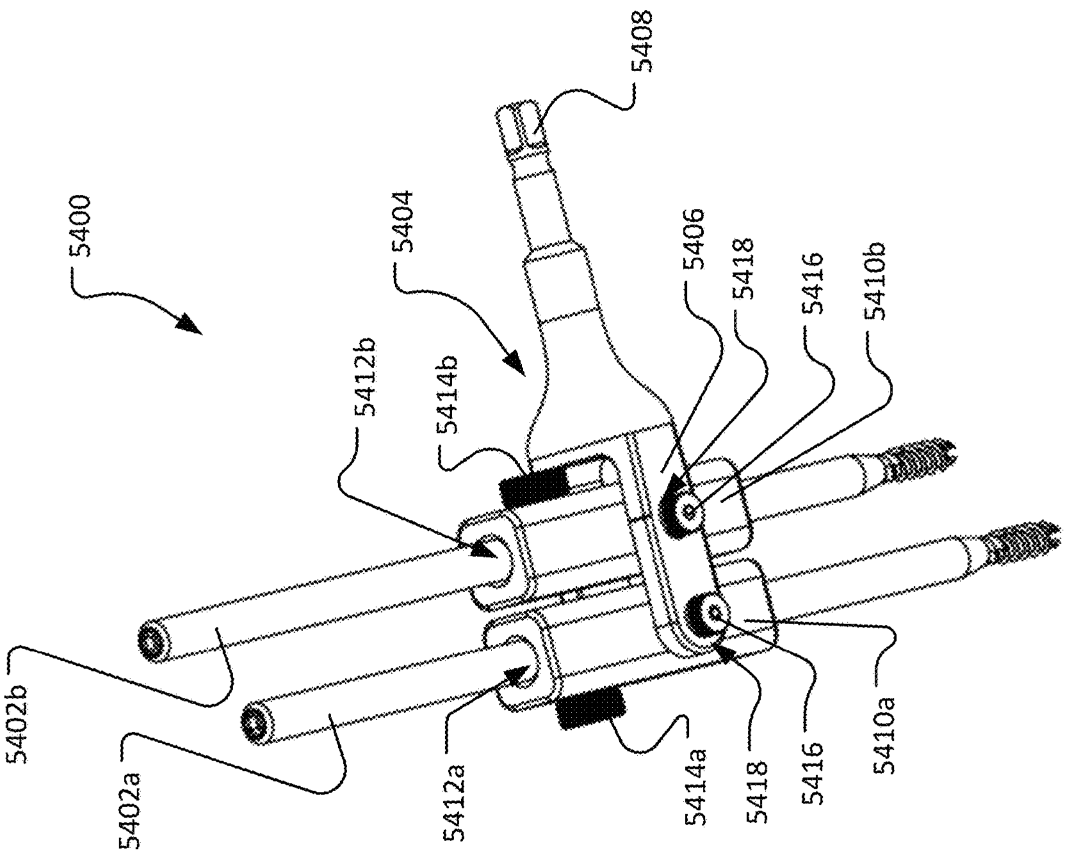
FIG. 54A is an isometric front view of a clevis guide supporting a pair of bone pins in a first parallel orientation.
Figure 54C:
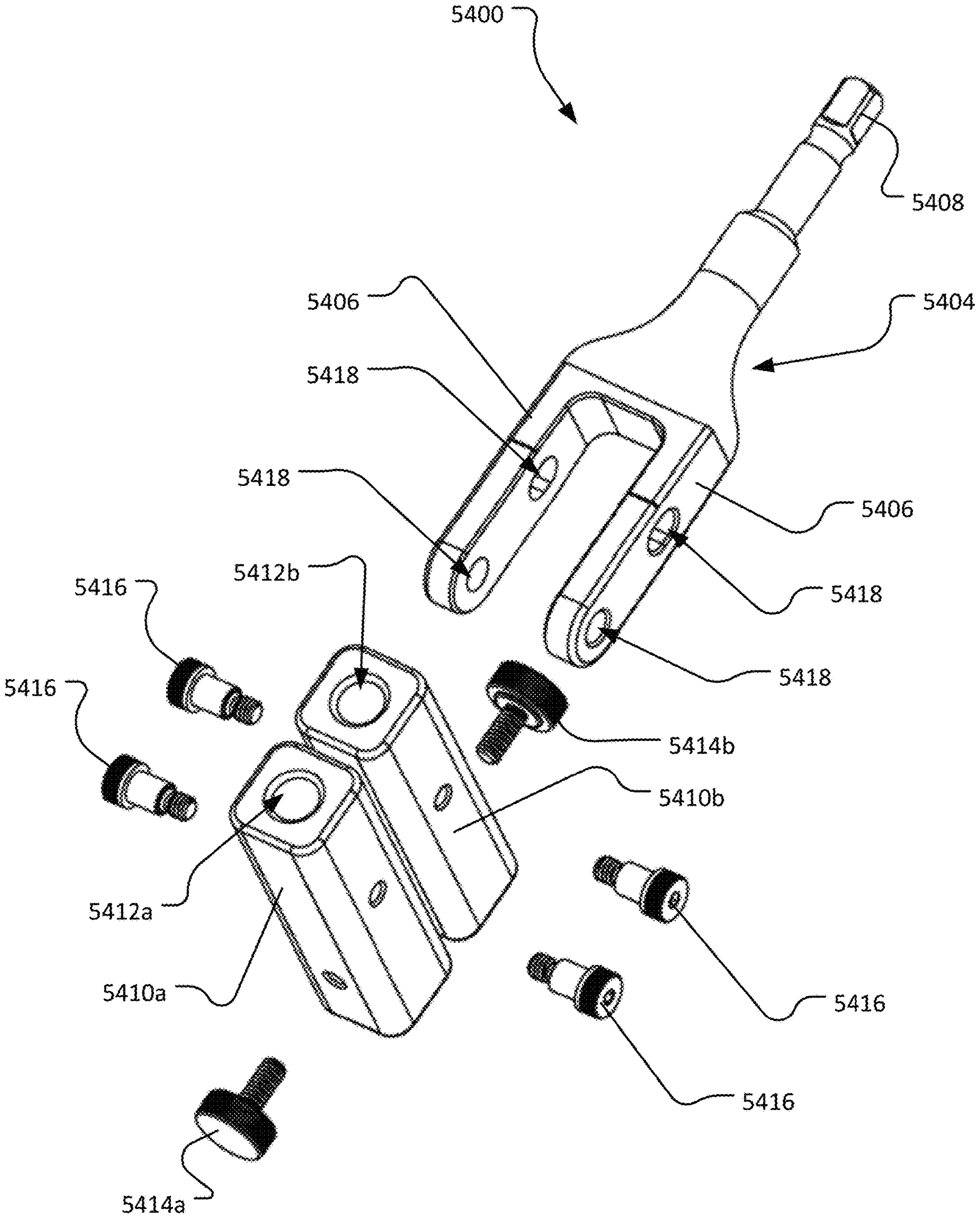
FIG. 54C is an isometric exploded view of the clevis guide.

FIGS. 54A-54C illustrate various view of a clevis guide 5400. More particularly, FIG. 54A is an isometric front view of a clevis guide 5400 supporting a pair of bone pins 5402 in a first parallel orientation. FIG. 54B is an isometric front view of the clevis guide 5400 supporting the pair of bone pins 5402 in a second parallel orientation where the bone pins 5402 are moved longitudinally relative to each other relative to their positions in the first parallel orientation. FIG. 54C is an isometric exploded view of the clevis guide 5400.

As seen in the figures, the clevis guide 5400 may include a clevis 5404 having a pair of prongs 5406 at one end and a tool engaging structure 5408 (e.g., square-end handle quick connect adapter) at the opposite end. The clevis guide 5400 may couple to a pair of guide blocks 5410*a*, 5410*b*, each of which may include a guide hole 5412*a*, 5412*b* extending longitudinally through the guide block 5410*a*, 5410*b*. The guide blocks 5410*a*, 5410*b* may include a thumb-screw 5414*a*, 5414*b* that, when engaged, causes a tip of the shaft to extend into the guide holes 5412*a*, 5412*b* so as to contact and retain the bone pins 5402*a*, 5402*b* positioned therein.

Each of the guide blocks 5410*a*, 5410*b* may be supported relative to the prongs 5406 via a pair of pins 5416 that extend through apertures 5418 in the prongs 5406. It can be seen in FIGS. 54B and 54C that the aperture 5418 nearest the body of the clevis 5404 is elongated so as to permit the pins 5416 to slide slightly distal-proximal, which permits the guide blocks 5410*a*, 5410*b* to remain in a parallel orientation during use.

In use, the clevis guide 5400 may be used to displace the bone pins 5402*a*, 5402*b* longitudinally relative to each other. For example, FIG. 54A depicts the guide blocks 5410*a*, 5410*b* in a neutral orientation where the blocks are parallel to each other and the tops and bottom surfaces of the blocks are, respectively, coplanar. From this orientation, the tool engaging structure 5408 may be moved down (assuming the bone pins 5402*a*, 5402*b* are secured to a patient's bone surface), which causes the most distal bone pin 5402*a* (the one farthest from the tool engaging structure 5408) to move up relative to the other bone pin 5402*b*. With this type of movement, the proximal bone pin 5402*b* acts as a fulcrum. While not shown, the tool engaging structure 5408 may be moved upwards, which causes the most distal bone pin 5402*a* to move down relative to the other bone pin 5402*b*.

Figure 55A:
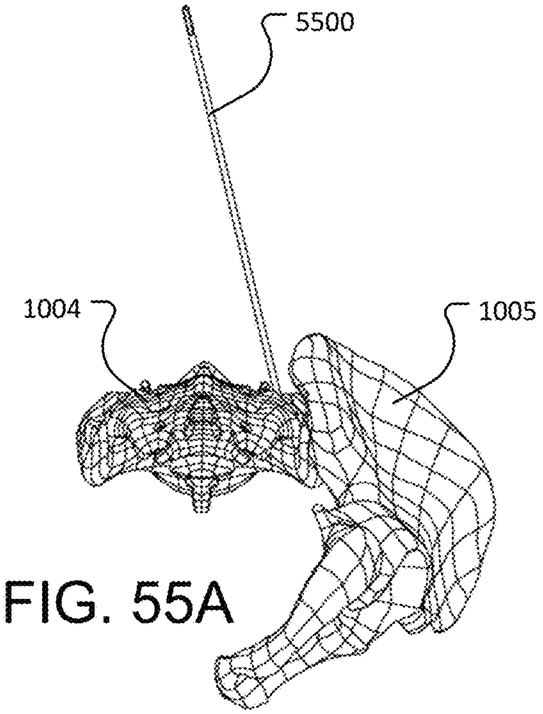
FIG. 55A is an inferior view of a sacrum and an ilium with a guide wire delivered into the sacrum.
Figure 55B:
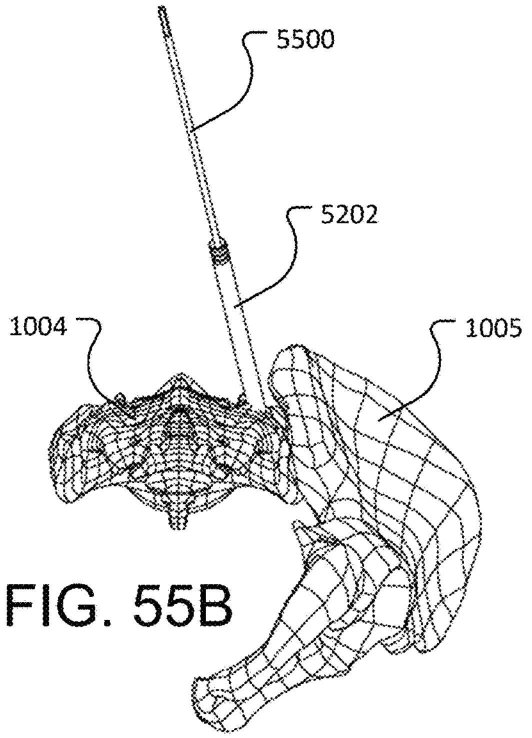
FIG. 55B is an inferior view of the sacrum and the ilium with a first dilator positioned over the guide wire.
Figure 55C:
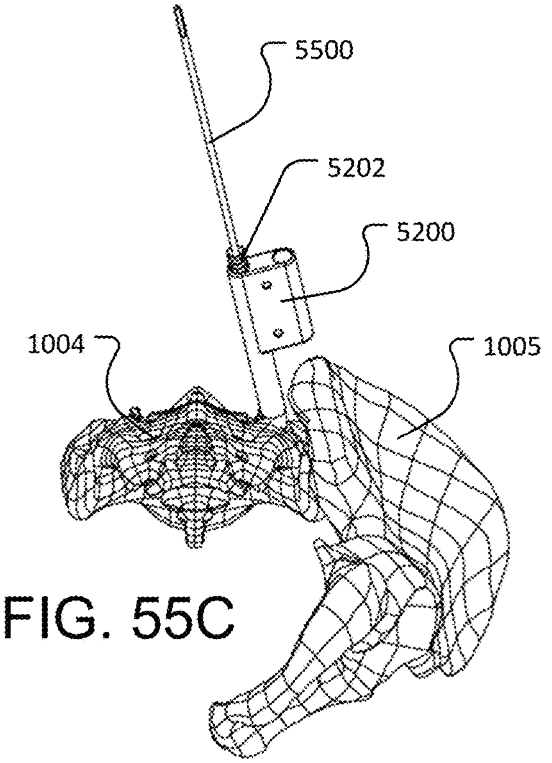
FIG. 55C is an inferior view of the sacrum and the ilium with the parallel pin guide positioned over the first dilator.
Figure 55D:
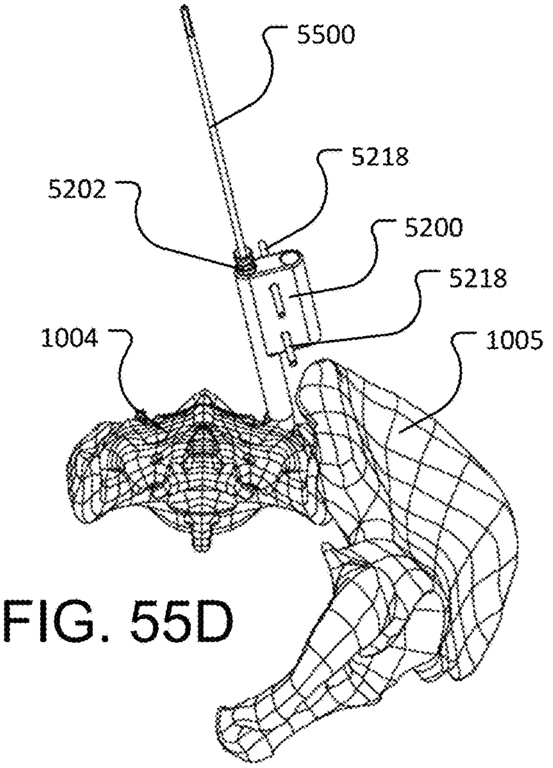
FIG. 55D is an inferior view of the sacrum and the ilium with a pair of radiographic contrasting cylinders positioned through the radiographic guides of the parallel pin guide.
Figure 55G:
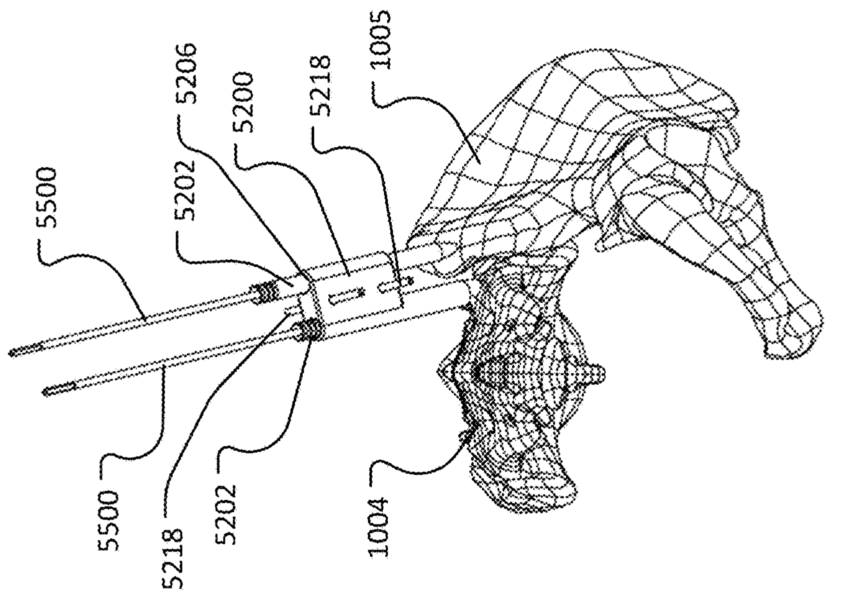
FIG. 55G is an inferior view of the sacrum and the ilium with a second guide wire positioned through the second dilator and into the ilium.
Figure 55F:
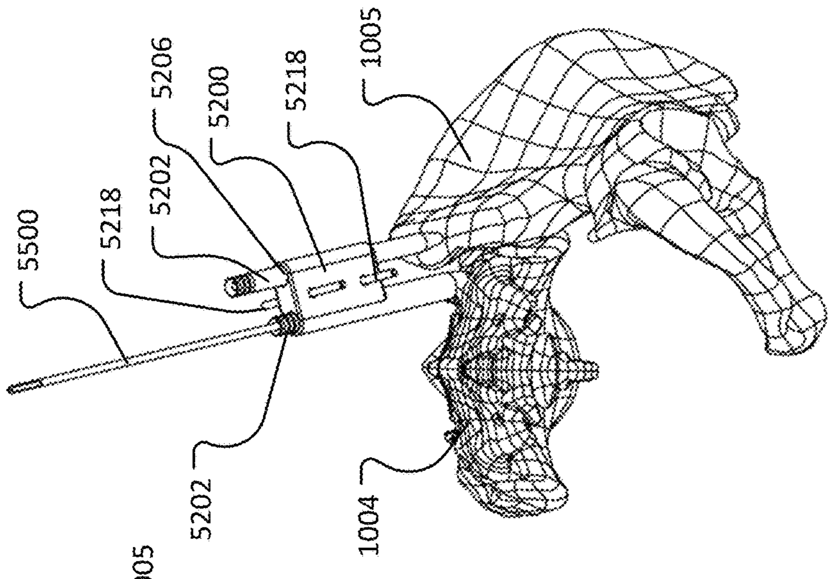
FIG. 55F is an inferior view of the sacrum and the ilium with a second dilator positioned up against the ilium and through a guide hole of the parallel pin guide.
Figure 55E:
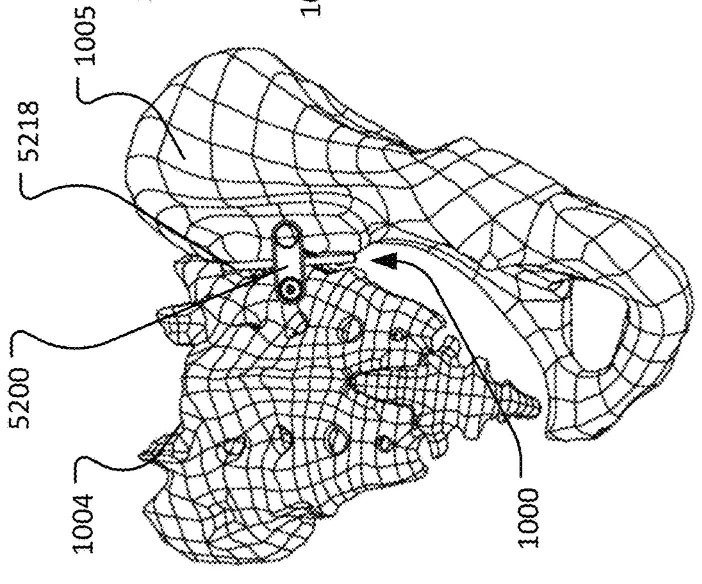
FIG. 55E is a posterior view of the sacrum and the ilium showing the pair of radiographic contrasting cylinders parallel with each other and generally parallel with a joint line of the sacroiliac joint.
Figure 55I:
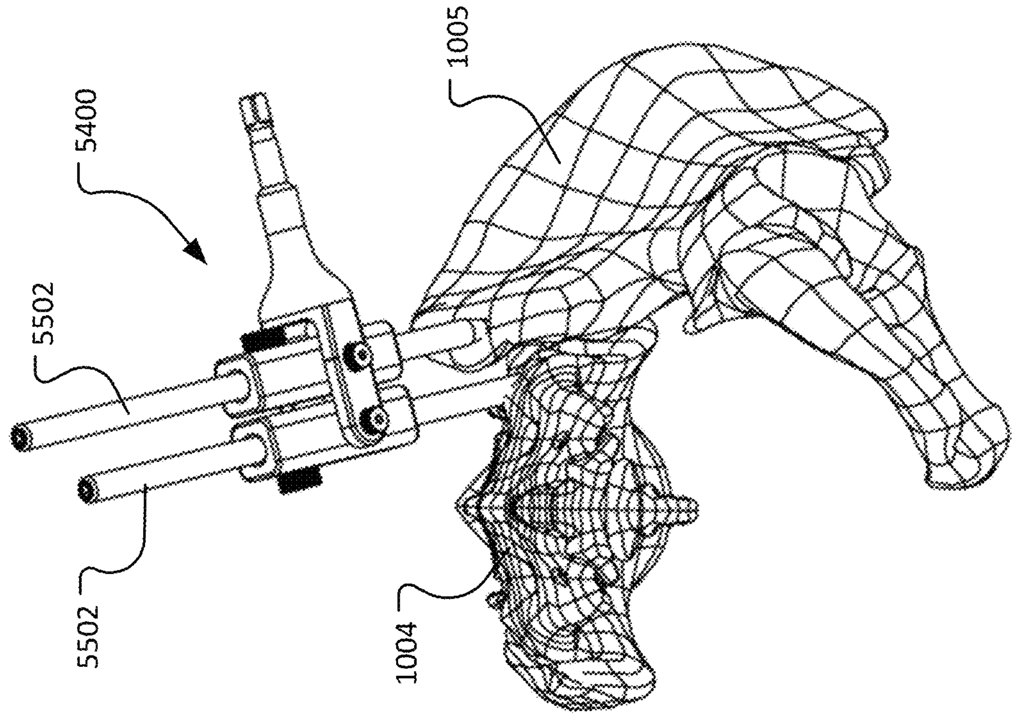
FIG. 55H is an inferior view of the sacrum and the ilium with the dual-axis pliers secured to a pair of pins (positioned in the sacrum and ilium where the guide wires were previously).
Figure 55H:
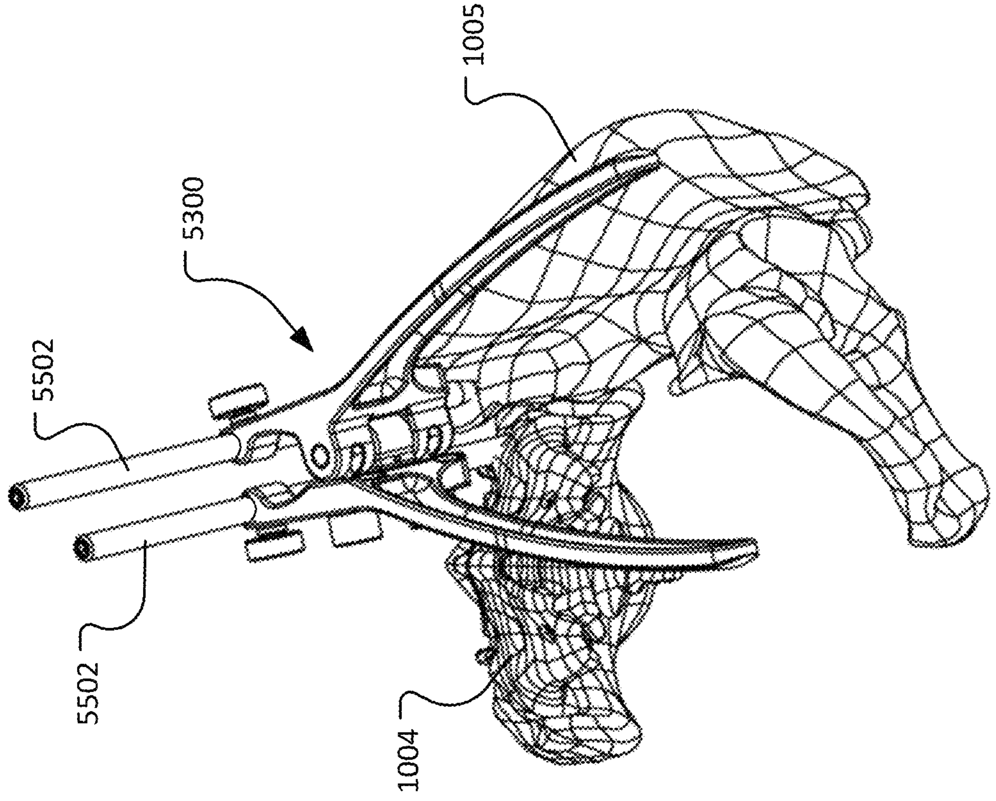

FIGS. 55A-55G depict exemplary steps in a surgical procedure. FIG. 55A is an inferior view of a sacrum 1004 and an ilium 1005 with a guide wire 5500 delivered into the sacrum 1004. FIG. 55B is an inferior view of the sacrum 1004 and the ilium 1005 with a first dilator 5202 positioned over the guide wire 5500. FIG. 55C is an inferior view of the sacrum 1004 and the ilium 1005 with the parallel pin guide 5200 positioned over the first dilator 5202. FIG. 55D is an inferior view of the sacrum 1004 and the ilium 1005 with a pair of radiographic contrasting cylinders 5218 positioned through the radiographic guides 5216 of the parallel pin guide 5200. FIG. 55E is a posterior view of the sacrum 1004 and the ilium 1005 showing the pair of radiographic contrasting cylinders 5218 parallel with each other and generally parallel with a joint line of the sacroiliac joint 1000. FIG. 55F is an inferior view of the sacrum 1004 and the ilium 1005 with a second dilator 5202 positioned up against the ilium 1005 and through a guide hole 5206 of the parallel pin guide 5200. FIG. 55G is an inferior view of the sacrum 1004 and the ilium 1005 with a second guide wire 5500 positioned through the second dilator 5202 and into the ilium 1005. FIG. 55H is an inferior view of the sacrum 1004 and the ilium 1005 with the dual-axis pliers 5300 secured to a pair of pins 5502 (positioned in the sacrum 1004 and ilium 1005 where the guide wires 5500 were previously). FIG. 55I is an inferior view of the sacrum 1004 and the ilium 1005 with the clevis guide 5400 secured to the pair of pins 5502 (positioned in the sacrum 1004 and ilium 1005 where the guide wires 5500 were previously).

The systems disclosed above may include a digital and or analog indicators and readout. Additionally or alternatively, the systems may include various forms of motion control (e.g., between components of the system and or the patient or a frame in proximity to the patient) with accurate position/velocity/torque capabilities operating in either open or closed loop mode. For example, open loop stepping drives may send motion commands to stepper motors, but receive no information about the result while closed loop servo systems may have feedback devices at the motor shaft to verify or adjust the resulting motion. Additionally or alternatively, the systems may include: linear motion slides and actuators, drive couplings, sensors, encoders, rotary encoders for detecting position and speed, sensors for detecting proximity, pressure, temperature, level, flow, current and voltage, limit switches for detecting states such as presence or end-of-travel limits, discrete or analog outputs, optical rotary encoders, inductive proximity sensors, magnetic proximity sensors, capacitive proximity sensors, photoelectric sensors, laser sensors, area sensors, fiber optic sensors, color sensors, contrast sensors, fork sensors, ultrasonic proximity sensors, pressure sensors, pressure gauges, thermometers, temperature sensors and transmitters, level sensors and controllers, flow sensors, current & voltage sensors (ac & dc), ground fault sensors, limit switches, hmi (human machine interface) providing a textual or graphical view of system conditions and operations offering monitoring, control, status reporting and other functions, programmable controllers (providing accurate, reliable, easily-modified control with discrete and process functions including motion, data logging and web server access), mechanical power transmission components, mechanical drivetrains to create movement, gearboxes, timing belts/pulleys/bushings, shaft couplings, bore reducers, linear shafts, and linear shaft supports.

Neuromonitoring may be conducted simultaneously with the diagnostic procedure utilizing any of the systems or methods described herein in order to monitor the status of the nerves in proximity to the diagnostic or treatment site whether to assess the location of the pins or to assess the influence of joint movement or pin movement on the nerves.

The foregoing merely illustrates the principles of the embodiments described herein. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the embodiments described herein and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A method for fusing a sacroiliac joint having a sacrum, an ilium, a joint plane, a posterior inferior aspect, an intra-articular region, a posterior inferior access region, and a sacroiliac joint space defined between the sacrum and the ilium, the method comprising:

a. positioning an implant up to the posterior inferior aspect of the sacroiliac joint, the implant having an implant longitudinal axis, an implant length, a distal end, a proximal end, a pair of longitudinally extending finger members extending the length and including a sacral member and an iliac member spaced apart from one another by a connecting portion coupled therebetween, the iliac and sacral members extending further distally than the connecting portion and defining an opening bound by the pair of longitudinally extending finger members and the connecting portion;

b. aligning the implant such that the implant longitudinal axis is generally in line with the joint plane; and c. delivering the implant at the sacroiliac joint such that: the iliac member enters the ilium lateral to the sacroiliac joint space; the sacral member enters the sacrum medial to the sacroiliac joint space; and the opening extends across the sacroiliac joint space, wherein the connecting portion comprises a planar member having opposing planar surfaces and a distance between the opposing planar surfaces defining a connecting portion thickness; and wherein each of the sacral member and the iliac member have a maximum thickness which is greater than the connecting portion thickness.

2. The method of claim 1, wherein the opening comprises a width extending between the pair of longitudinally extending finger members which is wider than a width of a portion of the sacroiliac joint space at the intra-articular region of the sacroiliac joint.

3. The method of claim 1, further comprising: selecting an implant configuration and size where the opening comprises a width extending between the pair of longitudinally extending finger members which is wider than a width of a portion of the sacroiliac joint space at the intra-articular region of the sacroiliac joint where the implant is delivered.

4. The method of claim 1, wherein the iliac and sacral members extend further distally than the connecting portion by approximately 5 mm.

5. The method of claim 1, wherein the planar member has a width extending between the pair of longitudinally extending finger members that is wider than a width of a portion of the sacroiliac joint space at the intra-articular region of the sacroiliac joint.

6. The method of claim 5, wherein, in delivering the implant, the implant is oriented to pass through the posterior inferior access region and positioned such that the iliac member enters the ilium inferior to the posterior superior iliac spine and the connecting portion bridges the sacroiliac joint.

7. The method of claim 1, further comprising, prior to positioning the implant up to the posterior inferior aspect of the sacroiliac joint, aligning a guidance tool including a body having a first bore spaced apart from and parallel to a second bore with the sacroiliac joint such that the first bore is positioned over the sacrum medial to the intra-articular region and the second bore is positioned over the ilium lateral to the intra-articular region, wherein each of the first and second bores is configured to guide a surgical tool, and wherein, in delivering the implant at the sacroiliac joint, the implant is oriented to pass through the posterior inferior access region and be positioned such that the iliac member enters the ilium inferior to the posterior superior iliac spine and the connecting portion bridges the sacroiliac joint.

8. The method of claim 7, wherein the body of the guidance tool further includes a center alignment bore extending therethrough and disposed between the first and second bores, and wherein, in aligning the implant, the center alignment bore is positioned in alignment with the joint plane.

9. A method for fusing a sacroiliac joint having a sacrum, an ilium, a joint plane, a posterior inferior aspect, an intra-articular region, a posterior inferior access region, and a sacroiliac joint space defined between the sacrum and the ilium, the method comprising:

a. positioning an implant up to the posterior inferior aspect of the sacroiliac joint, the implant having an implant longitudinal axis, an implant length, a distal end, a proximal end, a connecting portion at the proximal end, a pair of longitudinally extending finger members extending distally from the connecting portion and defining an opening bounded by the pair of longitudinally extending finger members and the connecting portion, the pair of longitudinally extending finger members extending the length and including a sacral member and an iliac member, the sacral member extending from a sacral side of the connecting portion, the iliac member extending from an iliac side of the connecting portion, the iliac member and the sacral member extending further distally than the connecting portion, the opening spanning unobstructed between the sacral member and the iliac member at the connecting portion;

b. aligning the implant such that the implant longitudinal axis is generally in line with the joint plane; and C. delivering the implant at the sacroiliac joint such that: the iliac member enters the ilium lateral to the sacroiliac joint space; the sacral member enters the sacrum medial to the sacroiliac joint space; and the opening extends across the sacroiliac joint space.

10. The method of claim 9, further comprising, prior to positioning the implant up to the posterior inferior aspect of the sacroiliac joint, aligning a guidance tool including a body having a first bore spaced apart from and parallel to a second bore with the sacroiliac joint such that the first bore is positioned over the sacrum medial to the intra-articular region and the second bore is positioned over the ilium lateral to the intra-articular region, wherein each of the first and second bores is configured to guide a surgical tool, and wherein, in delivering the implant at the sacroiliac joint, the implant is oriented to pass through the posterior inferior access region and be positioned such that the iliac member enters the ilium inferior to the posterior superior iliac spine and the connecting portion bridges the sacroiliac joint.

11. The method of claim 10, wherein the body of the guidance tool further includes a center alignment bore extending therethrough and disposed between the first and second bores, and wherein, in aligning the implant, the center alignment bore is positioned in alignment with the joint plane.

* * * * *